(12) United States Patent
Capone et al.

(10) Patent No.: US 9,057,363 B2
(45) Date of Patent: Jun. 16, 2015

(54) CONTINUOUS FLUID DELIVERY SYSTEM

(75) Inventors: Christopher D. Capone, Pittsburgh, PA (US); Richard A. Seman, Delmont, PA (US); Jason L. Bazala, North Huntington, PA (US)

(73) Assignee: Bayer Medical Care, Inc., Indianola, PA (US)

( * ) Notice: Subject to any disclaimer, the term of this patent is extended or adjusted under 35 U.S.C. 154(b) by 1091 days.

(21) Appl. No.: 12/745,849

(22) PCT Filed: Dec. 10, 2008

(86) PCT No.: PCT/US2008/086209
§ 371 (c)(1),
(2), (4) Date: Sep. 15, 2010

(87) PCT Pub. No.: WO2009/076429
PCT Pub. Date: Jun. 18, 2009

(65) Prior Publication Data
US 2011/0002802 A1    Jan. 6, 2011

Related U.S. Application Data

(60) Provisional application No. 61/012,626, filed on Dec. 10, 2007.

(51) Int. Cl.
*F04B 19/00* (2006.01)
*F04B 37/00* (2006.01)
(Continued)

(52) U.S. Cl.
CPC .. *F04B 13/02* (2013.01); *F04B 7/00* (2013.01)

(58) Field of Classification Search
CPC ............ F04B 1/02; F04B 33/005; F04B 7/00; D04B 35/28; E21B 43/121

USPC ............ 417/442, 521, 486, 487, 488; 222/94, 222/132, 135, 136, 137, 141, 142, 144.5, 222/145.1, 252, 255, 256, 259, 260, 265, 222/266, 270, 278
See application file for complete search history.

(56) References Cited

U.S. PATENT DOCUMENTS 378,073 A    2/1888    Alexander
660,040 A    10/1900   Baker
(Continued)

FOREIGN PATENT DOCUMENTS

EP    1817499         6/2006
GB    2038929 A       7/1980
(Continued)

*Primary Examiner* — Charles Freay
*Assistant Examiner* — Lilya Pekarskaya
(74) *Attorney, Agent, or Firm* — Joseph L. Kent; David Schramm; James R. Stevenson

(57) ABSTRACT

The continuous fluid delivery systems includes a fluid pumping device comprising a pump housing comprising a base member with a plurality of inlet ports and at least one outlet port and at least two pairs of opposing pistons movably associated with the housing. Each pair of opposing pistons at least in part defines a respective pumping chamber of the fluid pumping device. The pistons in each pair of opposing pistons may be independently controlled such that any one of the plurality of inlet ports or the at least one outlet port is independently selectable to be in fluid communication with one of the respective pumping chambers. A drive system may be interfaced with the respective pistons to at least reciprocally operate the pistons relative to the base member. The pump housing and the at least two pairs of opposing pistons may comprise a disposable unit.

20 Claims, 99 Drawing Sheets

(51) Int. Cl.
    *F04B 13/02*     (2006.01)
    *F04B 7/00*     (2006.01)

(56) References Cited

U.S. PATENT DOCUMENTS

| | | | |
|---|---|---|---|
| 711,128 A | 10/1902 | Schirmer | |
| 726,069 A | 4/1903 | Josse | |
| 878,073 A | 2/1908 | Lancia | |
| 1,085,963 A | 2/1914 | Bresnahan | |
| 1,234,684 A | 7/1917 | Niebling | |
| 1,383,997 A | 7/1921 | Pease | |
| 1,452,318 A | 4/1923 | Spiker et al. | |
| 1,511,962 A | 10/1924 | Hanson | |
| 1,516,032 A | 11/1924 | White | |
| 1,531,698 A | 3/1925 | Janes | |
| 1,590,940 A | 6/1926 | Hallett | |
| 1,595,688 A | 8/1926 | Porter | |
| 1,614,389 A | 1/1927 | Rainer | |
| 1,689,419 A | 10/1928 | Bronander | |
| 1,703,389 A | 2/1929 | Coles | |
| 1,716,127 A | 6/1929 | Hamlin | |
| 1,748,810 A | 2/1930 | Wandel | |
| 1,805,741 A | 5/1931 | Prestage | |
| 1,850,273 A | 3/1932 | Thayer | |
| 1,866,217 A | 7/1932 | Mayer | |
| 1,973,351 A | 9/1934 | Meeker | |
| 2,028,161 A | 1/1936 | Mann | |
| 2,038,155 A | 4/1936 | Aldridge | |
| 2,062,285 A | 12/1936 | Bergman | |
| 2,086,162 A | 7/1937 | Janicke | |
| 2,102,121 A | 12/1937 | Janicke | |
| 2,160,687 A | 5/1939 | Stubbs | |
| 2,169,807 A | 8/1939 | Lyon | |
| 2,183,318 A | 12/1939 | Burton | |
| 2,258,055 A | 10/1941 | Holloway et al. | |
| 2,306,364 A | 12/1942 | Skaredoff | |
| 2,435,361 A | 2/1948 | Mallory | |
| 2,486,185 A | 10/1949 | Mallory | |
| 2,648,290 A | 8/1953 | Ashton et al. | |
| 2,783,713 A | 3/1957 | Klein et al. | |
| 2,793,593 A | 5/1957 | Klein et al. | |
| 2,821,926 A | 2/1958 | Miller et al. | |
| 2,842,124 A | 7/1958 | James | |
| 2,853,982 A | 9/1958 | Bachle et al. | |
| 2,867,375 A | 1/1959 | Petersen | |
| 3,013,394 A | 12/1961 | Musser | |
| 3,075,473 A | 1/1963 | Finley | |
| 3,083,895 A | 4/1963 | Welles, Jr. | |
| 3,145,660 A | 8/1964 | Bush | |
| 3,168,872 A | 2/1965 | Pinkerton | |
| 3,202,062 A | 8/1965 | Burden | |
| 3,229,640 A | 1/1966 | Williams | |
| 3,249,052 A | 5/1966 | Karlak | |
| 3,256,821 A | 6/1966 | Brederhoff | |
| 3,313,291 A | 4/1967 | Marshall | |
| 3,435,819 A | 4/1969 | Reynolds et al. | |
| 3,447,468 A | 6/1969 | Kinne | |
| 3,464,359 A | 9/1969 | King et al. | |
| 3,471,079 A | 10/1969 | Myers | |
| 3,556,691 A | 1/1971 | Buri | |
| 3,586,129 A | 6/1971 | Cass | |
| 3,695,788 A | 10/1972 | Loomans | |
| 3,838,948 A | 10/1974 | McCorvey | |
| 3,882,899 A | 5/1975 | Ginsberg et al. | |
| 3,916,931 A | 11/1975 | Shaw et al. | |
| 3,932,065 A | 1/1976 | Ginsberg et al. | |
| 3,935,971 A | 2/1976 | Papoff et al. | |
| 3,974,810 A | 8/1976 | Yajima | |
| 3,993,065 A | 11/1976 | Szabo et al. | |
| 4,008,003 A | 2/1977 | Pinkerton | |
| 4,010,611 A | 3/1977 | Zachery | |
| 4,014,629 A | 3/1977 | Elsworth | |
| 4,030,495 A | 6/1977 | Virag | |
| 4,063,553 A | 12/1977 | Karsh | |
| 4,067,668 A | 1/1978 | Nimell | |
| 4,136,708 A | 1/1979 | Cosentino et al. | |
| 4,178,240 A | 12/1979 | Pinkerton | |
| 4,236,880 A | 12/1980 | Archibald | |
| 4,274,327 A | 6/1981 | Olsgaard | |
| 4,315,582 A | 2/1982 | Micallef | |
| 4,336,000 A | 6/1982 | Jorgensen et al. | |
| 4,405,294 A | 9/1983 | Albarda | |
| 4,407,644 A | 10/1983 | Brotherston et al. | |
| 4,431,009 A | 2/1984 | Marino, Jr. et al. | |
| 4,479,759 A | 10/1984 | Zeitz | |
| RE31,873 E | 4/1985 | Howes | |
| 4,508,103 A | 4/1985 | Calisi | |
| 4,536,140 A | 8/1985 | Guthrie | |
| 4,560,327 A | 12/1985 | Bez et al. | |
| 4,575,317 A | 3/1986 | Lindner | |
| 4,687,408 A | 8/1987 | Klambauer | |
| 4,708,605 A | 11/1987 | Orlita | |
| 4,790,728 A | 12/1988 | Dwyer | |
| 4,824,342 A | 4/1989 | Buck | |
| 4,850,972 A | 7/1989 | Schulman et al. | |
| 4,909,783 A | 3/1990 | Morrison | |
| 4,941,809 A | 7/1990 | Pinkerton | |
| 4,947,856 A | 8/1990 | Beard | |
| 5,015,157 A | 5/1991 | Pinkerton | |
| 5,020,980 A | 6/1991 | Pinkerton | |
| 5,024,587 A | 6/1991 | Maurer | |
| 5,033,650 A | 7/1991 | Colin et al. | |
| 5,044,889 A | 9/1991 | Pinkerton | |
| 5,044,900 A | 9/1991 | Cavallaro | |
| 5,047,012 A | 9/1991 | Leuschner et al. | |
| 5,048,537 A | 9/1991 | Messinger | |
| 5,053,003 A | 10/1991 | Dadson et al. | |
| 5,062,774 A * | 11/1991 | Kramer et al. | 417/413.1 |
| 5,092,037 A | 3/1992 | Pinkerton | |
| 5,097,840 A | 3/1992 | Wallace et al. | |
| 5,100,380 A | 3/1992 | Epstein et al. | |
| 5,135,500 A | 8/1992 | Zdeb | |
| RE34,114 E | 10/1992 | Lindner | |
| 5,156,538 A | 10/1992 | Lee | |
| 5,188,603 A | 2/1993 | Vaillancourt | |
| 5,246,347 A | 9/1993 | Davis | |
| 5,246,354 A | 9/1993 | Pardinas | |
| 5,286,178 A | 2/1994 | Schaef | |
| 5,312,233 A | 5/1994 | Tanny et al. | |
| 5,314,416 A | 5/1994 | Lewis et al. | |
| 5,322,423 A | 6/1994 | Heck et al. | |
| 5,378,231 A | 1/1995 | Johnson et al. | |
| 5,411,382 A | 5/1995 | Duensing | |
| 5,413,566 A | 5/1995 | Sevrain et al. | |
| 5,415,528 A | 5/1995 | Ogden et al. | |
| 5,423,323 A | 6/1995 | Orth | |
| 5,429,485 A | 7/1995 | Dodge | |
| 5,431,627 A | 7/1995 | Pastrone et al. | |
| 5,472,320 A | 12/1995 | Weisbrodt | |
| 5,482,448 A | 1/1996 | Atwater et al. | |
| 5,489,196 A | 2/1996 | Lee | |
| 5,529,463 A * | 6/1996 | Layer et al. | 417/403 |
| 5,547,470 A | 8/1996 | Johnson et al. | |
| 5,588,816 A | 12/1996 | Abbott et al. | |
| 5,638,793 A | 6/1997 | Rapp et al. | |
| 5,639,220 A | 6/1997 | Hayakawa | |
| 5,718,569 A * | 2/1998 | Holst | 417/479 |
| 5,718,570 A | 2/1998 | Beckett et al. | |
| 5,720,415 A | 2/1998 | Morningstar | |
| 5,733,105 A | 3/1998 | Beckett et al. | |
| 5,741,126 A | 4/1998 | Stearns et al. | |
| 5,741,710 A | 4/1998 | Ek | |
| 5,749,854 A | 5/1998 | Shen | |
| 5,803,712 A | 9/1998 | Davis et al. | |
| 5,806,519 A | 9/1998 | Evans, III et al. | |
| RE35,997 E | 12/1998 | Pinkerton | |
| 5,916,197 A | 6/1999 | Reilly et al. | |
| 5,961,303 A | 10/1999 | King | |
| 5,992,691 A | 11/1999 | Post et al. | |
| 6,039,011 A | 3/2000 | Agalarov et al. | |
| 6,105,829 A | 8/2000 | Snodgrass et al. | |
| RE36,871 E | 9/2000 | Epstein et al. | |
| 6,146,109 A | 11/2000 | Davis et al. | |
| 6,197,000 B1 | 3/2001 | Reilly et al. | |

(56) References Cited

U.S. PATENT DOCUMENTS

| | | | |
|---|---|---|---|
| 6,210,361 B1 | 4/2001 | Kamen et al. | |
| 6,220,487 B1 | 4/2001 | Srivastava et al. | |
| 6,224,346 B1 | 5/2001 | Denenburg | |
| 6,244,838 B1 | 6/2001 | Couillard et al. | |
| 6,293,756 B1 | 9/2001 | Andersson | |
| 6,312,227 B1 | 11/2001 | Davis | |
| 6,398,513 B1 | 6/2002 | Amsler et al. | |
| 6,488,660 B1 | 12/2002 | Futterknecht | |
| 6,540,486 B2 | 4/2003 | Amsler et al. | |
| 6,544,228 B1 | 4/2003 | Heitmeier | |
| 6,558,125 B1 | 5/2003 | Futterknecht | |
| 6,568,923 B2 | 5/2003 | Ikuta | |
| 6,623,455 B2 | 9/2003 | Small et al. | |
| 6,634,871 B2 | 10/2003 | Ikuta | |
| 6,640,689 B2 | 11/2003 | Mitsui et al. | |
| 6,685,673 B2 | 2/2004 | Minezaki et al. | |
| 6,688,211 B1 | 2/2004 | Viet | |
| 6,702,557 B2 | 3/2004 | Kim et al. | |
| 6,726,656 B2 | 4/2004 | Kamen et al. | |
| 6,742,992 B2 | 6/2004 | Davis | |
| 6,749,402 B2 | 6/2004 | Hogan et al. | |
| 6,755,630 B2 | 6/2004 | Kim et al. | |
| 6,786,885 B2 | 9/2004 | Hochman et al. | |
| 6,945,431 B2 | 9/2005 | Miller | |
| 6,945,954 B2 | 9/2005 | Hochman et al. | |
| 6,958,058 B1 | 10/2005 | Hunter, Sr. et al. | |
| 7,041,081 B2 | 5/2006 | Minezaki et al. | |
| 7,144,382 B2 | 12/2006 | Broek et al. | |
| 7,156,056 B2 | 1/2007 | Lemke et al. | |
| 7,169,128 B2 | 1/2007 | Kriesel et al. | |
| 7,169,135 B2 | 1/2007 | Duchon et al. | |
| 7,267,532 B2 | 9/2007 | Krebs | |
| 7,331,770 B2 | 2/2008 | Oyaski | |
| 7,337,538 B2 | 3/2008 | Moutafis et al. | |
| 7,347,837 B2 | 3/2008 | Azzolini | |
| 7,367,358 B2 | 5/2008 | Malcolm | |
| 7,451,742 B2 * | 11/2008 | Gibson et al. | 123/446 |
| 7,935,077 B2 * | 5/2011 | Thor et al. | 604/67 |
| 2002/0025267 A1 | 2/2002 | Lieber et al. | |
| 2002/0081223 A1 | 6/2002 | Ikuta | |
| 2002/0115933 A1 | 8/2002 | Duchon et al. | |
| 2002/0165490 A1 | 11/2002 | Minezaki et al. | |
| 2002/0197164 A1 | 12/2002 | Hogan et al. | |
| 2003/0060766 A1 | 3/2003 | Kamen et al. | |
| 2003/0171670 A1 * | 9/2003 | Gumb et al. | 600/411 |
| 2004/0082912 A1 | 4/2004 | Minezaki et al. | |
| 2004/0228736 A1 | 11/2004 | Moutafis et al. | |
| 2005/0019195 A1 | 1/2005 | Schnabl | |
| 2005/0033232 A1 | 2/2005 | Kriesel | |
| 2006/0122555 A1 * | 6/2006 | Hochman | 604/67 |
| 2006/0127252 A1 | 6/2006 | Caddell | |
| 2006/0140793 A1 | 6/2006 | Krebs | |
| 2006/0153716 A1 | 7/2006 | Shoji et al. | |
| 2006/0173419 A1 | 8/2006 | Malcolm | |
| 2006/0175832 A1 | 8/2006 | Mueller et al. | |
| 2007/0055195 A1 | 3/2007 | Browne | |
| 2007/0071616 A1 | 3/2007 | Owen et al. | |
| 2007/0088268 A1 * | 4/2007 | Edwards | 604/136 |
| 2007/0129680 A1 | 6/2007 | Hagg et al. | |
| 2007/0148010 A1 | 6/2007 | Michels et al. | |
| 2007/0167910 A1 * | 7/2007 | Tennican et al. | 604/110 |
| 2007/0196223 A1 | 8/2007 | Hogan | |
| 2007/0237658 A1 | 10/2007 | Burns et al. | |
| 2008/0089799 A1 | 4/2008 | O'Connell | |
| 2008/0281265 A1 * | 11/2008 | Hochman | 604/110 |

FOREIGN PATENT DOCUMENTS

| | | | | |
|---|---|---|---|---|
| GB | 2139708 A | | 11/1984 | |
| JP | 521502 | | 1/1977 | |
| JP | 57102578 | | 6/1982 | |
| JP | 4241778 | | 8/1992 | |
| JP | 6142199 A | | 5/1994 | |
| JP | 6142200 A | | 5/1994 | |
| JP | 1997-506316 | | 6/1997 | |
| JP | 2006-520875 A5 | | 12/2006 | |
| JP | 4268658 B1 * | | 5/2009 | F04B 39/00 |
| WO | 9320864 A1 | | 10/1993 | |
| WO | 2006002817 A1 | | 1/2006 | |
| WO | 2007141681 A2 | | 12/2007 | |
| WO | 2008086349 A1 | | 7/2008 | |

* cited by examiner

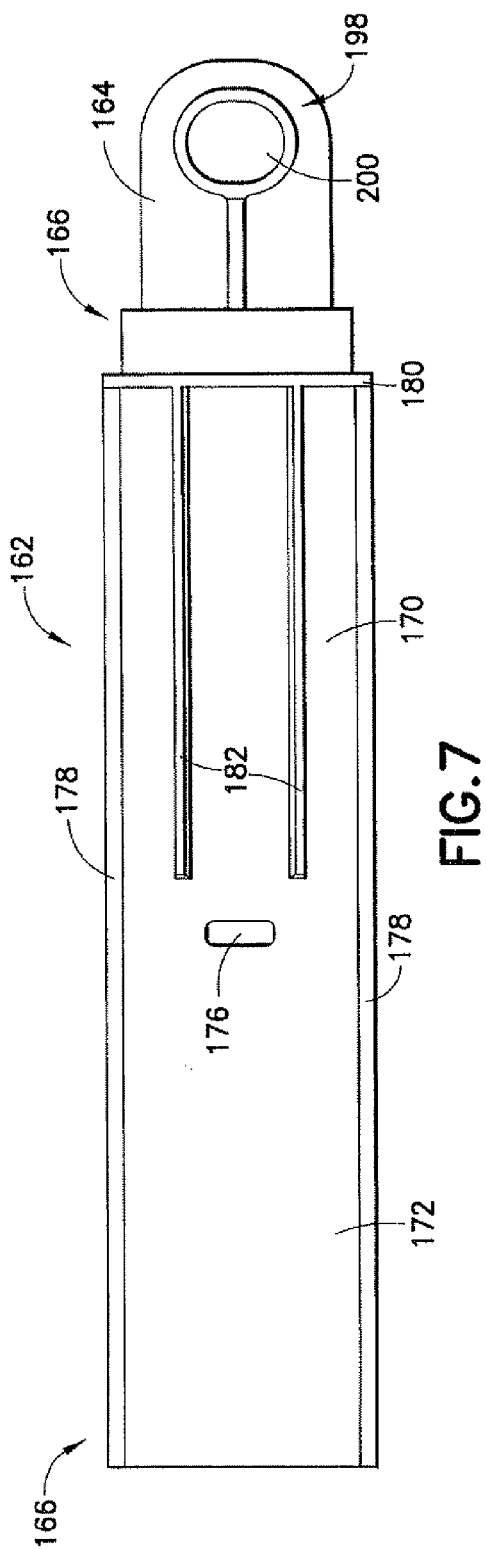
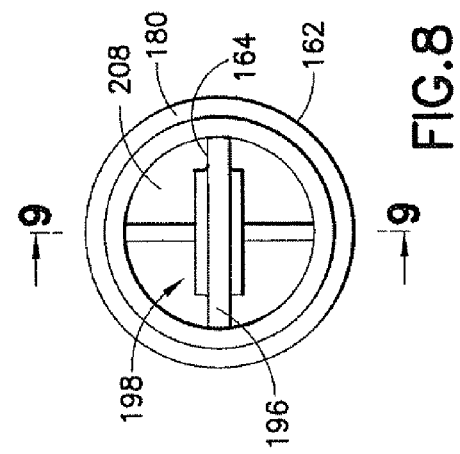

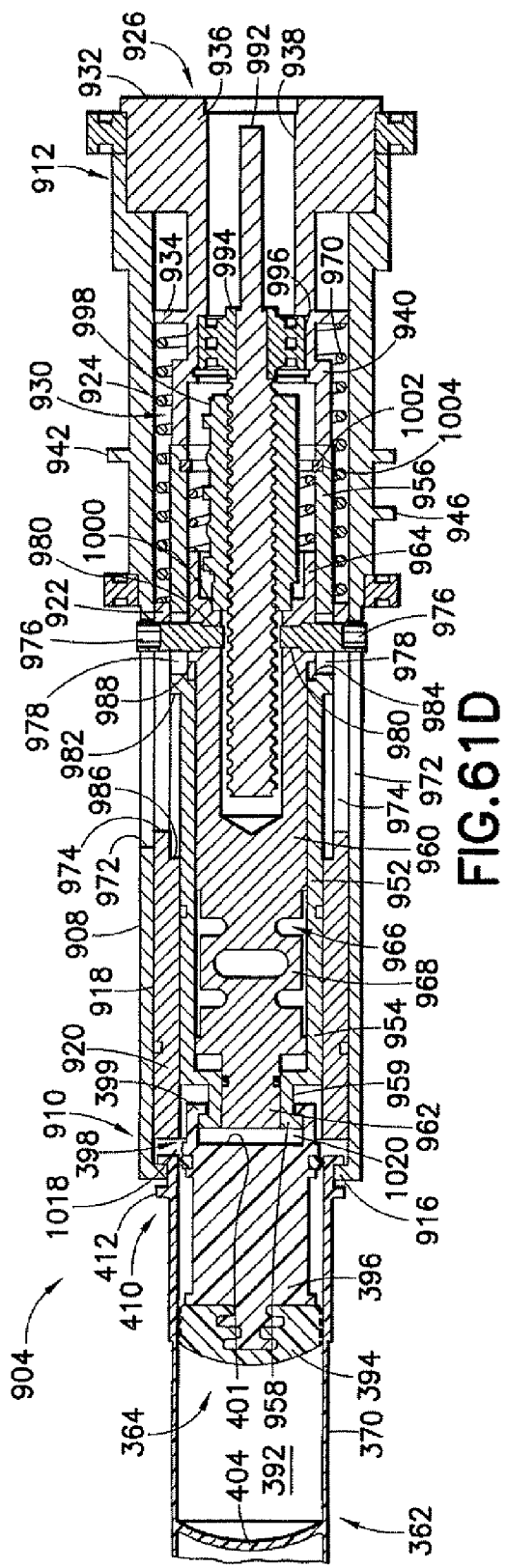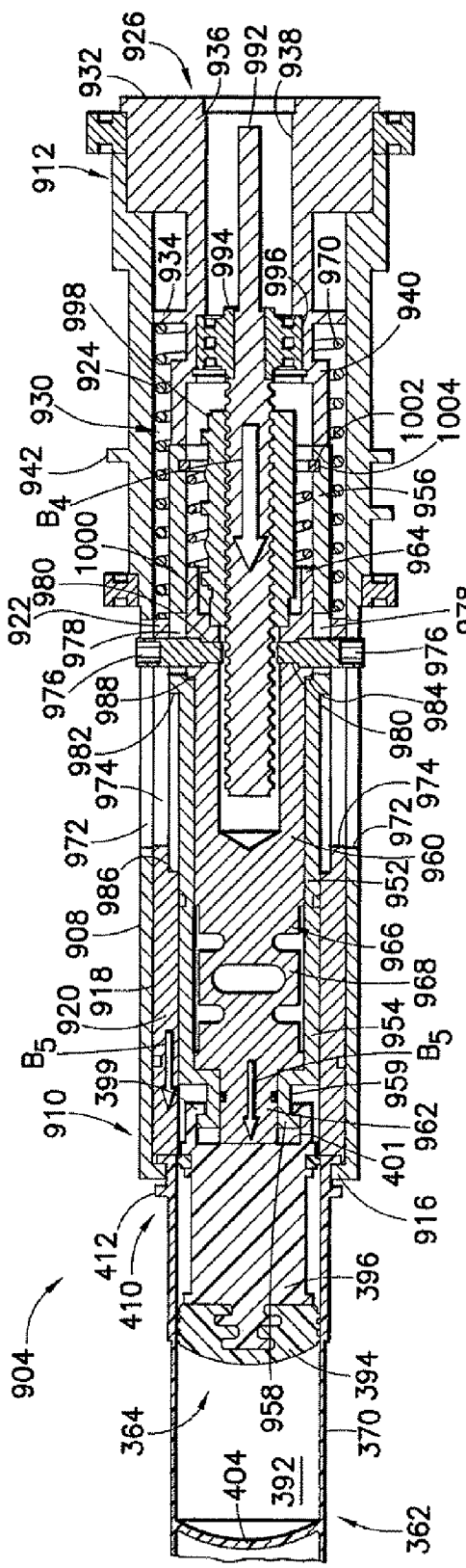

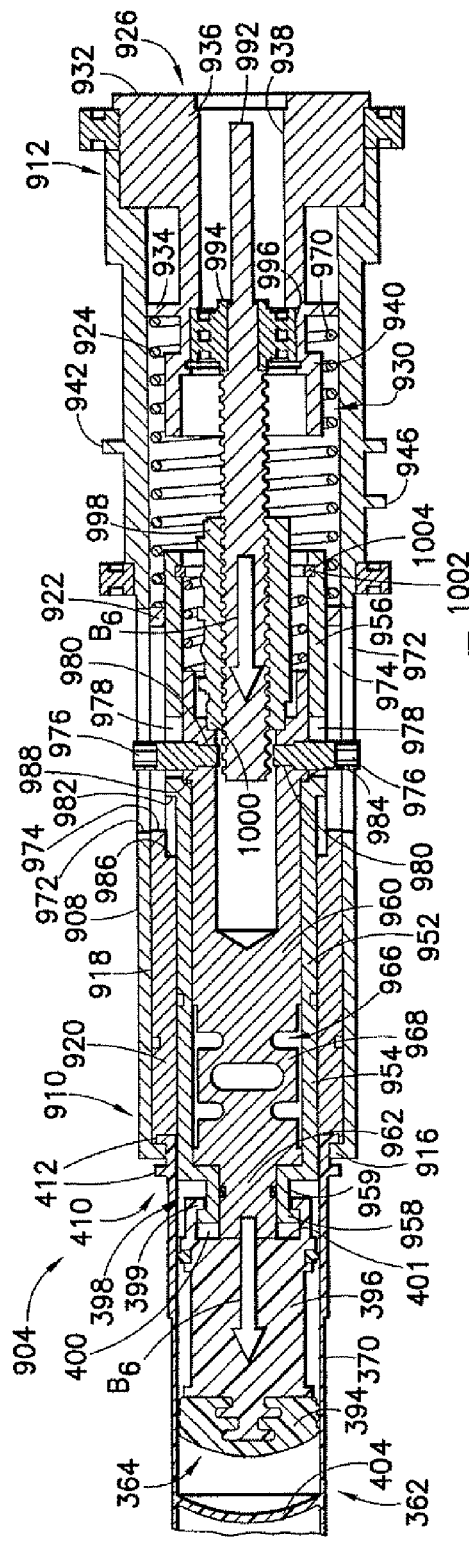
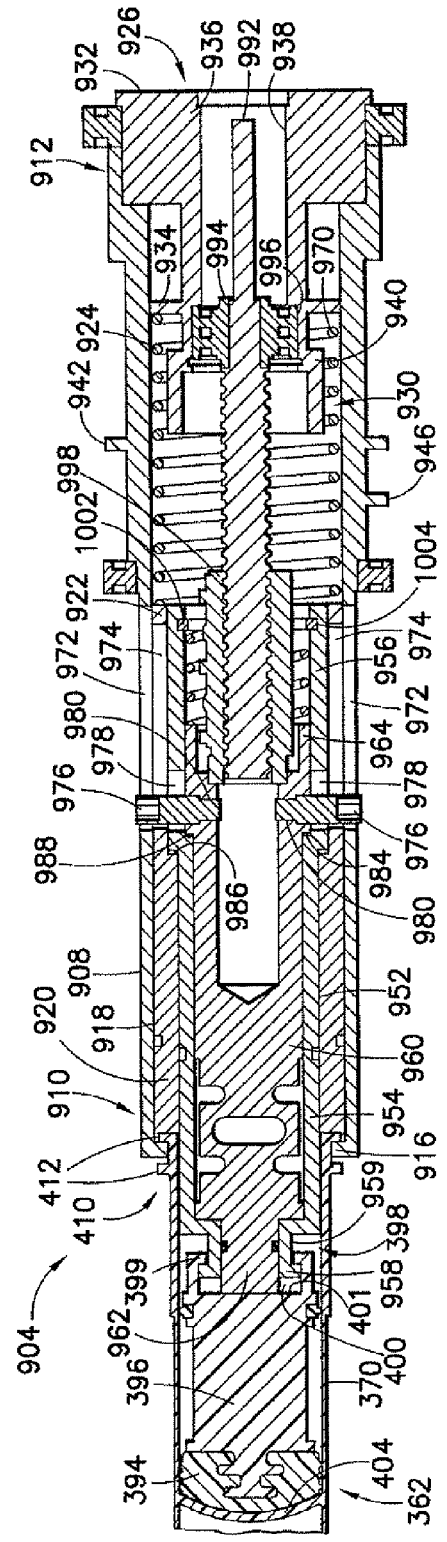
FIG.61F
FIG.61G

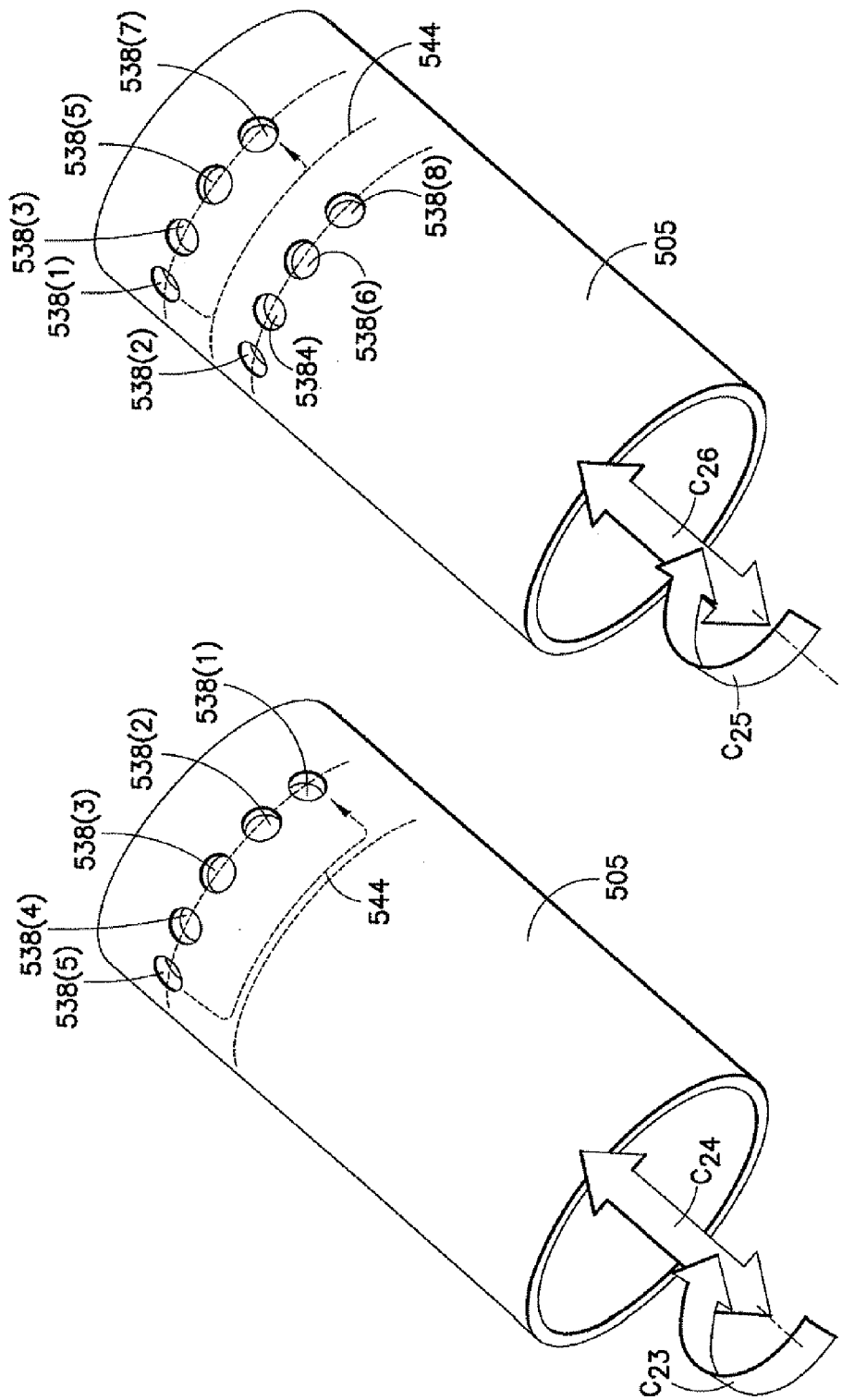

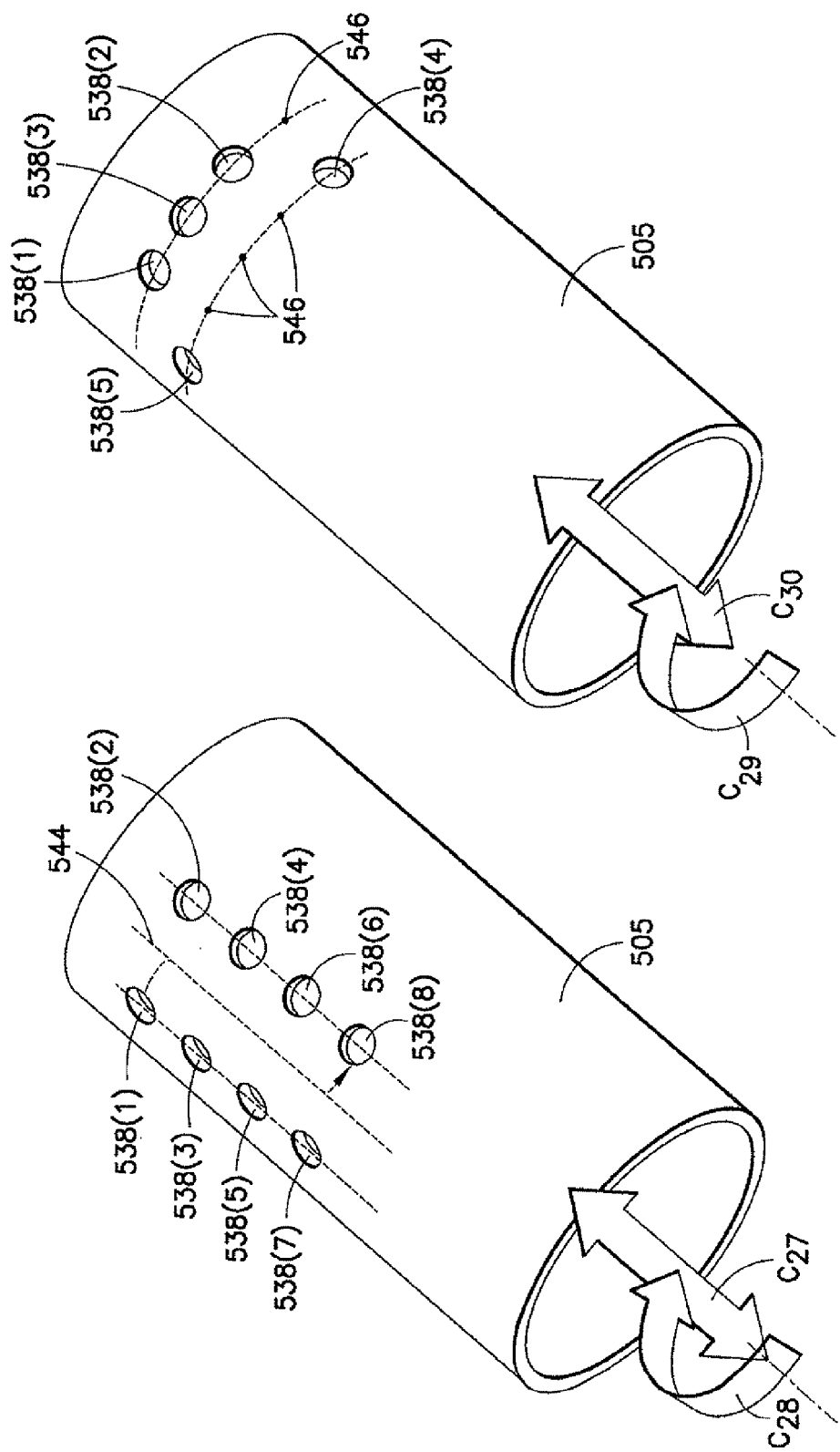

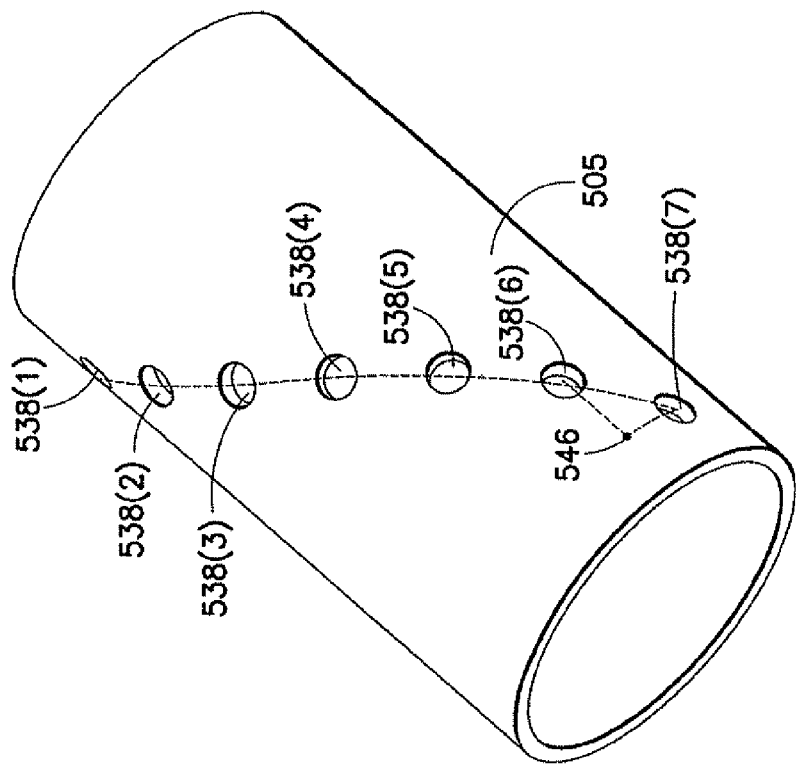
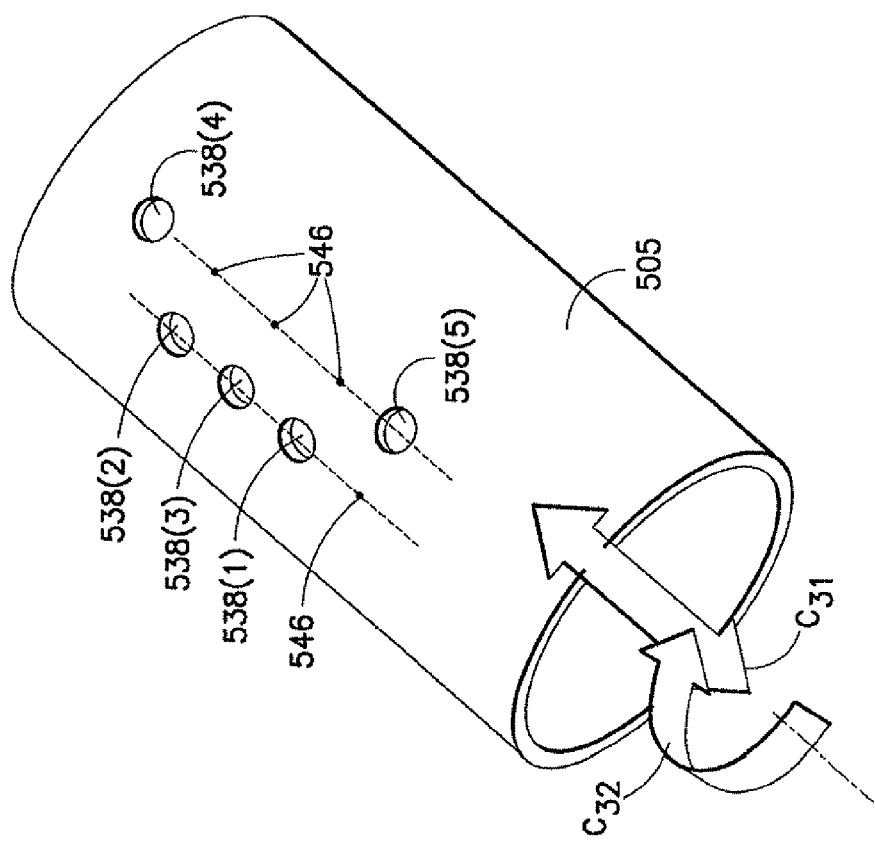

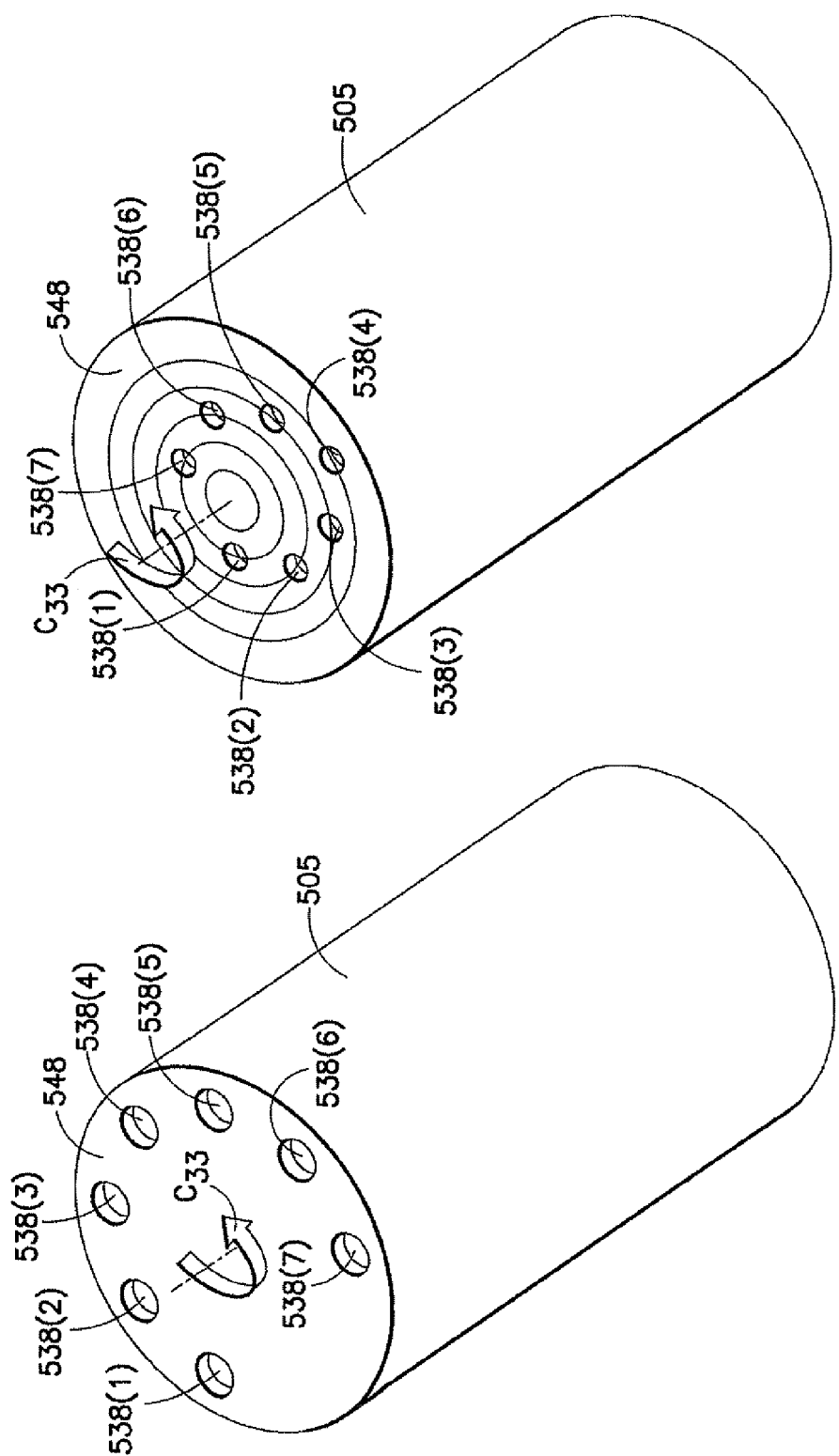

CONTINUOUS FLUID DELIVERY SYSTEM

CROSS REFERENCE TO RELATED APPLICATION

This application claims the benefit of U.S. Provisional Patent Application Ser. No. 61/012,626 filed Dec. 10, 2007, the contents of which are incorporated herein by reference.

BACKGROUND OF THE INVENTION

1. Field of the Invention

The invention described herein is directed to a fluid delivery system comprising a fluid pumping device and an associated drive system for continuous fluid delivery applications in medical diagnostic and therapeutic procedures wherein one or more fluids are infused/injected into a patient.

2. Description of Related Art

In the medical field, fluid delivery devices used to provide fluids to patients are generally well-known and exist in many different forms. A system commonly used for this purpose is a gravity-feed system wherein a fluid containing bag is supported above the level of the patient's body and wherein the flow rate to the patient is controlled by the gross pressure of a clamp upon the flexible tube extending between the bag and the patient. It will be readily apparent that the flow rate of fluid through the tube is a function of the amount of constriction of the tube. Manually operated devices are known in the medical field for delivery of fluid under pressure to a patient. Examples of such manually-operated pumping devices are known from U.S. Pat. No. 3,464,359 to King et al.; U.S. Pat. No. 2,062,285 to Bergman; and U.S. Pat. No. 1,748,810 to Wandel, as examples.

Syringe-based infusion pumps and peristaltic pumps have also been used in the medical field for delivering fluids to patients under pressure and provide more precise control over the flow rate and volumetric delivery of fluids to patients. An example of a syringe pump adapted to deliver fluid to a patient is described in U.S. Pat. No. 5,529,463 to Layer et al., which discloses a multi-syringe pump for this purpose. A peristaltic pump system suitable for delivering a constant flow of fluid under pressure to a patient is described in U.S. Pat. Nos. 6,558,125 and 6,488,660, both to Futterknecht.

There are a number of medical procedures which require the delivery of fluids to a patient in a precisely controlled manner. One such application involves the delivery of contrast media fluid to a patient during a diagnostic computed tomography (CT) scan to provide enhanced x-ray images. Traditionally, such contrast media fluid has been delivered to the patient using a syringe-based injection system. Such injection systems require the contrast media fluid to be transferred from its original container to a disposable syringe. The injection system then pressurizes the fluid within the syringe to deliver the fluid to the patient at a controlled flow rate, precisely when needed. Some syringe-based injection systems are capable of accommodating two separate syringes to facilitate sequential or simultaneous delivery of two different types of fluid.

One limitation of a syringe-based fluid injection system is the need to refill and replace the disposable syringes prior to each patient procedure. U.S. Pat. No. 5,806,519 to Evans, III et al. describes a fluid delivery system which could be used to deliver fluid to multiple patients in succession without the need to refill and replace syringes for each patient. Another fluid delivery system that purports to overcome this limitation is disclosed in U.S. Pat. Nos. 6,558,125 and 6,488,660 (Futterknecht). These latter patents disclose a fluid delivery system that utilizes a peristaltic pump to deliver fluid directly from contrast media bottles to the patient. While this system eliminates the need to replace disposable syringes after each patient, the use of a roller-type peristaltic pump inherently limits the pressure capability of the system to approximately 200 psi. Unfortunately, many CT procedures and virtually all angiographic procedures require fluid to be delivered at higher pressures.

In order to provide more precise control of flow rates and volumetric delivery of fluids to patients, positive displacement pump platforms have been developed in the medical field. These devices eliminate the use of syringes and provide increased pressure ranges over peristaltic pumps. One such positive displacement pump device is disclosed in U.S. Pat. Nos. 5,196,197 and 6,197,000 to Reilly et al., which describe a system for the continuous delivery of contrast media fluid to a patient that uses a cam-driven multi-piston pump. Such a pump is capable of delivering fluids at relatively high pressures in a controlled manner. Another example of a positive displacement pump platform intended for use in delivering fluid to a patient undergoing a medical procedure is disclosed in International Publication No. WO 2006/056828, which discloses a volumetric pump with reciprocating and rotating pistons that are adapted to deliver a controlled and continuous flow rate of fluid during a medical procedure. Japanese Publication Nos. JP 61-42199 and JP 61-4220, both assigned to Nemoto Kiyourindou KK, disclose another multi-piston cylinder pump which enables the controlled and continuous delivery of fluids during a medical procedure.

Examples of positive displacement pumps for non-medical applications are well-known. For example, U.S. Pat. No. 5,961,303 to King and U.S. Pat. No. 3,168,872 to Pinkerton disclose positive displacement pumps that comprise rotational and reciprocally operable pistons. Other non-medical positive displacement pumps are known that comprise multiple working pistons for dispensing fluids such as U.S. Pat. No. 5,639,220 to Hayakawa which discloses an "ink" pump with two pistons; Japanese Reference No. JP 4-241778 to Takashima et al. which discloses an automatic metering device for a viscous fluid that utilizes multiple pistons; and U.S. Pat. No. 4,405,294 to Albarda which discloses a dosing pump with two pistons. An older example of a positive displacement pump with multiple pistons is disclosed in U.S. Pat. No. 1,689,419 to Bronander. All of the foregoing listed patents and publications are incorporated herein by reference in their entirety.

In order to provide more precise control of flow rates and volumetric delivery of fluids to patients, positive displacement pump platforms have been developed in the medical field. These devices eliminate the use of syringes and provide increased pressure ranges over peristaltic pumps. One such positive displacement pump device is disclosed in U.S. Pat. Nos. 5,916,197 and 6,197,000 to Reilly et al., which describe a system for the continuous delivery of contrast media fluid to a patient that uses a cam-driven multi-piston pump. Such a pump is capable of delivering fluids at relatively high pressures in a controlled manner. Another example of a positive displacement pump platform intended for use in delivering fluid to a patient undergoing a medical procedure is disclosed in International Publication No. WO 2006/056828, which discloses a volumetric pump with reciprocating and rotating pistons that are adapted to deliver a controlled and continuous flow rate of fluid during a medical procedure. Japanese Publication Nos. JP 61-42199 and JP 61-42200, both assigned to Nemoto Kiyourindou KK, disclose another multi-piston cylinder pump which enables the controlled and continuous delivery of fluids during a medical procedure.

Another disadvantage present in the foregoing positive displacement pump examples, particularly multi-piston positive displacement pumps, is that as the pistons in multi-piston positive displacement pumps sequentially deliver pressurized fluid to the pump outlet, there are fluctuations or "pulsatility" in the flow rate as the fluid source transitions from one piston to the next. This pulsatility can be reduced with the inclusion of additional pistons but can never be completely eliminated. Moreover, multi-piston pumps often include passive check valves and like devices which are used to direct fluid into and out of piston chambers. Such passive valves are often unable to respond quickly enough at high cycle rates and this can lead to volumetric inefficiencies and leakage at high pressures.

SUMMARY OF THE INVENTION

In view of the foregoing, there is a need for a positive displacement pump platform which can continuously deliver fluids at positively controlled flow rates and which is suitable for use in medical procedures involving infusing/injecting fluid into a patient. A continuous fluid delivery system in accordance with this disclosure and which meets the foregoing need comprises, at least in part, a fluid pumping device comprising a pump housing comprising a base member comprising a plurality of inlet ports and at least one outlet port and a pair of opposing pistons movably associated with the base member housing and at least in part defining a pumping chamber of the fluid pumping device. The pistons may be independently controlled such that any one (or more) of the plurality of inlet ports or the at least one outlet port is independently selectable to be in fluid communication with the pumping chamber.

The base member supports the pistons to at least reciprocally operate relative to the base member. The base member may comprise a manifold portion defining the plurality of inlet ports and the at least one outlet port. A manifold cap may be provided on the manifold portion and define the plurality of inlet ports and the at least one outlet port desirably in combination with the manifold portion. The manifold portion may comprise a plurality of fluid passageways respectively connected to the plurality of inlet ports and the at least one outlet port. The base member may comprise at least one opening in each fluid passageway to enable fluid communication between the pumping chamber and the plurality of inlet ports and the at least one outlet port via the passageways. The base member may comprise a manifold portion defining the plurality of inlet ports and the at least one outlet port, and the plurality of inlet ports and the at least one outlet port may be disposed on lateral sides of the manifold portion.

One of the pistons may comprise a sleeve portion and the other of the pistons is at least partially disposed in the sleeve portion to define the pumping chamber. The sleeve portion defines an opening for fluid communication with a selected inlet port or the at least one outlet port to establish fluid communication between the selected inlet port or the at least one outlet port and the pumping chamber. A fluid seal element may be disposed between the base member and the sleeve portion.

In another embodiment, the fluid pumping device comprises a pump housing comprising a base member comprising a plurality of inlet ports and at least one outlet port and at least two pairs of opposing pistons may be movably associated with the base member. Each pair of opposing pistons at least in part defines a respective pumping chamber of the fluid pumping device. The pistons in each pair of opposing pistons may be independently controlled such that any one (or more) of the plurality of inlet ports or the at least one outlet port is independently selectable to be in fluid communication with one of the respective pumping chambers.

The base member supports the at least two pairs of opposing pistons to reciprocally operate relative to the base member. The base member may comprise a manifold portion defining the plurality of inlet ports and the at least one outlet port. A manifold cap may be provided on the manifold portion and define the plurality of inlet ports and the at least one outlet port desirably in combination with the manifold portion. The manifold portion may comprise a plurality of fluid passageways respectively connected to the plurality of inlet ports and the at least one outlet port. The base member may comprise at least one opening in each fluid passageway to enable fluid communication between the pumping chamber and the plurality of inlet ports and the at least one outlet port via the passageways. The base member may comprise a manifold portion defining the plurality of inlet ports and the at least one outlet port, and the plurality of inlet ports and the at least one outlet port may be disposed on lateral sides of the manifold portion.

One of the pistons in each pair of opposing pistons may comprise a sleeve portion and the other of the pistons in each pair of opposing pistons is at least partially disposed in the sleeve portion to define the respective pumping chambers. The sleeve portion defines an opening for fluid communication with a selected inlet port or the at least one outlet port to establish fluid communication between the selected inlet port or the at least one outlet port and the respective pumping chambers. Respective fluid seal elements may be disposed between the base member and the sleeve portion in each pair of opposing pistons.

Another embodiment is directed to a fluid delivery system, comprising the fluid pumping device and a drive system. The fluid pumping device comprises a pump housing comprising a base member comprising a plurality of inlet ports and at least one outlet port, and a pair of opposing pistons movably associated with the base member. The pistons at least in part define a pumping chamber of the fluid pumping device and the pistons are independently controlled such that any one of the plurality of inlet ports or the at least one outlet port is independently selectable to be in fluid communication with the pumping chamber. The drive system is interfaced with the pistons to at least reciprocally operate the pistons relative to the base member.

The drive system may comprise respective piston positioning devices interfaced with each piston. The piston positioning devices may be disposed on opposite sides of the base member to interface with the respective pistons. The piston positioning devices may each be disposed on the same side of the base member to interface with the respective pistons. Additionally, the piston positioning devices may be disposed commonly on a carriage. The carriage may be movable by a carriage drive system. The carriage may be bi-directional linearly movable by the carriage drive system.

A position sensor may be associated with the drive system to interface with the carriage to ascertain at least one position of the carriage. A support device may be used to support at least one of the pistons in the drive system. A position sensor may also be associated with the drive system to interface with at least one of the piston positioning devices to ascertain at least one position of the piston positioning device.

In another aspect, a method is disclosed for operating a fluid pumping device. Such a method comprises providing a fluid pumping device comprising a pump housing comprising a base member comprising plurality of inlet ports and at least one outlet port and a pair of pistons movably associated with the base member and at least in part defining a pumping chamber of the fluid pumping device. The pistons may be independently controlled pistons such that any one (or more) of the plurality of inlet ports or the at least one outlet port is independently selectable to be in fluid communication with the pumping chamber.

One of the pistons may comprise a sleeve portion defining an opening and the other of the pistons is at least partially disposed in the sleeve portion to define the pumping chamber, and the method may further comprise establishing fluid communication between the opening and a selected inlet port or the at least one outlet port to establish fluid communication between the selected inlet port or the at least one outlet port and the pumping chamber.

Additionally, the method may comprise independently controlling the pistons to select one of the plurality of inlet ports to be in fluid communication with the pumping chamber, moving one of the pistons relative to the opposing piston to draw fluid into the pumping chamber from a fluid source associated with the selected inlet port, and moving both pistons to select another inlet port or the at least one outlet port to be in fluid communication with the pumping chamber. The method may further comprise moving one of the pistons relative to the opposing piston to eject fluid from the pumping chamber into the at least one outlet port.

In still a further aspect, the fluid pumping device may comprise at least two pairs of opposing pistons movably associated with the base member, with each pair of opposing pistons at least in part defining a respective pumping chamber of the fluid pumping device, and the method may further comprise independently controlling the pistons in each pair of opposing pistons such that any one (or more) of the plurality of inlet ports or the at least one outlet port is independently selectable to be in fluid communication with one of the respective pumping chambers. The method may further comprise independently controlling the pistons in the respective pairs of opposing pistons in a sequence comprising: independently controlling the pistons to select one of the plurality of inlet ports to be in fluid communication with one of the respective pumping chambers, moving one of the pistons relative to the opposing piston to draw fluid into the pumping chamber from a fluid source associated with the selected inlet port, and moving both pistons to select another inlet port of the at least one outlet port to be in fluid communication with the pumping chamber. The method may further comprise moving one of the pistons relative to the opposing piston to eject fluid from the pumping chamber into the at least one outlet port. The respective pairs of opposing pistons may operate in a substantially staggered sequence such that substantially continuous fluid flow is delivered by the fluid pumping device at the least one outlet port.

A drive system may be interfaced with the pistons and the method may comprise the drive system at least reciprocally operating the pistons relative to the base member. The method may further comprise at least reciprocally operating the pistons from opposite sides of the base member. Additionally, the method may comprise at least reciprocally operating the pistons from a same side of the base member.

The drive system may comprise respective piston positioning devices interfaced with each piston and disposed on opposite sides of the base member and the method may comprise at least reciprocally operating the pistons from opposite sides of the base member with the respective piston positioning devices. Alternatively, the drive system may comprise respective piston positioning devices interfaced with each piston and disposed on a same side of the base member and the method may comprise at least reciprocally operating the pistons from the same side of the base member with the respective piston positioning devices. The piston positioning devices may be disposed commonly on a carriage movable by a carriage drive system and the method may comprise moving the carriage with the carriage drive system. The carriage may move in a bi-directional linear movement.

Further details and advantages will become clear upon reading the following detailed description in conjunction with the accompanying figures.

BRIEF DESCRIPTION OF THE DRAWINGS

FIG. 7 is a top view of the fluid pump shown in FIG. 6.

FIG. 8 is an end view of the fluid pump shown in FIG. 6.

FIGS. 61A-61G are cross-sectional views illustrating the sequence for associating the pistons of a fluid pump with the fluid pump actuator shown in FIG. 49.

FIGS. 92A-92J are perspective views of one cylindrical member of the base member of the pump housing of the fluid pumping device of FIG. 65, each illustrating a different configuration for the fluid ports in the base member of the pump housing.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices, features, and components illustrated in the accompanying drawing figures and described herein are simply exemplary and should not be considered as limiting.

Figure 13:
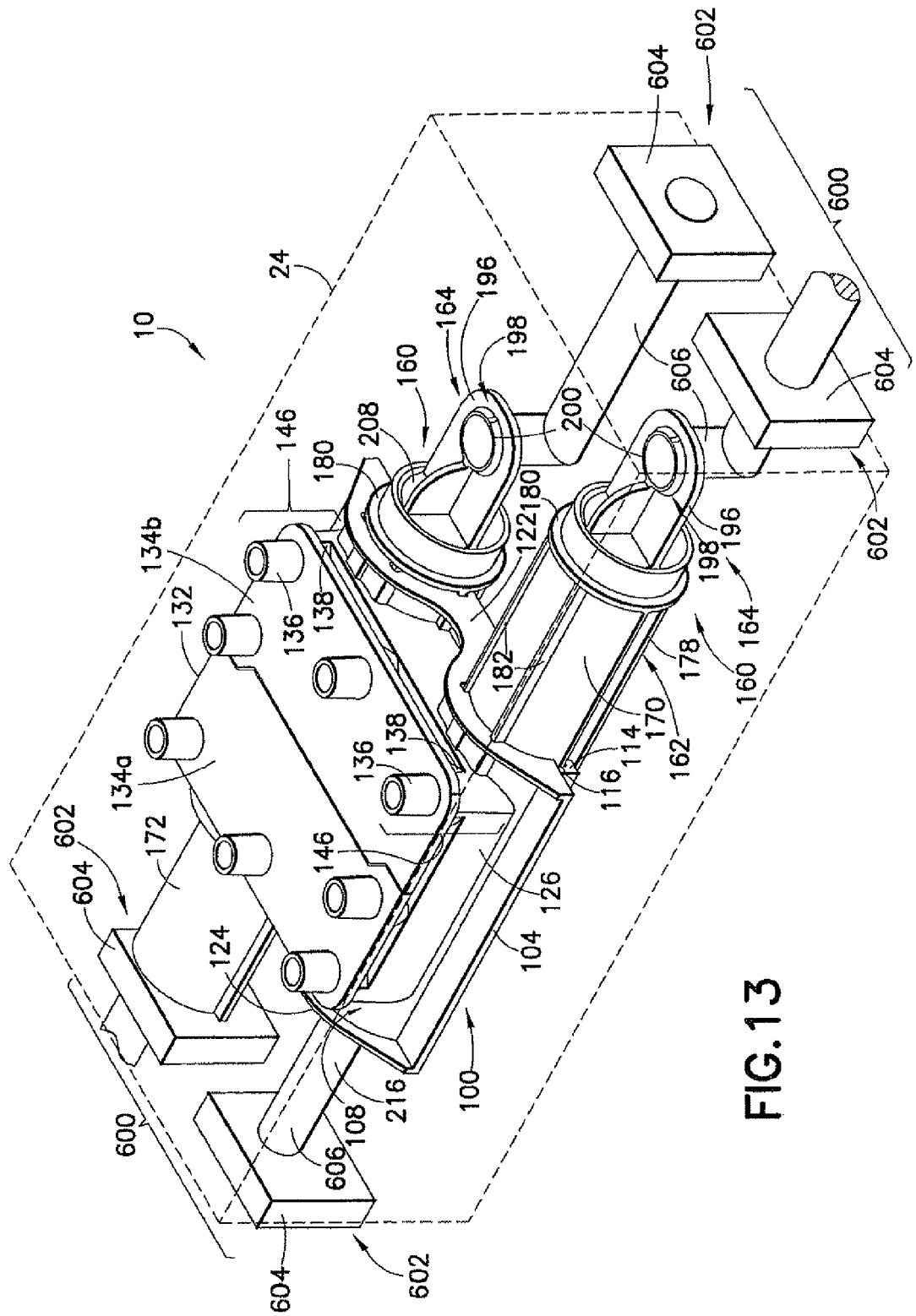
FIG. 13 is a perspective showing a fluid delivery system comprising the fluid pumping device of FIG. 1A and an associated and schematically represented drive system.

An embodiment of a fluid pumping device 100 is shown in FIGS. 1-12. Desirably, fluid pumping device 100 is used as part of a fluid delivery system or platform 10, a schematic representation thereof is depicted in FIG. 13 discussed herein. Referring briefly to FIG. 13, in such an embodiment, fluid delivery system 10 generally comprises fluid pumping device 100 and a drive system 600 that provides motive forces used to operate movable components of fluid pumping device 100. A desirable feature of fluid pumping device 100 is to provide the fluid pumping device 100 as a disposable component, for example, as a disposable cartridge, cassette, or unit, which may be associated with a reusable drive system 600 for one use or a discrete number of uses and then disposed of. Such a disposable version of fluid pumping device 100 has particular use in the medical field such as in the delivery of fluids to a patient undergoing a medical infusion/injection procedure. One such procedure described previously involves the delivery of contrast media fluid to a patient during a diagnostic computed tomography (CT) scan to provide enhanced x-ray images. As described previously in connection with this procedure, syringe-based infusion devices are typically used in this procedure for delivery of contrast media fluid to the patient. One limitation of a syringe-based fluid injection system is the need to refill and replace disposable syringes prior to each patient procedure, as described previously. As further described previously, techniques have been developed in the medical field (as described in U.S. Pat. No. 5,806,519 as an example) to provide a fluid delivery system that may be adapted to deliver fluid to multiple patients in succession without the need to refill and replace syringes for each patient. A disposable form of fluid pumping device 100 will allow use of the fluid pumping device 100 for a single patient or, desirably, multiple patients typically up to a preset or discrete number of patients or number of uses.

Figure 1A:
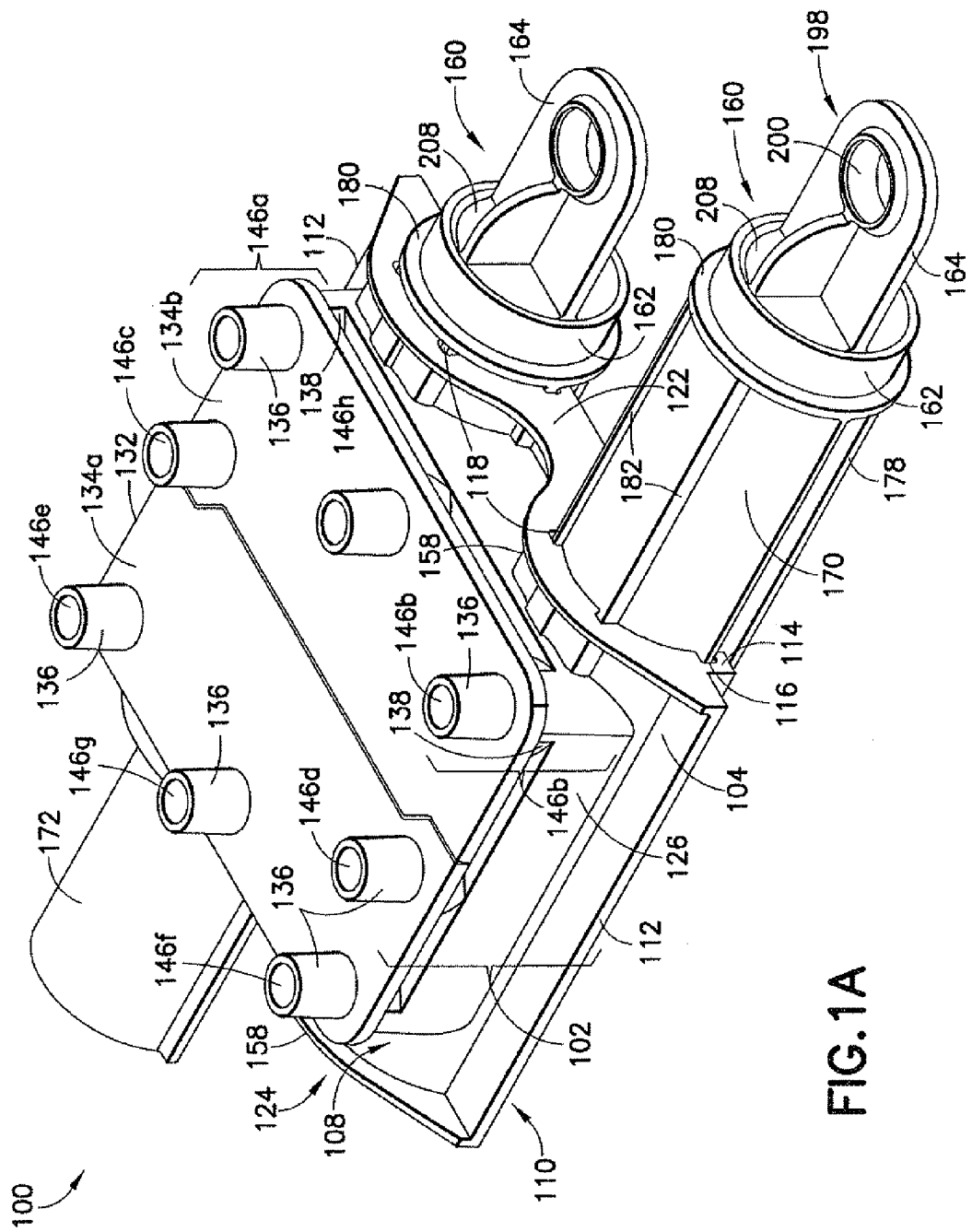
FIG. 1A is a perspective view of an embodiment of a fluid pumping device comprising two or more fluid pumps in accordance with the disclosure herein.
Figure 1B:
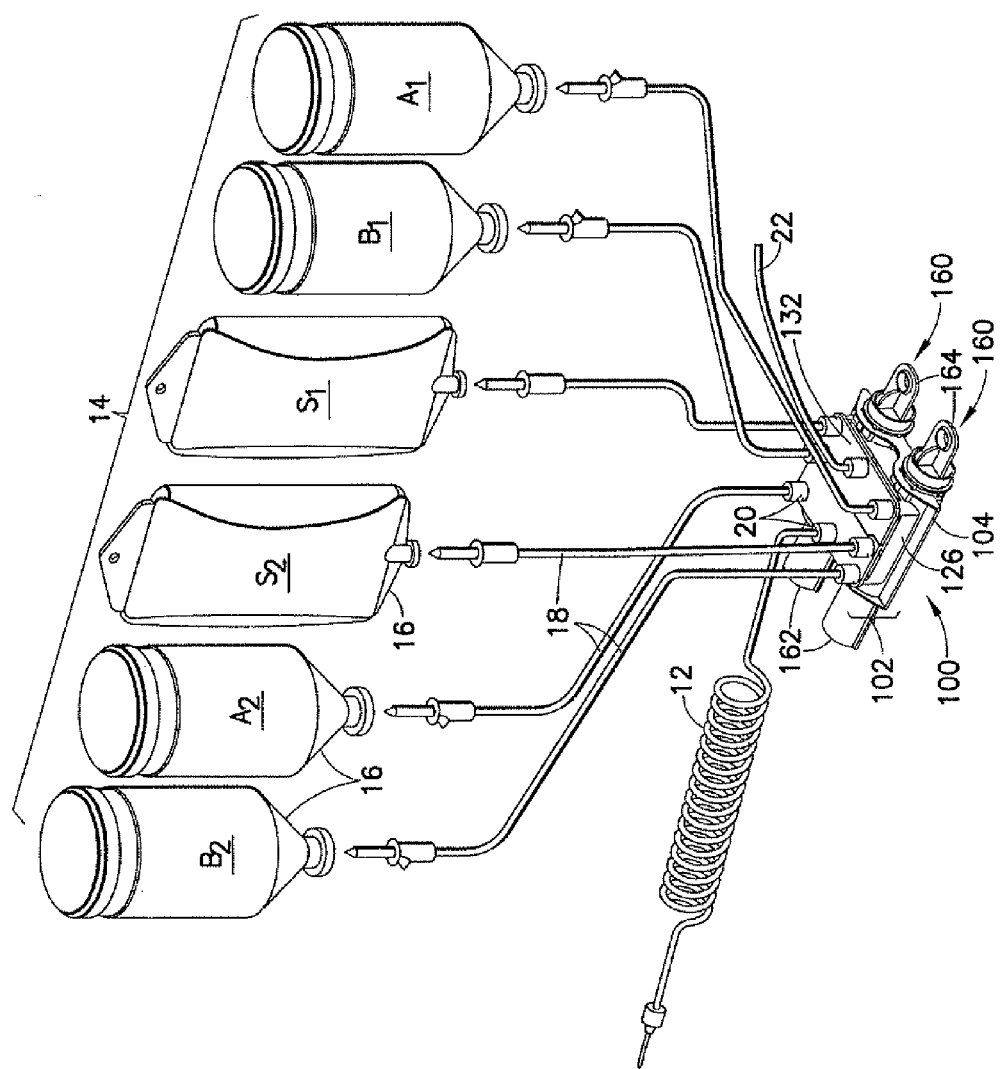
FIG. 1B is a perspective view of the fluid pumping device of FIG. 1A shown associated with multiple bulk fluid sources.
Figure 2:
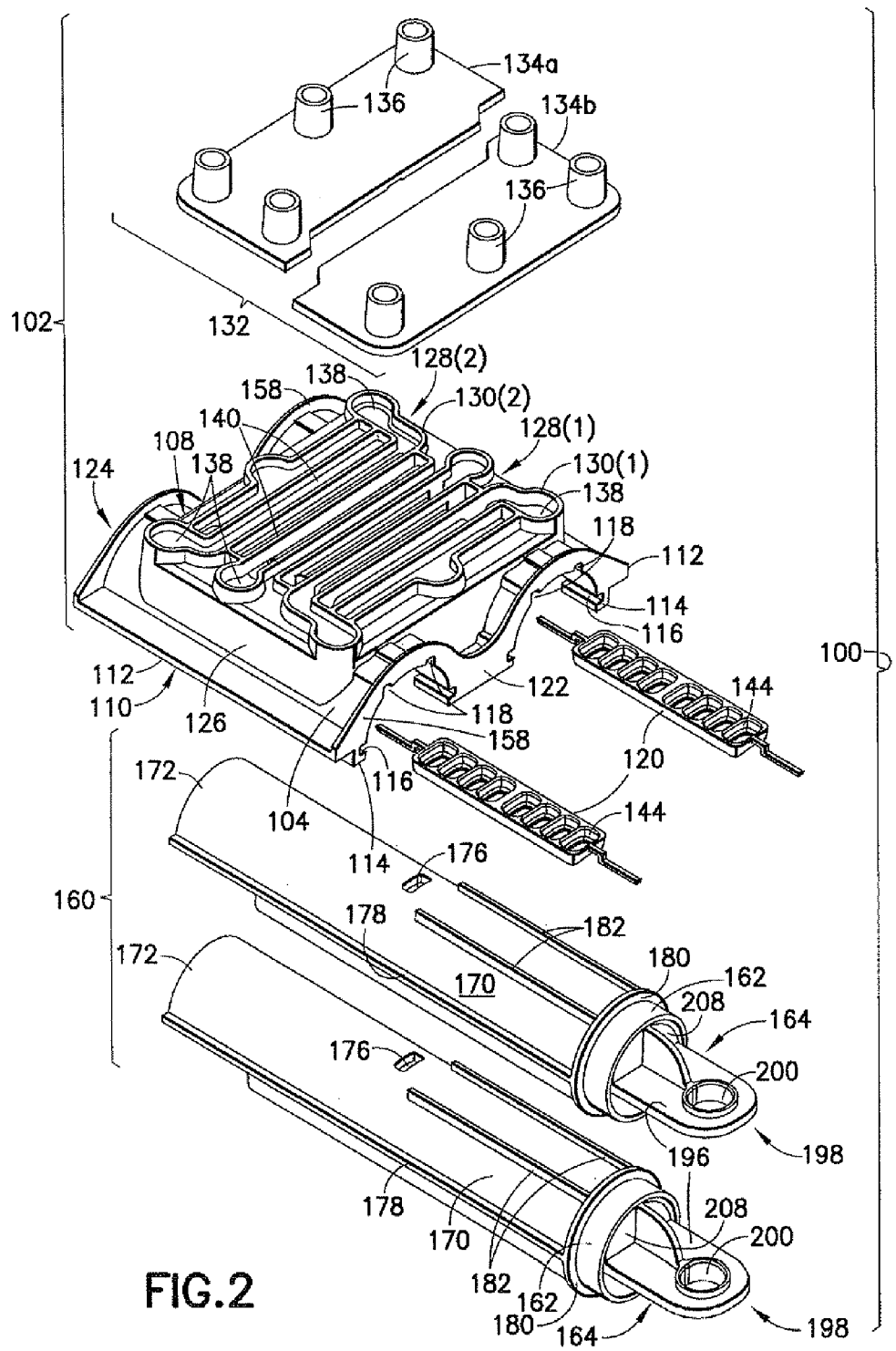
FIG. 2 is an exploded perspective view of the fluid pumping device of FIG. 1A showing a housing including a base member and the fluid pumps of the fluid pumping device.

The following discussion initially sets forth the general structure and arrangement of fluid pumping device 100, after which a discussion of drive system 600 is provided along with a discussion of the interaction between fluid pumping device 100 and drive system 600 to effect operation of fluid pumping device 100. Fluid pumping device 100 is a multi-component device comprising a pump housing 102 and one or more fluid pumps 160 which constitute the movable components of fluid pumping device 100 for delivering fluid under pressure to a desired end point, such as a patient fluid path 12 delivering fluid to a patient undergoing a fluid infusion/injection procedure. An exemplary patient fluid path 12 is shown in FIG. 1B and may connect to a catheter and like patient interface apparatus as is known in the medical field. Pump housing 102 serves several purposes including as a support component or structure for the movable components of fluid pumping device 100, namely, fluid pumps 160, as well as a connection point for connecting patient fluid path 12 to the fluid pumping device 100. As further shown in FIG. 1B, fluid pumping device 100 may be connected to multiple bulk fluid sources 14. Preferably, multiple different fluids are available for fluid pumping device 100 to draw upon. The bulk fluid sources 14 each comprise a fluid container 16, connecting fluid line 18, and a suitable connector 20 adapted for fluid connection to the pump housing 102 as described herein. For the illustrative purposes only, bulk fluids in fluid containers 16 may comprise two different types of contrast media fluid. In FIG. 1B a first type, concentration, or brand of contrast fluid is labeled as "$A_1, A_2$" and a second type, concentration, or brand of contrast fluid is labeled "$B_1, B_2$". Two different sources of bulk saline are labeled "$S_1, S_2$" in FIG. 1B. As further shown in FIG. 1B, a waste fluid line 22 may also be provided and is typically connected to an appropriate medical fluid waste receptacle (not shown).

Pump housing 102 typically includes a base member 104 to which a separate manifold cap 132 is secured. Manifold cap 132 may be considered to be a component or part of pump housing 102 in accordance with the disclosure and optionally may be formed integral with base member 104 in this and other embodiments described herein. In the present embodiment, pump housing 102 may be considered to be a multi-piece component comprising at least base member 104 and manifold cap 132. Base member 104 and manifold cap 132 may be injection-molded plastic components or pieces which are assembled together to form or complete pump housing 102 by suitable assembly methods such as ultrasonic welding, laser welding, adhesive, solvent bonding, by direct mechanical attachment, and like methods. Manifold cap 132 may be a unitary or a multi-piece component as discussed herein.

Base member 104 may have any desirable configuration and one such configuration is that of a generally plate-shaped component or element that defines one or more, and desirably at least two adjacent and generally parallel cavities 106. Cavities 106 are adapted to accept two identical fluid pumps 160 which form the movable components of fluid pumping device 100 as identified previously and which are described in detail herein. While the illustrated configuration of base member 104 comprises two adjacent cavities 106 defined in base member 104 for accepting two like fluid pumps 160, this illustration is not intended to restrict the possibility of base member 104 forming an additional or several additional cavities 106 to accept an additional or several fluid pumps 160 respectively therein. For simplicity and expediency, the following discussion describes fluid pumping device 100 with two like fluid pumps 160 as a non-limiting embodiment of the fluid pumping device 100. Cavities 106 define a generally concave shape to receive fluid pumps 160 therein and, as illustrated, a typical or desirable shape of cavities 106 for such a purpose is that of two generally half-cylindrical cavities for accepting generally cylindrical-shaped fluid pumps 160 therein. For purposes of explaining the spatial orientation of additional features or components of fluid pumping device 100, base member 104 may be considered to have a first side or top side 108, a second side, bottom side, or underside 110, and opposing lateral sides 112.

To maintain the association of fluid pumps 160 with base member 104, base member 104 comprises a plurality of individual securing members 114 depending from bottom side or underside 110 of the base member 104. Securing members 114 are provided as opposed and spaced apart pair sets so that the securing members 114 are provided on opposite sides of cavities 106 to support both lateral sides of the individual fluid pumps 160. Securing members 114 are adapted to support fluid pumps 160 to base member 104 while permitting movement of fluid pumps 160 relative to base member 104 and, desirably, sliding reciprocal movement of fluid pumps 160 relative to base member 104. Securing members 114 each define a slot 116 for receiving a cooperating structure, such as a lip, rib, flange, and the like, on fluid pumps 160 to allow sliding reciprocal movement of the fluid pumps 160 relative to base member 104 and, thus, pump housing 102 generally. Securing members 114 depend or extend from the underside 110 so that slots 116 face inward toward one another. While securing members 114 are generally illustrated as a plurality of depending tab-like structures that are adapted to cooperate with corresponding structure on lateral sides of fluid pumps 160, these may be replaced by a series of rings (not shown) depending from the bottom side 110 of base member 104 and which are adapted to coaxially receive the fluid pumps 160. For example, two such rings may depend from the underside 110 of base member 104 below each cavity 106 at the locations currently occupied by securing members 114 and through which the two fluid pumps 160 may extend, respectively. It is also within the scope of this disclosure to provide continuous securing members 114 on both lateral sides of each cavity 106, or replace the depending securing members 114 with two completely formed cylindrical structures defined by base member 104 and which define barrels which accept the respective fluid pumps 160 therein.

Figure 4:
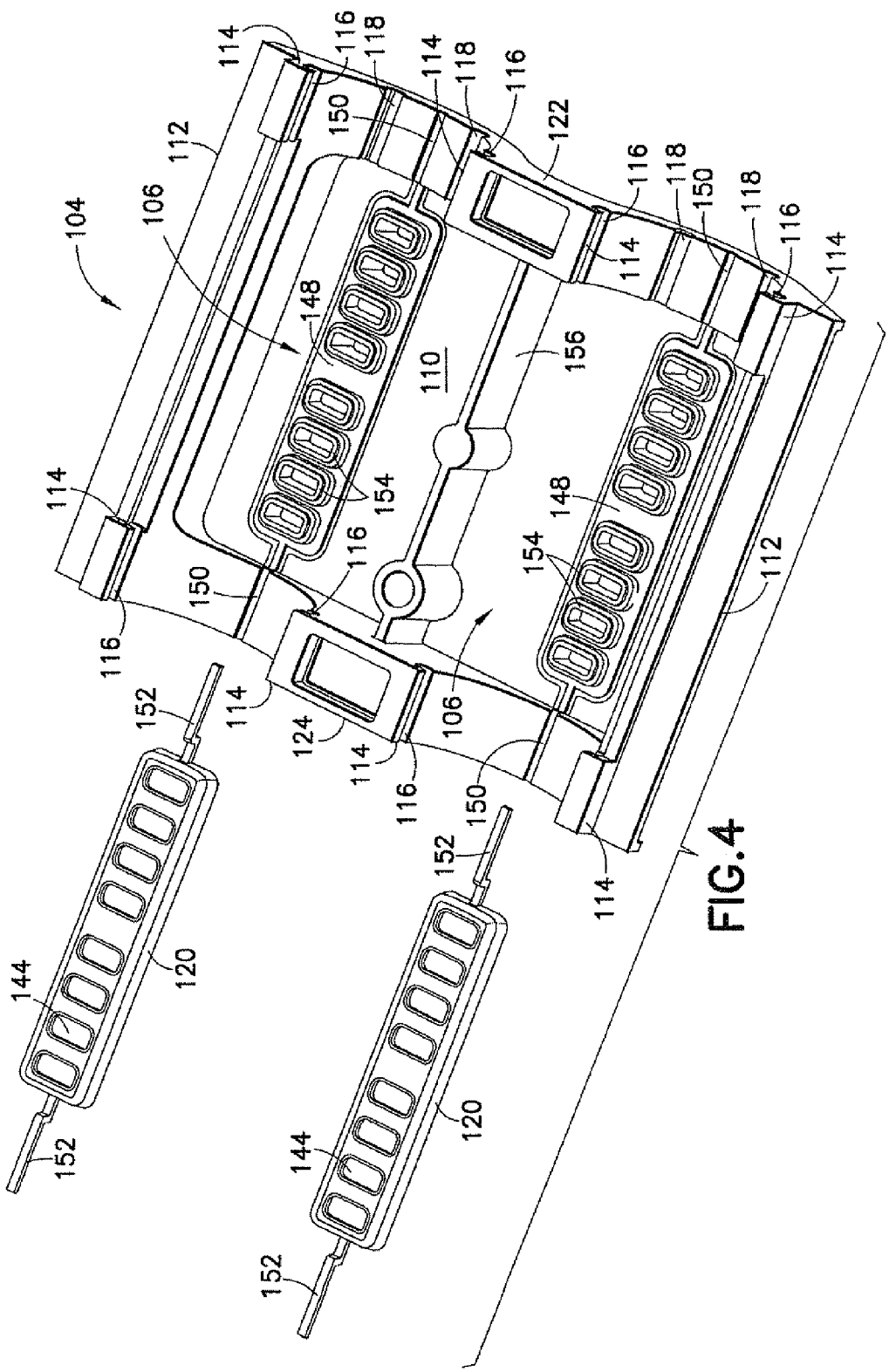
FIG. 4 is a bottom perspective view of the base member of the housing of the fluid pumping device of FIG. 1A and showing fluid seal elements exploded from the base member.
Figure 5:
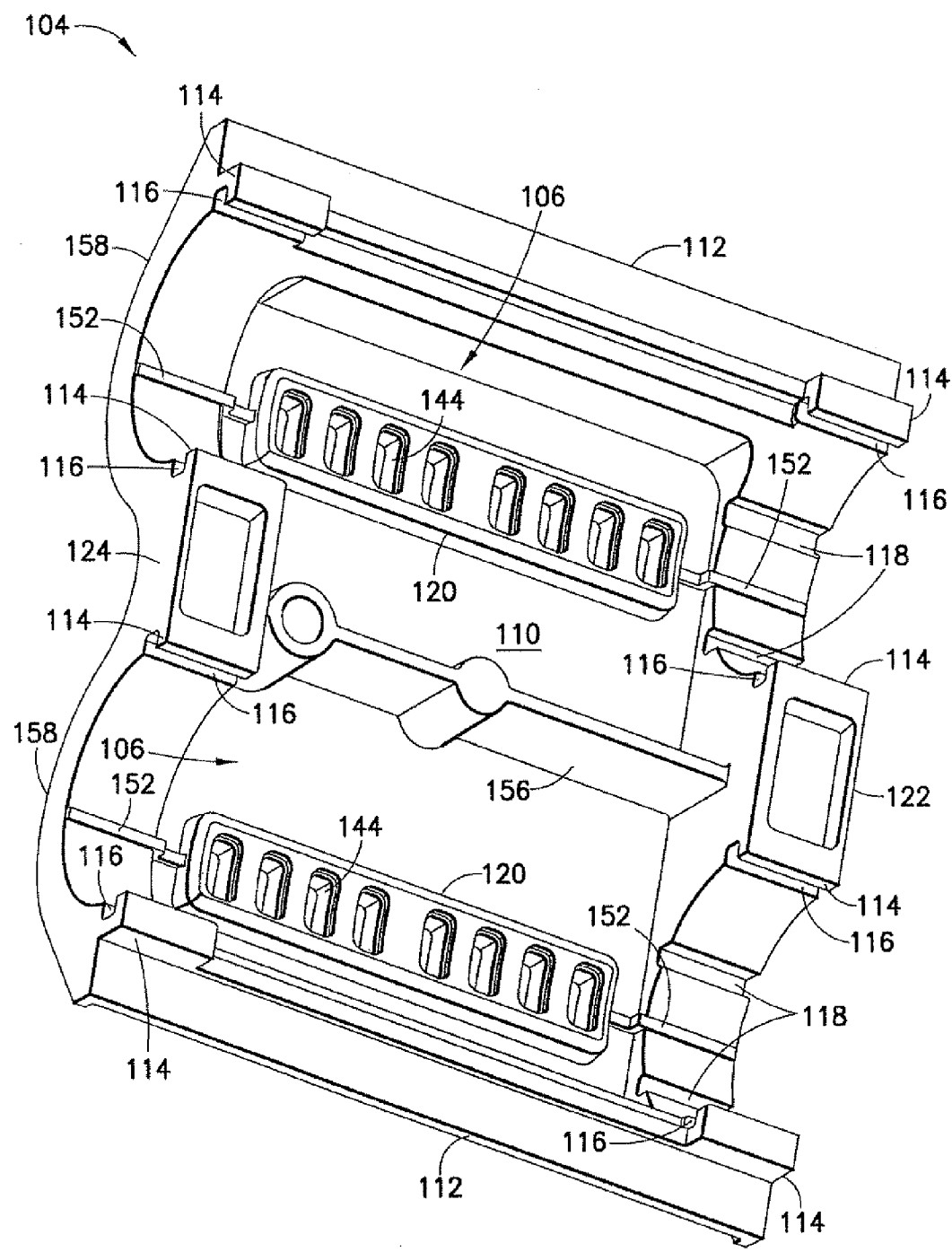
FIG. 5 is a bottom perspective view of the base member of the housing of the fluid pumping device of FIG. 1A and showing the fluid seal elements assembled to the base member.
Figure 6:
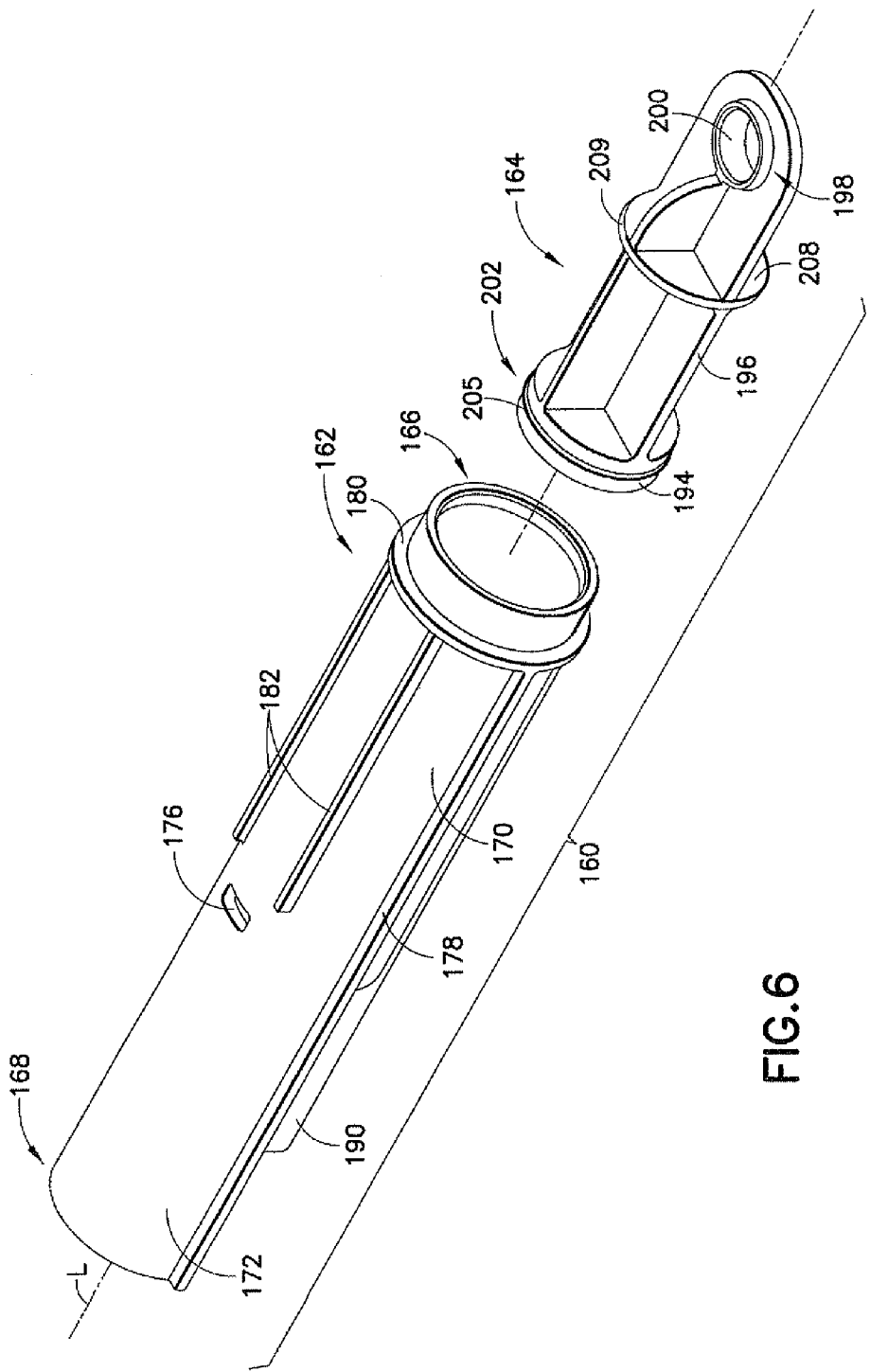
FIG. 6 is an exploded perspective view of one of the fluid pumps of the fluid pumping device of FIG. 1A.
Figure 9:
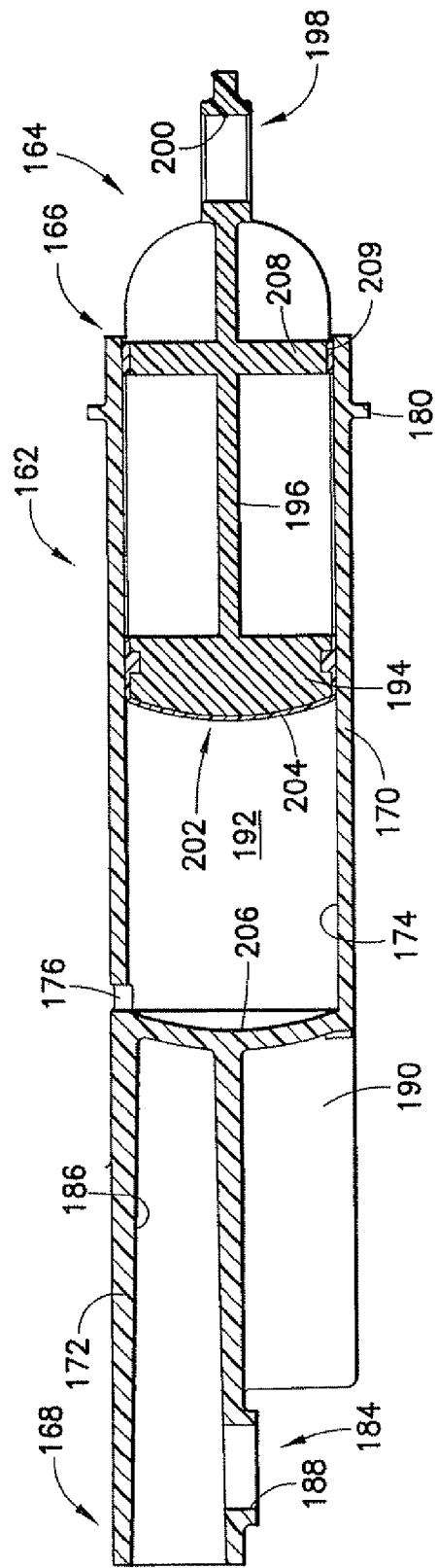
FIG. 9 is a cross-sectional view taken along line 9-9 in FIG. 8.
Figure 10:
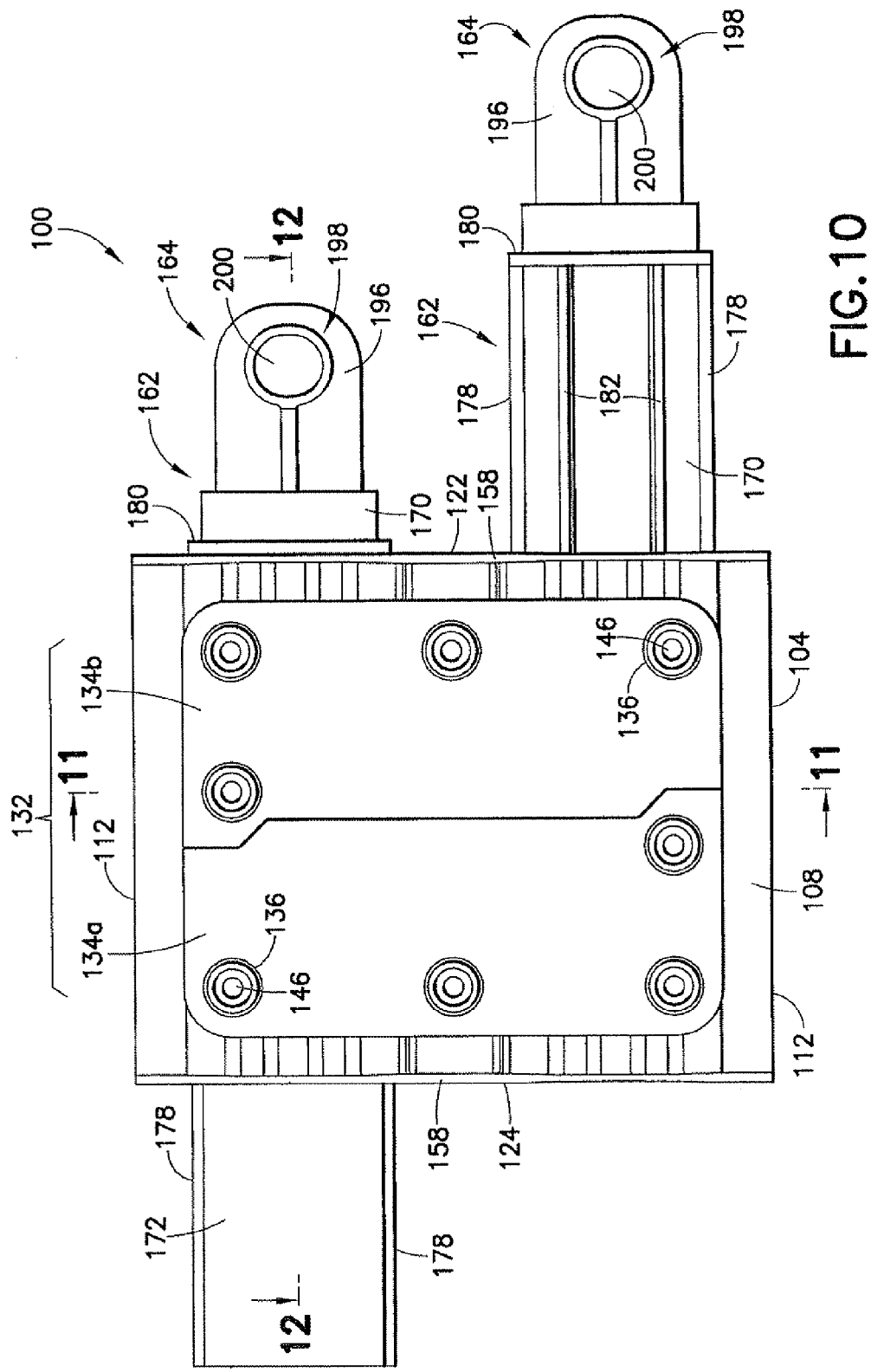
FIG. 10 is a top view of the fluid pumping device of FIG. 1A.
Figure 11:
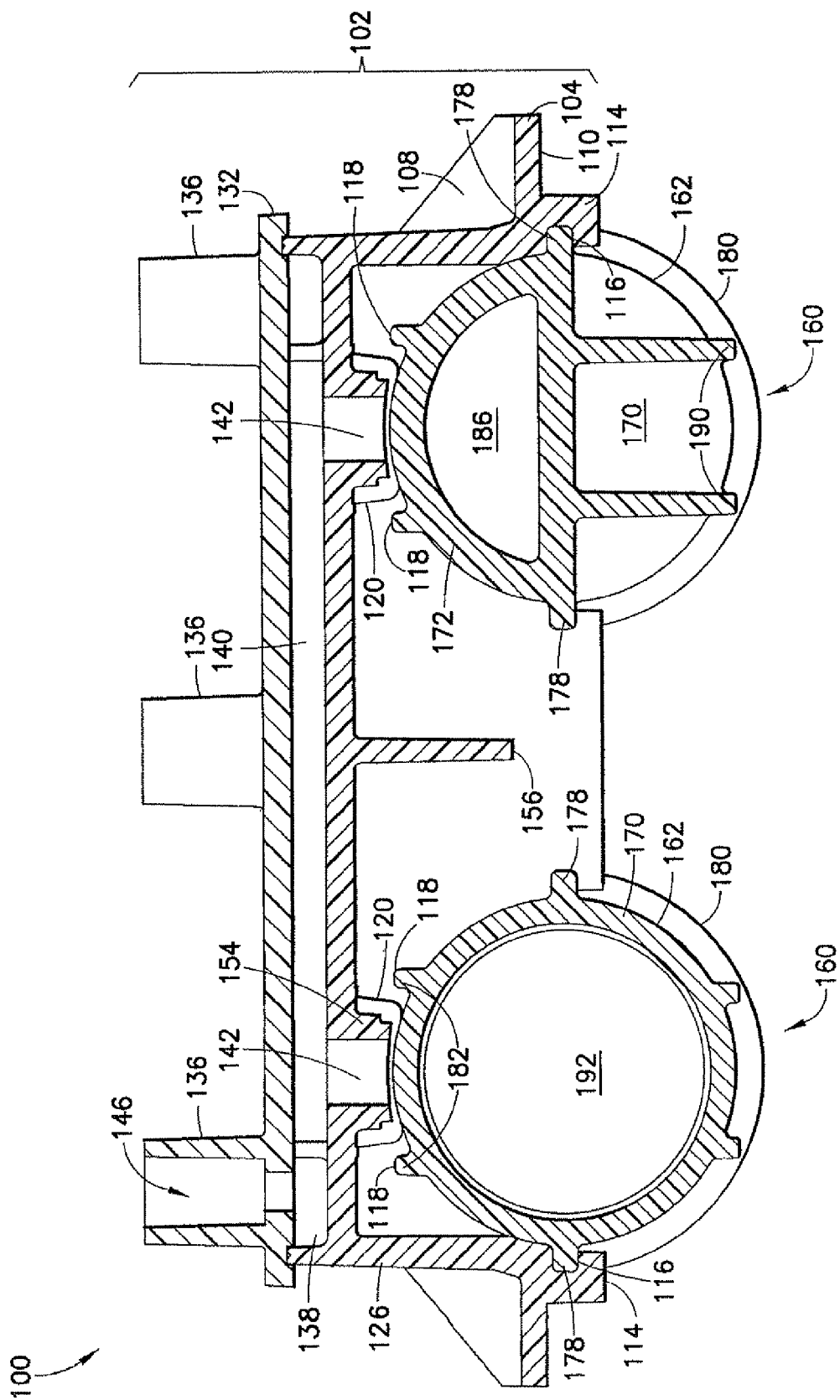
FIG. 11 is a cross-sectional view taken along line 11-11 in FIG. 10.
Figure 12:
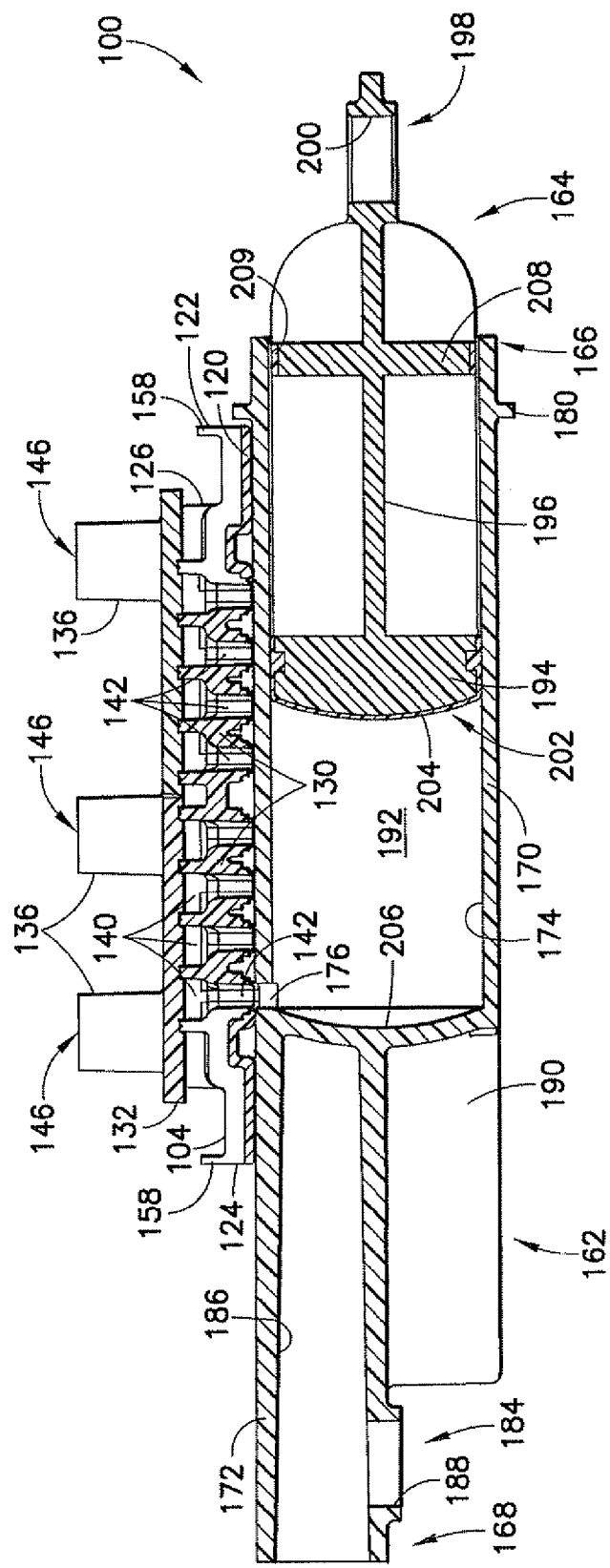
FIG. 12 is a cross-sectional view taken along line 12-12 in FIG. 10.

Referring, in particular, to FIGS. 4-5 a pair of longitudinally-directed alignment slots or alignment channels 118 may be provided within each cavity 106 which accept cooperating structures on fluid pumps 160, again, such as a lip, rib, flange, and the like. The engagement of these cooperating structures associated with fluid pumps 160 with alignment channels 118 serves several purposes including maintaining axial alignment between the respective fluid pumps 160 and cavities 106, guiding the sliding reciprocal movement of the fluid pumps 160 in cavities 106 during operation of fluid pumping device 100, and as a keying feature to ensure that fluid pumps 160 are associated with base member 104 in the proper manner, desirably by inserting piston 162 into engagement with base member 104 from end 122 of base member 104. Additionally, a fluid seal element 120 is desirably provided within each cavity 106 and is used to provide a sealing association between base member 104 and fluid pumps 160 disposed in the respective cavities 106. In this manner, a generally fluid seal engagement is provided between each fluid pump 160 and base member 104 within each cavity 106 during operation of fluid pumping device 100. In one desirable construction, fluid seal elements 120 may be over-molded to base member 104 within each cavity 106 in a subsequent over-molding process to the typical injection-molding process used to form base member 104. Base member 104 and manifold cap 132 are typically formed of rigid or stiff plastic material such as polycarbonate, acrylic, polyethylene terephthalate (PET), or cyclo-olefin polymer (COP). Fluid seal elements 120 are typically formed of elastomeric material such as thermoplastic elastomers (TPE's), thermoplastic polyurethanes (TPU's), or thermoformed rubbers such as nitrile rubber or ethylene propylene diene monomer rubber (EPDM). A soft plastic material may also be used for fluid seal elements 120 such as polypropylene, polyethylene, ultra-high molecular weight polyethylene (UHMW), or fluoropolymers such as polytetrafluoroethylene (PTFE). Further, a thermosetting rubber may be used for fluid seal elements 120 such as nitrile rubber (acrylonitrile butadiene rubber) or ethylene propylene diene monomer rubber (EPDM).

Base member 104 generally comprises two opposing ends 122, 124. Typically, securing members 114 depend from the underside 110 of base member 104 immediately adjacent opposing ends 122, 124 of the base member 104. However, if desired, securing members 114 may be continuous along the opposing lateral sides 112 of base member 104 as explained previously. Base member 104 further comprises a manifold portion 126 on top side 108, generally centered between opposing ends 122, 124 of base member 104. Manifold portion 126 extends upward or is generally upstanding from the top side 108 of base member 104 and defines one or more banks 128 of fluid channels and associated ports. In the illustrated embodiment, two individual banks 128(1), 128(2) of fluid channels are provided. Each fluid channel bank 128(1), 128(2) is defined by an individual upstanding, circumferential wall 130(1), 130(2) formed as part of manifold portion 126. An area of separation S is defined between the adjacent fluid channel banks 128(1), 128(2) and which separates the fluid channel banks 128(1), 128(2). It will be apparent that the provision of two distinct circumferential walls 130(1), 130(2) to form distinct fluid port banks 128(1), 128(2) may be replaced by a single wall 130 that forms the perimeter of both fluid channel banks 128(1), 128(2). As will be further appreciated from inspection of FIGS. 1-2, manifold cap 132 is used to enclose fluid channel banks 128(1), 128(2) and may be bifurcated into two cap halves 134*a*, 134*b* for this purpose. However, if desired, bifurcated manifold cap 132 may be unitary to enclose both fluid port banks 128(1), 128(2) simultaneously. Manifold cap 132 further comprises a series of connector ports 136, the arrangement and function of which are described herein. However, generally connector ports 136 are adapted to interface with connectors 20 at the end of the fluid line 18 associated with the respective fluid containers 16 to form a generally leak proof connection with the connectors 20. If desired, manifold portion 126 may also be formed as a separate component that is joined to base member 104 by joining methods customary in the art such as ultrasonic welding, laser welding, adhesive, by direct mechanical attachment, and like methods.

Figure 3:
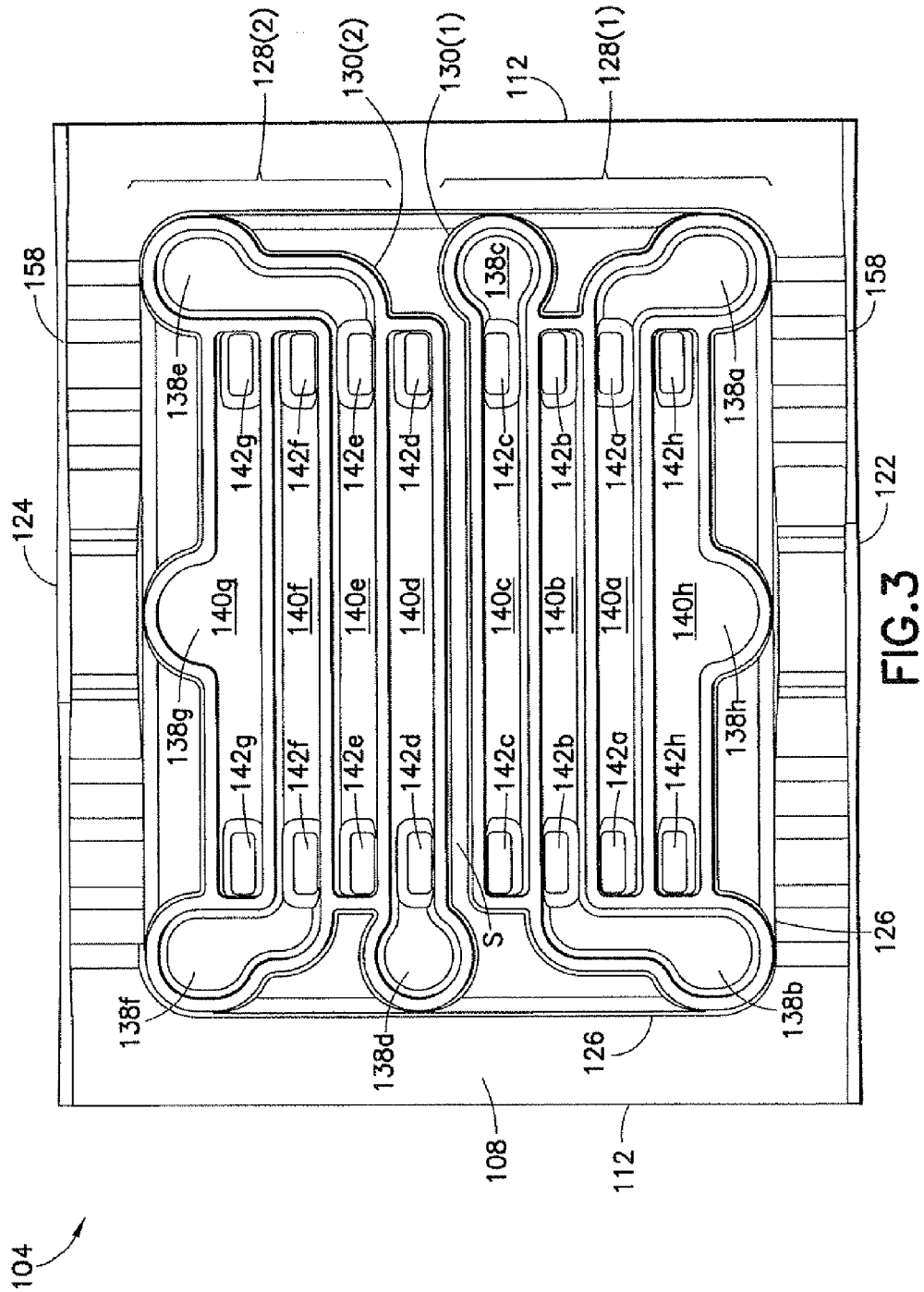
FIG. 3 is a top view of the base member of the housing of the fluid pumping device of FIG. 1A.

From FIG. 3, it will be understood that circumferential walls 130(1), 130(2) associated with manifold portion 126 define a series of fluid ports 138 each having an associated or connected fluid passageway 140. In the accompanying figures, each fluid port 138 and associated fluid passageway 140 is given an alphabetical identifier (a-h) for ease in discerning one fluid port 138 and associated or connected fluid passageway 140 from an adjacent fluid port 138 and associated or connected passageway 140. Fluid ports 138 and associated fluid passageways 140 are defined by the respective walls 130(1), 130(2), but a single such wall 130 on the manifold portion 126 may likewise produce the same formation, as indicated previously. Additionally, each fluid port 138 and associated fluid passageway 140 is desirably fluid-isolated from each neighboring fluid port 138 and associated fluid passageway 140 by the respective walls 130(1), 130(2) or a single such wall 130. However, it is within the scope of this disclosure to fluidly interconnect adjacent fluid ports 138 by providing fluid-connecting apertures (not shown) in the respective walls 130(1), 130(2) or a single such wall 130 to fluidly connect adjacent fluid passageways 140 if desired.

A pair of manifold openings or apertures 142 is defined in base member 104 within each fluid passageway 140 to provide fluid communication between each fluid passageway 140 and the respective fluid pumps 160 disposed in cavities 106. As noted previously, the illustrated embodiment of fluid pumping device 100 comprises two fluid pumps 160 and two manifold openings 142 are, therefore, needed in each fluid passageway 140 to register with the respective fluid pumps 160 as explained further herein. However, as indicated previously, this configuration is for exemplary purposes only and may be expanded beyond two fluid pumps 160. In such an arrangement, base member 104 may define an additional or several additional cavities 106 and manifold portion 126 may be expanded to encompass this additional or several additional cavities 106 and the accompanying or associated fluid pump(s) 160 disposed therein. For example, if one additional fluid pump 160 is associated with base member 104 in a third cavity 106 (not shown), manifold portion 126 will comprise a third manifold opening or aperture 142 in each fluid passageway 140 to register with the additional fluid pump 160. As manifold portion 126 is typically integrally-formed with base member 104 such as during an injection molding process, in this variation manifold portion 126 would be formed on base member 104 to extend and encompass the additional fluid pump 160.

As explained previously, fluid seal elements 120 are disposed in each cavity 106 to provide a generally fluid tight seal between base member 104 and fluid pumps 160 during operation of the fluid pumps 160. Fluid seal elements 120 define a series of openings or apertures 144 which are positioned to generally coincide with the manifold openings 142 in base member 104 so that the fluid seal elements 120 may seal against the base member 104 and, thereby, allow generally fluid-tight communication between fluid ports 138 and associated fluid passageways 140 and fluid pumps 160. Further, it will be apparent from the accompanying figures, particularly FIG. 2, that manifold connector ports 136 generally coincide and register with fluid ports 138 and, when manifold cap 132 is secured to manifold portion 126 of base member 104, manifold connector ports 136 and fluid ports 138 coincide or register to define a series of manifold ports 146 on manifold portion 126 of base member 104 suitable as inlet ports for providing one or more fluids to fluid passageways 140 or as one or more outlet ports for delivering a single fluid or a mixture of fluids to patient fluid path 12 or, possibly to waste fluid line 22 leading to an appropriate medical fluid waste container. Manifold ports 146 are given an alphabetic identifier (a-h) corresponding to that assigned to the associated fluid passageways 140.

As shown in FIGS. 4-5, base member 104 further defines a recessed area 148 in each cavity 106 wherein fluid seal elements 120 are respectively disposed. Recessed areas 148 include axially-extending grooves 150 and the fluid seal elements 120 comprise corresponding axial appendages 152 in axial grooves 150. Axial appendages 152 are a result of a typically injection molding process used to dispose fluid seal elements 120 in recessed areas 148. As noted previously, fluid seal elements 120 may be over-molded to base member 104 and, thus, fluid seal elements 120 may be over-molded directly into recessed areas 148 in each cavity 106 pursuant to this disclosure. Moreover, base member 104 may comprise depending flange or rim flanges 154 which, at least in part, define the respective manifold openings 142 and provide depending structure around which fluid seal elements 120 may be over-molded, for example. Rim flanges 154 may extend into fluid seal openings or apertures 144 and may in part define these openings 144. FIGS. 4-5 further show a central support bridge 156 formed on the bottom side or underside 110 of base member 104 as a reinforcing structure for base member 104. Moreover, as shown in FIGS. 4-5, opposing ends 122, 124 of base member 104 are formed with radial flanges 158 which provide abutment walls or limits that limit linear travel of fluid pumps 160 relative to the base member 104 during operation of fluid pumping device 100 as described herein.

Turning next to fluid pumps 160, fluid pumps 160 are located within the respective cavities 106 defined in base member 104, as generally described previously. Fluid pumps 160 each comprise two opposing pistons 162, 164, which may be referred to herein as a first piston or sleeve piston 162 and a second piston or insertion piston 164 for identification purposes. As each fluid pump 160 is identical having identical pistons 162, 164, the following discussion outlines the structure of one such fluid pump 160 used in fluid pumping device 100. A suitable configuration for pistons 162, 164 of fluid pump 160 is shown, for example, in FIGS. 6-12. In the illustrated configuration, opposing pistons 162, 164 are configured such that insertion piston 164 may be disposed or inserted at least partially into sleeve piston 162. For this purpose, sleeve piston 162 may have a generally cylindrical configuration with opposing first and second ends 166, 168. Sleeve piston 162 comprises a sleeve portion 170 wherein piston 164 may be inserted or disposed and which forms or defines the first end 166 of the sleeve piston 162. Sleeve piston 162 further comprises an extended interface portion 172 that extends from sleeve portion 170 and defines the second end 168 of the sleeve piston 162. Interface portion 172 is generally adapted to interface with drive system 600 as described herein. Sleeve portion 170 defines an internal cavity 174 accessible via a sleeve access opening or sleeve port 176. Sleeve piston 162 further comprises lateral flanges or ribs 178 on opposing lateral sides thereof and which extend generally parallel to a central longitudinal axis L of fluid pump 160. Lateral flanges or ribs 178 form or define the cooperating structures mentioned previously that engage slots 116 in depending securing members 114 associated with base member 104. The engagement of lateral flanges or ribs 178 with securing members 114 supports fluid pump 160 to base member 104. This engagement, in particular, serves to secure fluid pump 160 in its respective cavity 106 while allowing sliding reciprocal movement between sleeve pistons 164 and base member 104. Sleeve piston 162 is also provided with an end flange 180 formed as part of sleeve portion 170. End flange 180 forms an interfering structure proximate to first end 166 of sleeve piston 162 to engage radial end flange 158 formed at end 122 of base member 104 to limit linear travel of sleeve piston 162 relative to base member 104. Radial end flanges 158 at opposing ends 122, 124 of base member 104 also serve to structurally reinforce the base member 104.

A further feature of sleeve piston 162 is the provision of alignment tabs or ribs 182 on sleeve portion 170 and generally coextensive with the sleeve portion 170. Alignment tabs or ribs 182 are provided in a suitable location and configuration to engage the pair of longitudinally-directed alignment slots or channels 118 in base member 104 and, more particularly, within each cavity 106 in the base member 104. Alignment tabs 182 define the cooperating structures mentioned previously which engage alignment channels 118. The engagement of alignment tabs 182 in alignment channels 118 acts to orient fluid pump 160 within cavity 106, maintains axial alignment between the fluid pump 160 and cavity 106 and, more particularly, between sleeve piston 162 and base member 104 during sliding reciprocal movement of the sleeve piston 162 in cavity 106 in base member 104 during operation of fluid pump 160, and operate as a keying feature as noted previously.

Interface portion 172 on sleeve piston 162 comprises a drive interface portion 184 which is adapted to engage piston drive elements of drive system 600 (described herein) to effect motion of sleeve piston 162 relative to base member 104. Interface portion 172 may be formed with an open or hollow cross-sectional shape or space 186, for example, of generally semi-circular transverse or vertical cross-section. Interface portion 172 defines an interface or attachment aperture 188 which provides a location or structure for interfacing with a piston drive element or component of drive system 600. In particular, interface aperture 188 may be adapted to provide a location whereby sleeve piston 162 may physically interface or connect with a piston drive element or component of drive system 600 used to operate sleeve piston 162 and move the sleeve piston 162 relative to base member 104 and relative to insertion piston 164. Interface portion 172 may comprise one or more depending flanges 190 that depend or extend downward from interface portion 172 and enhance the structural strength of interface portion 172 and may have additional functions in this embodiment and other embodiments described herein. Interface aperture 188 may be located proximal of flanges 190 (e.g., behind) and axially between the flanges 190.

As noted previously, insertion piston 164 is adapted to access internal cavity 174 defined by sleeve portion 170 of sleeve piston 162. Insertion piston 164 is reciprocally movable within sleeve portion 170 of sleeve piston 162 and, with piston 164 disposed within sleeve portion 170, pistons 162, 164 cooperate to form or define a fluid pumping chamber of 192 of each fluid pump 160. Piston 164 comprises a piston head 194 and a proximally extending piston rod 196. Piston head 194 and piston rod 196 may be an integral structure as illustrated or be separate structures that are joined together by the joining methods outlined previously. Piston rod 196 comprises a generally X-shaped configuration and terminates at a proximal end thereof with a drive interface portion 198 defining a second interface aperture or attachment aperture 200 of similar configuration to first interface aperture or attachment aperture 188. In a similar manner to first drive interface portion 184 and first interface aperture 188, second drive interface portion 198 and second interface aperture 200 provide a location whereby insertion piston 164 may physically interface or connect with a piston driving element or component of drive system 600 used to operate piston 164 and move the piston 164 relative to sleeve piston 162 and, further, base member 104.

Piston head 194 desirably exhibits a generally curved or arcuate-shaped distal end 202. A polymeric cover or layer 204 is desirably provided on piston head 194 to form the arcuate-shaped distal end 202 thereof. Polymeric layer 204 desirably defines one or more circumferential sealing ribs 205 to form a fluid seal with the inner wall of sleeve portion 170 of sleeve piston 162. The curved, arcuate shape of distal end 202 of piston head 194 is desirably shaped to cooperate or engage with a correspondingly curved or arcuate-shaped internal end wall 206 within sleeve portion 170 and opposing the piston head 194 when piston 164 is disposed in sleeve portion 170 of sleeve piston 162. The corresponding shapes of distal end 202 of piston head 194 and end wall 206 are desirable for several reasons including because the curved shape of end wall 206 permits sleeve portion 170 to withstand high pressures without significant deformation due to its domed shape. While only a single sealing rib 205 is shown on piston head 194 in the present embodiment, additional spaced sealing ribs may be on polymeric cover or layer 204 as desired, and as provided for herein in connection with other embodiments.

Piston rod 196 may have a generally X-shaped cross-section defined by individual flange elements 207 and is desirably reinforced with a proximal disc element 208 located distally forward of second drive interface portion 198 as illustrated. Proximal disc element 208 may have a polymeric layer 209 provided on the outer circumferential edge of disc element 208. Polymeric layer 209 is desirably a similar material to polymeric layer 204 on piston head 194. Proximal disc element 208 enhances stability of piston 164 as it operates within sleeve portion 170 of sleeve piston 162. It will be appreciated that polymeric layer 204 and, particularly, sealing rib(s) 205 forms a generally fluid tight seal between piston head 194 and the inner wall of sleeve portion 170 of sleeve piston 162 such that pumping chamber 192 is a generally fluid tight chamber during a static, non-moving situation of pistons 162, 164 or during a dynamic, operational movement of pistons 162, 164. Polymeric layer 204 and polymeric layer 209 may be formed of any of the materials detailed previously in connection with fluid seal elements 120 and are desirably overmolded polyurethane layers and the like. Proximal disc element 208 and the applied polymeric layer 209 provide additional fluid sealing assistance as piston 164 operates in sleeve portion 170 and aids in keeping pumping chamber 192 sealed and free from external sources of contamination. Other embodiments described herein disclose that a polymeric layer may also be provided on the outward edges of individual flange elements 207 for additional sealing and stability advantages. Any polymeric layer on the outward edges of flange elements 207 is typically a result of an injection molding process used to apply polymeric material to form polymeric cover 204 and polymeric seal layer 209 and may or may not engage the inner wall of sleeve portion 370 in accordance with this disclosure.

As noted previously, in one desirable embodiment of fluid pumping device 100, fluid pumping device 100 may be provided in a cassette or cartridge form that is optionally disposable after a single or a multiple number of discrete uses. In such an embodiment, fluid pumping device 100 may be part of fluid delivery system 10 comprising fluid pumping device 100 and drive system 600, as schematically illustrated in FIG. 13. Drive system 600 desirably comprises a cabinet-like component that defines an enclosure or compartment 24 adapted to receive fluid pumping device 100. Fluid pumping device 100 is desirably inserted or loaded into pump compartment 24 to interface with drive system 600. In the foregoing embodiment of fluid pumping device 100 comprising two fluid pumps 160, drive system 600 generally comprises two essentially identical actuators 602, one for each fluid pump 160. Each fluid pump actuator 602 comprises two essentially identical piston positioning or movement devices 604, a total of four such devices 604. Each piston positioning or movement device 604 includes a piston positioning or movement member 606 adapted to engage or interface with pistons 162, 164. As noted previously, pistons 162, 164 have respective piston drive interface portions 184, 198 with respective interface apertures 188, 200. It will be generally appreciated from FIG. 13 that interface apertures 188, 200 are desirably identical so that four identical devices 604 are used to operate the four pistons 162, 164 associated with fluid pumps 160. Accordingly, fluid pump actuators 602 each have a piston positioning device 604 associated with a sleeve piston 162 and have a second piston positioning device 604 associated with insertion piston 164 in each fluid pump 160. A further aspect of fluid pump actuators 602 is that the individual piston positioning devices 604 may be individually controlled to effect individualized motion, movement, or positioning of the pistons 162, 164 in the respective fluid pumps 160. In other words, fluid pump actuators 602 each have two independent, desirably linear, axes of motion, wherein one piston positioning device 604 moves piston 164 axially in sleeve portion 170 of sleeve piston 162 while the other piston positioning device 604 moves sleeve piston 162 relative to base member 104 during operation of fluid pumps 160.

Piston positioning devices 604 could be provided in several different forms to effect movement, typically linear reciprocal movement, of pistons 162, 164 in fluid pumps 160. For example, piston positioning devices 604 could be a ball screw shaft driven by a motor, a voice coil actuator, a rack-and-pinion gear drive, a linear motor, and the like. While it is often desirable that piston positioning devices 604 be identical devices, this should not be considered as foreclosing the possibility that different configurations may be used to effect movement of pistons 162, 164 in each fluid pump 160. For example, it is possible to use a rack and pinion gear drive to effect movement of sleeve piston 162 while using a linear motor to effect movement of insertion piston 164 in each fluid pump 160 and vice versa. In other words, various types of controlled mechanical devices may be mixed and matched for piston positioning devices 604 in fluid pump actuators 602 of drive system 600.

It is also be possible for pistons 162, 164 in each fluid pump 160 to share a single or common piston positioning device 604 which would form the fluid pump actuator 602. For example, such a common or single piston positioning device 604 could be in the form of a single ball screw shaft that has two ball nuts attached, permitting pistons 162, 164 to be positioned independently on a single screw in each fluid pump 160. No matter what format is used for piston positioning or movement devices 604 in fluid pump actuators 602, a desirable feature is that the position, velocity, and acceleration of each piston positioning or movement device 604 may be controlled independently, for example, by a control device interfaced with the respective piston positioning devices 604. Such a control device (not shown) may be a controller or computer with an algorithm that can operate the individual piston positioning devices 604 associated with fluid pump actuators 602. Such a control device may receive inputs from piston positioning devices 604 relating to the position of piston positioning member 606 associated with each piston positioning device 604 and this information is used to effect controlled movement of pistons 162, 164 in each fluid pump 160.

Referring further to FIGS. 14-20, exemplary operation of fluid pumping device 100 will now be described. As noted previously, fluid pumping device 100 comprises two fluid pumps 160 in the illustrated and non-limiting embodiment in the accompanying figures. Moreover, manifold portion 126 and manifold cap 132 together define a series of eight manifold ports 146 having the configuration described in detail hereinabove. Of these eight manifold ports 146, it may be desirable to have six of these manifold ports 146 be inlet ports (146a-146f) and the remaining two manifold ports 146 be outlet ports (146g, 146h), as labeled in FIG. 3 (see also FIG. 1B). As an example, in the context of using fluid pumping device 100 for delivering contrast media fluid to a patient during a radiographic imaging procedure, the six inlet manifold ports 146 may be divided as follows: two manifold inlet ports 146 for saline $S_1$, $S_2$ (146a, 146d); two manifold inlet ports 146 for one type, concentration, or brand of contrast media fluid $A_1$, $A_2$ (146b, 146e); and two manifold inlet ports 146 for a different type, concentration, or brand of contrast media fluid $B_1$, $B_2$ (146c, 146f), such as a different concentration of contrast media fluid or different type or brand of contrast media fluid. The two remaining manifold ports 146 may be divided into a patient administration port (146g) and a waste outlet port (146h). It will be clear that manifold ports 146 may be configured in a way to make suitable connections with connectors 20 associated with fluid lines 18 connected to the various bulk fluid containers 16 illustrated in FIG. 1B. While the foregoing example limits the following discussion to eight manifold ports 146, it is possible within the scope of this disclosure to add additional manifold ports 146 for additional inlet and outlet ports if desired based on the details provided hereinabove. Moreover, it will be apparent that the various manifold ports 146 may be associated with the bulk fluids sources 14 in any manner desired and that the specific arrangement set forth in the foregoing is merely exemplary.

As noted previously, fluid pumps 160 are configured such that, under the action of drive system 600, pistons 162, 164 in each fluid pump 160 may be separately controlled and, therefore, are separately positionable relative to one another. Stated another way, each insertion piston 164 is movable relative to its opposing sleeve piston 164 and vice versa. Base member 104 forming pump housing 102 forms a static support structure from which pistons 162, 164 may move relative to one another during the operation of fluid pumping device 100. Accordingly, it is possible for insertion piston 164 to move while the opposing sleeve piston 164 remains stationary and vice versa as desired. For clarity in explaining operation of fluid pumps 160 in fluid pumping device 100, the following discussion will describe the operation of one fluid pump 160, namely, the fluid pump 160 immediately below and adjacent manifold inlet ports 146a; 146c; 146e. It will be appreciated that the additional or "second" fluid pump 160(2) in fluid pumping device 100 may be operated in the same manner and, additionally, in a staggered mode from the "first" fluid pump 160(1) so that continuous fluid delivery may be provided at patient administration manifold outlet port 146g, as described herein.

Figure 14:
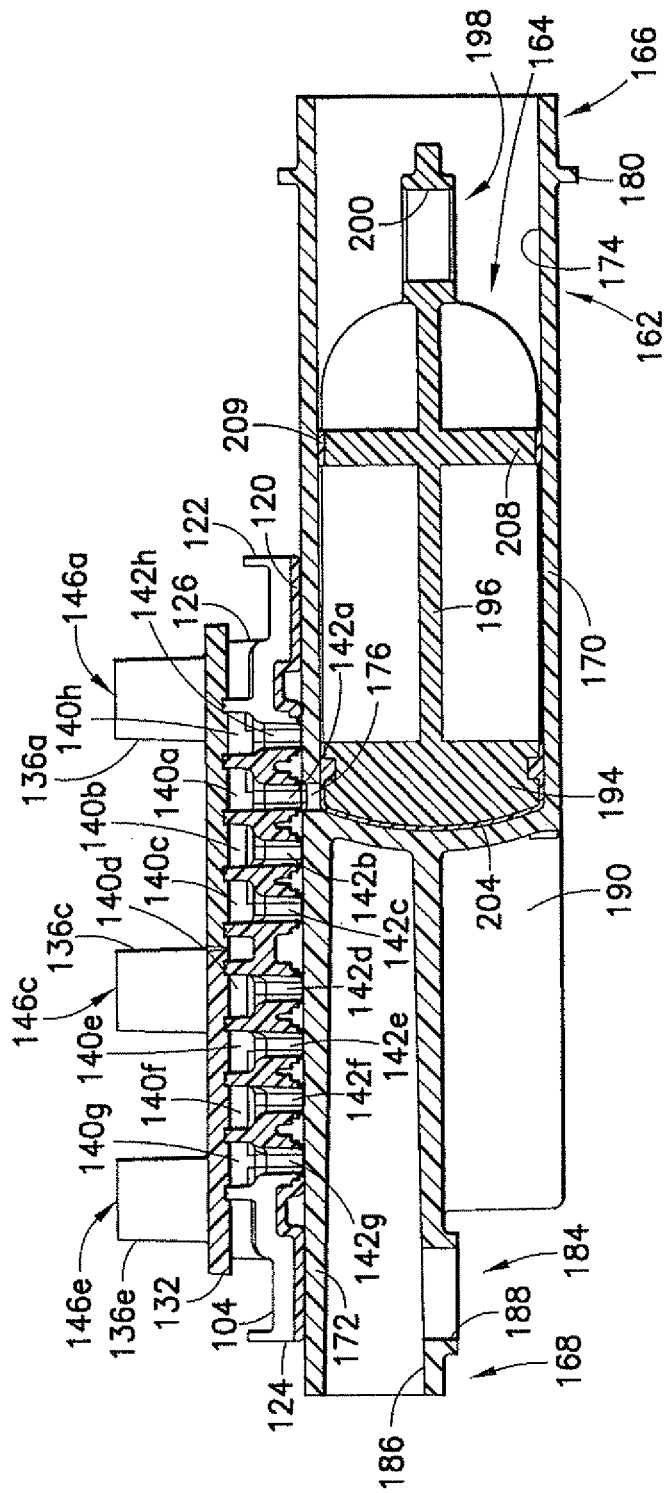
FIGS. 14-20 are cross-sectional views showing one complete fluid fill and ejection cycle of one of the fluid pumps in the fluid pumping device of FIG. 1A.
Figure 15:
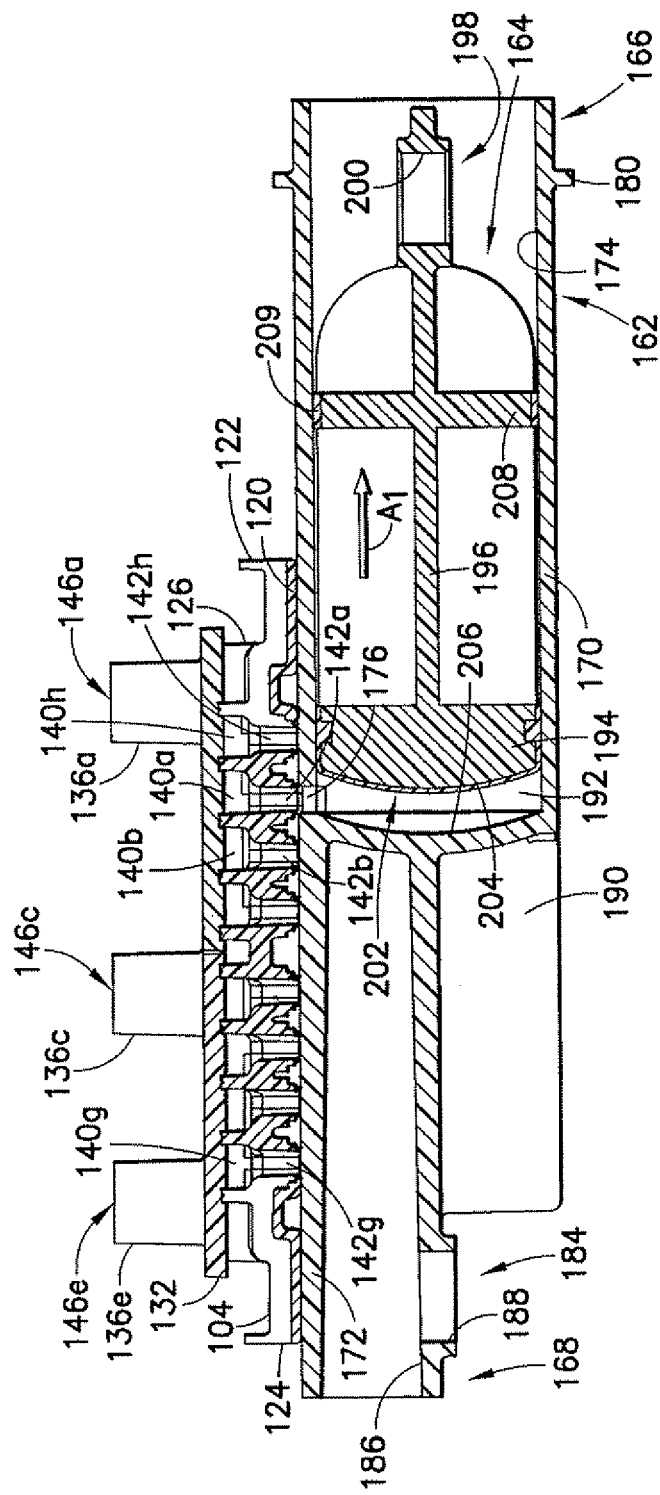
Figure 16:
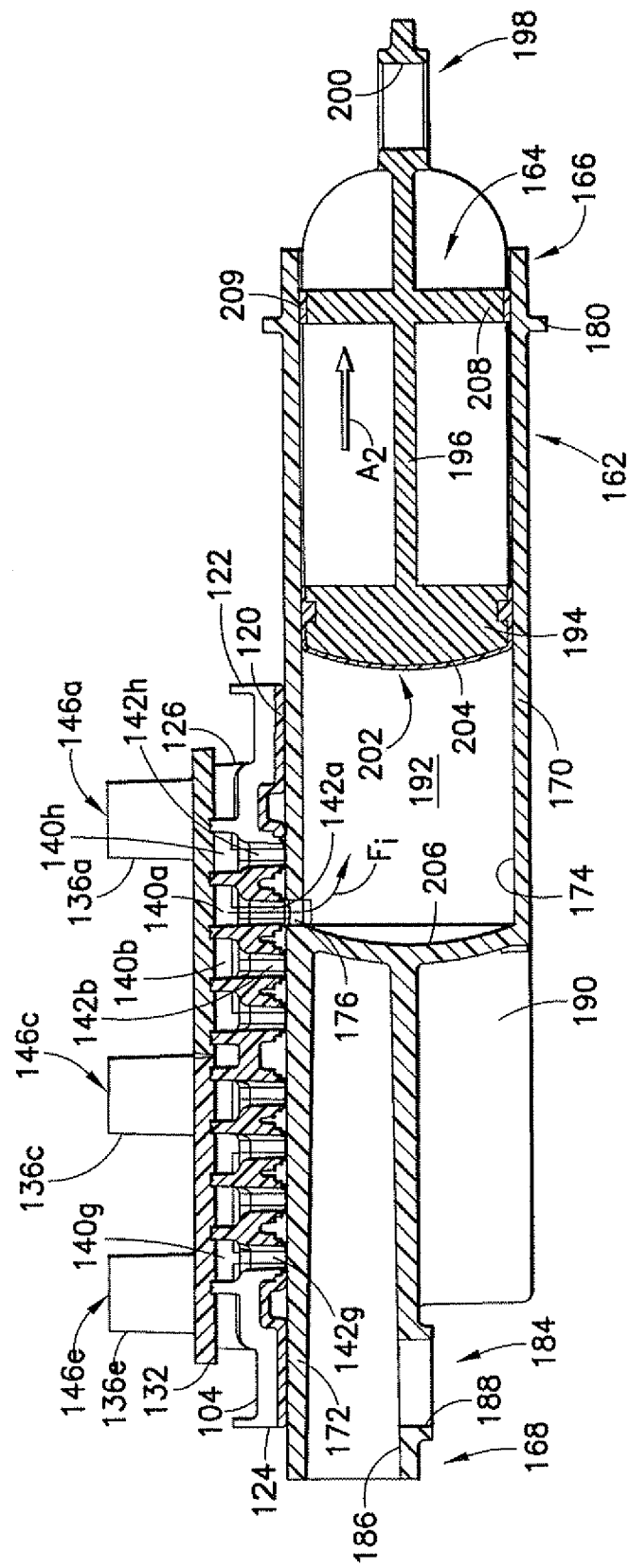
Figure 17:
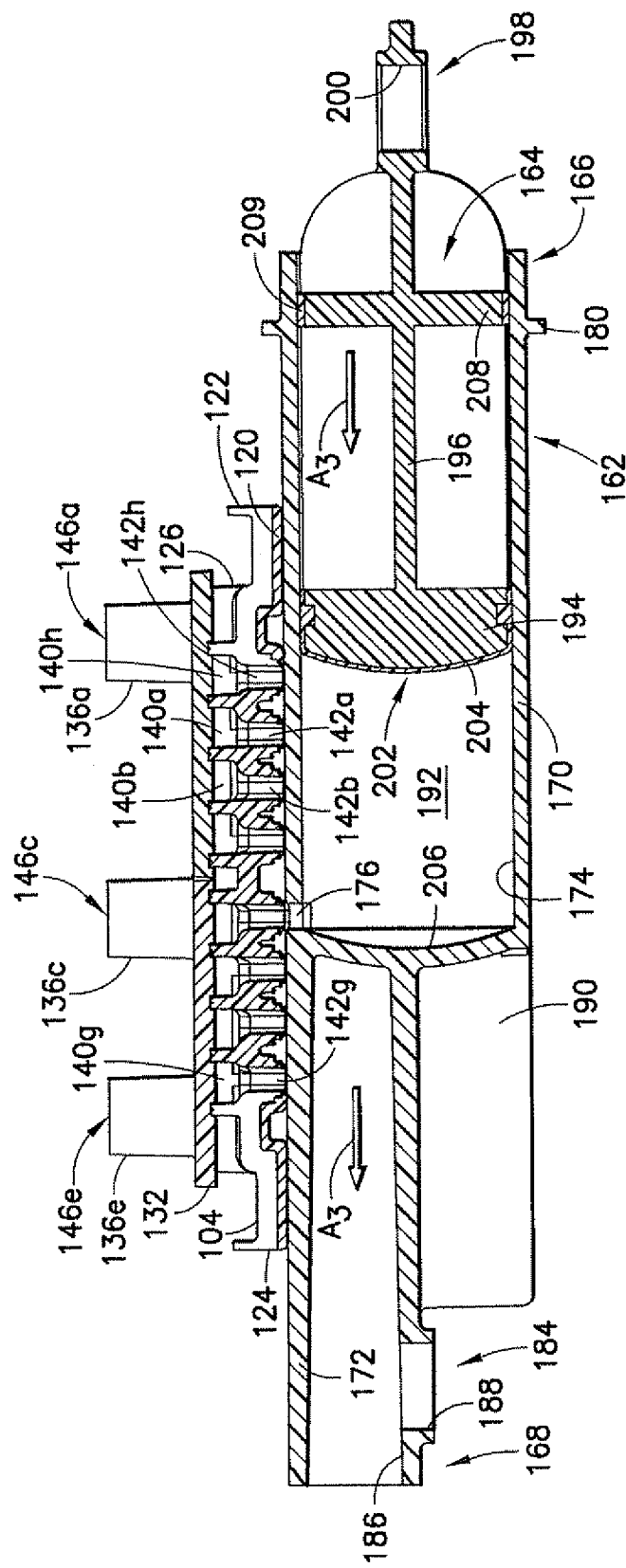

The ability of pistons 162, 164 to move independently under the motive force provided drive system 600 allows, for example, sleeve piston 162 to remain stationary proximate to one of manifold openings 142 in base member 104 so that sleeve opening or sleeve port 176 in sleeve portion 170 of sleeve piston 162 is associated with a selected manifold opening 142 or, possibly, two or more adjacent manifold openings 142 with proper (elongated) sizing of sleeve port 176. As a reminder, it is noted that manifold openings 142 coincide with the respective openings 144 in fluid seal elements 120. As a further reminder, it is noted that each manifold opening 142 is in fluid communication or connection with one of the manifold ports 146, respectively, via an associated connecting fluid port 138 and fluid passageways 140. In the present example, it may be assumed that sleeve piston 162 is positioned such that sleeve port 176 in sleeve portion 170 is located proximate to manifold opening 142a connecting to fluid passageway 140a and associated fluid port 138a, as shown in FIG. 14. While not specifically shown in FIG. 14, sealing rib 205 on piston head 194 is desirably located just proximal of sleeve port 176 such that there is desirably a slight clearance around the distal end 202 of the piston head 194 to enable fluid to be ejected from pumping chamber 192 during an ejection or pumping stroke of insertion piston 164 as described herein.

As described previously, fluid port 138a and manifold connector port 136a together define manifold inlet port 146a which, in the instant example, is associated with a bulk "saline" source 14 contained in fluid container 16 identified as saline $S_1$ in FIG. 1B, meaning that this manifold inlet port 146*a* is associated with an external source of saline $S_1$. As sleeve piston 162 is held positioned at the selected manifold opening 142*a* by its associated piston positioning device 604, opposing piston 164 may be moved axially and generally linearly away from sleeve piston 162 by its associated piston positioning device 604. As this movement occurs as represented by an arrow $A_1$ in FIG. 15, piston head 194 generally clears sleeve port 176, so that a substantially unimpeded inlet fluid path is established between bulk "saline $S_1$" container 16 and pumping chamber 192. In particular, this inlet fluid path is generally defined by manifold inlet port 146*a*, connecting fluid passageway 140*a*, manifold opening 142*a* and sleeve port 176 in sleeve portion 170 leading to pumping chamber 192. As sleeve piston 162 is maintained at the selected manifold opening 142*a* by its associated piston positioning device 604, further movement of piston 164 axially and generally linearly away from sleeve piston 162 by its associated piston positioning device 604 (as represented by the arrow $A_2$ in FIG. 16) draws in fluid (saline $S_1$ in the present example) as represented by arrow $F_1$ into pumping chamber 192 under negative pressure caused by this relative movement. In particular, saline $S_1$ is drawn into pumping chamber 192 from bulk saline $S_1$ container 16 via manifold inlet port 146*a*, associated fluid passageway 140*a*, manifold opening 142*a*, and sleeve port 176. As only a single opening, namely, sleeve port 176, is provided in sleeve portion 170 of sleeve piston 162, the remaining manifold openings 142 in line with manifold inlet port 146*a* are blocked by the sleeve portion 170 preventing fluid communication with pumping chamber 192. When a desired amount of saline $S_1$ is drawn into pumping chamber 192 under the moving action of piston 164, both pistons 162, 164 may be moved substantially synchronously to establish another inlet fluid path, such as an inlet fluid path associated with manifold inlet port 146*b* or, alternatively, to establish an outlet fluid path such as one associated with manifold outlet port 146*g* (patient), or manifold outlet port 146*h* (waste). During this movement to another fluid path, whether to establish a fluid path with manifold inlet port 146*b* or another manifold inlet port 146 or to establish a fluid path one of the manifold outlet ports 146*g*, 146*h*, pistons 162, 164 are driven or moved substantially in synch with one another by the respective piston positioning devices 604 associated with fluid pump actuator 602 in order to prevent unwanted pressure or vacuum in pumping chamber 192. An example of this substantially synchronous movement is illustrated by arrows $A_3$ in FIG. 17.

Once the next manifold port 146 is selected, for example, manifold inlet port 146*b*, sleeve piston 162 is halted with sleeve portion 170 positioned such that sleeve port 176 aligns with manifold opening 142*b* to allow fluid communication between pumping chamber 192 and the manifold inlet port 146*b*. At this location, fluid communication is present between pumping chamber 192 and manifold inlet port 146*b* via fluid passageway 140*b*, manifold opening 142*b*, and sleeve port 176 in the manner described previously. As sleeve piston 162 is held positioned at the selected manifold opening 142*b*, opposing piston 164 may again be moved axially and generally linearly away from sleeve piston 162. As this movement occurs, fluid, now contrast media from bulk "contrast $A_1$" container 16 is drawn into pumping chamber 192 under the negative pressure caused by the movement of piston 164. In particular, contrast $A_1$ fluid is drawn into manifold inlet port 146*b*, passes to connecting fluid passageway 140*b*, and enters pumping chamber 192 via the alignment of sleeve port 176 and manifold opening 142*b*. As contrast $A_1$ fluid enters pumping chamber 192, the contrast $A_1$ fluid mixes with saline $S_1$ present in pumping chamber 192 which dilutes the contrast $A_1$ fluid. It will be appreciated that the amount of saline $S_1$ and contrast $A_1$ fluid drawn into pumping chamber 192 may be controlled by the distance piston 164 is retracted relative to sleeve piston 162 in each of the foregoing "fill" procedures; this retracted distance defines a specific volume of fluid drawn into pumping chamber 192. Accordingly, the proportion of the two fluids in pumping chamber 192 is controlled by the axial distance piston 164 is withdrawn within sleeve portion 170 of sleeve piston 162 in each of the foregoing "fill" procedures.

As the generally linear movement of piston 164 is incrementally controlled by fluid pump actuator 602 and fluid pump actuator 602 is typically controlled by the control device, and such a control device may be used to precisely control the amount of volume of contrast $A_1$ fluid and the amount or volume of saline $S_1$ that is present in pumping chamber 192 and, thereby, control the mixture or concentration of contrast media fluid to be delivered to a patient. Such a control device may include a user interface device such as a touch screen, keyboard, handcontroller, or a wireless device, for example, in the form of a personal data assistant, which is used to enter data inputs to the control device. The control device includes software programming that converts the data inputs into specific movements of pistons 162, 164 to arrive, for example, at specific contrast media concentrations or mixtures in pumping chamber 192. When a desired amount of contrast $A_1$ fluid is drawn into pumping chamber 192 under the moving action of piston 164, both pistons 162, 164 may be moved substantially synchronously to establish another inlet fluid path, if desired, such as an inlet fluid path associated with manifold inlet port 146*b* to receive additional contrast media fluid (in this case "contrast $A_1$" fluid) or another fluid altogether or, alternatively, pistons 162, 164 may be moved (substantially in synch for the reasons noted previously) to a selected manifold outlet port 146, such as manifold outlet port 146*g* which serves as a patient fluid administration port connected to patient fluid path 12 in the instant example.

Figure 18:
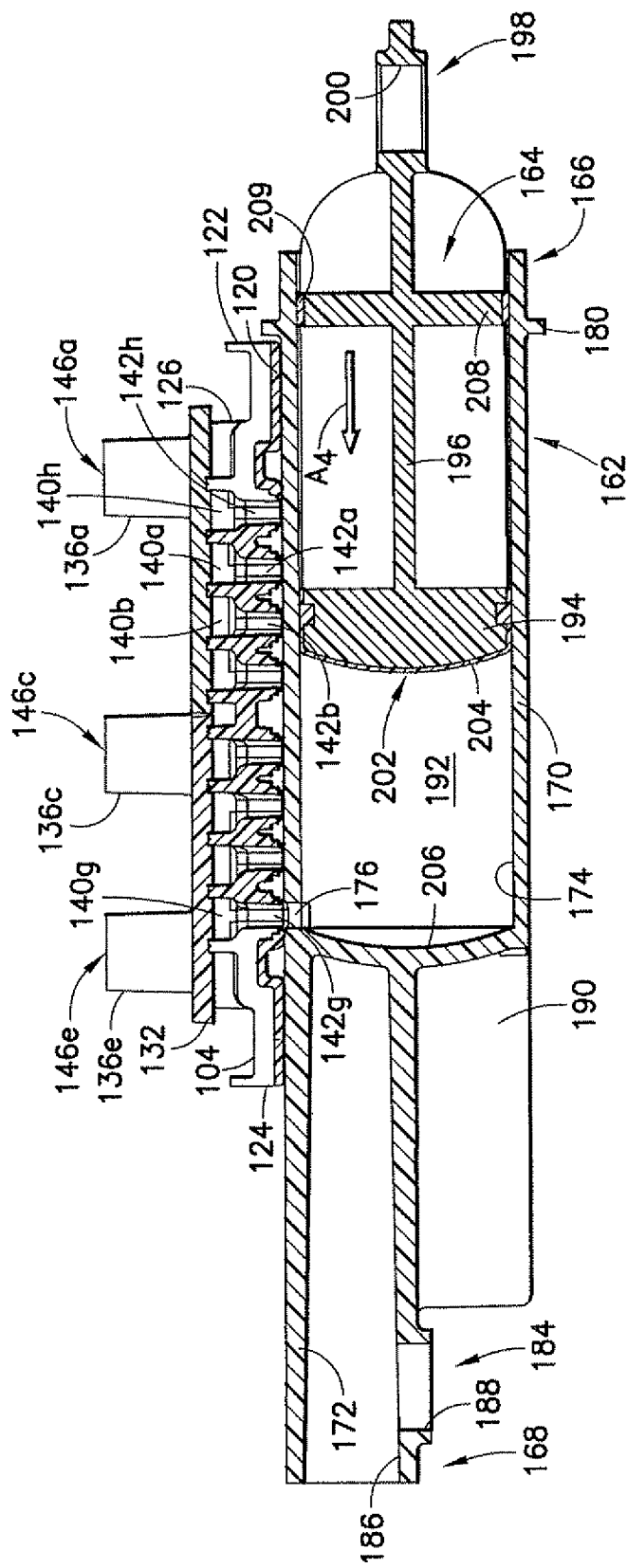
Figure 19:
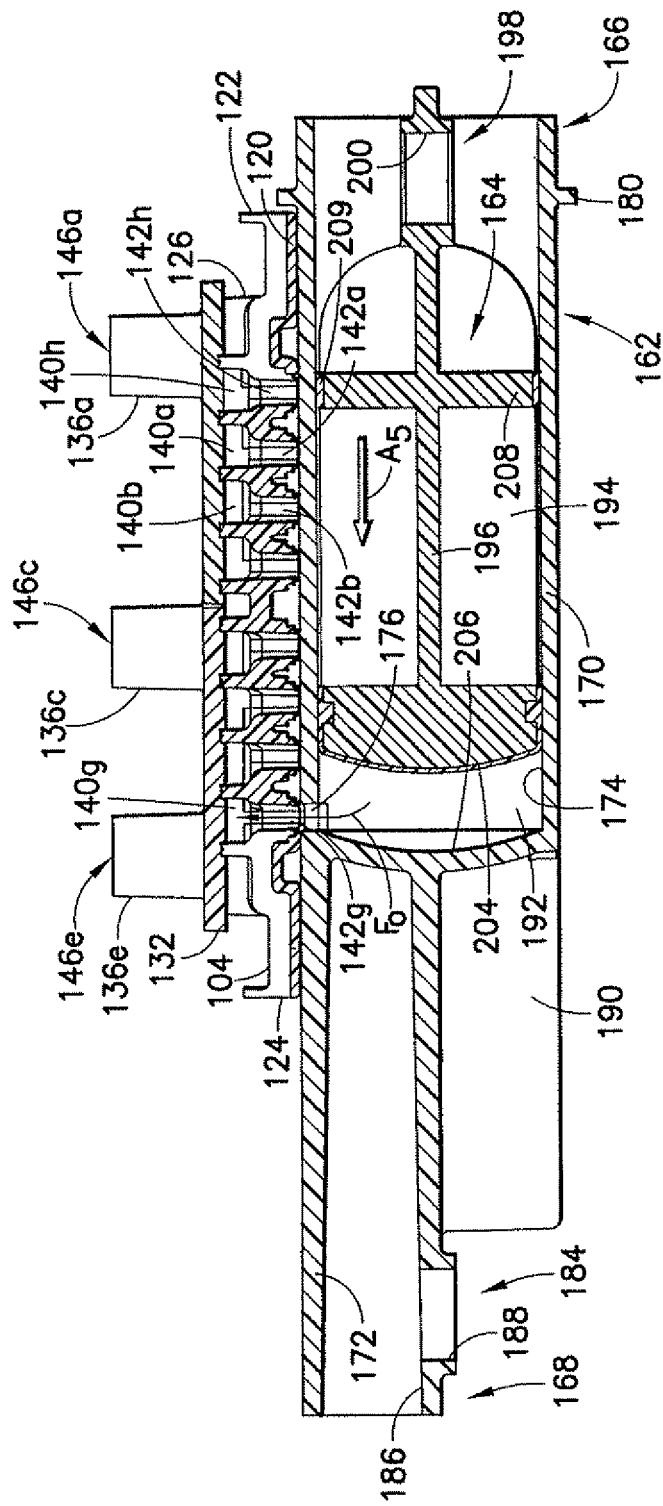
Figure 20:
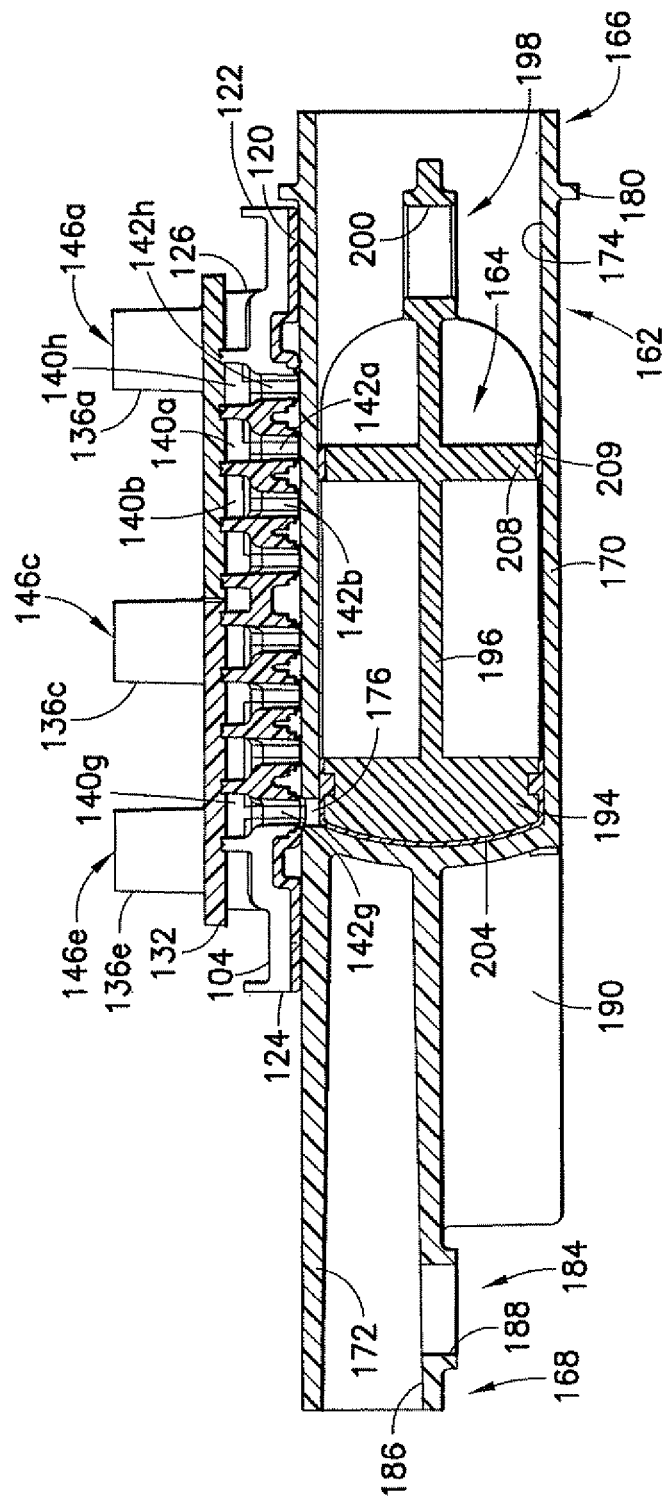
Figure 21:
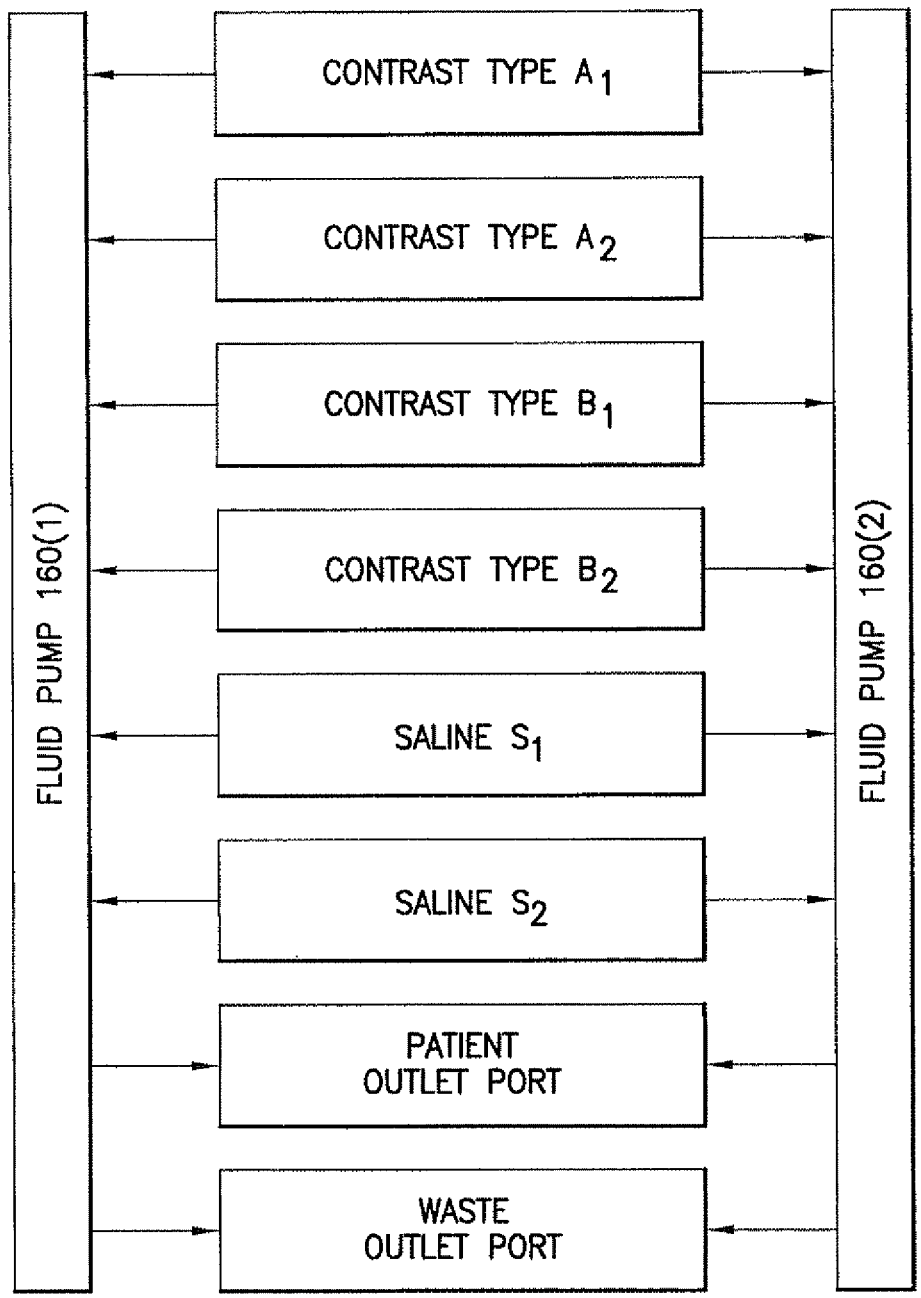
FIG. 21 is a functional block diagram illustrating how the fluid pumps in the fluid pumping device of FIG. 1A are able to independently draw fluid from any one of the bulk fluid sources fluid depicted in FIG. 1B.

If it is assumed that patient manifold outlet port 146*g* is selected, pistons 162, 164 move substantially in synch with one another to manifold opening 142*g* associated with manifold outlet port 146*g*, with sleeve piston 162 desirably stopping proximate to manifold opening 142*g*, thereby establishing an outlet fluid path from pumping chamber 192 to patient manifold outlet port 146*g*. In particular, at this location, sleeve port 176 in sleeve portion 170 of sleeve piston 162 substantially aligns with the selected "outlet" manifold opening 142*g*. As this alignment occurs, fluid communication is established between pumping chamber 192 and fluid passageway 140*g*. As described previously, fluid passageway 140*g* fluidly connects to fluid port 138*g*, and fluid port 138*g* and manifold connector port 136*g* together define patient manifold outlet port 146*g*. Desirably, a suitable fluid connection is made between patient manifold outlet port 146*g* and patient fluid path 12 leading to the patient. Once the foregoing fluid communication path is established, the piston positioning device 604 associated with sleeve piston 162 "fixes" the location of sleeve piston 162. As sleeve piston 162 is held substantially stationary, piston 164 may be moved by its associated piston positioned device 604 to begin a pumping or ejection stroke or movement. In the pumping or ejection stroke, as illustrated in FIGS. 18-19, piston 164 moves into sleeve piston 162 as represented by arrows $A_4$-$A_5$ in FIGS. 18-19 to pressurize the proportional mixture contained in pumping chamber 192 and expels this fluid, a mixture of contrast $A_1$ fluid and saline $S_1$ in the present example, through the patient fluid path 12 to deliver the fluid mixture under pressure to the patient. In FIG. 19 the expelling or ejection of fluid from pumping chamber 192 into sleeve port 176 in sleeve portion 170 of sleeve piston 162 and fluid passageway 140g is represented by arrow $F_o$. In FIG. 20, at the conclusion of the ejection stroke, the curved or arcuate distal end 202 of piston head 194 mates with the curved or arcuate-shaped end wall 206 in sleeve portion 170 of sleeve piston 162. As noted previously, it is desirable for the sealing rib 205 on piston head 194 to be located just proximal of sleeve port 176 such that there is desirably a slight clearance around the distal end 202 of piston head 194 to enable substantially all fluid to be ejected from pumping chamber 192 during the foregoing ejection or pumping stroke of insertion piston 164. As the ejection cycle is now complete, another fill cycle as described previously may begin again. FIG. 21 illustrates as a functional block diagram that each of the fluid pumps 160(1), 160(2) is able to independently draw fluid from any one of the six bulk fluid sources 14 described previously and eject fluid to either of the two manifold outlet ports 146g, 146h.

While the foregoing example describes how two fluids may be received and mixed in pumping chamber 192, this is only intended as a representative example of how fluid pumping device 100 may operate. As noted in the foregoing, additional fluids may be received into pumping chamber 192 by the method described hereinabove so that a multi-fluid mixture comprising at least three fluids may be present in pumping chamber 192. Moreover, it may be desirable only to load one type of fluid into pumping chamber 192. As an example, after the fluid mixture of contrast $A_1$ fluid and saline $S_1$ is injected into the patient according to the foregoing description, it may be desirable to clear the patient-connecting fluid path 12 of residual contrast media fluid. In such a circumstance, saline $S_1$ alone may loaded into pumping chamber 192 by "selecting" only manifold inlet port 146a according to the foregoing method and injecting this saline bolus into the patient fluid path 12 via patient manifold outlet port 146g.

Figure 22A:
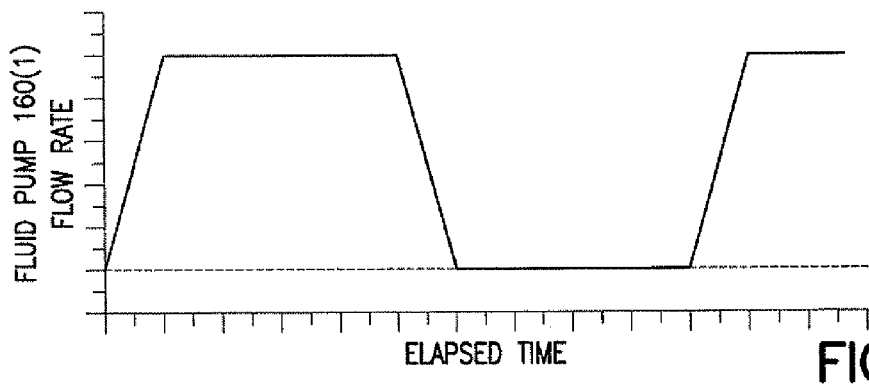
FIGS. 22A-22D graphically illustrate staggered operation of the fluid pumps in the fluid pumping device of FIG. 1A to deliver a continuous net fluid flow output.
Figure 22B:
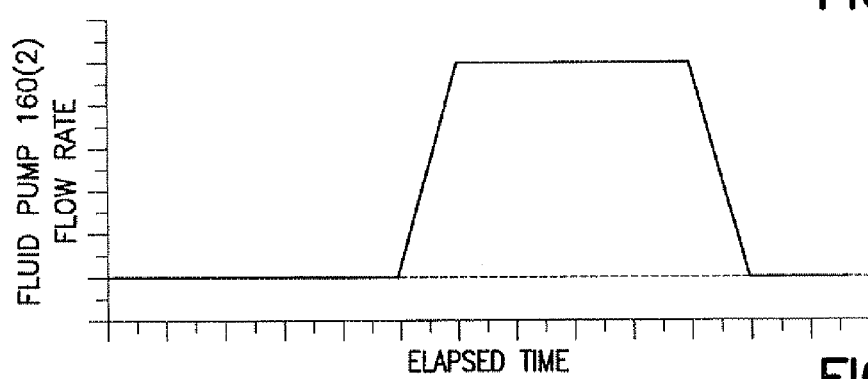
Figure 22C:
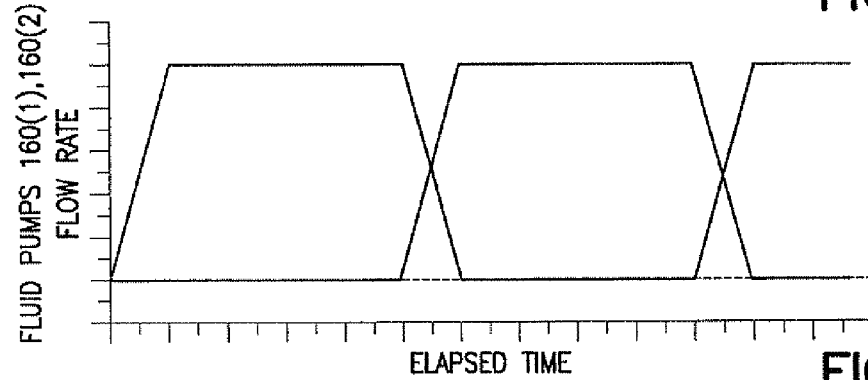

In actual practice, as illustrated in FIGS. 22A-22D, fluid pumping device 100 will typically operate so that the respective fluid pumps 160 have staggered operations. In other words, as one fluid pump 160, arbitrarily identified as fluid pump 160(2) in FIG. 22B, is in a fill cycle at an arbitrary point in time wherein its associated pistons 162, 164 are operating to load a selected fluid or fluids into pumping chamber 192 as described in the foregoing description, the other or "second" fluid pump 160, arbitrarily identified as fluid pump 160(1) in FIG. 22A, is in a staggered ejection cycle, wherein its associated pistons 162, 164 are associated with one of manifold outlet ports 146g, 146h and expelling fluid to a downstream end point, such as a patient undergoing a radiographic imaging procedure or a waste container. Such a staggered operation of fluid pumps 160 in fluid pumping device 100 results in generally constant fluid flow at the selected manifold outlet port 146g, 146b as shown by the overlaying of the cyclical operation of fluid pumps 160(1), 160(2) in FIG. 22C and the resulting continuous net fluid flow output result shown graphically in FIG. 22D.

Figure 22D:
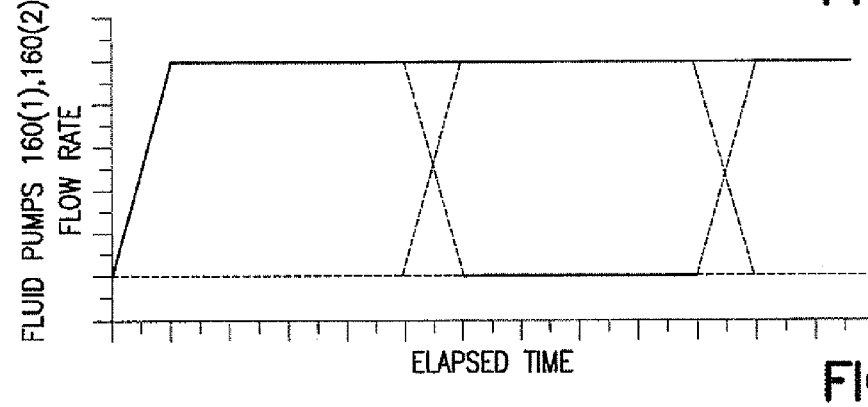
Figure 22E:
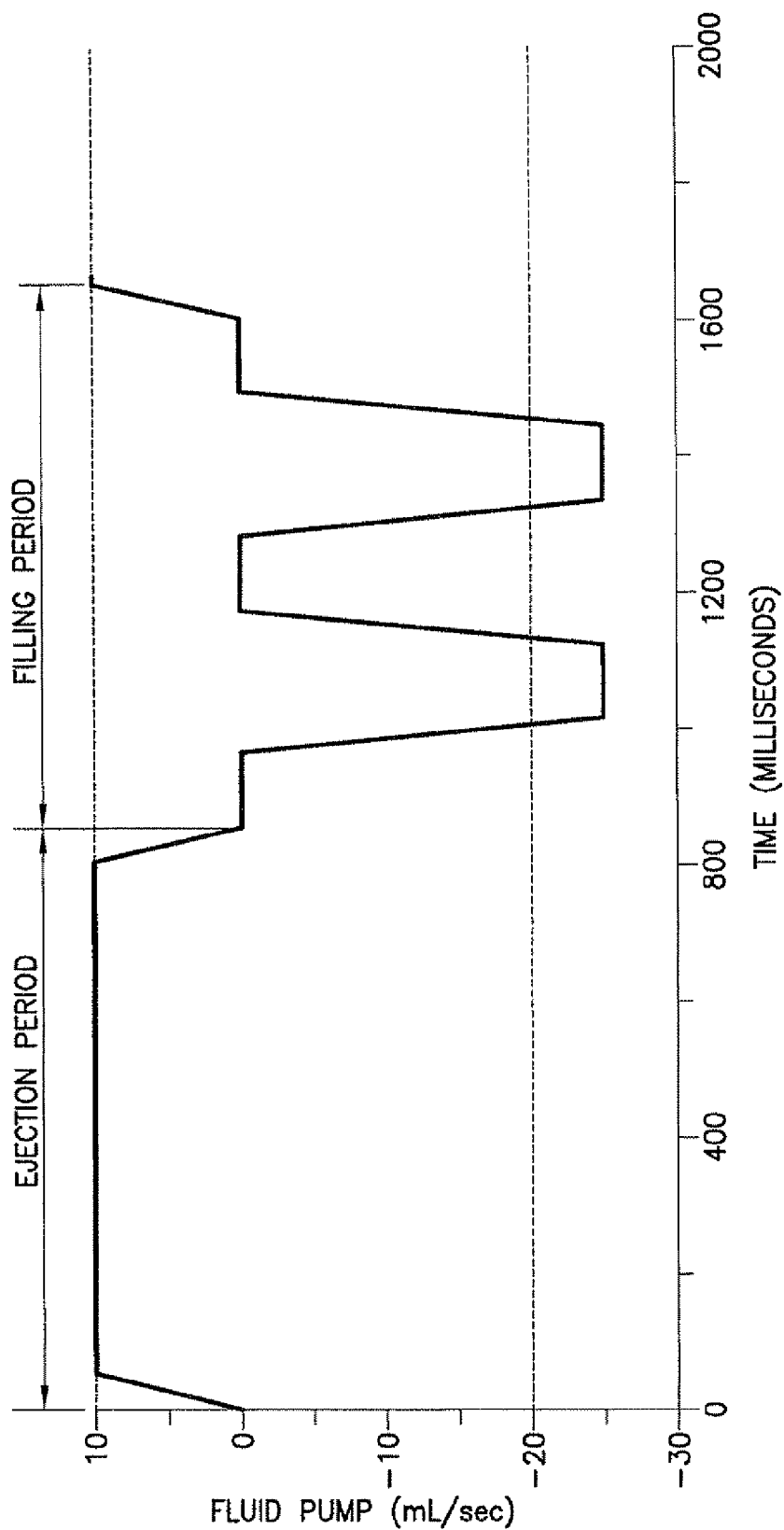
FIG. 22E graphically illustrates that a fill cycle for the fluid pumps occurs at a slightly faster rate than an ejection cycle for the fluid pumps in the fluid pumping device of FIG. 1A.

Accordingly, in summary, staggered operation of fluid pumps 160 allows fluid to be supplied continuously. While one fluid pump 160(2) is filling with fluid (FIG. 22B), the second fluid pump 160(1) is ejecting fluid (FIG. 22A). For example, in the staggered operation of fluid pumps 160, as the insertion piston 164 of fluid pump 160(1) reaches the end of its pumping or ejection stroke, the fluid pump actuator 602 associated with the fluid pump 160(1) smoothly reduces the linear speed of insertion piston 164, as illustrated in FIG. 22A to begin a fill cycle. Simultaneously, the fluid pump actuator 602 associated with fluid pump 160(2) accelerates the movement of insertion piston 164 associated with the fluid pump 160(2) to eject fluid from "filled" pumping chamber 192 of the second fluid pump 160(2). The insertion piston 164 of fluid pump 160(2) reaches its full "ejection" velocity at approximately the same moment that the insertion piston 164 in fluid pump 160(1) comes to a complete stop after ejection of fluid. Thus, the total flow rate delivered by both fluid pumps 160 together is substantially constant (FIG. 22D). In general, as shown in FIG. 22E, it is desirable for the fill cycle described in the foregoing description to occur at a slightly faster rate than the ejection cycle as this will allow sufficient time for the "filling" pistons 162, 164 to stop, reverse direction, and begin to accelerate before the "ejecting" pistons 162, 164 completely empty the pumping chamber 192 of the ejecting fluid pump 160. This slightly faster fill rate is needed because filling of the pumping chamber 192 and selection of a desired manifold port(s) 146 for one fluid pump 160, fluid pump 160(2) in the present example, must be completed while the staggered fluid pump 160, fluid pump 160(1), is ejecting fluid; therefore, the filling process must generally occur at a higher flow rate than the ejection process. The sequence described above provides a generally uniform, constant flow rate from fluid pumping device 100 without pulsatility (FIG. 22D).

From the foregoing, it will be appreciated that several distinct advantages are provided by fluid pumping device 100 over the prior art discussed previously. First, fluid pumping device 100 may deliver two or more types of fluid sequentially or as a mixture and it is possible to have one fluid delivery system 10 including fluid pumping device 100 with two fluid pumps 160 to deliver a large number of different types of fluid, again, either sequentially or as a mixture. Additionally, a controlled proportional mixture of two or more types of fluid may easily be delivered. The mixture may be a blend of two, three, or even four different fluids; the only limitation is the number of available manifold inlet ports 146. The proportion of each type of fluid may be controlled with substantial precision since the proportion is determined by the position of insertion piston 164 relative to sleeve piston 162 in each fluid pump 160. Moreover, since mixing occurs within each pumping chamber 192 of fluid pumps 160, the resulting mixture will be more homogenous than that delivered by a fluid delivery system in which mixing occurs in an outlet channel or means downstream of a pump as is conventional in art.

Further, it is also possible to pump fluid in both directions (i.e., reverse flow), if desired. This may be accomplished via suitable programming of the control device associated fluid pumping device 100 to allow sequencing of pistons 162, 164 through "reverse" operating steps in fluid pumps 160. This feature enables fluid pumping device 100 to flush and/or purge air from the respective fluid paths associated with each manifold port 146a-f described previously and patient fluid path 12 associated with patient manifold outlet port 146g, as well as waste manifold outlet port 146h if desired. Typically, saline is used as a flushing fluid and flushing and/or air purging may be accomplished at any time by drawing in saline from a saline fluid source such saline $S_1$, $S_2$ containers 16 depicted in FIG. 1B and pumping it through all other portions of fluid pumps 160 and, typically, the patient fluid path 12. To flush pumping chambers 192 and the patient fluid path 12 associated with patient manifold outlet port 146g, saline is pumped "forwardly" according to the principles outlined previously. To flush the contrast supply manifold inlet ports 146, saline is drawn from, for example, from one of saline $S_2$, $S_2$ containers 16 shown in FIG. 1B and then pumped "backwards" through the various contrast supply manifold inlet ports 146. The ability to operate fluid pumping device 100 in "reverse" also allows for automated patency checks to be performed, wherein a small amount of fluid may be drawn from patient manifold outlet port 146g into pumping chamber 192 (temporarily) and then ejected back into the patient manifold outlet port 146g to confirm proper installation of a catheter. It is noted that blood drawn from the patient does not enter pumping chamber 192 during this process but is only drawn into patient fluid path 12 to confirm patency and a check valve in the fluid passageway 140 associated with patient manifold outlet port 146g may be provided to prevent any such entrance into pumping chamber 192.

In operation, fluid pumping device 100 provides a smooth, generally uniform flow of fluid because each piston 162, 164 in fluid pumps 160 is independently controlled. By also synchronizing the motion of two fluid pumps 160 such that one fluid pump 160 is in a fill cycle while the other is in an ejection cycle, it is possible to deliver substantially non-pulsatile flow on a continuous basis with only two fluid pumps 160. As noted previously, the magnitude of deceleration of the insertion piston 164 in one fluid pump 160 ordinarily substantially matches the acceleration magnitude of the insertion piston 164 in the second fluid pump 160 to provide a seamless delivery of fluid at the selected manifold outlet port 146g, 146h. The ability to deliver fluids at a generally constant, uniform controlled flow rate may be effected regardless of outlet pressure because an actively-controlled manifold port system is provided. As a result, volumetric efficiency of fluid pumping device 100 does not vary as a function of outlet pressure and/or flow rate.

Moreover, because fluid pumping device 100 comprises an actively controlled manifold port system, the dimensions of manifold ports 146, connecting passageways 140, and manifold openings 142 may be optimized to minimize pressure losses and may be of virtually any shape or dimension. As a result, dimensions of the fluid paths formed by manifold ports 146, connecting passageways 140, and manifold openings 142 may be sized to minimize pressure drops and maximize the overall performance of the respective fluid pumps 160 and, further, minimize the potential for pump cavitation due to inlet port restrictions.

Another feature described previously is the provision of only a single access opening or port 176 to pumping chamber 192. This configuration has the benefit of isolating almost all of the manifold openings 142 in base member 104 from the effects of high pressures; only the manifold outlet ports 146g, 146h are subjected to the high pressures of the fluid ejection cycle. An accompanying benefit of the foregoing configuration is minimizing the potential for reverse flow due to leakage from high-pressure manifold outlet ports 146g, 146h to low-pressure manifold inlet ports 146a-f.

Furthermore, another advantage of fluid pumping device 100 and fluid delivery system 10 incorporating the same is the ability to discard or dispose of fluid pumping device 100 after a single use or a discrete number of uses. As a result, fluid pumping device 100 may be made from relatively inexpensive materials and by well-known processes so as to be disposable while a "permanent" drive system 600 is reused. As is evident from FIG. 13 described previously, the connections between fluid pumping device 100 and drive system 600 may be relatively simple connections, if desired, thereby minimizing the number and complexity of interfaces between "disposable" components and "permanent" components.

As generally described in connection with FIG. 13, drive system 600 provides motive forces used to operate movable components of fluid pumping device 100. As noted previously, a desirable feature of fluid pumping device 100 is to provide the fluid pumping device 100 as a disposable component, for example, as a disposable cartridge, cassette, or unit, which may be associated with a reusable drive system 600 for one use or a discrete number of uses and then disposed of. Moreover, as described previously, drive system 600 generally comprises two essentially identical fluid pump actuators 602, one for each fluid pump 160. Each fluid pump actuator 602 comprises two essentially identical piston positioning or movement devices 604, a total of four such devices 604. Each piston positioning or movement device 604 includes a piston positioning or movement member 606 adapted to engage pistons 162, 164. As will be apparent from FIG. 23, for each fluid pump actuator 602, one piston positioning device 604 is located to interface with insertion piston 164 while the second piston positioning device 604 is located at the opposite end of pump compartment 24 to interface with sleeve piston 162. As noted previously, pistons 162, 164 have respective piston drive interface portions 184, 198 with respective interface apertures 188, 200. Interface apertures 188, 200 are desirably identical so that four identical devices 604 may be used to operate the four pistons 162, 164 associated with the two fluid pumps 160 in the embodiment described hereinabove. Accordingly, fluid pump actuators 602 each comprise a piston positioning devices 604 associated with sleeve piston 162 and a second piston positioning devices 604 associated with insertion piston 164 in each fluid pump 160. A further aspect of fluid pump actuators 602 is that the individual piston positioning devices 604 may be individually controlled to effect individualized motion, movement, or positioning of pistons 162, 164 in the respective fluid pumps 160. In other words, fluid pump actuators 602 each have two independent, desirably linear, axes of motion, wherein one piston positioning device 604 moves piston 164 axially in sleeve portion 170 of sleeve piston 162 while the other piston positioning device 604 moves the sleeve piston 162 relative to base member 104 during operation of fluid pumps 160.

Piston positioning devices 604 could be provided in several different forms to effect movement, typically linear movement, of pistons 162, 164 in each fluid pumps 160, specific examples of which were detailed previously. Furthermore, as noted previously, it is also possible for pistons 162, 164 in each fluid pump 160 to share a single or common piston positioning device 604 which would form the fluid pump actuator 602. No matter what format is used for the respective piston positioning or movement devices 604 in fluid pump actuators 602, a desirable feature is that the position, velocity, and acceleration of each piston positioning or movement device 604 may be controlled independently, for example, by a control device interfaced with the respective piston positioning devices 604. Such a control device, as noted previously, may be a controller or computer with an algorithm which can operate the individual piston positioning devices 604 associated with each fluid pump actuators 602. Such a control device may receive inputs from piston positioning devices 604 relating to the position of the piston positioning member 606 associated with each piston positioning device 604 and this information used to effect movement of pistons 162, 164 in each fluid pump 160.

Figure 23:
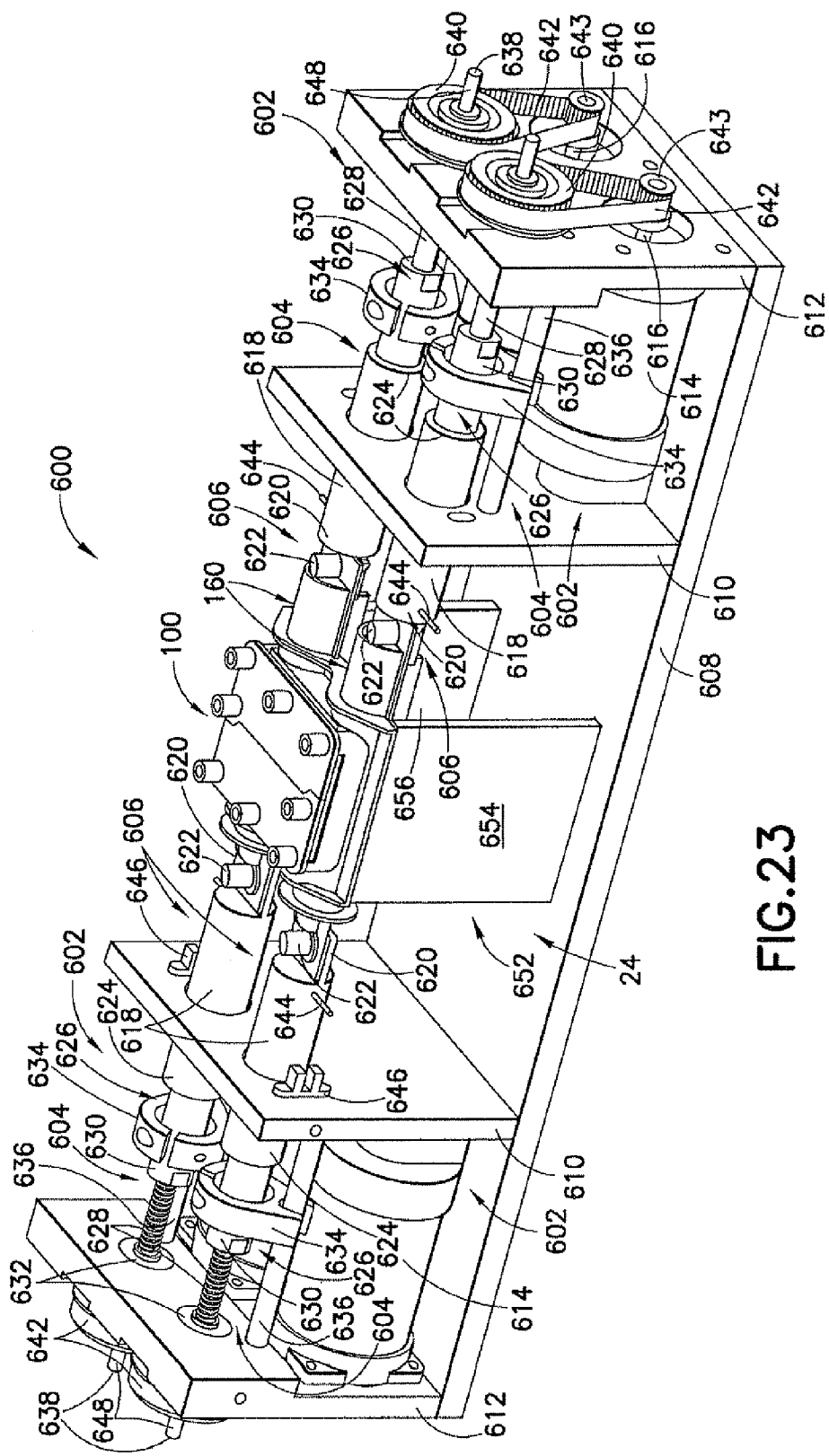
FIG. 23 is a perspective view of a fluid delivery system comprising the fluid pumping device of FIG. 1A and an embodiment of a drive system for operating the fluid pumping device.
Figure 24:
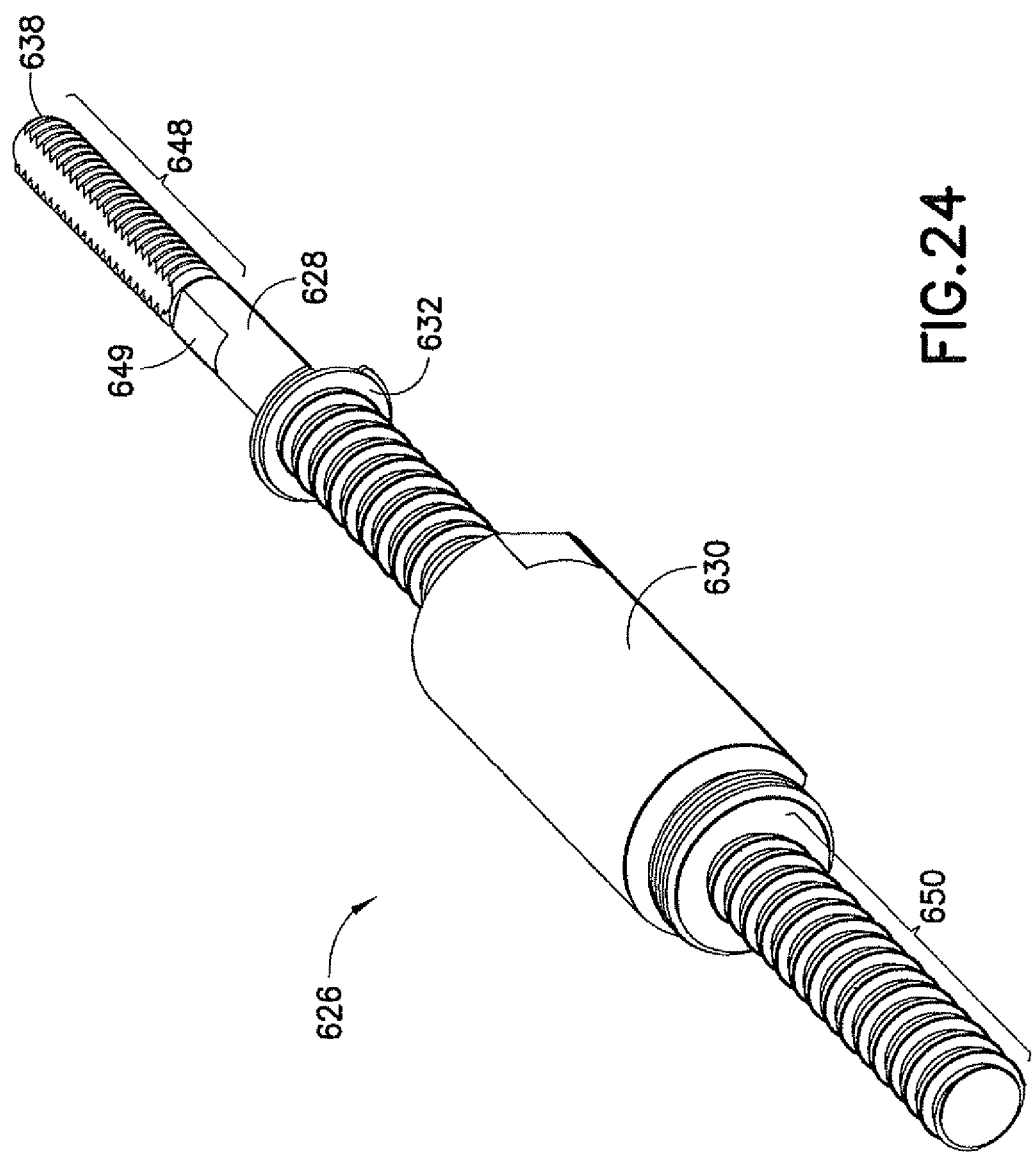
FIG. 24 is a perspective view of a linkage device provided in the drive system shown in FIG. 23.

Referring now to FIGS. 23-24, drive system 600 will now be described in further detail. As noted in the foregoing, each piston positioning device 604 in each of the two fluid pump actuators 602 is substantially identical. Accordingly, the following discussion describes the components comprising one of the piston positioning devices 604 for expediency in explaining each of the four piston positioning devices 604 and their operation. For background purposes, it is noted that pump enclosure or compartment 24, discussed previously, may comprise a support base 608 and two pairs of opposed support walls 610 at opposed ends of the pump compartment 24 between which fluid pumping device 100 is disposed and two outside walls 612 are provided for enclosing the various components comprising drive system 600 between two respective sets of opposed support walls 610, 612. Each piston positioning device 604 comprises a drive motor 614 supported, for example, between the opposed support walls 610, 612 and comprises a drive shaft 616 extending through rear or proximal support wall 612 to provide motive forces to the piston positioning device 604. As noted previously, each piston positioning device 604 comprises a piston positioning member 606 for interfacing with pistons 162, 164. In the illustrated embodiment, piston positioning member 606 comprises a piston drive element 618 which terminates at a distal end 620 in a simple peg 622 for engaging with the interface apertures 188, 200 defined in pistons 162, 164. Such a simple "pegged" interface for associating piston positioning member 604 with pistons 162, 164 is merely exemplary and numerous alternative removable interface configurations may be substituted such as a fixed, or "hard" interface connection provided by removable mechanical fasteners, and other like removable interface connections.

Piston drive element 618 is desirably hollow and is open at its proximal end 624 to interface with a linkage device 626 which is used to transfer the motive forces provided by drive motor 614 and drive shaft 616 to piston positioning member 606 generally and piston drive element 618 in particular. Linkage device 626 may take many known mechanical forms for converting the rotational drive output of drive motor 614 and drive shaft 616 to translational movement of piston positioning member 606 so that pistons 162, 164 may exhibit the linear movement described previously in this disclosure which, as should be clear from the foregoing discussion, is intended to be bi-directional linear movement. Linkage device 626 in the illustrated exemplary embodiment comprises a ball screw shaft 628 rotationally journaled in a ball screw nut 630, namely, by threaded engagement as is known in the mechanical arts. Ball screw nut 630 is connected to the proximal end 624 of piston drive element 618 of piston positioning member 606. As an example, ball screw nut 630 may be fixed internally in the open proximal end 624 of piston drive element 618, for example, by a threaded engagement. Ball screw shaft 628 extends through an opening in proximal or rear supporting wall 612. A thrust washer 632 (and bearing located behind the thrust washer 632) may be disposed in the opening in proximal or rear supporting wall 612 to support rotational movement of ball screw shaft 628 in the opening. An anti-rotation collar 634 is connected to ball screw nut 630 and, further, is connected to a fixed guide rail 636 extending between supports walls 610, 612 to prevent rotation of the ball screw nut 630 when ball screw shaft 628 is rotating. It is noted that four such fixed guide rails 636 are provided to enable operation of each of the four piston positioning devices 604. As illustrated, anti-rotation collar 634 is connected to guide rail 636 so as to slide along guide rail 636 such that ball screw nut 630 translates linearly under the threaded connection with ball screw shaft 628 when the ball screw shaft 628 is rotating. A proximal end 638 of ball screw shaft 628 extends through the opening in proximal support wall 612 for interfacing with drive motor 614 and drive shaft 616. In particular, a pulley 640 is mounted to ball screw shaft 628 and a timing belt 642 is reeved about pulley 640 and a second pulley 643 mounted to the end of drive shaft 616 and is used to rotationally interface the drive shaft 616 and the ball screw shaft 628. The pulley 640 and timing belt 642 permit rotational movement of drive shaft 616 to be imparted to ball screw shaft 628 as will apparent to those skilled in the mechanical arts. A sensor pin 644 desirably extends laterally outward from piston drive element 618 of piston positioning member 606 in each piston positioning device 604, which is positioned to engage a home sensor 646 provided on the pump-facing side or front side of distal support wall 610 to provide an indication of a "zero" or "home" position of pistons 162, 164 in each fluid pumping device 160. Accordingly, four such home sensors 646 are present in connection with drive system 600.

In operation, to effect movement of piston positioning member 606, motor drive shaft 616 is driven by drive motor 614 and this rotational movement is imparted to the pulley 640 mounted to ball screw shaft 628 via timing belt 642. As ball screw shaft 628 rotates, ball screw nut 630 translates (forward or backward) along the ball screw shaft 628 due to their threaded engagement. Ball screw nut 630 is prevented from rotating by the engagement of anti-rotation collar 634 with guide rail 636. As described previously, ball screw nut 630 is connected to piston drive element 618 of piston positioning member 606, for example, by a threaded connection. As ball screw nut 630 translates, piston drive element 618 and, hence, piston positioning member 606 generally, moves with the ball screw nut 630. By this translational movement of ball screw nut 630 on ball screw shaft 628, bi-directional linear movement of pistons 162, 164 may be effected. As noted previously, each of the two pump actuators 602 comprises a pair of piston positioning devices 604, one to interface with sleeve piston 162 and one to interface with insertion piston 164 for each of the two fluid pumps 160. In the previous discussion regarding the filling and ejecting cycles for the two fluid pumps 160 in fluid pumping device 100, it was noted that while one of the fluid pumps 160 is filling with fluid, the other will be ejecting fluid into patient fluid path 12 for delivery to a patient (and vice versa). In general, as noted in the foregoing, it is desirable for the fill cycle to occur at a slightly faster rate than the ejection cycle. This slightly faster rate allows sufficient time for the "filling" pistons 162, 164 to stop, reverse direction, and begin to accelerate before the "ejecting" pistons 162, 164 completely empty the associated pumping chamber 192 for the ejecting fluid pump 160. Drive system 600 allows each of the four piston positioning devices 604 to be independently controlled by a control device to effect such operation as described previously.

A basic operating sequence for the adjacent fluid pumps 160 will now be discussed. In operation, the pump actuator 602 associated with one of the fluid pumps 160 is controlled by the control device so that the drive motors 614 associated with the opposed piston positioning devices 604 are driven substantially synchronously (at the same speed) to move pistons 162, 164 associated with that fluid pump 160 substantially in unison. Since there is substantially no relative motion between pistons 162, 164, fluid will not be pulled into pumping chamber 192 as they move together. The pistons 162, 164 are moved until sleeve opening or port 176 in the sleeve portion 170 of sleeve piston 162 is aligned with a desired manifold inlet port 146. The position of sleeve piston 162 is held constant by its associated piston positioning device 604 while insertion piston 164 is retracted by its associated piston positioning device 604 by actuation of the drive motor 614 associated with this piston positioning device 604 in the opposite direction. This action causes pumping chamber 192 to fill with fluid from the selected manifold inlet port 146. If desired, pistons 162, 164 may be moved together to an additional manifold inlet port 146, again substantially in unison by substantially synchronous operation of the drive motors 614, so that fluid will not be pulled into pumping chamber 192 as they move together. Upon reaching the next manifold inlet port 146, only insertion piston 164 is moved by its associated piston positioning device 604 by reverse operation drive motor 614 to draw in fluid from the next source. The pistons 162, 164 are then moved substantially synchronously, again by substantially synchronous (at the same speed) operation of the drive motors 614 associated with the respective piston positioning devices 604 to a selected manifold outlet port 146. Again, since there is no relative motion between pistons 162, 164 during this translational movement, fluid will not be expelled from pumping chamber 192. Once sleeve port 176 in sleeve piston 162 is aligned with the selected manifold outlet port 146, movement of sleeve piston 162 is stopped by, for example, the associated control device stopping operation of the drive motor 614 associated with the piston positioning device 604 operating sleeve piston 162. The opposed insertion piston 164 is then moved into sleeve piston 162 to eject fluid through sleeve port 176 in sleeve portion 170 of sleeve piston 162 and out through the selected manifold outlet port 146. This movement is effected, for example, by operation of the drive motor 614 associated with piston positioning device 604 operating the insertion piston 164. It will be apparent that the adjacent or second fluid pump 160 operates in an identical manner but out of phase or "staggered" from the operation of the first fluid pump 160 so that substantially constant flow is provided by fluid pumping device 100 generally, as described previously.

For the associated control device to accurately control the staggered operation of fluid pumps 160, in an initial or start-up mode both pistons 162, 164 are actuated to move together until the sensor pin 644 associated with the piston positioning device 604 operating sleeve piston 162 engages and actuates its associated home sensor 646. The home sensor 646 may use, for example, an infrared LED and photosensor to detect the presence of sensor pin 644 mounted to the piston drive element 618 of the piston positioning member 606 of the piston positioning device 604. With sleeve piston 162 then held stationary, the opposing piston 164 is moved by its associated piston positioning device 604 until its home sensor 646 is actuated in the same manner. From this point on, the computer-based control device keeps track of the positions of pistons 162, 164 so the "zero" or "home" positions of both pistons 162, 164 are now known. As shown in FIG. 24, a proximal portion 648 of ball screw shaft 628 may have a smaller diameter than a distal portion 650 thereof which is in threaded engagement with ball screw nut 630. Proximal portion 648 defines an attachment location 649 for mounting pulley 640 to ball screw shaft 628 so rotation of the pulley 640 and timing belt 642 combination results in rotation of the ball screw shaft 628 and, thereby, translational movement of the ball screw nut 630 for a given rotation of the ball screw shaft 628. A further feature associated with drive system 600 comprises a pump support structure 652 for supporting fluid pumping device 100 from below during operation of the fluid pumps 160. As illustrated, such a pump support structure 652 may simply comprise a pair of support walls 654, 656 supporting the lateral sides 112 of base member 104 of pump housing 102 of fluid pumping device 100, but other fluid pump support arrangements or device may be provided such as that described herein in connection with FIGS. 28-35. While not shown in FIG. 23, pump compartment 24 may comprise a cover plate (not shown, but a suitable cover plate is described herein in connection with an alternative drive system 700 described herein) to enclose fluid pumping device 100 and, possibly, the components of drive system 600 in the pump compartment 24. Such a cover plate may optionally contact the top of manifold cap 132 to apply pressure to fluid seal elements 120 for assisting in fluidly sealing each fluid pump 160 in its receiving cavity 106 in base member 104 of pump housing 102.

Figure 25:
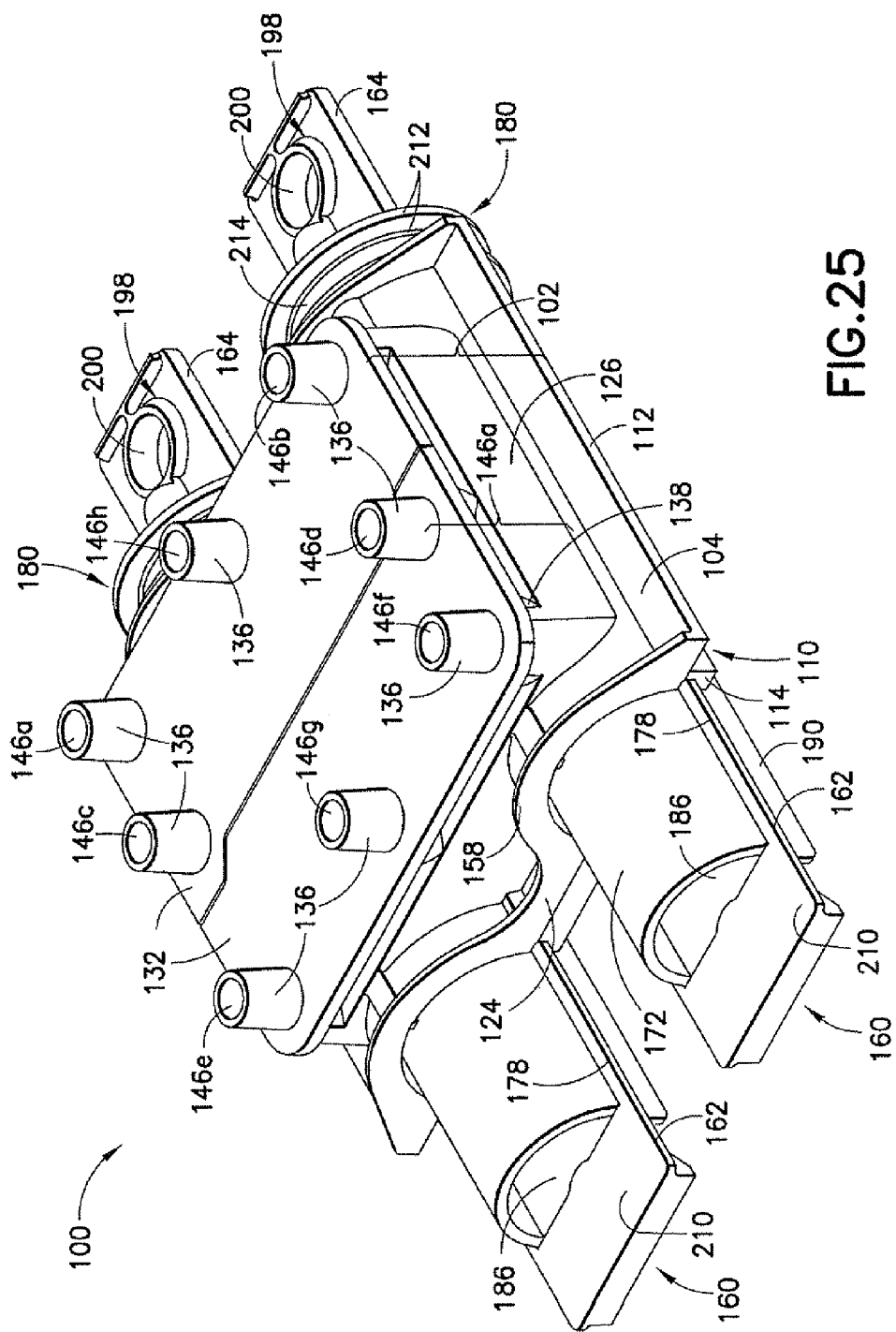
FIG. 25 is a top perspective view of another embodiment of the fluid pumping device of FIG. 1A.
Figure 26:
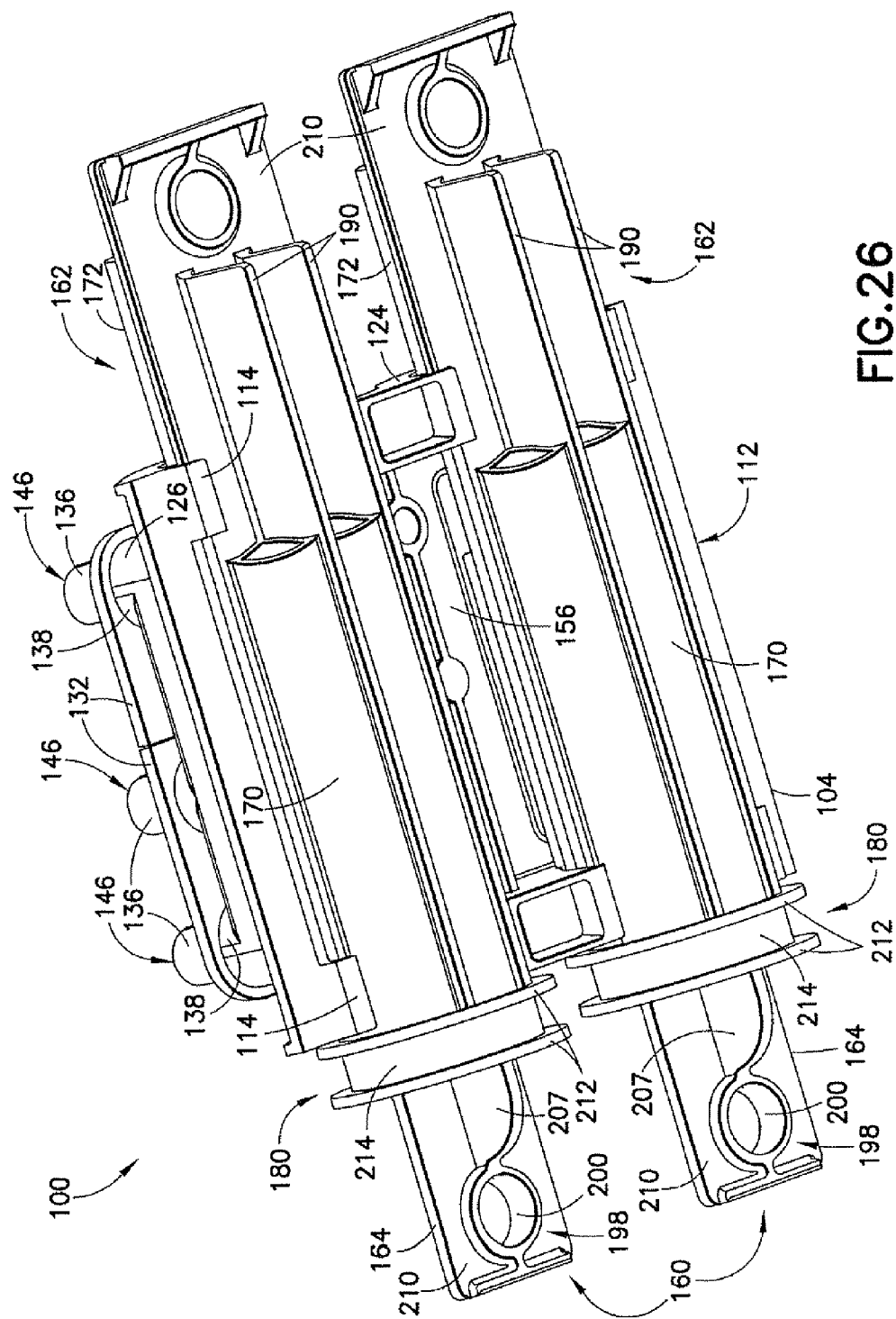
FIG. 26 is a bottom perspective view the embodiment of the fluid pumping device shown in FIG. 25.
Figure 27:
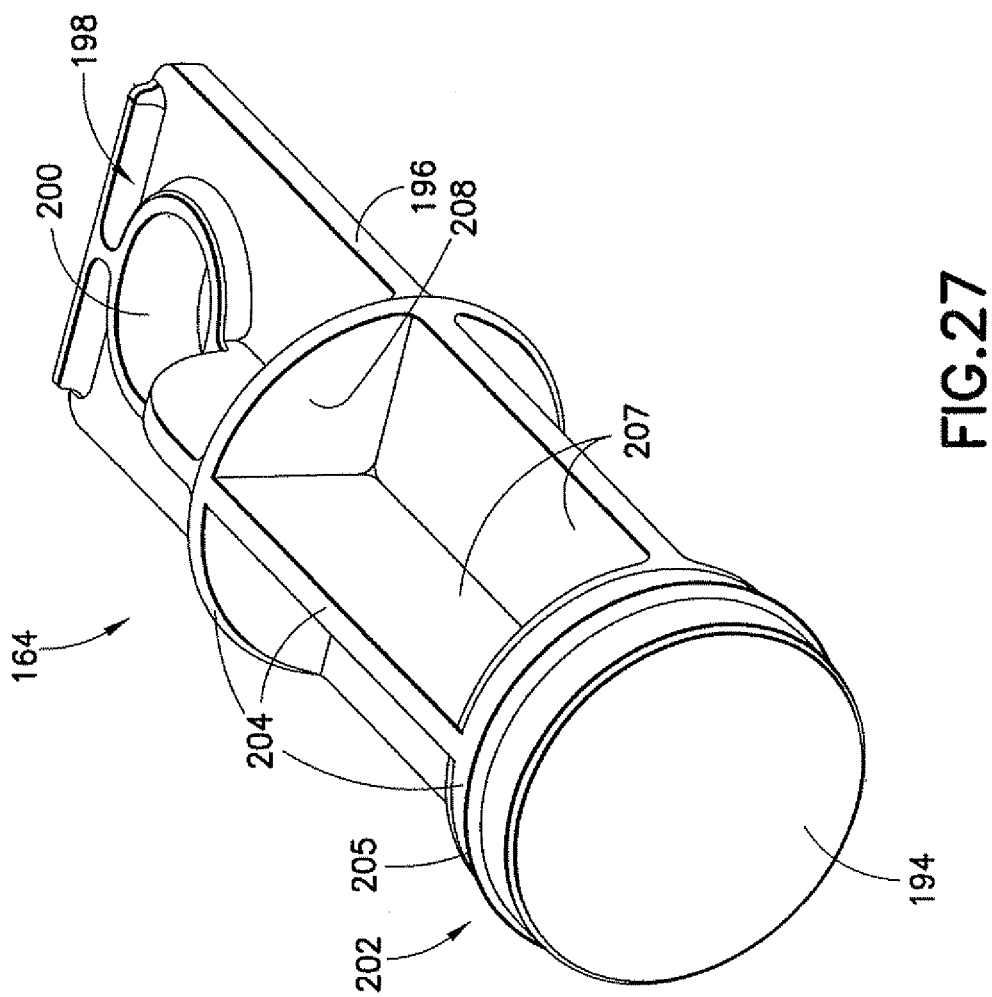
FIG. 27 is a perspective of an insertion piston used in fluid pumps in the embodiment of the fluid pumping device shown in FIG. 25.

Referring to FIGS. 25-27, another embodiment of fluid pumping device 100 is shown and wherein like parts are designated with like reference numerals used in the description of the foregoing embodiment. Fluid pumping device 100 has the same basic components as described previously with a modification as to how pistons 162, 164 are driven. In the present embodiment of fluid pumping device 100, the fluid pumping device 100 is adapted such that pistons 162, 164 for each fluid pump 160 may be driven from the same side of the fluid pumping device 100. In particular, pistons 162, 164 for each fluid pump 160 are now adapted to be driven from the same end 122 of base member 104 forming pump housing 102 of fluid pumping device 100 by an appropriately modified drive system 700, described herein in connection with FIGS. 28-35. Drive system 700 described herein comprises several features in common with drive system 600 discussed hereinabove. As to specific differences over the previously discussed embodiment of fluid pumping device 100, in the present embodiment interface portion 172 of sleeve piston 162 no longer requires an interface or attachment aperture 188 for interfacing with a piston positioning member 606 associated with the piston positioning devices 604 in the drive system 600 discussed previously. In the present embodiment, interface portion 172 may terminate in a generally planar end flange portion 210. Interface portion 172 still desirably defines an open or hollow cross-sectional shape with an interior space 186 of, for example, generally semi-circular transverse cross-section. Additionally, interface portion 172 still comprises one or more depending flanges 190 that depend or extend downward from interface portion 172 and enhance the structural strength of interface portion 172. As shown in FIG. 26, flanges 190 may extend nearly the length of sleeve piston 162.

In contrast to that discussed previously, sleeve piston 162 in the present embodiment is provided with a dual or double rim end flange 180 which is likewise formed as part of sleeve portion 170. End flange 180 comprises two spaced apart rim flange elements 212 which define an intervening space 214 for interfacing with piston attachment or interfacing elements (discussed herein) associated with drive system 700 and specifically suited to operation of fluid pumping device 100 according to the present embodiment. A distal or "interior" one of the two spaced rim flange elements 212 still forms an interfering structure at first end 166 of sleeve piston 162 to engage radial end flange 158 at end 122 of base member 104 to limit linear travel of the sleeve piston 162 relative to base member 104, as described previously in this disclosure.

FIG. 27 illustrates insertion piston 164 which operates with sleeve piston 162 in the manner described previously. Insertion piston 164 is generally similar in overall appearance and function to that described previously. However, as is apparent in FIG. 27, a single polymeric layer 204 may be provided to cover piston head 194 and, further, be provided on proximal disc element 208 and on flange elements 207 defining the generally X-shaped cross-sectional shape of piston rod 196. Polymeric layer 204 is desirably a single or unitary layer which may be overmolded onto piston head 194 and, further, overmolded onto the circumferential edge of proximal disc element 208 (taking the place of polymeric layer 209) and the outward edges of the individual flange elements 207 forming piston rod 196. The presence of such a polymeric layer 204, as described previously, desirably forms a generally fluid tight seal between piston head 194 and the inner wall of sleeve portion 170 of sleeve piston 162, thereby substantially assuring that pumping chamber 192 is a generally fluid tight chamber during a static, non-moving situation of pistons 162, 164 or during dynamic, operational movement of pistons 162, 164. Desirably, polymeric layer 204 is a unitary layer and may be formed of any of the materials detailed previously in connection with fluid seal elements 120 and is desirably an overmolded layer of polyurethane and the like. It is noted that piston rod 196 comprises the same drive interface portion 198 as described previously comprising a defined interface aperture 200 in the body of piston rod 196.

Referring now to FIGS. 28-35, an alternative drive system 700 which is adapted to operate the alternative fluid pumping device 100 described in the immediate foregoing disclosure is shown and will now be discussed. In drive system 700, pistons 162, 164 for each fluid pump 160 are driven by a dedicated fluid pump actuator 702 in much the same as described previously in connection with drive system 600. However, the fluid pump actuators 702 are each now located adjacent to one end 122 of base member 104 of pump housing 102 of fluid pump apparatus 100. Accordingly, in the present drive system 700, the two piston positioning devices 704 in each of the two fluid pump actuators 702 are combined into one operational device and are operable to move pistons 162, 164 in each fluid pump 160 from the same end of the pistons 162, 164. In view of the foregoing, the following discussion describes the components comprising one of the fluid pump actuators 702 used to operate one of the fluid pumps 160 and it will be apparent that the adjacent fluid pump actuator 702 operating the adjacent fluid pump 160 is of similar construction and operation to that described herein. It is generally noted that pump enclosure or compartment 24 in this embodiment comprises a support base 708 and two pairs of opposed support walls 710, 712 between which fluid pumping device 100 is located. Proximal wall 712 separates the various components of drive system 700 from the pump compartment 24.

As noted, each fluid pump actuator 702 in drive system 700 again utilizes two piston positioning devices 704, designated 704(1) and 704(2) hereinafter for convenience. As described herein, piston positioning devices 704(1) and 704(2) are concurrently supported on a movable support device. One of such piston positioning devices 704(1) is substantially identical to the piston positioning devices 604 described hereinabove in connection with drive system 600. This piston positioning device 704(1) is adapted in a similar manner to piston positioning device 604 to interface with insertion piston 164. Piston positioning device 704(1) comprises a drive motor 714 having a motor housing 715 and a drive shaft 716 to provide motive forces to the piston positioning device 704(1). Piston positioning device 704(1) comprises a piston positioning member 706 for interfacing with insertion piston 164. Piston positioning member 706 comprises a piston drive element 718 which terminates at a distal end 720 in a simple peg 722 for engaging with interface aperture 200 in drive interface portion 198 of piston rod 196 of piston 164. Such a simple "pegged" interface for associating piston positioning member 706 with piston 164 is again merely exemplary and numerous removable interface configurations may be substituted as indicated previously.

Figure 32:
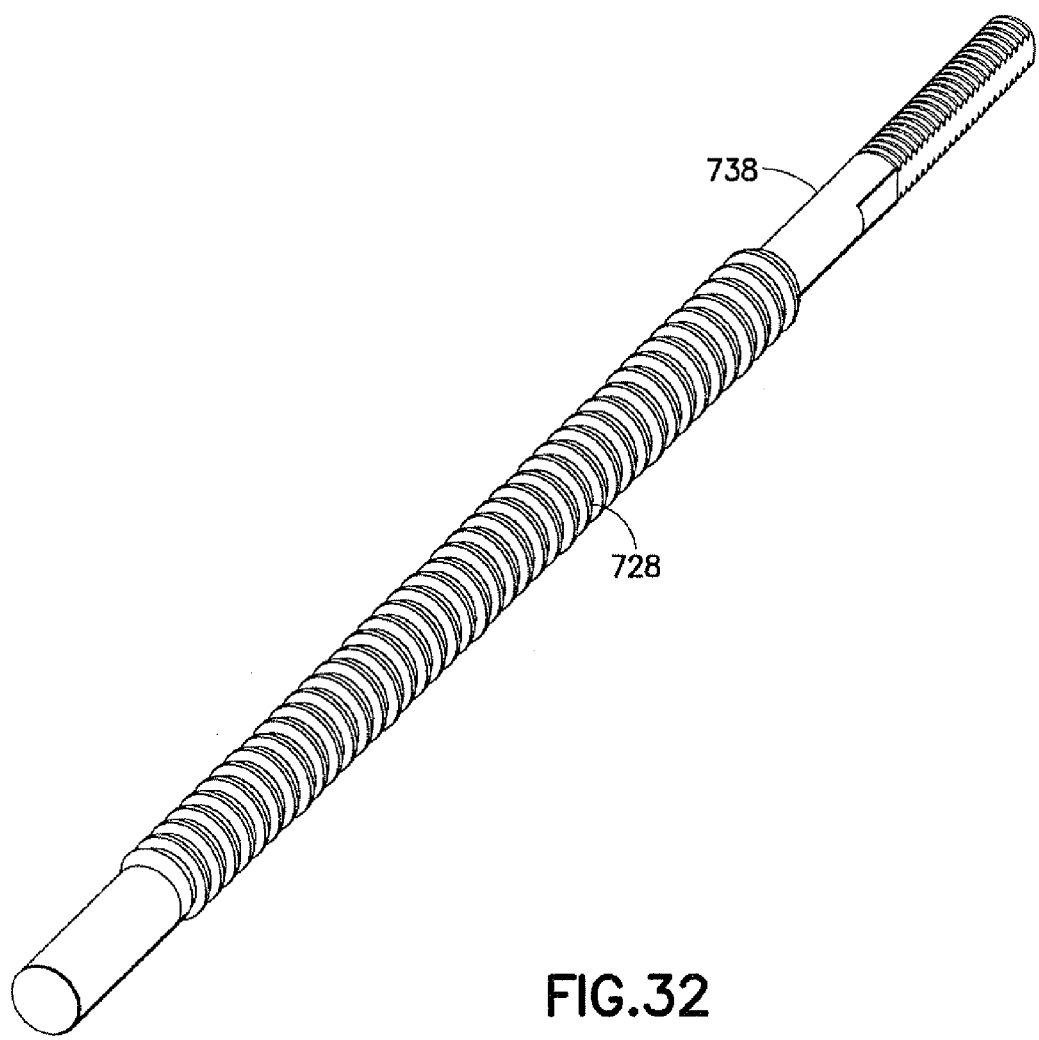
FIG. 32 is a ball screw shaft of the piston positioning device shown in FIG. 31.
Figure 33:
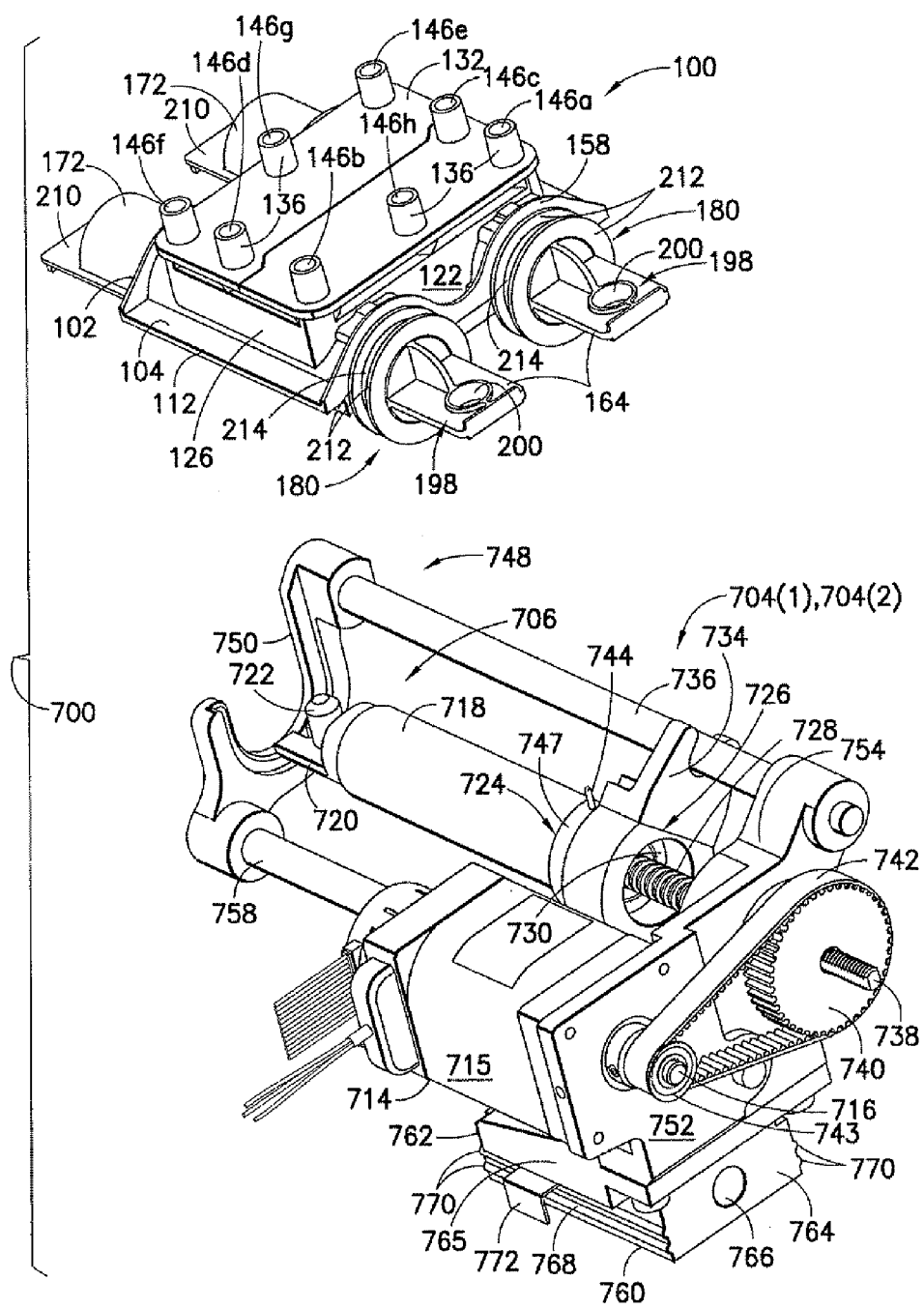
FIG. 33 is a perspective view illustrating the interfacing of the fluid pumping device of FIGS. 25-26 with the piston positioning device of FIG. 31.
Figure 34A:
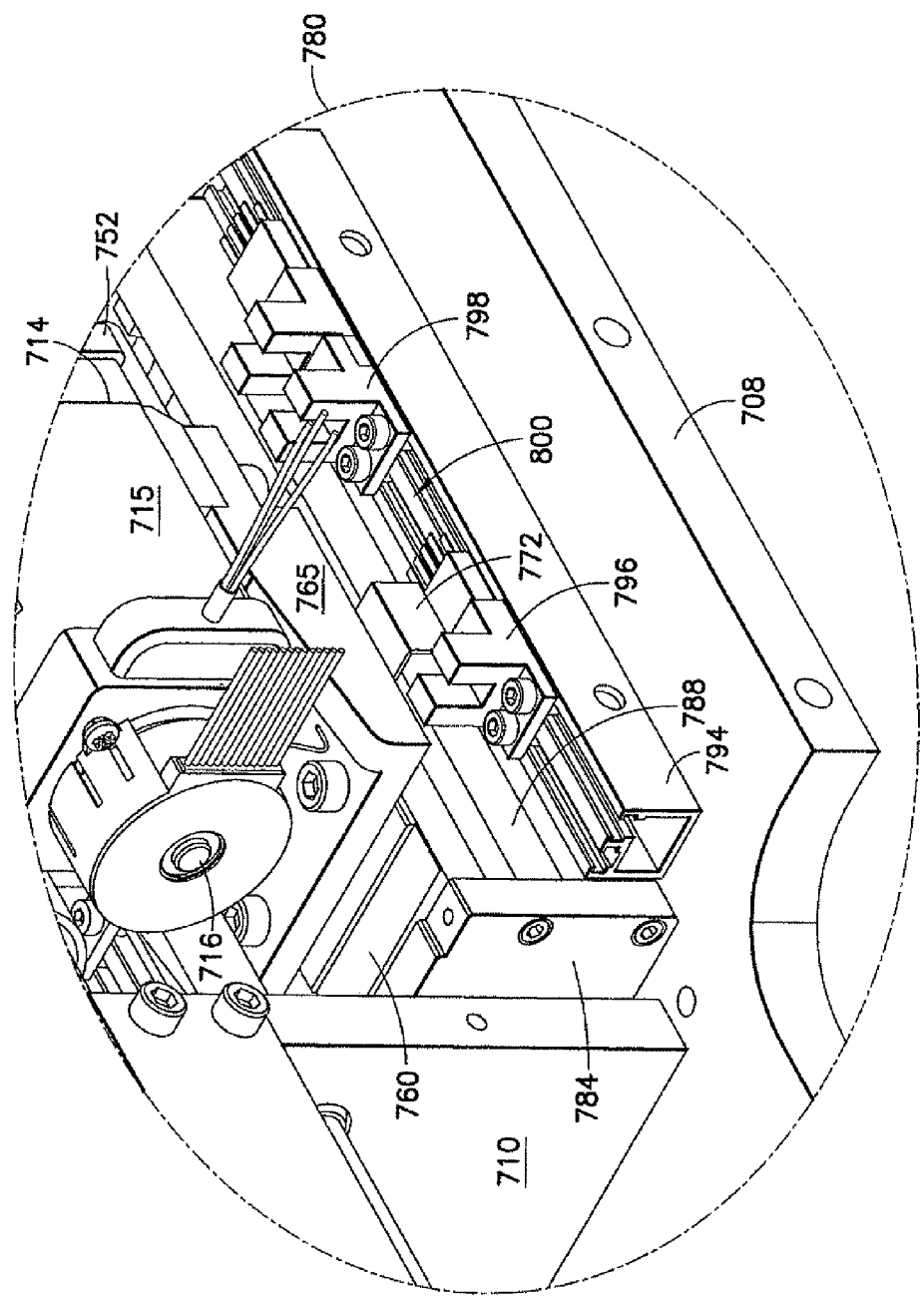
FIG. 34A is a detail view of Detail 34A in FIG. 29.
Figure 34B:
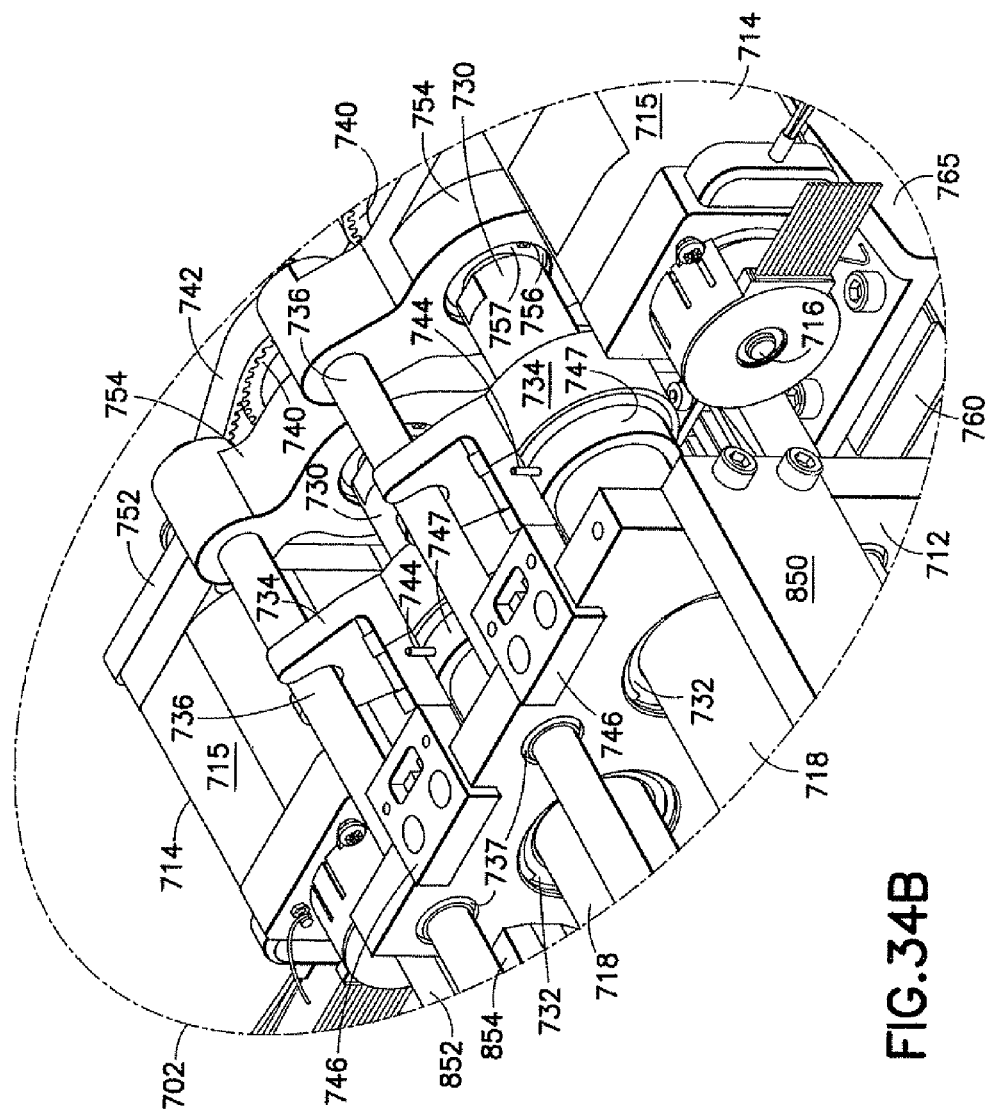
FIG. 34B is a detail view of Detail 34B in FIG. 29.

Piston drive element 718 is desirably hollow and may be open (not shown) at its proximal end 724 to interface with a linkage device 726 which is used to transfer the motive forces provided by drive motor 714 and drive shaft 716 to piston positioning member 706 generally and piston drive element 718 in particular. Linkage device 726 may again take many known mechanical forms for converting the rotational drive output of drive motor 714 and drive shaft 716 to translational movement of piston positioning member 706 so that the second piston 164 may exhibit the bi-directional linear movement described previously in this disclosure. Linkage device 726 in the illustrated exemplary embodiment again comprises a ball screw shaft 728 rotationally journaled in a ball screw nut 730, namely, by threaded engagement as described previously. FIG. 32 reveals that ball screw shaft 728 is substantially similar to ball screw shaft 628 discussed previously in connection with FIG. 24. The ball screw nut 730 is connected to the proximal end 724 of piston drive element 718 of piston positioning member 706. As an example, ball screw nut 730 may be fixed internally in the proximal end 724 of piston drive element 718, for example, by a threaded engagement. Such a connection was detailed previously in connection with drive system 600 and reference may be made to this foregoing description.

In contrast to drive system 600 discussed previously, piston drive element 718 now extends through an opening 732 in proximal or rear supporting wall 712 extending upward from support base 708 in pump compartment 24. An anti-rotation collar 734 is connected to ball screw nut 730 and, further, is connected to a guide rail 736 which passes through an opening 737 in proximal support wall 712. In drive system 600, a similar guide rail extended between supports walls 610, 612 to prevent rotation of ball screw nut 630 when ball screw shaft 628 is rotating. In the present embodiment, guide rail 736 is supported by a piston interface structure connected to the motor housing 715 of drive motor 714 as described herein. As illustrated, anti-rotation collar 734 may connect to guide rail 736 so as to slide along guide rail 736 such that ball screw nut 730 translates linearly under the threaded connection with ball screw shaft 728 when the ball screw shaft 728 is rotating. Ball screw shaft 728 comprises a proximal end portion 738 and the ball screw shaft 728 is operatively associated with a pulley 740 and a timing belt 742 combination. In particular, pulley 740 is mounted to the proximal end portion 738 of ball screw shaft 728 and timing belt 742 is reeved about pulley 740 and a second pulley 743 mounted to the end of drive shaft 716 and is used to rotationally interface the drive shaft 716 and the ball screw shaft 728; this arrangement is similar to ball screw shaft 628 and pulley 640 described previously and reference may be made to this previously discussed arrangement. The pulley 740 and timing belt 742 permit rotational movement of drive shaft 716 to be imparted to ball screw shaft 728 as will be apparent to those skilled in the mechanical arts. A sensor pin 744 desirably extends upward from a collar portion 747 provided at the proximal end 724 of piston drive element 718 of piston positioning member 706 in piston positioning device 704(1). Sensor pin 744 is positioned to engage a home sensor 746 mounted to proximal support wall 712 to provide an indication of a "zero" or "home" position of the insertion piston 164 in each fluid pumping device 160 of fluid pumping device 100. Accordingly, two such home sensors 746 are present in connection with drive system 700, one for each fluid pump actuator 702, to obtain sensor information of the "zero" or "home" position of insertion piston 164 in each fluid pump 160.

In contrast to drive system 600 described previously, each fluid pump actuator 702 comprises a modified or second piston positioning device 704(2) which is different from the piston positioning device 604 described previously and piston positioning device 704(1) described in the immediate foregoing disclosure. Second or modified positioning device 704(2) is substantially adapted to interface with sleeve piston 162 in the fluid pumps 160 of fluid pumping device 100. Piston positioning device 704(2) comprises a piston interface and support structure 748 for interfacing with sleeve piston 162 and, in particular, with dual or double rim end flange 180 associated with the sleeve piston 162. As noted in the foregoing, end flange 180 comprises two spaced apart rim flange elements 212 which define an intervening space 214. Piston interface structure 748 comprises a U-shaped saddle element 750 which is adapted to engage the intervening space 214 between rim flange elements 212. Saddle element 750 is connected to and supported at least on one side thereof by guide rail 736 which extends between the saddle element 750 and a rear support plate 752. Rear support plate 752 is desirably secured to the rear or proximal side of the motor housing 715 of drive motor 714 and may be considered to be part of the piston interface structure 748. Rear support plate 752 comprises cylindrical support portion 754 that defines a recessed cavity 756 sized to permit passage into or at least limited entry therein of the proximal end 724 of piston drive element 718. Rear support plate 752 defines an opening (not shown) in cavity 756 which permits passage of ball screw shaft 728 so the ball screw shaft 728 may operatively interface with pulley 740. Guide rail 736 is affixed at its distal end to cylindrical support portion 754 of rear support plate 752. In an analogous manner to that described in connection with drive system 600, a thrust washer 757, similar to thrust washer 632, and an associated bearing (not shown) located behind thrust washer 757 may be used to rotationally support ball screw shaft 728 in the opening (not shown) in rear support plate 752. Piston interface structure 748 further comprises a support rail 758 opposite from guide rail 736 and which extends between the opposite side of saddle element 750 and, desirably, extends proximally to be connected (not shown) to rear support plate 752 and may likewise be considered part of piston interface structure 748 in drive system 700.

Piston positioning devices 704(1), 704(2) are supported on a supporting sled carriage 760 which is provided to support the drive motor 714 and the components secured to the motor housing 715 of drive motor 714, for example, piston interface structure 748. Sled carriage 760 comprises a distal end 762 and a proximal end 764 and defines a central aperture 766 therethrough from the distal end 762 to the proximal end 764. As illustrated, drive motor 714 is mounted to sled carriage 760 by virtue of a mechanical connection between rear support plate 752 with the proximal end 764 of the sled carriage 760. A support block 765 is also used to mechanically secure the motor housing 715 of drive motor 714 to the sled carriage 760. Opposed lateral sides 768 of sled carriage 760 each comprise one or more rail elements 770, and a sensor plate 772 is provided on at least one lateral side 768 of the sled carriage 760. Sensor plate 772 is operable in combination with a home sensor, described herein and, possibly, additional position sensors which may be used to track positioning and movement of sled carriage 760 and/or for other purposes. Additionally, while not shown, a ball screw nut is provided or formed internally in central aperture 766 to interface with a sled ball screw shaft, also discussed herein, to cause translational movement of sled carriage 760 in this embodiment.

Sled carriage 760 is coupled to and driven by a sled drive system 780 for effecting translational movement of the sled carriage 760 and, hence, all the components supported by the sled carriage 760. Sled drive system 780 is likewise a component of the fluid pump actuator 702. Sled drive system 780 comprises a base portion 782 having two upstanding walls, namely, a distal wall 784 and a proximal wall 786. Base portion 782 is desirably securely affixed to support base 708 of pump compartment 24. Lateral side walls 788 connect the distal and proximal end walls 784, 786, and the end walls 784, 786 and side walls 788 define a receiving cavity 790 for reception of sled carriage 760 therein. Each lateral side wall 788 defines mating tracks 792 for engaging the rail elements 770 on the corresponding lateral sides 768 of sled carriage 760. A sensor support channel 794 desirably extends laterally outward from one lateral side wall 788. Sensor support 794 supports a sled drive home sensor 796 and a rear or proximal position sensor 798. It will be apparent that with sled carriage 760 received in receiving cavity 790, sensor plate 772 is disposed in an intervening space 800 defined between home sensor 796 and proximal sensor 798 and, hence, sufficient forward and backward movement of sled carriage 760 causes sensor plate 772 to actuate home sensor 796 and proximal sensor 772, respectively. In particular, sensor plate 772 may interface with home sensor 796 to determine a "zero" or "home" position of sled carnage 760 which, consequently, identifies the "zero" or "home" position of sleeve piston 162. Additionally, in a similar manner to that described in connection with sensor pin 644 and home sensor 646 in drive system 600, sensor pin 744 interfaces with home sensor 746 to identify the "zero" or "home" of insertion piston 164. Both home sensors 746, 796 and their interaction with sensor pin 744 and sensor plate 772, respectively, are described further herein.

Figure 28:
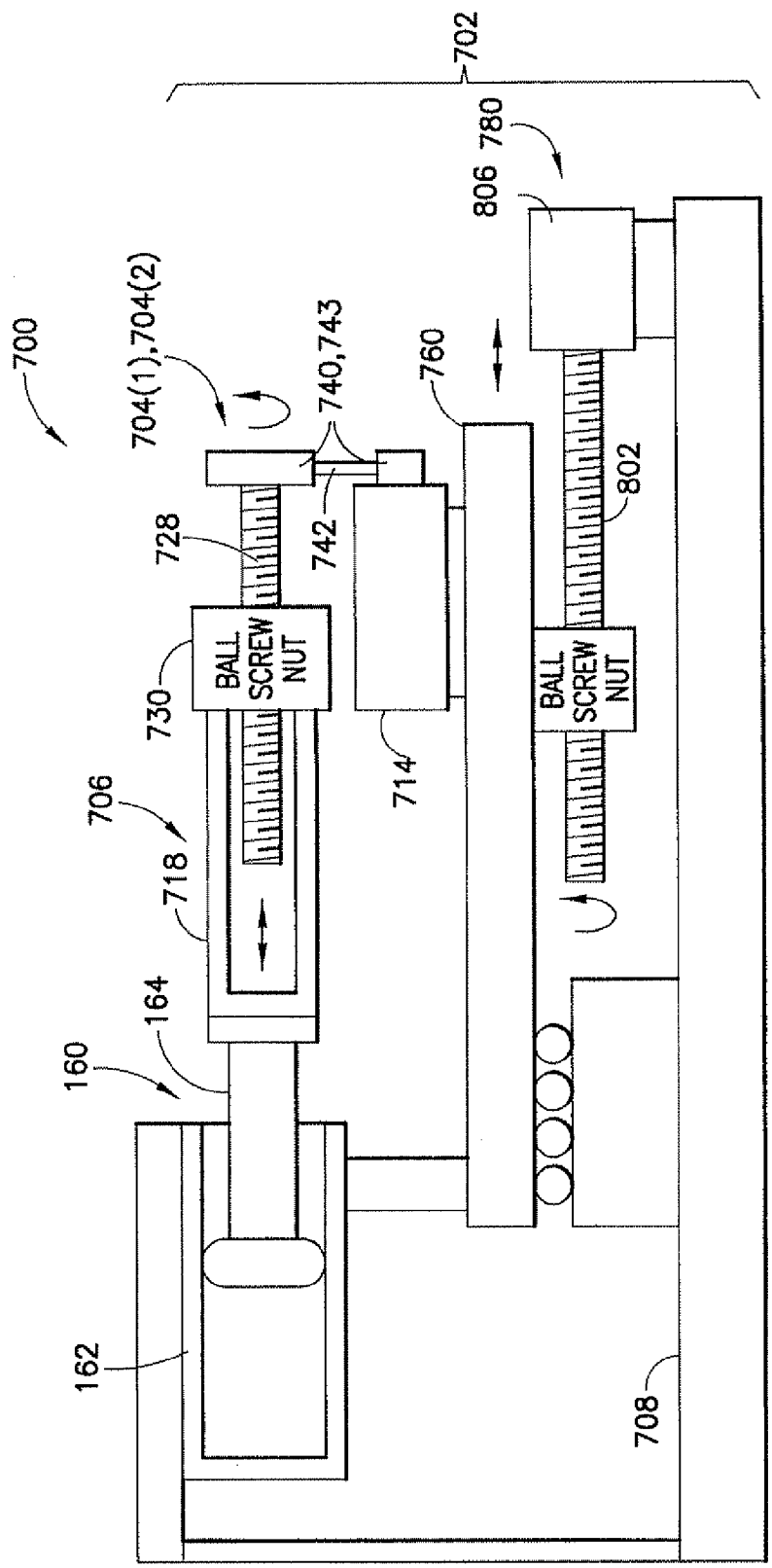
FIG. 28 is a schematic representation of a drive system embodiment adapted for operating the fluid pumping device of FIGS. 25-26.
Figure 29:
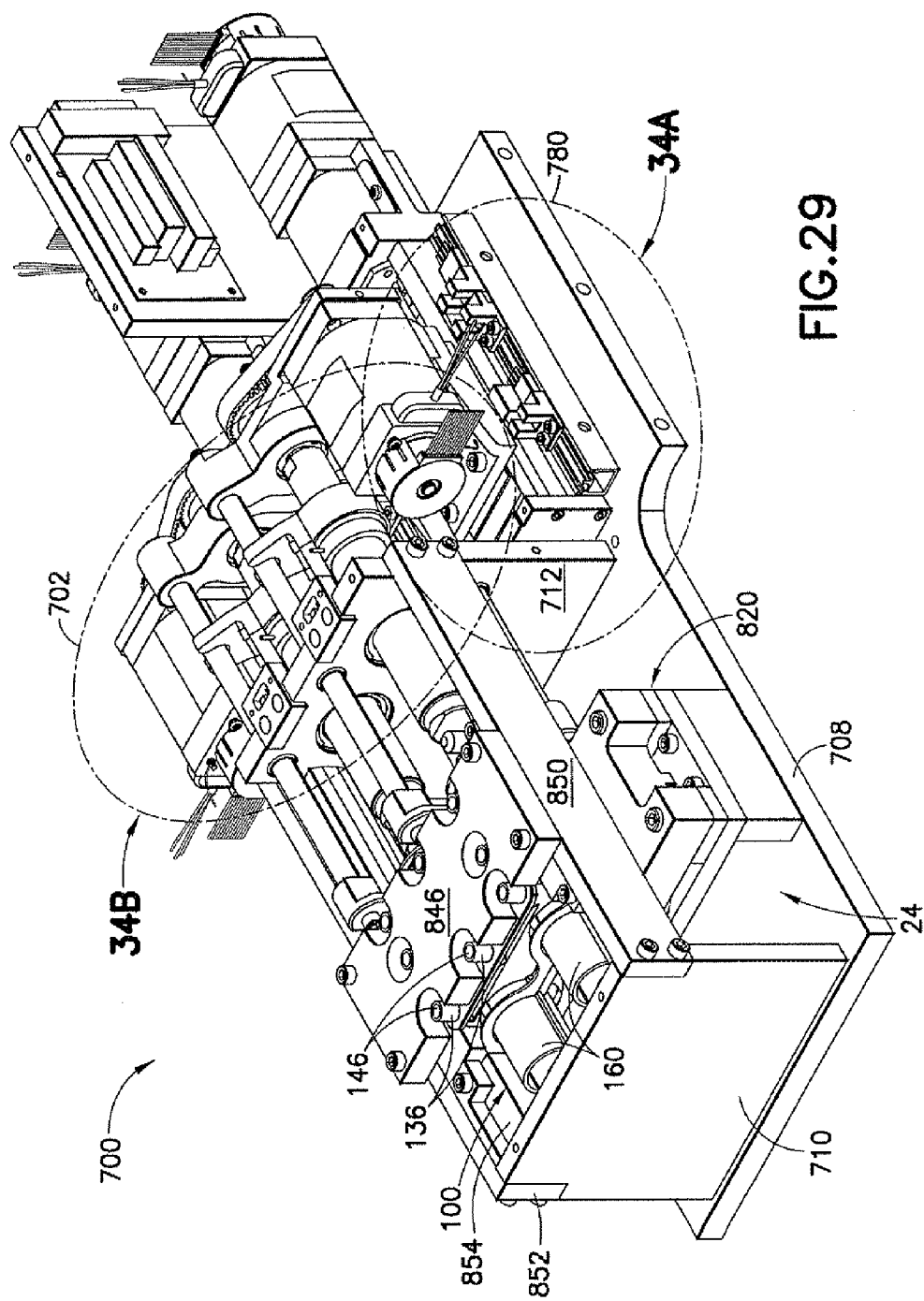
FIG. 29 is a perspective view of the drive system schematically represented in FIG. 28.
Figure 30:
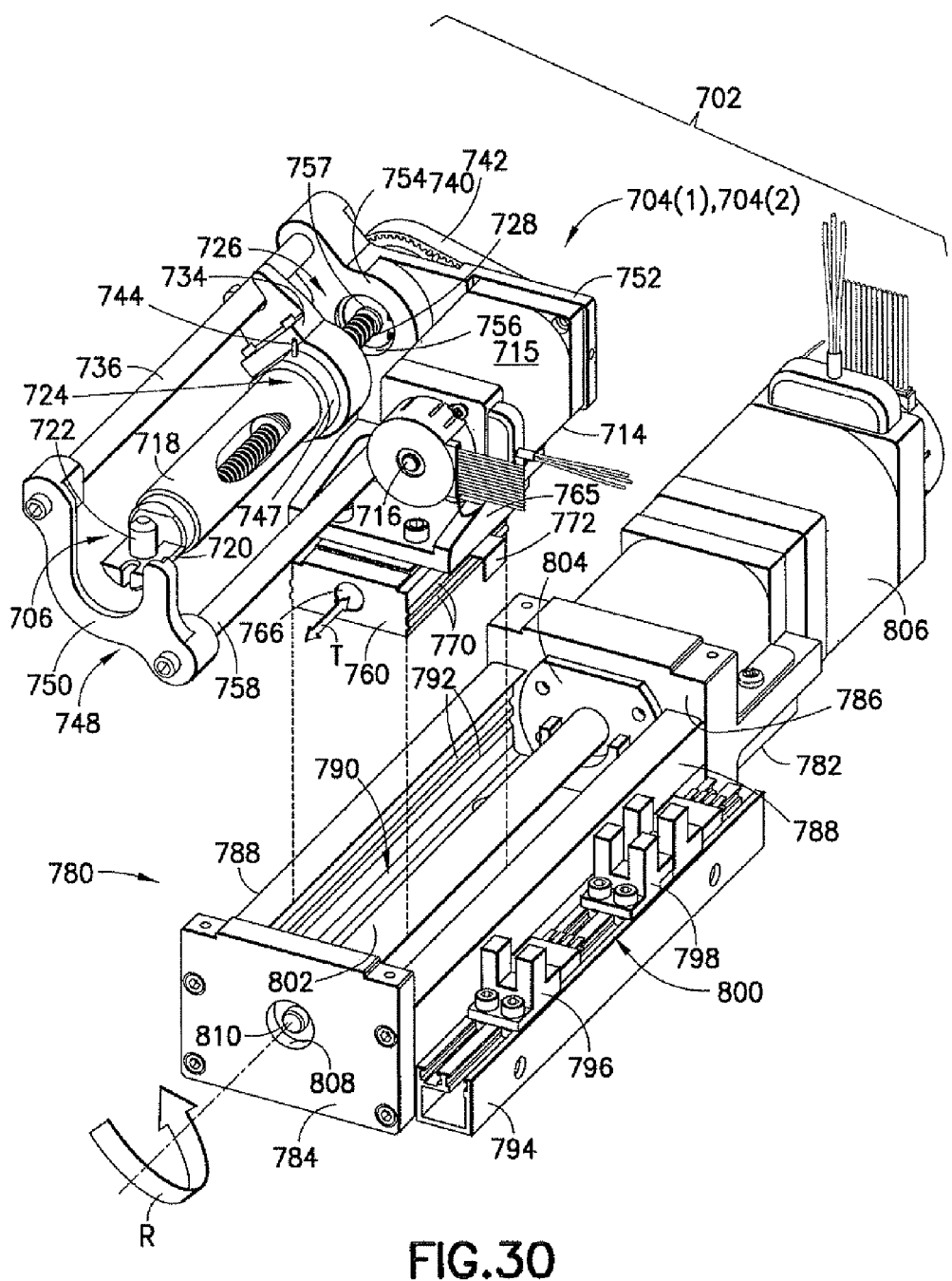
FIG. 30 is a perspective view of a fluid pump actuator of the drive system shown in FIG. 29.
Figure 31:
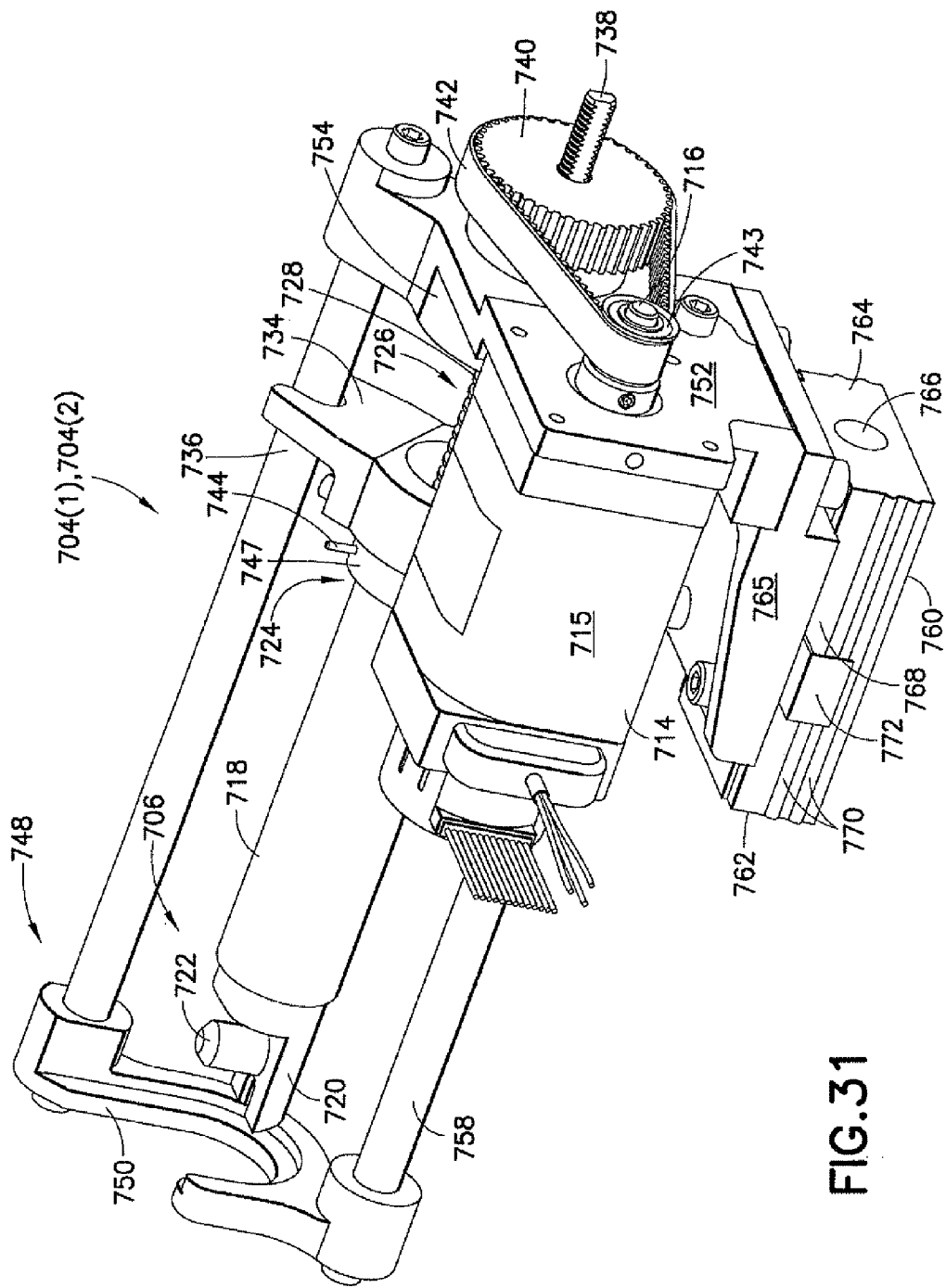
FIG. 31 is a perspective view of a piston positioning device of the fluid pump actuator shown in FIG. 30.

A sled drive ball screw shaft 802 is supported in an opening (not shown) in rear or proximal wall 786 extending upward from base portion 782 by a bearing plate 804 disposed on the front side of the proximal wall 786. Sled ball screw shaft 802 is operatively engaged and driven by a sled drive motor 806 via a motor drive shaft (not shown) in a conventional manner. Sled drive motor 806 may be mounted to the rear side of proximal support wall 786 for driving sled ball screw shaft 802. A front opening 808 may be provided in front or distal wall 784 to permit passage of a distal end 810 of sled ball screw shaft 802 during operation of the sled ball screw shaft 802. When the sled carriage 760 is associated with the sled drive system 780, the sled ball screw shaft 802 extends into the central aperture 766 in sled carriage 760 and rotationally engages with the ball screw nut (not shown) provided in or formed internally in the central aperture 766; a schematic representation of sled carriage 760 comprising an internal ball screw nut is shown in FIG. 28. Accordingly, when sled drive motor 806 is in operation, rotation of the sled motor drive shaft (not shown) causes rotation of sled ball screw shaft 802. As indicated, the sled motor drive shaft is directly coupled to the sled ball screw shaft 802 by conventional methods. When the sled ball screw shaft 802 is under drive force imparted by sled drive motor 806, the rotational threaded engagement between the sled ball screw shaft 802 and the ball screw nut associated with the central aperture 766 in sled carriage 760 causes the sled carriage 760 to translate (distally forward or proximally backward) in receiving cavity 790. The rotation of sled ball screw shaft 802 by operation of sled drive motor 806 is depicted by arrow R in FIG. 30 and the resulting forward and backward translational movement imparted to sled carriage 760 is depicted by arrow T in FIG. 30 for illustrative purposes. It will be apparent that the translational movement of sled carriage 760 simultaneously moves the various components of piston positioning devices 704(1), 704(2) as these devices are mounted to the sled carriage 760. The engagement of rail elements 770 on lateral sides 768 of sled carriage 760 with mating tracks 792 in side walls 788 prevents the rotational motion imparted to the sled ball screw shaft 802 from rotating or lifting the sled carriage 760 in receiving cavity 790. Accordingly, the threaded engagement of sled ball screw shaft 802 and internal ball screw nut in sled carriage 760 converts the rotational motion imparted to the sled ball screw shaft 802 by sled drive motor 806 to translational movement of sled carriage 760 in receiving cavity 790, distally forward or proximally backward in the receiving cavity 790.

Figure 35A:
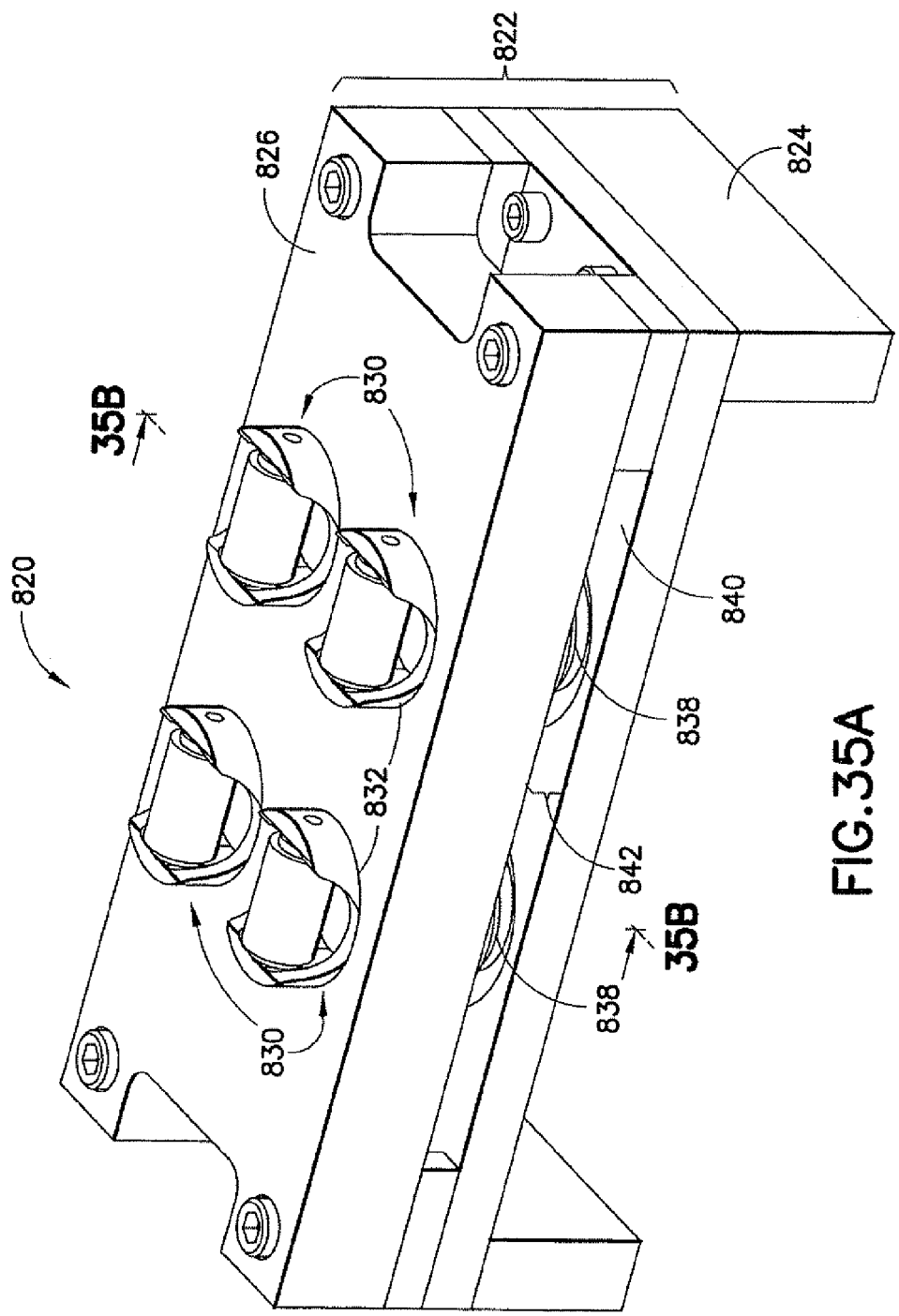
FIG. 35A is a perspective view of a pump support device of the drive system shown in FIG. 29.
Figure 35B:
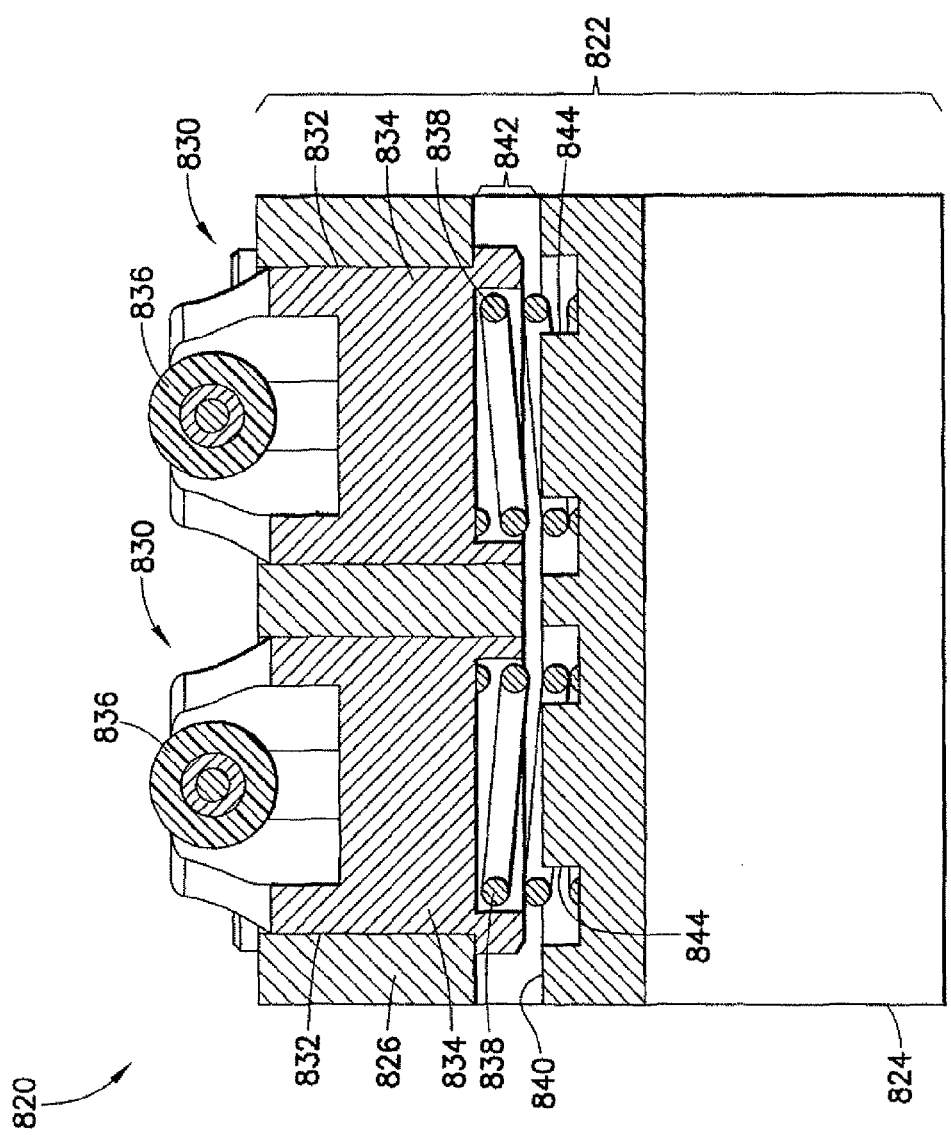
FIG. 35B is a cross-sectional view taken along line 35B-35B in FIG. 35A.
Figure 36:
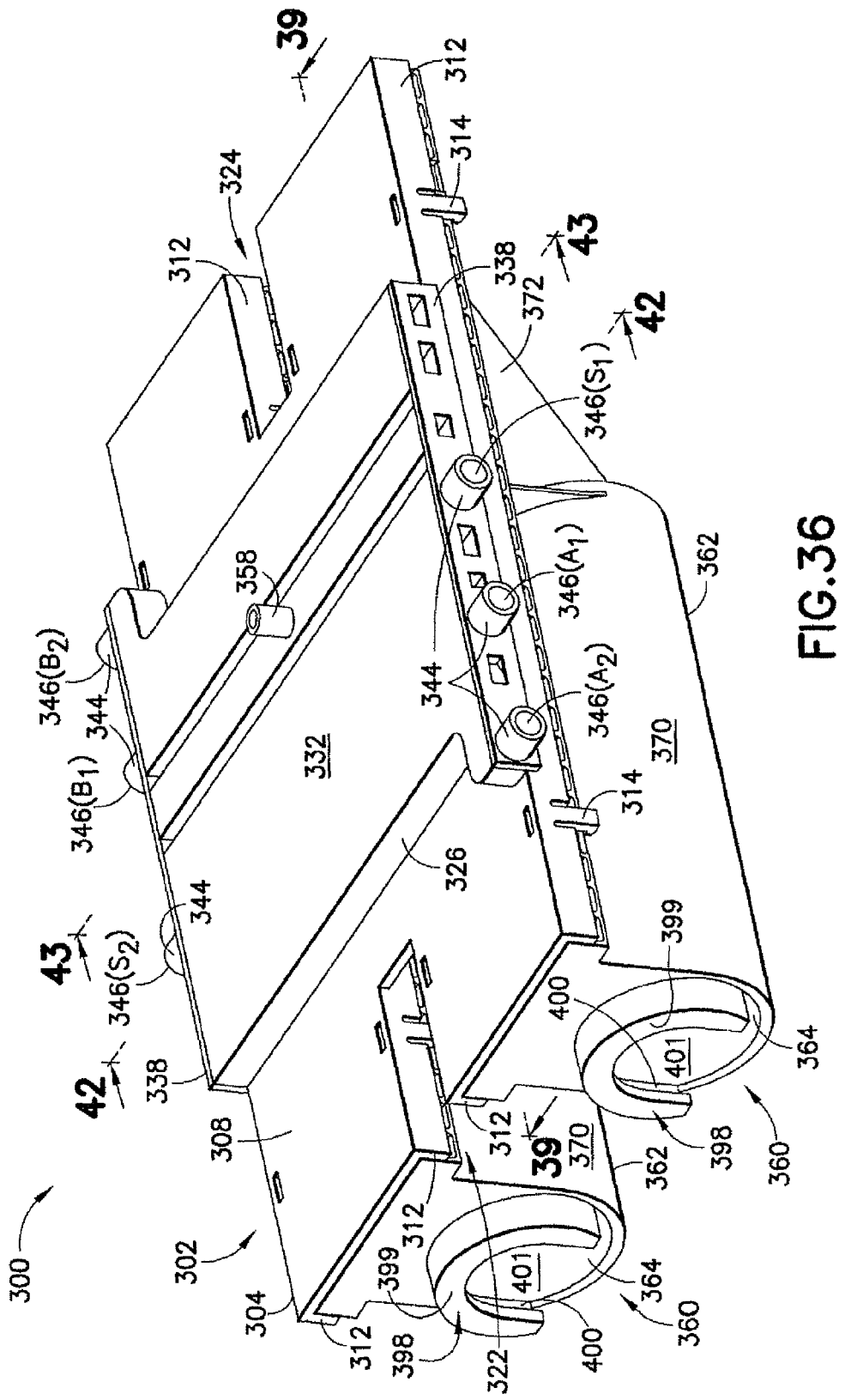
FIG. 36 is a top perspective view of another embodiment of the fluid pumping device comprising two or more fluid pumps in accordance with the disclosure herein.
Figure 37:
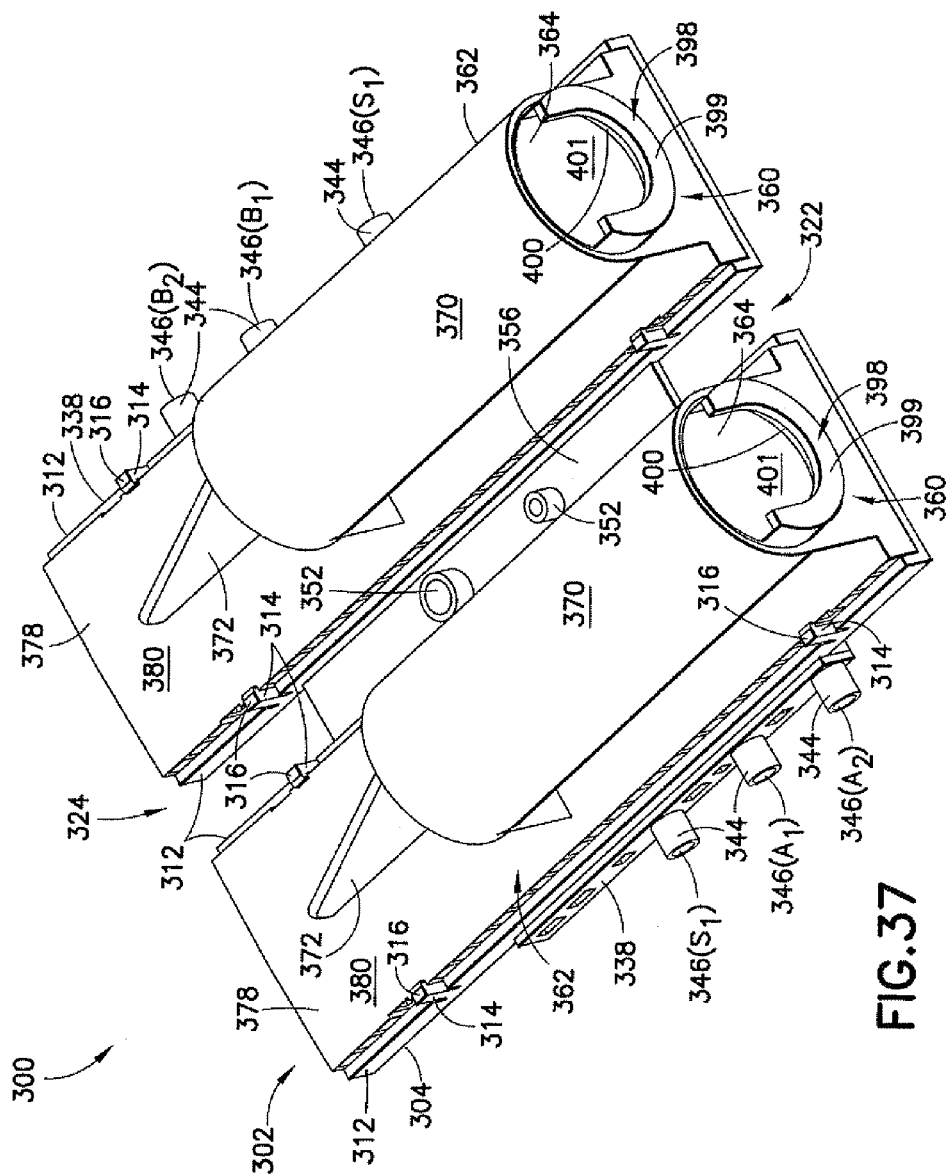
FIG. 37 is a bottom perspective view of the fluid pumping device of FIG. 36.

With specific reference to FIGS. 35A-35B, when fluid pumping device 100 is associated with drive system 700, the respective adjacent fluid pump actuators 702 interface with the respective adjacent fluid pumps 160 in fluid pumping device 100. In this association, for each fluid pump actuator 702, piston positioning device 704(1) is interfaced with a corresponding insertion piston 164. This interface connection is made by inserting peg 722 at the distal end 720 of piston drive element 718 in piston positioning device 704(1) into the interface aperture 200 in drive interface portion 198 of piston rod 196 of the corresponding insertion piston 164. Similarly, the second piston positioning device 704(2) in each fluid pump actuator 702 is interfaced with a corresponding sleeve piston 162. This interface connection is made by associating the rim flange elements 212 on end flange 180 of sleeve portion 170 of each sleeve piston 162 with the piston interface structure 748 in the respective piston positioning devices 704(2). In particular, for each piston positioning device 704(2), U-shaped saddle element 750 of the piston interface structure 748 is placed in engagement between the rim flange elements 212 on end flange 180 of the corresponding sleeve piston 162 and engages the intervening space 214 between the two spaced apart rim flange elements 212. This engagement is provided for each sleeve piston 162 associated with fluid pumps 160 in fluid pumping device 100. Once fluid pumping device 100 is associated with drive system 700, the adjacent fluid pump actuators 702 respectively operate the fluid pumps 160 in the fluid pumping device 100.

In order to support fluid pumping device 100 during operation and, further, to maintain sufficient pressure on fluid seal elements 120 associated with fluid pumps 160 for a generally fluid tight seal to exist between base member 104 and the fluid pumps 160, a pump support and seal device 820 is incorporated into drive system 700. Pump support device 820 is positioned generally under fluid pumping device 100 to support the same from underneath. Generally, pump support device 820 comprises a two-tier platform 822, comprising a table-shaped support portion 824 and a top plate 826. Support portion 824 may be secured to support base 708 in pump compartment 24 by mechanical securing methods and the like.

A plurality of spring-backed rollers 830 are disposed in respective openings 832 defined in top plate 826. Spring-backed rollers 830 each comprise a roller holder 834, a roller element 836, and a supporting or backing spring 838. As illustrated, top plate 826 is spaced apart from a top surface 840 of table support portion 824 and support or backing springs 838 may be disposed in this open area 842. Desirably, individual spring support guides 844 are provided on the top surface 840 of support portion 824 to support the compression and extension of the individual support springs 838, which support the respective roller holders 834. Typically, the spring-backed rollers 830 are disposed so as to engage the depending flanges 190 that depend or extend downward from interface portion 172 of each of the sleeve pistons 162 in fluid pumps 160, particularly in fluid pumping device 100 described in connection with FIGS. 25-26. Accordingly, spring-backed rollers 830 support the respective sleeve pistons 162 in each fluid pump 160 during reciprocal operation of pistons 162, 164 in the respective fluid pumps 160. It will be appreciated that the foregoing described pump support device 820 may be provided in place of the pump support structure 652 described in connection with drive system 600 to support the fluid pumping device 100 described in connection with FIGS. 1-20. If such a modification is provided in connection with drive system 600, depending flanges 190 associated with sleeve pistons 162 in this earlier embodiment of fluid pumping device 100 may extend the length of the sleeve pistons 162 in a similar manner to the sleeve piston 162 shown in FIG. 26.

In operation, the spring-backed rollers 830 apply force directly to the bottom surface of each of the sleeve pistons 162 in fluid pumps 160 via contact engagement with depending flanges 190. The spring-backed or loaded rollers 830 allow the sleeve pistons 162 to be moved in an axial direction with little friction. By using spring-loaded or loaded rollers 830, the effect of manufacturing tolerances within fluid pumping device 100 is minimized. The spring-backed or loaded rollers 830 are adapted to "push" upward until contact is made with sleeve pistons 162, regardless of the actual position of the sleeve pistons 162 or their wall thickness.

Moreover, to ensure that pump support device 820 applies sufficient pressure to fluid seal elements 120 associated with fluid pumps 160 during operation of the fluid pumps 160, a cover plate 846 may be placed in engagement with manifold cap 132 of fluid pumping device 100. Such a cover plate 846 ensures that the upward force applied by pump support device 820 and the spring-backed or loaded rollers 830 is applied directly to fluid seal elements 120. Without the presence of cover plate 846, this upward force may possibly misalign the insertion engagement between pistons 162, 164 and degrade operation of fluid pumps 160. Cover plate 846 may be secured to two lateral support beams 850, 852 extending between opposing support walls 710, 712 in pump compartment 24 and, thereby, support beams 850, 852 form part of the pump compartment 24. As illustrated, support beams 850, 852 may each define an inner ledge 854 to which the lateral sides 112 of base member 104 of pump housing 102 of fluid pumping device 100 may be secured by mechanical connection and the like. Cover plate 846, if desired, may be integrated as part of an enclosure cover for pump chamber 24 which seats against the top surface of manifold cap 132 when the enclosure cover is in a closed, covering position enclosing the pump compartment 24. Such an enclosure cover, for example, a hinged enclosure cover, ideally covers at least the open area defined between opposing support walls 710, 712 in pump compartment 24. Cover plate 846 additionally keeps manifold portion 126 from bowing upward under system pressure.

As noted previously, fluid pumping device 100, according to the embodiment shown in FIGS. 25-26, comprises only differences regarding operation of the fluid pumps 160 from the same side or end by drive system 700 from the fluid pumping device 100 described in connection with FIGS. 1-20 and operated by drive system 600. Accordingly, fluid pumping device 100, according to the embodiment shown in FIGS. 25-26, operates in an identical manner to the operational sequence described in connection with FIGS. 14-20. Accordingly, in operation, drive system 700 operates fluid pumping device 100 of FIGS. 25-26 in a manner similar to drive system 600 described previously, in that while one fluid pump 160 is filling with fluid, the other fluid pump 160 is ejecting fluid into patient fluid path 12 (and vice versa). Drive system 700 allows each fluid pump actuator 702 to be independently controlled by a control device in a similar manner to that described previously. As each fluid pump actuator 702 comprises piston positioning devices 704(1), 704(2), each of these devices may be independently controlled by the control device. In a basic operational sequence of drive system 700, the control device operates sled drive motor 806 associated with one fluid pump actuator 702 to rotate sled ball screw shaft 802 in the central aperture 766 in sled carriage 760. As described previously, the threaded engagement between sled ball screw shaft 802 and a corresponding ball screw nut provided in the central aperture 766 causes the sled carriage 760 to exhibit translational movement. This translational movement is imparted to sleeve piston 162 via piston interface structure 748 mounted to sled carriage 760. As noted, U-shaped saddle element 750 engages rim flange elements 212 on end flange 180 of the sleeve piston 162 to operatively interface piston positioning device 704(2) with the sleeve piston 162. As a fixed connection exits between piston interface structure 748 and sled carriage 760 via rear support plate 752, motor housing 715 of drive motor 714, and support block 765, translational movement of the sleeve piston 162 simultaneously occurs when sled drive motor 806 is operated.

Since piston position device 704(1) is also mounted to sled carriage 760 via rear support plate 752 and engagement of anti-rotation collar with guide rail 736, the various components of piston position device 704(1) also move in synchronous movement with piston positioning device 704(2), and pistons 162, 164 likewise exhibit synchronous translational movement. As there is no relative motion between pistons 162, 164, fluid will not be pulled into pumping chamber 192 as they move together. Sled carriage 760 is moved by operation of sled drive motor 806 until the sleeve opening or port 176 in the sleeve portion 170 of the sleeve piston 162 is aligned with a desired manifold inlet port 146. The position of sled carriage 760 is then held constant while insertion piston 164 is retracted by actuation of piston positioning device 704(1), which causes the pumping chamber 192 to fill with fluid from the selected manifold inlet port 146. As piston positioning device 704(1) is identical to the piston positioning device 604 discussed previously, operation of piston positioning device 704(1) is also the same. In brief, to effect movement of the piston positioning member 706, drive shaft 716 is driven by drive motor 714 and this rotational movement is imparted to pulley 740 mounted to ball screw shaft 728 via timing belt 742. As ball screw shaft 728 rotates, ball screw nut 730 translates along the ball screw shaft 728, which effects translational linear movement of piston 164 to draw fluid into pumping chamber 192 from the selected manifold inlet port 146.

If it is desired to select an additional manifold inlet port 146, sled carriage 760 may be moved, distally or proximally, in receiving cavity 790, by operation of sled drive motor 806 under the direction of the control device such that sleeve piston 162 is positioned with sleeve port 176 in sleeve portion 170 of the sleeve piston 162 aligned with the next desired manifold inlet port 146. Upon reaching the next desired manifold inlet port 146, only piston positioning device 704(1) is actuated, for example, by the control device, so that piston 164 withdraws in sleeve portion 170 of sleeve piston 162 to draw in fluid into pumping chamber 192 via the second selected manifold inlet port 146.

Once the desired fluid volumes of similar or dissimilar fluids are present in pumping chamber 192, sled carriage 760 may be moved by operation of sled drive motor 806 in the manner described in the foregoing such that sleeve port 176 in sleeve portion 170 of sleeve piston 162 is aligned with a desired manifold outlet port 146, typically the manifold outlet port 146 connected to patient fluid path 12. As described, as sled carriage 760 mounts the components of both piston positioning devices 704(1), 704(2), there is no relative motion between pistons 162, 164 during the translational movement of sled carriage 760 and fluid is not expelled from sleeve portion 170 in sleeve piston 162 during the translational movement of sled carriage 760. Upon reaching the desired manifold outlet port 146, only piston positioning device 704 (1) is actuated by the control device so that piston 164 inserts into sleeve portion 170 of sleeve piston 162 to expel fluid from pumping chamber 192 via sleeve port 176 and into the selected manifold outlet port 146. It will be apparent that the adjacent or second fluid pump 160 operates in an identical manner but out of phase or "staggered" from the operation of the "first" fluid pump 160 as described in the foregoing so that substantially constant flow is provided by the fluid pumping device 100 generally.

For the control device to accurately control fluid pumps 160, in an initial or start-up mode or sequence both pistons 162, 164 are actuated to move together distally forward in cavity 790 until sensor plate 772 actuates home sensor 796. Home sensor 796 may use, for example, an infrared LED and photosensor to detect the presence of sensor plate 772. This actuation of home sensor 796 establishes a "zero" or "home" position of the sled carriage 760 and, hence, the "zero" or "home" position of sleeve piston 162 for the control device. With the sled carriage 760 held fixed by the operation of sled drive motor 806 by the control device and, thereby, with sleeve piston 162 held stationary, piston positioning device 704(1) is operated by the control device to move insertion piston 164 until sensor pin 744 engages and actuates its associated home sensor 746. The home sensor 746 may use, again, an infrared LED and photosensor to detect the presence of sensor pin 744 mounted to collar portion 747 on piston drive element 718 of piston positioning member 706 of piston positioning device 704(1). From this point on, the computer-based control device keeps track of the positions of pistons 162, 164 as the "zero" or "home" positions of both pistons 162, 164 are now known.

Drive system 700 has numerous advantages including that drive motors 714 and the pulley 740 and timing belt 742 combination associated with each piston positioning device 704(1) may be optimized for the high forces that are required to actuate insertion pistons 164 in each fluid pump 160 against high fluid pressures encountered during operation of fluid pumps 160. During operation of fluid pumps 160, peak forces may be as high as 600 lbs. Because the insertion pistons 164 move relatively slowly, their piston drives (drive motors 714 and the pulley 740 and timing belt 742 combinations) may use speed reduction (such as optimizing the pulleys and belts) to reduce the required motor torque. Additionally, the sled drive motors 806 may be optimized to drive the sled carriages 760 at high velocities, but with low force. The sled drive motors 806 only need to develop sufficient force overcome friction and inertia in the drive system 700; they are generally not subjected to the high forces that are required to actuate the insertion pistons 164 in fluid pumps 160. Since the required motor torque is low, the sled drive motors 806 are directly coupled to respective sled ball screw shafts 802 without any speed reduction. Accordingly, the drive elements associated with the insertion pistons 164 in fluid pumps 160 generally move with high force and low velocity, and the drive elements associated with the sleeve pistons 162 in fluid pumps 160 generally move with low force and high velocity. Further, the drive motor 714 and sled drive motor 806 do not have to be precisely synchronized because both piston positioning devices 704(1), 704(2) are mounted commonly on sled carriage 760 and there is no relative motion between pistons 162, 164 unless drive motor 714 is energized; this feature enhances volume accuracy of fluid pumping device 100 during operation.

Another embodiment of a fluid pumping device 300 is shown in FIGS. 36-48 and may be used as part of fluid delivery system 10. Accordingly, fluid delivery system 10 may comprise fluid pumping device 300 and the foregoing described drive system 700 which provides the motive forces used to operate movable components of fluid pumping device 300. As an alternative, fluid pumping device 300 may also interface with a modified version of drive system 700, described herein in connection with FIGS. 49-64 and identified as drive system 900. Adaptations to fluid pumping device 300 so that it may operate with drive system 700 or drive system 900 are described herein. Once again, a desirable feature of fluid pumping device 300 is to provide the fluid pumping device 300 as a disposable component, for example, as a disposable cartridge, cassette or unit, which may be associated with a reusable drive system 700, 900 for one use or a discrete number of uses and then disposed of.

Fluid pumping device 300 is again a multi-component device generally comprising a pump housing 302 and one or more fluid pumps 360 which constitute the movable components of fluid pumping device 300 for delivering fluid under pressure to a desired end point, such as patient fluid path 12 shown in FIG. 1B. The fluid path components described in connection with FIG. 1B used to associate the various bulk fluid sources with fluid pumping device 100 equally suited to use with fluid pumping device 300. Pump housing 302 serves as a support component or structure for the movable components of fluid pumping device 300, namely, fluid pumps 360, as well as a connection point for connecting the fluid path components described in connection with FIG. 1B. Pump housing 302 comprises a generally plate-shaped base member 304. In previous embodiments of fluid pumping device 100, a separate manifold cap 132 was attached to base member 104 and, accordingly, base member 104 and manifold cap 132 generally formed a multi-component pump housing 102. It was identified previously in this disclosure that these components, namely, base member 104 and manifold cap 132, may be formed integrally so that pump housing 302 is an integral structure. Pump housing 302 is an example of such an integral structure in one exemplary embodiment. Base member 304 is desirably formed as an injection-molded plastic component. Nonetheless, base member 304 (and manifold components associated therewith as described herein) forming pump housing 302 may alternatively be formed as individual components or pieces which are assembled together to form pump housing 302 by suitable assembly methods such as ultrasonic welding, laser welding, adhesive, solvent bonding, by direct mechanical attachment, and like methods.

Base member 304 may have any desirable configuration and one such configuration is that of a generally plate-shaped component or element that defines one or more and, desirably, at least two adjacent, generally parallel, and somewhat planar cavities 306. Generally planar cavities 306 are adapted to accept two identical fluid pumps 360. While the illustrated configuration of base member 304 comprises two adjacent planar cavities 306 defined in the underside or bottom side of base member 304 for accepting two like fluid pumps 360, this illustration is again not intended to restrict the possibility of base member 304 forming an additional or several additional planar cavities 306 to accept an additional or several fluid pumps 360 respectively therein. Such an alternative configuration was described previously in connection with the various embodiments of fluid pumping device 100 and reference may be made to the foregoing disclosure for implementing this alternative configuration. For simplicity and expediency, the following discussion describes fluid pumping device 300 with two like fluid pumps 360 as a non-limiting embodiment of fluid pumping device 300. In contrast to previous embodiments of fluid pumping device 100, planar cavities 306 are intended to interface with fluid pumps 360 having a slightly different configuration to fluid pumps 160 described previously which interfaced with generally concave cavities 106. For purposes of explaining the spatial orientation of additional features or components of fluid pumping device 300, base member 304 may again be considered to have a first or top side 308 and a second, bottom, or underside 310. Planar cavities 306 are each formed between two generally parallel side walls 312 depending from underside 310.

To maintain the association of fluid pumps 360 with base member 304, base member 304 comprises a plurality of individual securing members 314 depending from side walls 312 depending from the bottom or underside 310 of the base member 304. In the illustrated embodiment, each side wall 312 has two depending securing members 314 as an exemplary configuration and, therefore, four such securing members 314 are used to support each fluid pump 360 to base member 304 while permitting sliding reciprocal movement of the components of fluid pumps 360 relative to base member 304. Securing members 314 each comprise a distal tab element 316 for engaging a cooperating structure, such as a lip, rib, flange, edge, and the like, on fluid pumps 360 to allow sliding reciprocal movement of the components of fluid pumps 360 relative to base member 304. Tab elements 316 on securing members 314 face inward toward one another and the securing members 314 are spaced apart on the individual side walls 312. While securing members 314 are generally illustrated as depending tab-like structures, these may be replaced by other support configurations. For example, if desired, securing members 314 may be continuous along the opposing side walls 312 of base member 304 defining the planar cavities 306.

As in previous embodiments, fluid seal elements 320 are desirably provided within receiving recesses or grooves in each planar cavity 306 and are used to provide a sealing association between base member 304 and fluid pumps 360 disposed in the respective planar cavities 306. In this manner, a generally fluid seal engagement is provided between each fluid pump 360 and base member 304 within each planar cavity 306 during operation of fluid pumping device 300. In one desirable construction, fluid seal elements 320 may comprise a plurality of O-rings which, for example, may be over-molded to base member 304 within each planar cavity 306 in a subsequent over-molding process to the typical injection-molding process used to form base member 304. Base member 304, in like manner to that described previously, in this disclosure may be formed of rigid or stiff plastic material such as polycarbonate, acrylic, polyethylene terephthalate (PET), or cyclo-olefin polymer (COP). Fluid seal elements 320 are typically formed of elastomeric material such as thermoplastic elastomers (TPE's), thermoplastic polyurethanes (TPU's), or thermoformed rubbers such as nitrile rubber or ethylene propylene diene monomer rubber (EPDM). A soft plastic material may also be used for seal elements 320 such as polypropylene, polyethylene, ultra-high molecular weight polyethylene (UHMW), or fluoropolymers such as polytetrafluoroethylene (PTFE). Further, a thermosetting rubber may be used for seal elements 320 such as nitrile rubber (acrylonitrile butadiene rubber) or ethylene propylene diene monomer rubber (EPDM).

Base member 304 further comprises an integral manifold portion 326 on top side 308, generally centered between opposing ends 322, 324 of base member 304. Manifold portion 326 extends upward or is generally upstanding from the top side 308 of base member 304 and defines a fluid channel bank 328 comprising a plurality of individual fluid channels. The individual channels in fluid channel bank 328 are defined by a series of individual upstanding walls 330 which generally define the manifold portion 326. As in previous embodiments, a manifold cap 332 is used to enclose fluid channel bank 328 but, as noted, in the present embodiment manifold cap 332 is formed integral with manifold portion 326 and, hence, with base member 304. However, if desired, manifold cap 332 may be formed as a separate component and joined to upstanding walls 330 to enclose the fluid channel bank 328. In contrast to previous embodiments, manifold cap 332 does not comprise a series of upward-opening or "top" fluid ports. In the present embodiment, manifold portion 326 comprises a series of side-opening fluid ports 336 defined by upstanding walls 330 and manifold cap 332; side fluid ports 336 are described further herein.

In the present embodiment, side fluid ports 336 in manifold portion 326 of base member 304 are adapted engage with a pair of manifold side caps 338. Such manifold side caps 338 are adapted to engage the generally open lateral sides of manifold portion 326 defined by upstanding walls 330 and seal the open lateral sides and manifold portion 326. Manifold side caps 338 may be joined to the manifold portion 326 of base member 304 by any of the joining techniques outlined previously, namely, ultrasonic welding, laser welding, adhesive, solvent bonding, by direct mechanical attachment, and like methods. It will be apparent from the accompanying figures that fluid channel bank 328 comprises a plurality of individual fluid passageways or channels 340 defined by the upstanding walls 330 and which are enclosed by manifold cap 332. Side fluid ports 336 provide lateral openings to the respective fluid passageways or channels 340. In the accompanying figures, each fluid passageway 340 is again given an identifier, in the present embodiment, related to the type of fluid to be associated with the fluid passageway, namely a first type, concentration, or brand of contrast $A_1$, $A_2$, a different type, concentration, or brand of contrast $B_1$, $B_2$, and two different sources of bulk saline $S_1$, $S_2$, for ease in discerning one fluid passageway 340 from an adjacent fluid passageway 340 and, accordingly, it will be clear that the basic operation of fluid pumping device 300 is unchanged from previous embodiments of fluid pumping device 100. A pair of manifold openings or apertures 342 is defined in base member 304 within each fluid passageway 340 to provide fluid communication between each fluid passageway 340 and the respective fluid pumps 360 engaged in planar cavities 306. As noted previously, the illustrated embodiment of fluid pumping device 300 comprises two fluid pumps 360 and, consequently, two manifold openings 342 are provided in each fluid passageway 340 to provide fluid communication with the respective fluid pumps 360. However, as indicated previously, this configuration is for exemplary purposes only and may be expanded beyond two fluid pumps 360. In such an arrangement, base member 304 may define an additional or several additional planar cavities 306 and manifold portion 326 may be expanded to encompass this additional or several additional cavities 306 and the accompanying or associated fluid pump(s) 360 disposed therein.

As explained hereinabove, manifold side caps 338 are adapted to engage the generally open lateral sides of manifold portion 326. More particularly, manifold side caps 338 are used to fluidly seal the open lateral sides of manifold portion 326. Manifold side caps 338 are not intended to be interchangeable and, therefore, left and right manifold caps 338 are provided but manifold portion 326 may certainly be constructed to accept interchangeable manifold side caps if desired. Nonetheless, the left and right manifold side caps 338 have generally similar constructions, each comprising a plurality of outward-facing or projecting cylindrical elements 344 forming or defining a series of manifold ports 346 with respective side fluid ports 336 in manifold portion 326 and a plurality of inward-facing or hollow projections 347 which engage the remaining side fluid ports 336 in manifold portion 326 to block or fluidly seal such remaining side fluid ports 336. Projections 347 also reduce "dead" volume present in the respective fluid passageways 340. Manifold ports 346 are given a fluid identifier (contrast $A_1$, $A_2$, a different type of contrast $B_1$, $B_2$, and bulk saline $S_1$, $S_2$,) corresponding to that assigned to the associated fluid passageways 340.

As will be appreciated from the accompanying figures, in the illustrated embodiment, with the manifold side caps 338 in place in association with the left and right lateral sides of manifold portion 326, three manifold ports 346 are provided on each lateral side of the manifold portion 326 while each of the remaining side fluid ports 336 are sealed with respective projections 347 on the manifold side caps 338. Manifold side caps 338 may be secured to base member 304 to fluidly seal the open lateral sides of manifold portion 326 by any of the various joining methods described previously in this disclosure.

As noted in the foregoing, in contrast to previous embodiments, fluid seal elements 320 may comprise O-rings. In the present embodiment, the plurality of fluid seal elements 320, namely O-rings, are desirably positioned within respective recesses or grooves 348 defined in the underside or bottom side 310 of base member 304. In particular, each circumferential or perimetrical recess or groove 348 is defined about a respective manifold opening or aperture 342 defined in base member 304 to receive one the fluid seal elements 320 to individually seal these openings or apertures 342. Base member 304 may comprise depending interior rim flanges 349 which, at least in part, define the respective manifold openings 342. It will be apparent, for example, from FIG. 38 that one or more of the manifold openings 342 may not require a circumferential groove 348 containing a fluid seal element 320 as one or more of manifold openings 342 may be set aside as a dedicated waste port in each planar cavities 306 and which does not require a perimeter sealing structure so as to drain freely, for example, via a waste fluid line 22 to an appropriate medical waste fluid container (not shown). An additional outer circumferential groove 350 in the underside 310 of base member 304 may be provided around the entire series or bank of manifold openings or apertures 342 in each planar cavity 306 which will also receive an O-ring type fluid seal element 320 to provide a perimeter seal about each "bank" of manifold openings 342.

Also in contrast to previous embodiments, a dedicated waste outlet port 352 and a pressure sensor port 354 may be defined in base member 304, desirably in a central support bridge 356 which connects lateral halves of base member 304 that define the respective planar cavities 306. Waste outlet port 352 is formed to extend or project from the underside 310 of base member 304 so as to connect or interface with a connector on waste fluid line 22 which leads to an appropriate medical waste fluid container (not shown). Pressure sensor port 354 is similarly configured on the underside 310 of base member 304 for connection to a connector on a fluid conduit line leading to a pressure sensor (not shown). As shown, for example, in FIG. 42, a patient outlet port 358 is formed in manifold portion 326 on the top side 308 of base member 304 to desirably be coextensive or coincide with pressure sensor port 354, meaning that both the patient outlet port 358 and pressure sensor port 354 connect to the same fluid passageway 340 in the manifold portion 326. For labeling purposes, the fluid passageway 340 connecting to waste outlet port 352 is identified with a "W" identifier (i.e., 340(W)) and the fluid passageway connecting to patient outlet port 358 and pressure sensor port 354 is identified with a "P" (i.e., 340(P)) identifier in the accompanying figures. In view of the foregoing, it is desirable for a pressure sensor to be connected to pressure sensor port 354 so that system fluid pressure readings may be obtained or, possibly, a hemodynamic pressure sensor may be connected to pressure sensor port 354 so that blood pressure readings from a patient may be obtained, for example, when fluid pumping device 300 is not in active operation. Patient outlet port 358 disposed on manifold portion 326 on the top side 308 of base member 304 may connect or interface with patient fluid path 12 via a suitable medical connector. If desired, check valves 359 may be provided as part of each manifold side caps 338 and, in particular, be associated with projections 347 on the manifold side caps 338. Check valves 359 may be formed, for example, by an overmolding process to connect to the projections 347. The check valves 359 are desirably associated with the fluid passageway 340 connected to the waste outlet port 352 and the fluid passageway 340 connected to the pressure sensor port 354 and the patient outlet port 358 which, as indicated, share the same fluid passageway 340. Check valves 359 prevent reverse flow from the waste outlet port 352 and the patient outlet port 358 from entering the pumping chambers of fluid pump 360.

Turning to fluid pumps 360, fluid pumps 360 are located within the respective planar cavities 306 defined in base member 304, as generally described previously. Fluid pumps 360 each comprise two opposing pistons 362, 364, which may be referred to herein as a first piston or sleeve piston 362 and a second piston or insertion piston 364 for non-limiting identification purposes. As each fluid pump 360 is identical having identical pistons 362, 364, the following discussion again outlines the structure of one such fluid pump 360 used in fluid pumping device 300. In the illustrated embodiment, opposing pistons 362, 364 are configured such that piston 364 may be disposed or inserted at least partially into sleeve piston 362. For this purpose, sleeve piston 362 may have a generally cylindrical configuration with opposing first and second ends 366, 368. Sleeve piston 362 generally comprises a sleeve portion 370 wherein piston 364 may be inserted or disposed and which forms or defines first end 366 of the sleeve piston 362. Sleeve piston 362 further comprises an extended, somewhat triangular-shaped interface portion 372 that extends from sleeve portion 370. Sleeve portion 370 defines an internal cavity 374 accessible via a sleeve top opening or port 376.

Sleeve piston 362 further comprises a rectangular-shaped top portion 378 from which sleeve portion 370 depends. It will be apparent, for example, from FIGS. 44A-44B that sleeve portion 370 is desirably integral with top portion 378 and that interface portion 372 extends from sleeve portion 370 to connect to an underside or bottom side 380 of top potion 378. Top portion 378 may be cored or hollowed-out as illustrated to form a plurality of individual transversely-extending chambers 382 to enhance the stiffness and rigidity of top potion 378. A top or upper side 384 of top portion 378 may define two opposed and longitudinally-extending raised areas 386 which define a recessed center area 388 therebetween. This recessed central area 388 is intended to seat against fluid seal elements 320 associated with base member 304 of pump housing 302. Raised lateral areas 386 contact the underside 310 of base member 304 of pump housing 302 to ensure a uniform gap exists between recessed central area 388 and the underside 310 of the base member 304 for the O-rings forming fluid seal elements 320. Notches N may be defined in the lateral sides of top portion 378 providing locations for securing members 314 to snap-fit into engagement to secure sleeve piston 362 in a fixed position during storage and transport of fluid pumping device 300. As illustrated, each fluid pump 360 has the top portion 378 of its sleeve piston 362 disposed in a planar cavity 306 in base member 304. With top portion 378 disposed in planar cavity 306, side walls 312 depending from the underside 310 of the member 304 are disposed adjacent lateral side areas or edges 390 of the top portion 378 of the sleeve piston 362. The tab elements 316 provided on securing members 314 on side walls 312 depending from base member 304 engage the underside 380 of top portion 378 to mount the sleeve piston 362 to the base member 304. This engagement serves generally to secure each fluid pump 360 in its respective planar cavity 306 while allowing sliding reciprocal movement of each sleeve piston 362 relative to base member 304.

As noted previously, insertion piston 364 is adapted to access internal cavity 374 defined by sleeve portion 370 of sleeve piston 362. Insertion piston 364 is reciprocally movable within sleeve portion 370 of sleeve piston 362 and, with piston 364 disposed within sleeve portion 370, pistons 362, 364 cooperate to form or define a fluid pumping chamber 392 of fluid pump 360. Piston 364 comprises a piston head 394 and a proximally extending piston rod 396. Piston rod 396 comprises a generally X-shaped configuration and terminates at a proximal end thereof with a drive interface flange 398 comprising a flange lip 399 defining, in the illustrated embodiment, a generally U-shaped slot 400 for interfacing with drive system 900 described herein in connection with FIGS. 49-64. Drive interface flange 398 comprises a solid end wall 401 opposing flange lip 399 defining U-shaped slot 400. Drive interface flange 398 provides a location whereby piston 364 may physically interface or connect with piston attachment or interfacing components of drive system 900 used to operate piston 364 and move piston 364 relative to sleeve piston 362. While piston 364 is illustrated with piston rod 396 adapted to operate with the drive system 900 to be described herein, piston rod 396 may alternatively comprise the drive interface portion 198 described previously in this disclosure, wherein an interface aperture or attachment aperture 200 is used to associate previously-described piston rod 196 with drive system 700 described previously. Accordingly, drive system 700 may also be used to operate fluid pumping device 300 within this disclosure.

Piston rod 396 is desirably formed of a generally rigid plastic material such as polycarbonate and piston head 394 is desirably formed of a polymeric material such as polyurethane and the like that is overmolded onto a distal end of piston rod 396. Piston head 394 exhibits a generally curved or arcuate-shaped configuration. The polymeric material defining piston head 394 desirably defines one or more circumferential sealing ribs 402 to form a fluid seal with the inner wall of sleeve portion 370 of sleeve piston 362. The curved shape of piston head 394 is desirably shaped to cooperate or engage with a correspondingly curved or arcuate-shaped internal end wall 404 within sleeve portion 370 and opposing the piston head 394 when piston 364 is disposed in the sleeve portion 370 of sleeve piston 362. The "matching" shape between piston head 394 and end wall 404 is desirable because the curved shape of end wall 404 permits sleeve portion 470 to withstand high pressures without significant deformation due to its domed shape. While a pair of sealing ribs 402 is shown on piston head 394, additional spaced ribs or a single such rib may be provided as desired.

The generally X-shaped cross-section of piston rod 396 may be formed by individual flange elements 406 and be reinforced with a proximal disc element 408 located distally forward of drive interface flange 398 as illustrated. Proximal disc element 408 may comprise an overmolded polymeric layer 409 in a generally similar manner the polymeric material forming piston head 394. Polymeric covered proximal disc element 408 generally provides stability to piston 364 as it operates within sleeve portion 370 of sleeve piston 362. It will be appreciated that sealing ribs 402 on piston head 394 form a generally fluid tight seal between piston head 394 and sleeve portion 370 of sleeve piston 362 such that pumping chamber 392 is a generally fluid tight chamber during a static, non-moving situation involving pistons 362, 364 or during dynamic, operational movement of pistons 362, 364 relative to base member 304. While specific materials for forming piston head 394 and polymeric layer 409 were identified in the foregoing, other suitable materials may be used such as those detailed previously in connection with fluid seal elements 120. Desirably, piston head 394 and polymeric layer 409 are the same material, for example, polyurethane. If desired, polymeric layer 409 may be formed onto flange elements 406 so that polymeric layer 409 encompasses the circumferential edge of disc element 408 and, optionally, the outward facing edges of the individual flange elements 406 defining piston rod 396 so that the surfaces contacting the inner wall of sleeve portion 370 of sleeve piston 362 are contacted by polymeric coated elements for sealing and contamination prevention purposes as generally described previously in this disclosure. Again, any polymeric layer on the outward edges of flange elements 406 is typically a result of an injection molding process used to apply polymeric material to form piston head 394 and polymeric layer 409 and may or may not engage the inner wall of sleeve portion 370 in accordance with this disclosure.

While not shown in FIGS. 36-48, sleeve piston 362 may be provided with a dual or double rim end flange similar to end flange 180 which was discussed previously in connection with FIGS. 25-26. As described previously, in connection with FIGS. 25-26, end flange 180 on sleeve portion 170 of sleeve piston 162 comprises two rim flange elements 212 defining an intervening space 214 for interfacing with piston attachment or interfacing elements associated with drive system 700, namely, U-shaped saddle element 750 associated with piston interface structure 748 discussed previously. This modification allows the sleeve pistons 362 in fluid pumps 360 of fluid pumping device 300 to operate with drive system 700 described previously. Accordingly, it is within the scope of this disclosure that drive system 700 may be used to operate fluid pumping device 300.

Figure 50:
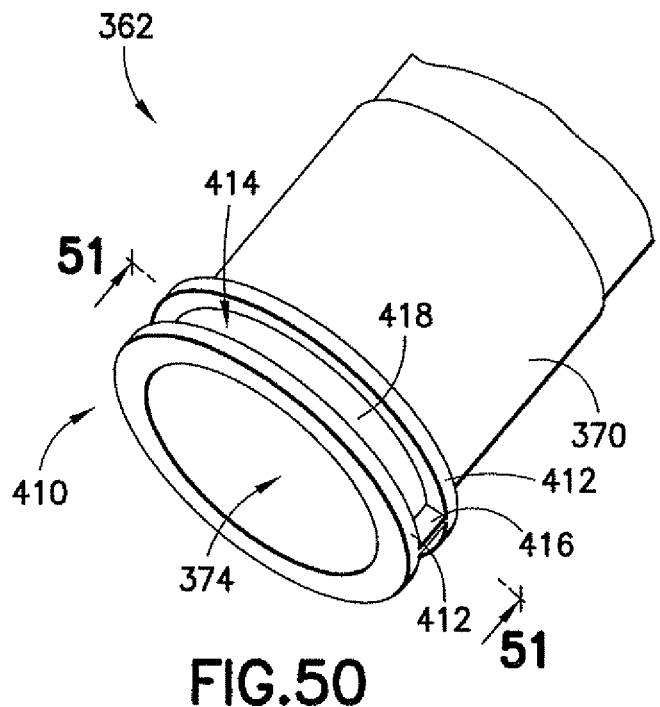
FIG. 50 is a perspective view of a proximal portion of a sleeve piston adapted to interface with the fluid pump actuator shown in FIG. 49.
Figure 51:
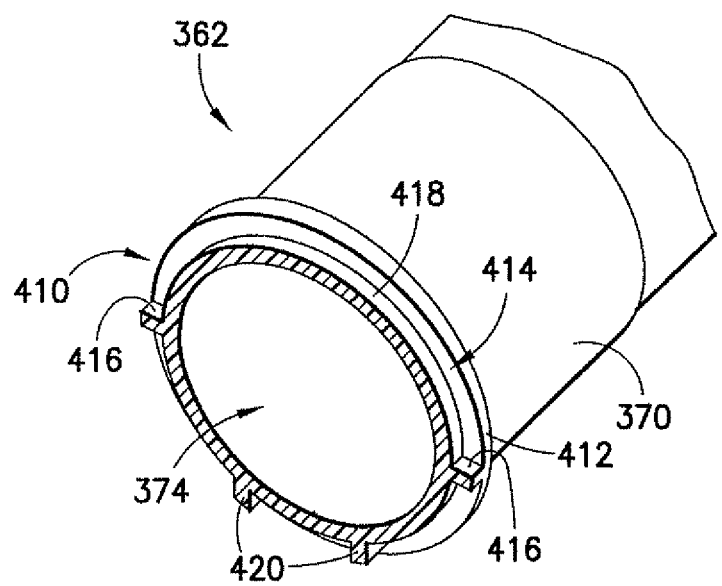
FIG. 51 is cross-sectional view taken along lines 51-51 in FIG. 50.
Figure 52:
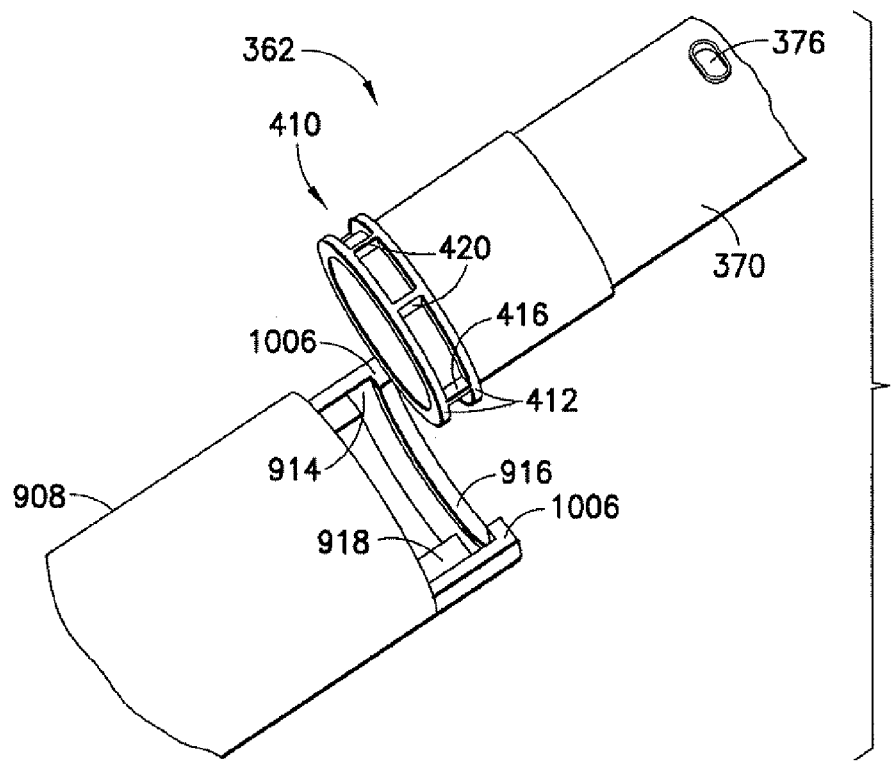
FIG. 52 is a perspective view illustrating a sequence for connecting the sleeve piston shown in FIGS. 50-51 with a sleeve piston positioning device of the fluid pump actuator shown in FIG. 49.
Figure 53:
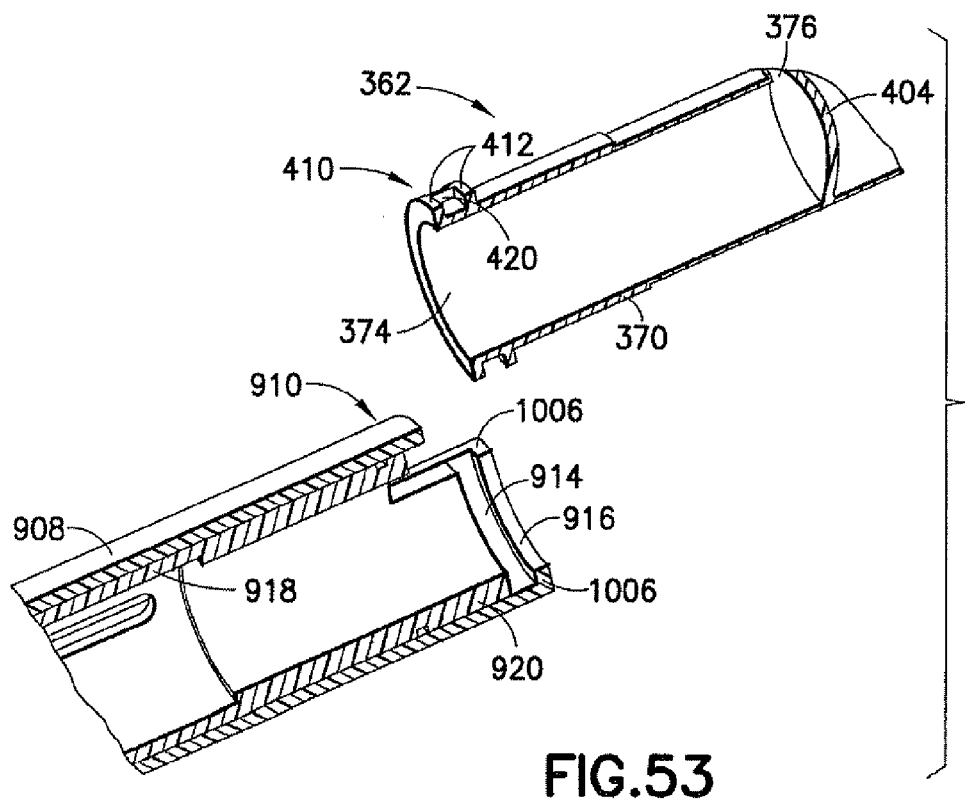
FIG. 53 is a cross-sectional view of the sequence shown in FIG. 52.
Figure 54:
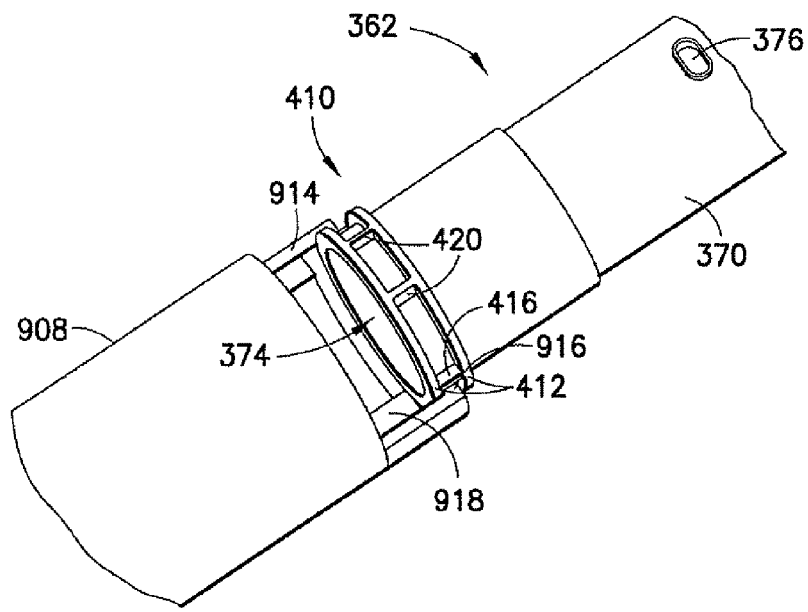
FIG. 54 is a perspective view illustrating the connection of the sleeve piston with the sleeve piston positioning device resulting from the sequence shown in FIGS. 50-51.
Figure 55:
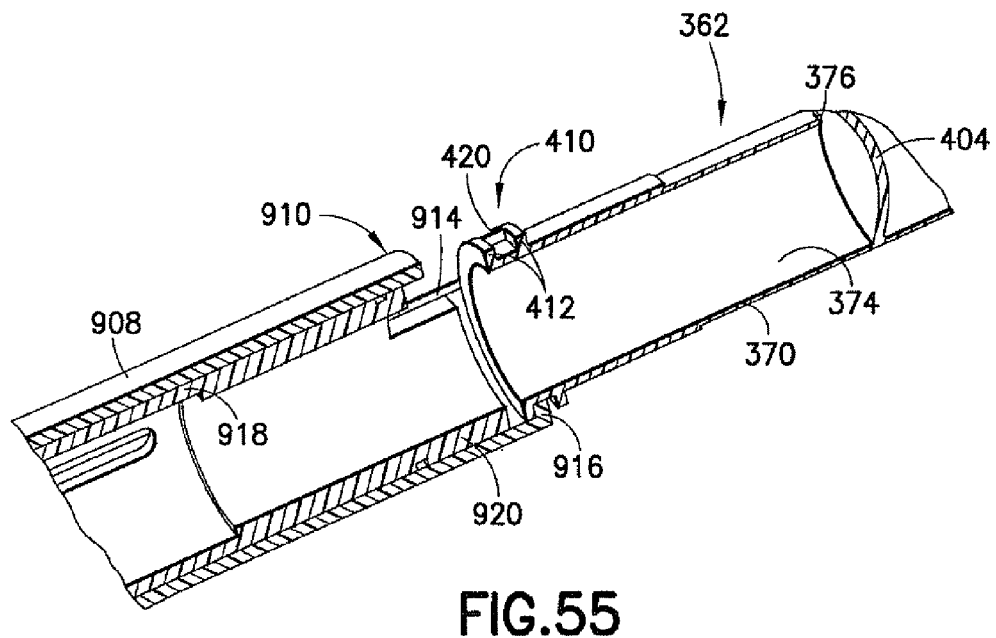
FIG. 55 is a cross-sectional view of the connection shown in FIG. 54.

As mentioned in the foregoing, drive system 900 is to be described herein and comprises certain modifications to drive system 700 detailed previously. In order for sleeve piston 362 to operate with the drive system 900, sleeve portion 370 of sleeve piston 362 may comprise an end flange 410 as generally shown in FIGS. 50-51. Referring briefly to FIGS. 50-51, end flange 410 comprises two spaced apart rim flange elements 412, like flange elements 212 described previously, which define an intervening space 414 for interfacing with piston interfacing elements associated with drive system 900. To ensure that end flange 410 on sleeve portion 370 of sleeve piston 362 will properly and securely engage with the components in drive system 900, laterally located ribs 416 may be provided in intervening space 414 to section the intervening space 414 into an engagement space 418 adapted for engagement with piston interfacing elements associated with the drive system 900. Additionally, it may be desirable to ensure that the engagement of end flange 410 on sleeve portion 370 of sleeve piston 362 with drive system 900 is orientation specific, meaning that the end flange 410 has only one possible or "correct" orientation for interfacing with drive system 900. For this purpose, additional intervening ribs 420 may be provided in intervening space 414 thereby blocking any potential incorrect association of interface of sleeve portion 370 of sleeve piston 362 with drive system 900 as described further herein.

Figure 47:
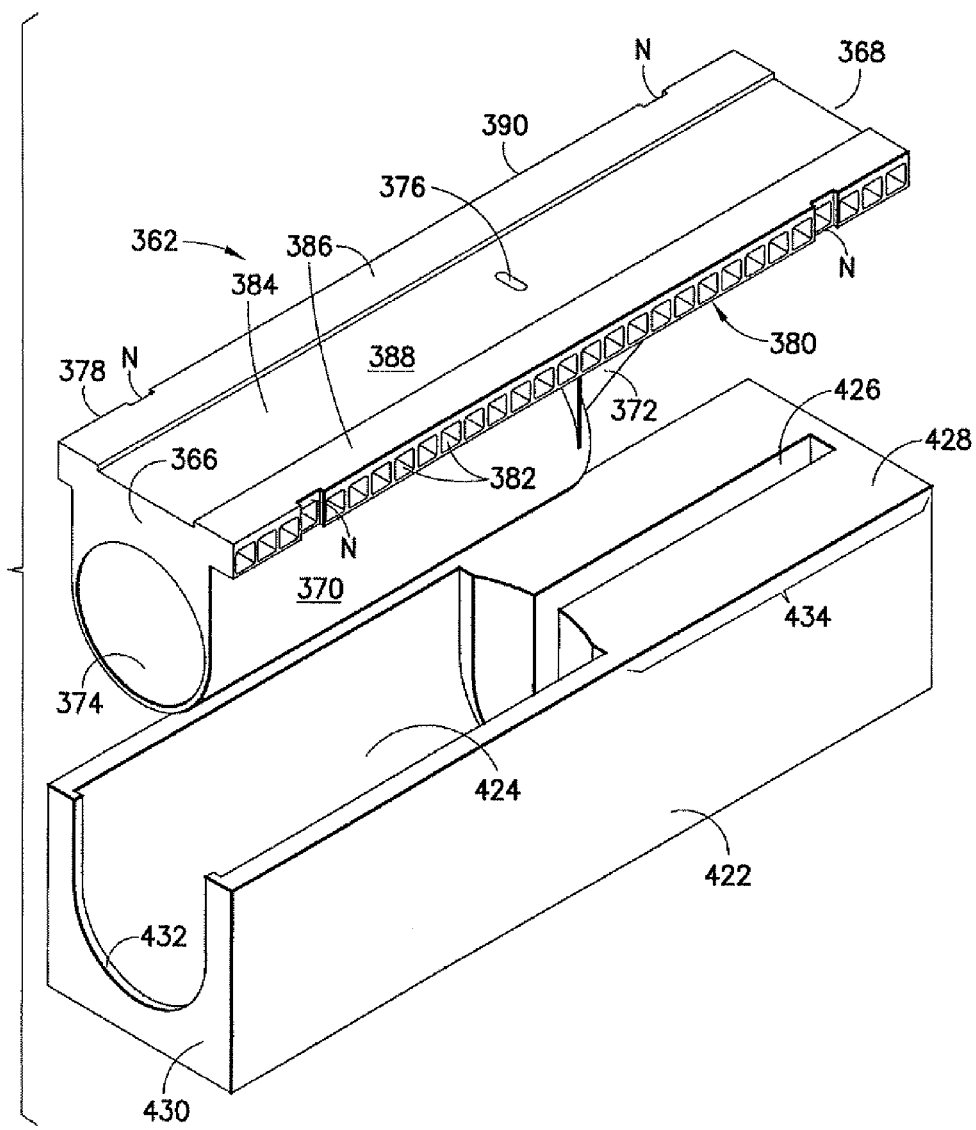
FIG. 47 is a perspective view showing the sleeve piston shown in FIGS. 43A-43B interfacing with a piston drive cradle optionally provided as part of the drive system of FIG. 29.

As described previously, pump support and seal device 820 is desirably incorporated into drive system 700 to support fluid pumping device 100 during operation and, further, to maintain sufficient pressure on fluid seal elements 120 associated with fluid pumps 160 for a generally fluid tight seal to exist between base member 104 and the fluid pumps 160. Pump support device 820 is positioned generally under fluid pumping device 100 to support the same from underneath. FIG. 47 illustrates an additional element that may be associated with pump support device 820. FIG. 47 illustrates a pump support "cradle" 422 which may be associated with pump support device 820 and used to support fluid pumping device 300 in drive system 700 or in drive system 900 to be described herein. Pump support cradle 422 comprises a receiving chamber 424 adapted to accept sleeve portion 370 of sleeve piston 362 therein. A narrow groove or slot 426 is defined in pump support cradle 422 proximal of receiving chamber 424 and opening to the receiving chamber 424 to accept the generally triangular-shaped interface portion 372 that extends rearward from sleeve portion 370 to connect to top portion 378 of sleeve piston 362. Narrow slot 426 provides alignment to the engagement of sleeve portion 370 of sleeve piston 362 in receiving chamber 424. The underside 380 of top portion 378 is seated on a top or upper surface 428 of pump support cradle 422. With sleeve piston 362 seated in pump support cradle 422 sufficient pressure is desirably applied against fluid seal elements 320 (i.e., O-rings) to provide a generally fluid tight seal between base member 304 and the respective fluid pumps 360. It will be appreciated that a front flange 430 defines a front opening 432 to receiving chamber 424. The front flange 430 provides a structure for interference engagement with end flange 180 if sleeve piston 362 is configured to be associated with drive system 700 or, alternatively, with end flange 410 if sleeve piston 362 is configured to be associated with drive system 900 described herein to limit linear movement of the sleeve portion 370 of sleeve piston 362 into pump support cradle 422.

Spring-backed rollers 830 discussed previously in connection with pump support device 820 are desirably used to press against the underside of pump support cradle 422. The force from spring-backed rollers 830 (not shown in FIG. 47, but illustrated in FIGS. 35A-35B discussed previously) is applied through pump support cradle 422 to sleeve portion 370 of sleeve piston 362 to force the sleeve portion 370 upward against fluid seal elements 320. The configuration of pump support device 820 may be altered slightly so that the upward force applied spring-backed rollers 830 to pump support cradle 422 applies this upward force to lateral side areas 390 of the top portion 378 of sleeve piston 362 so that these lateral side areas 390 seat against the underside 310 of base member 304 in planar cavity 306 to compress fluid seal elements 320 between the central area 388 defined between the lateral side areas 390 of the top portion 378 and the underside 310 of the base member 304. To properly direct this upward directed force, it will be appreciated that spring-backed rollers 830 may seat against the underside of pump support cradle 422 in a rear area 434 of the upper surface 428 of the pump cradle support 422, for example, with two spring-backed rollers 830 disposed on opposite sides of narrow slot 426. From the foregoing, it will be appreciated that pump support cradle 422 may, for example, simply seat overtop of pump support device 820 with spring-backed rollers 830 positioned as indicated, but slight adjustments may be needed to the configuration of two-tier platform 822 discussed previously used to support the spring-backed rollers 830 due to the presence of intervening narrow slot 426. Pump support cradle 422 minimizes concentrated forces on the bottom of the sleeve portion 370 from the spring-loaded rollers 830. Accordingly, pump support cradle is 422 is able to distribute applied forces over a larger area of the sleeve portion 370 of sleeve piston 362. Additionally, pump support cradle 422 allows a seal "preload" force to be applied near the top of the sleeve portion 370 of sleeve piston 362 closer to fluid seal elements 320, thereby minimizing deflection that can occur in the sleeve portion 370.

Figure 45:
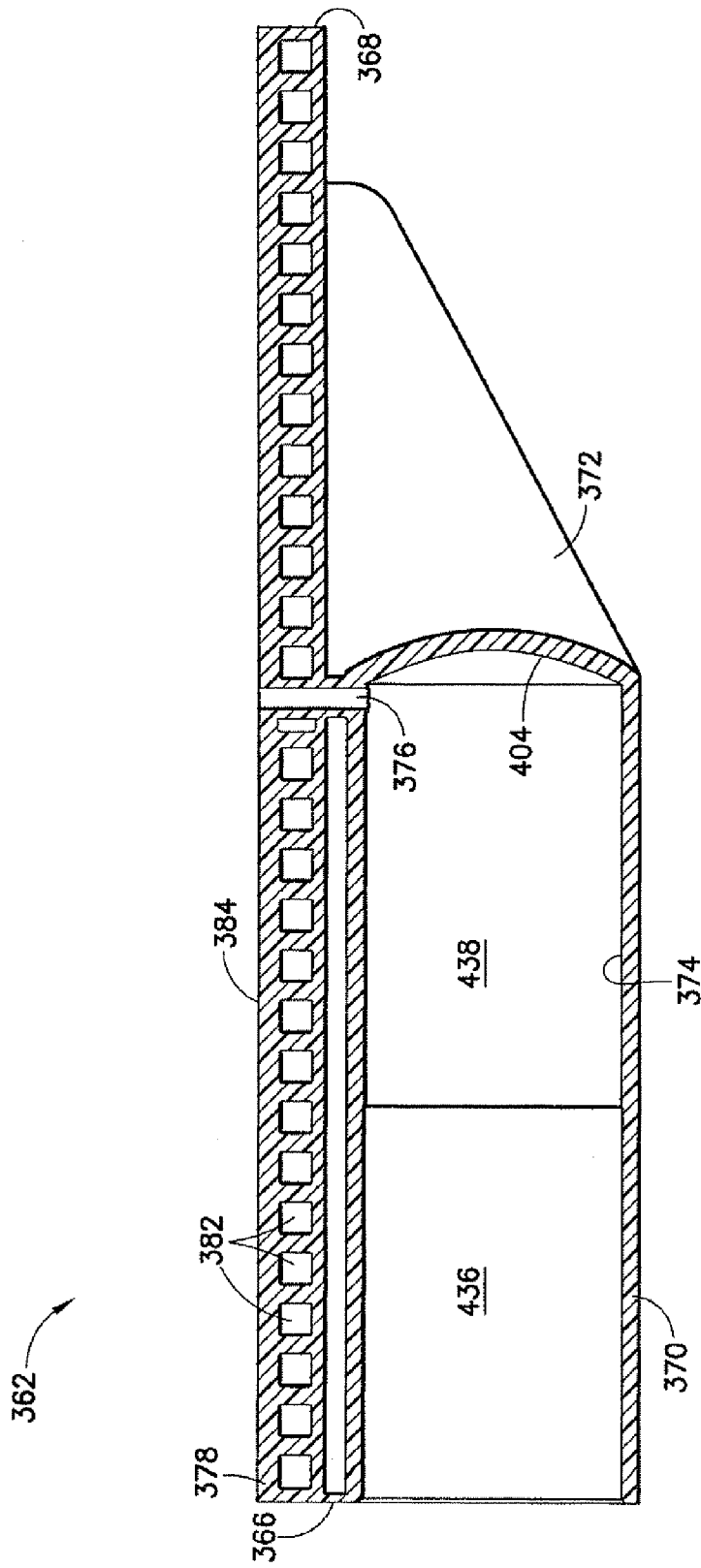
FIG. 45 is a longitudinal cross-sectional view of the sleeve piston shown in FIGS. 44A-44B.
Figure 46:
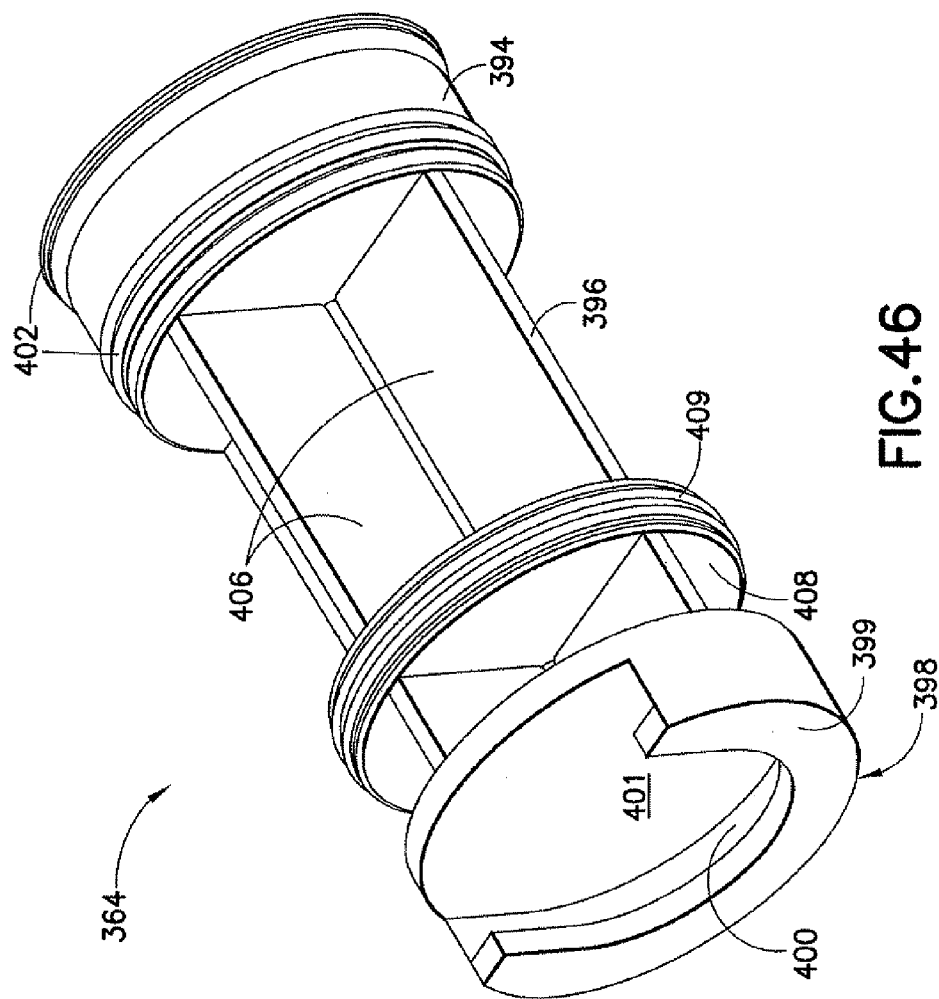
FIG. 46 is a perspective view of an insertion piston for the fluid pumps associated with the fluid pumping device of FIG. 36.

Referring to FIG. 45, it will be noted that the internal cavity 374 defined by sleeve portion 370 of sleeve piston 362 exhibits a slightly smaller diameter proximate to the first end 366 of the sleeve piston 362 than at the second end 368. This slight difference in diameter divides internal cavity 374 into a first portion 436 of slightly larger diameter than a second portion 438. This slight difference in diameter provides a storage position (first larger diameter 436) for piston 364 within sleeve internal cavity 374, and enhanced compression of fluid seal elements 402 on piston head 394 when piston 364 is operating within sleeve internal cavity 374; accordingly, the large diameter first portion 436 may be considered a storage zone for piston 164 wherein piston 364 is stored prior to use of fluid pumping device 300 while the smaller diameter second portion 438 may be considered the operational or working zone for piston 364 in internal cavity 374 during operation of fluid pumping device 300.

Generally, fluid pumping device 300 has only certain structural difference over previously discussed embodiments of fluid pumping device 100. These structural differences do not change the substantive overall operation of fluid pumping device 300 as compared to previous embodiments of fluid pumping device 100. As will be clear from the foregoing, a non-exhaustive listing of the structural differences include: (1) changes in the shape of sleeve piston 362 and base member 304 of pump housing 302; (2) locating manifold ports 346 on side of manifold portion 326 and forming manifold ports 346 as part of manifold side caps 338; and (3) providing a dedicated waste outlet port 352 and pressure sensing port 354 at the bottom of the fluid pumping device 300 and a dedicated patient outlet port 358 at the top of the fluid pumping device 300. As indicated, these changes do not change the substantive overall operation of fluid pumping device 300 as compared to previous embodiments of fluid pumping device 100. Accordingly, previous descriptions relating to the operation of the previous embodiments of fluid pumping device 100 are equally applicable to fluid pumping device 300.

Figure 38:
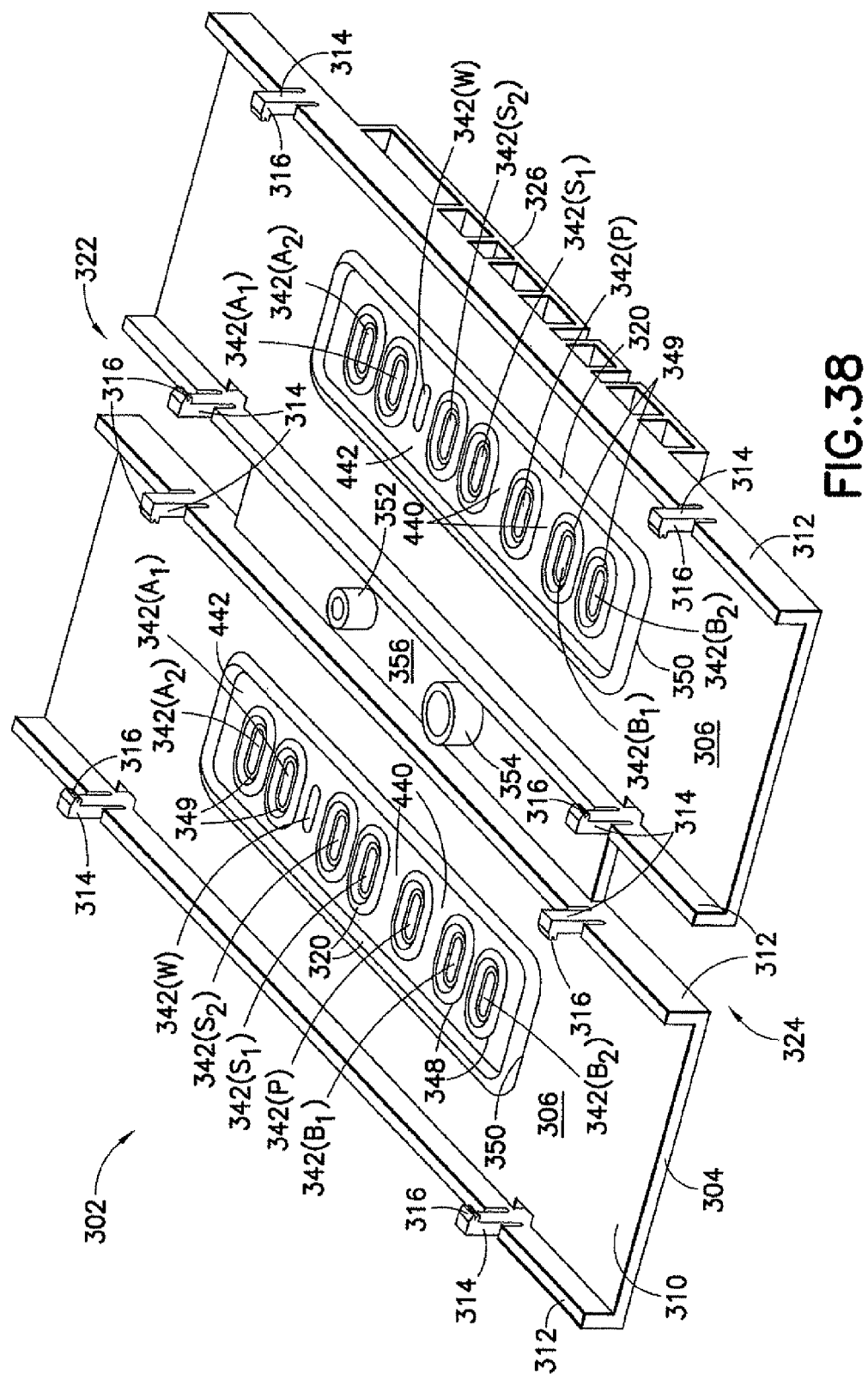
FIG. 38 is a bottom view of a base member of the fluid pumping device of FIG. 36 showing manifold openings in the base member and associated fluid seal elements.
Figure 39:
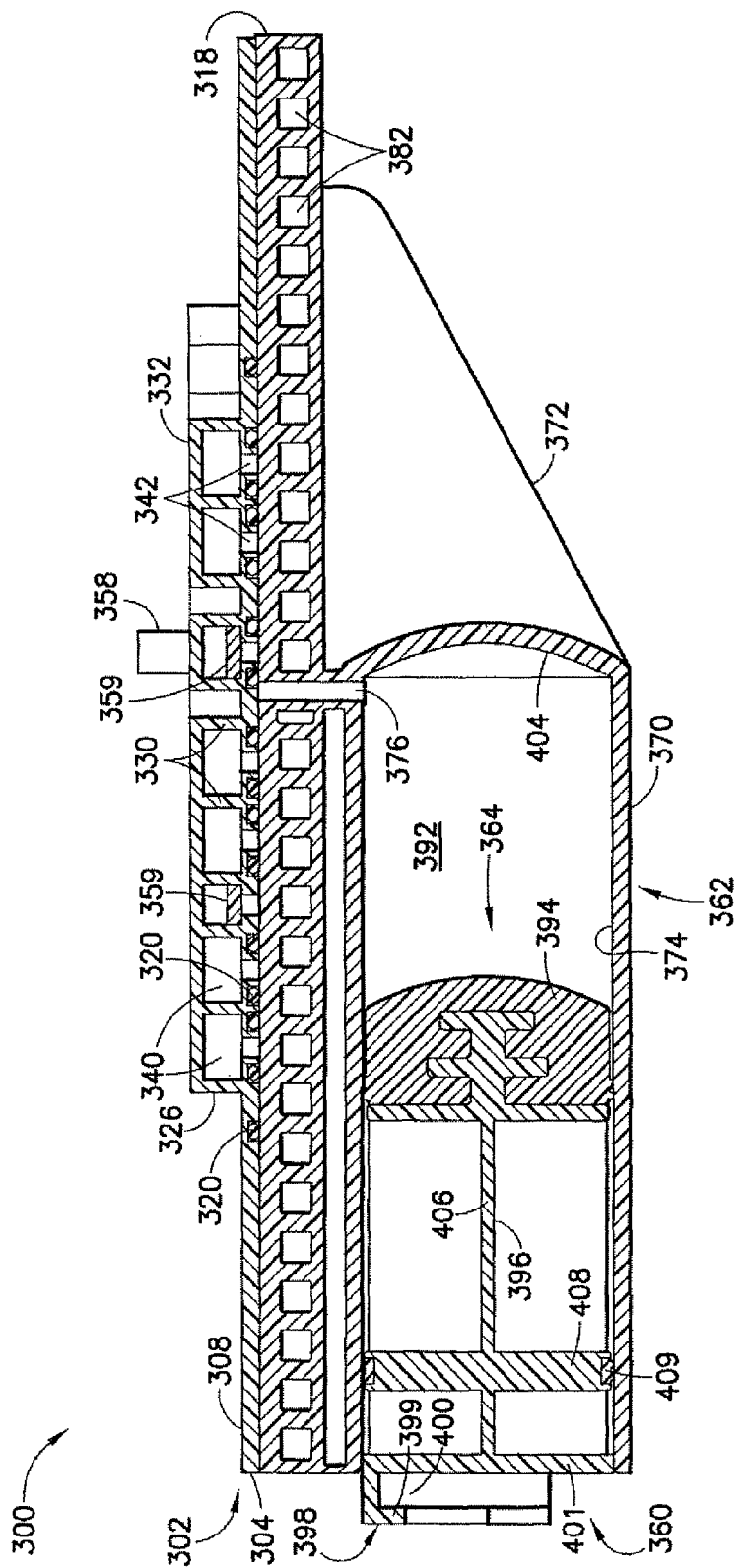
FIG. 39 is a cross-sectional view taken along line 39-39 in FIG. 36.
Figure 40:
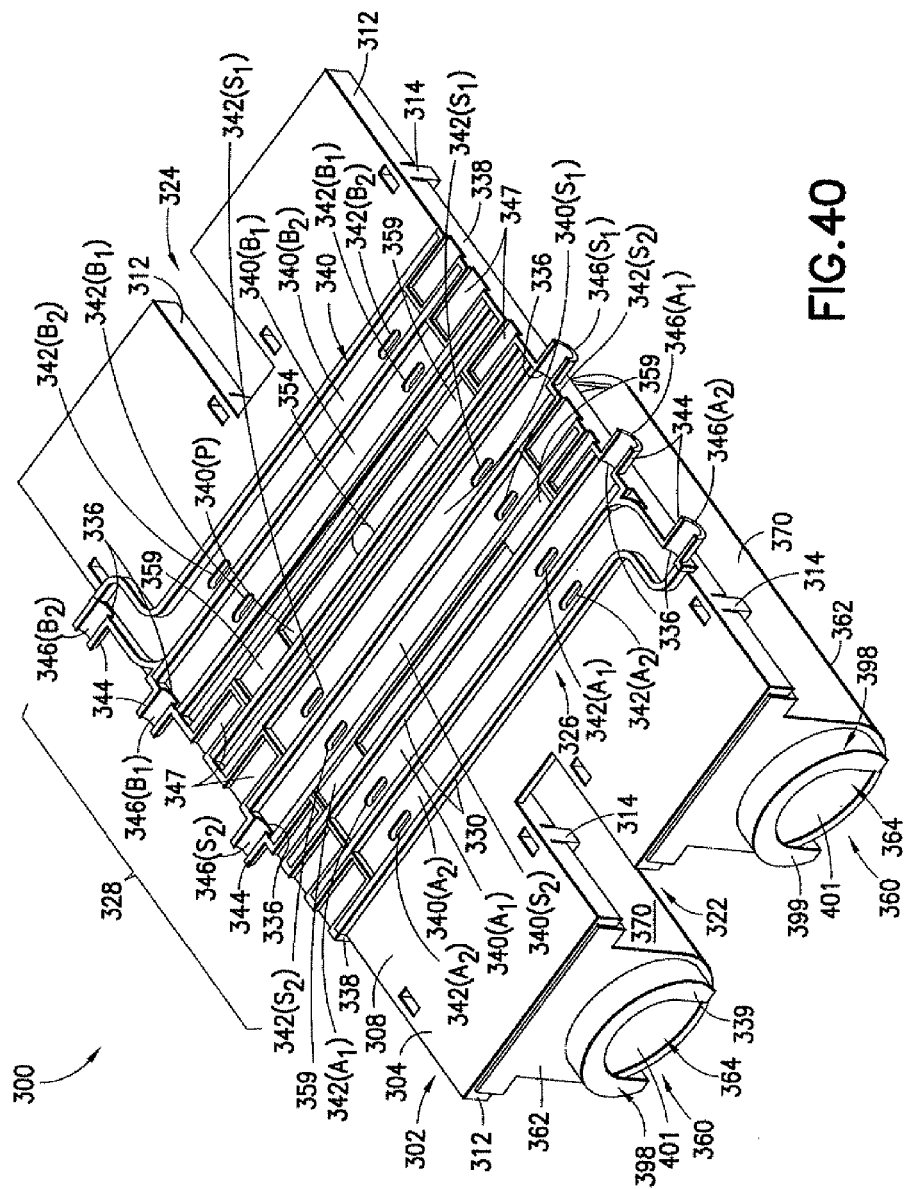
FIG. 40 is a top perspective view of the fluid pumping device of FIG. 36 in which a manifold portion is partially cut away to reveal hidden details.
Figure 41:
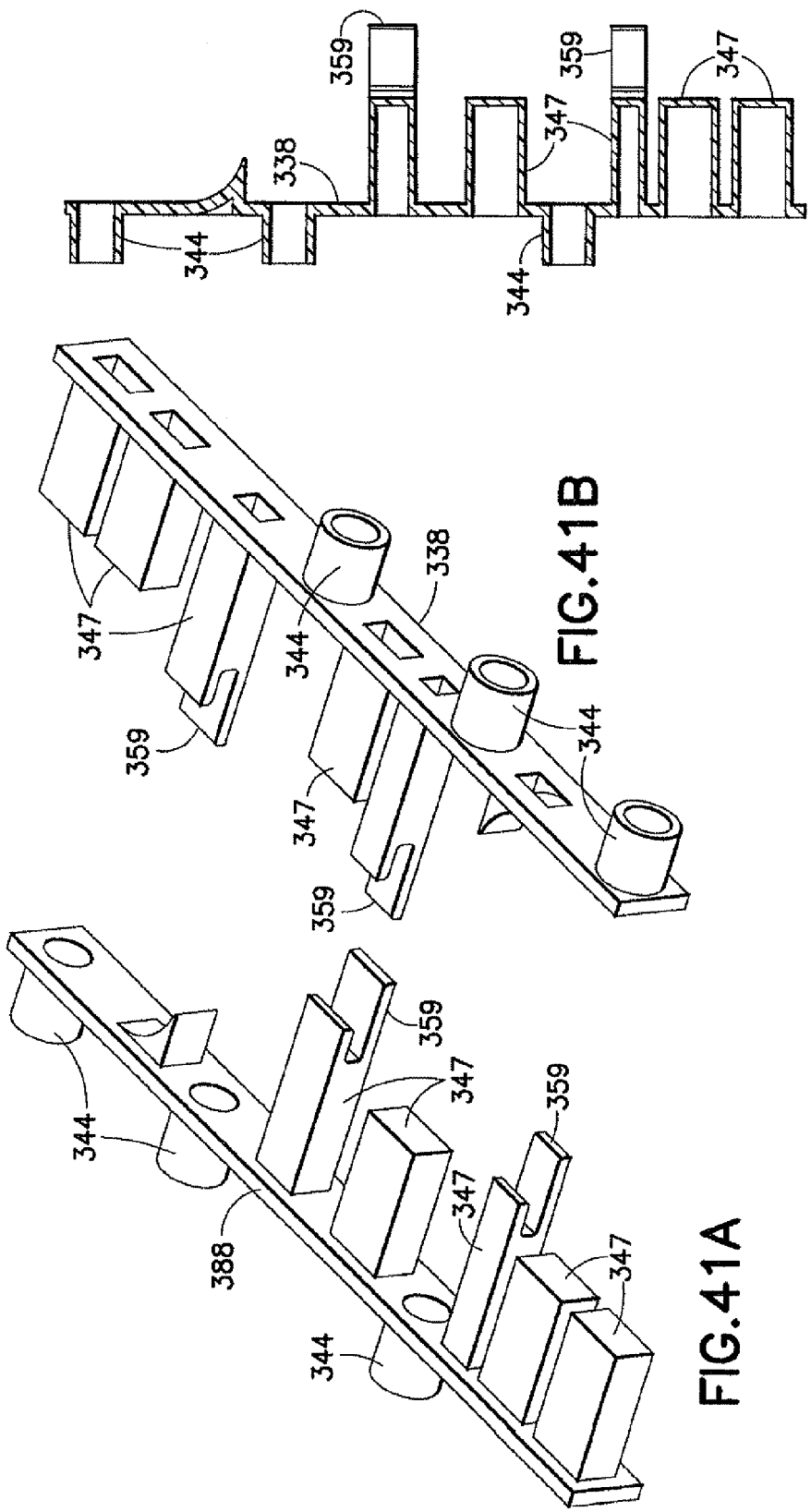
FIGS. 41A-41B are perspective views of manifold side caps associated with the revealed manifold portion shown in FIG. 40.
FIG. 41C is a cross-sectional view of the manifold side caps shown in FIGS. 41A-41B.
Figure 42:
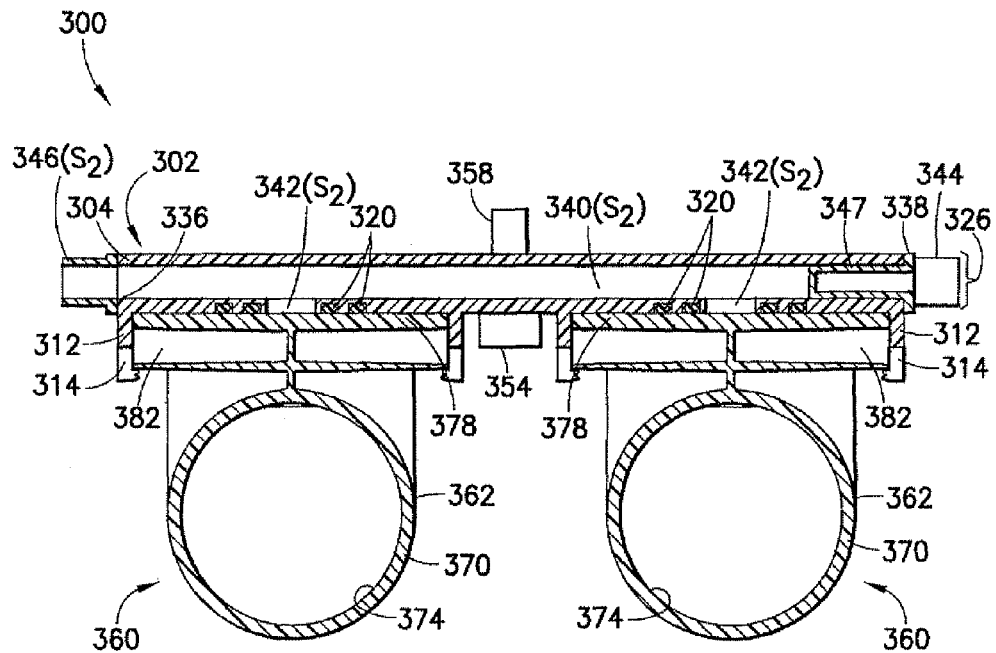
FIG. 42 is a cross-sectional view taken along line 42-42 in FIG. 36.
Figure 43:
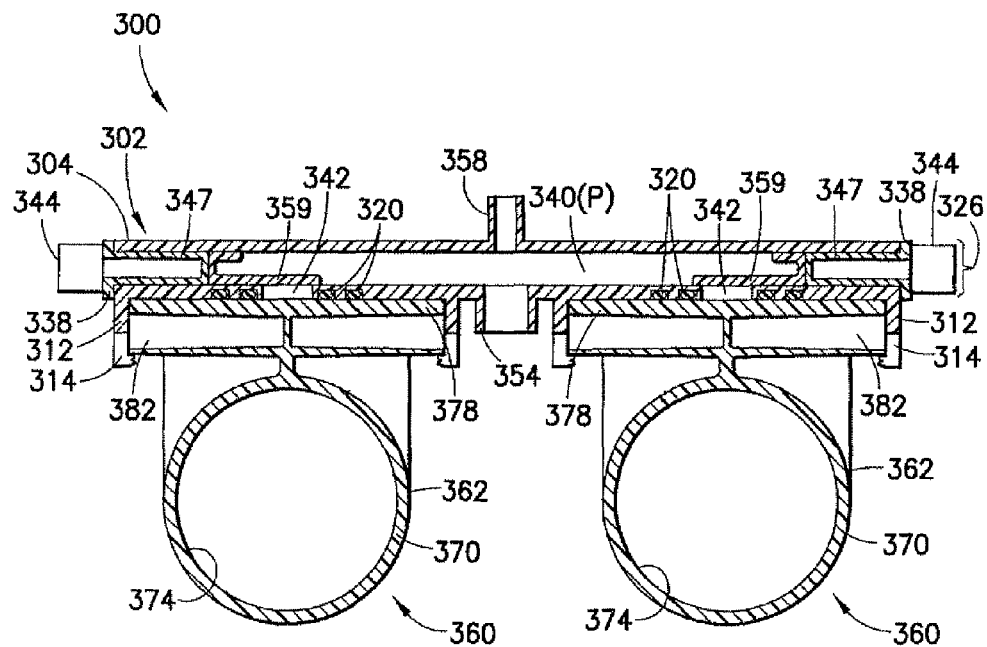
FIG. 43 is a cross-sectional view taken along line 43-43 in FIG. 36.
Figure 44A:
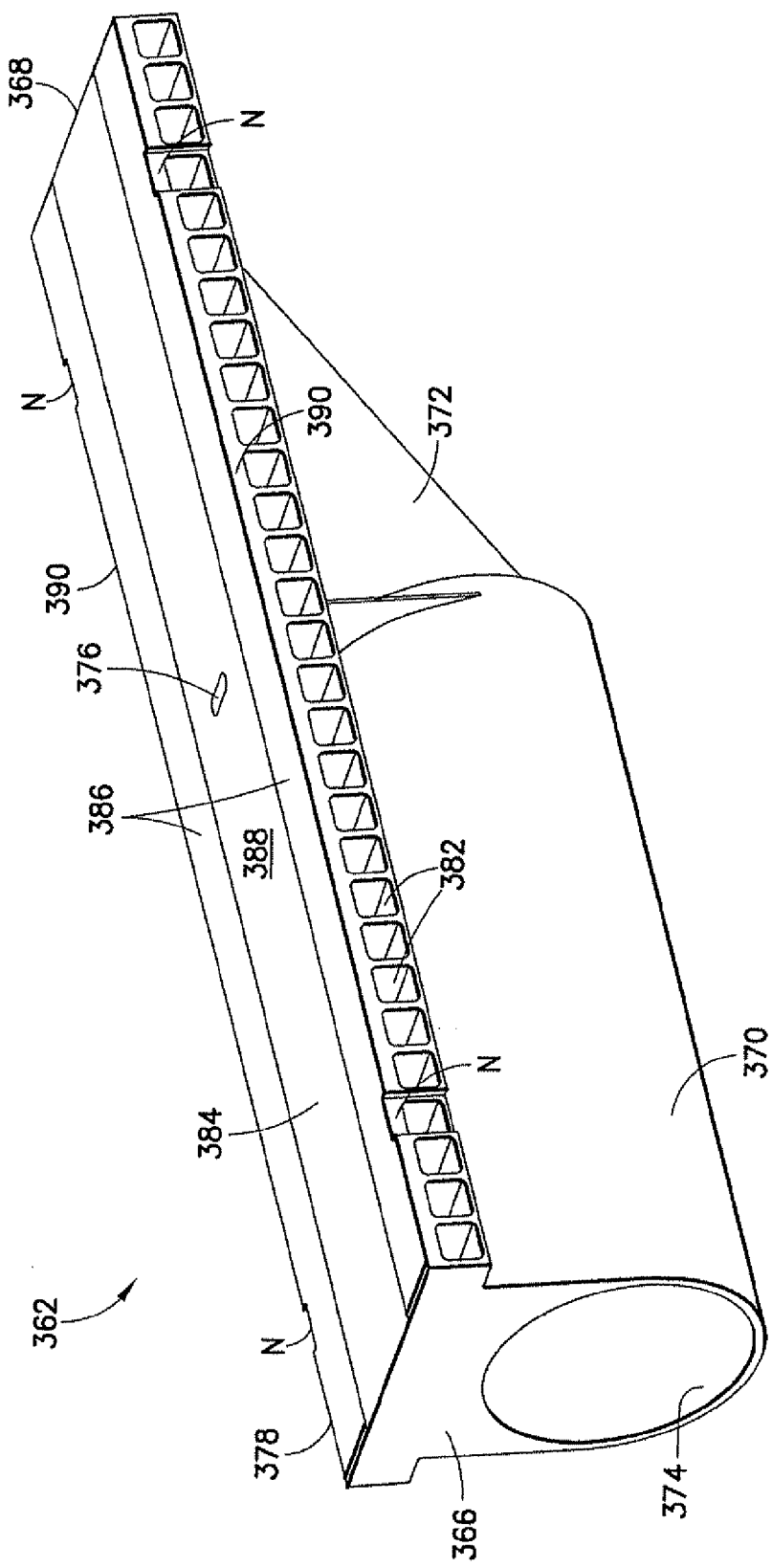
FIG. 44A is a perspective view of a sleeve piston for the fluid pumps associated with the fluid pumping device of FIG. 36.
Figure 44B:
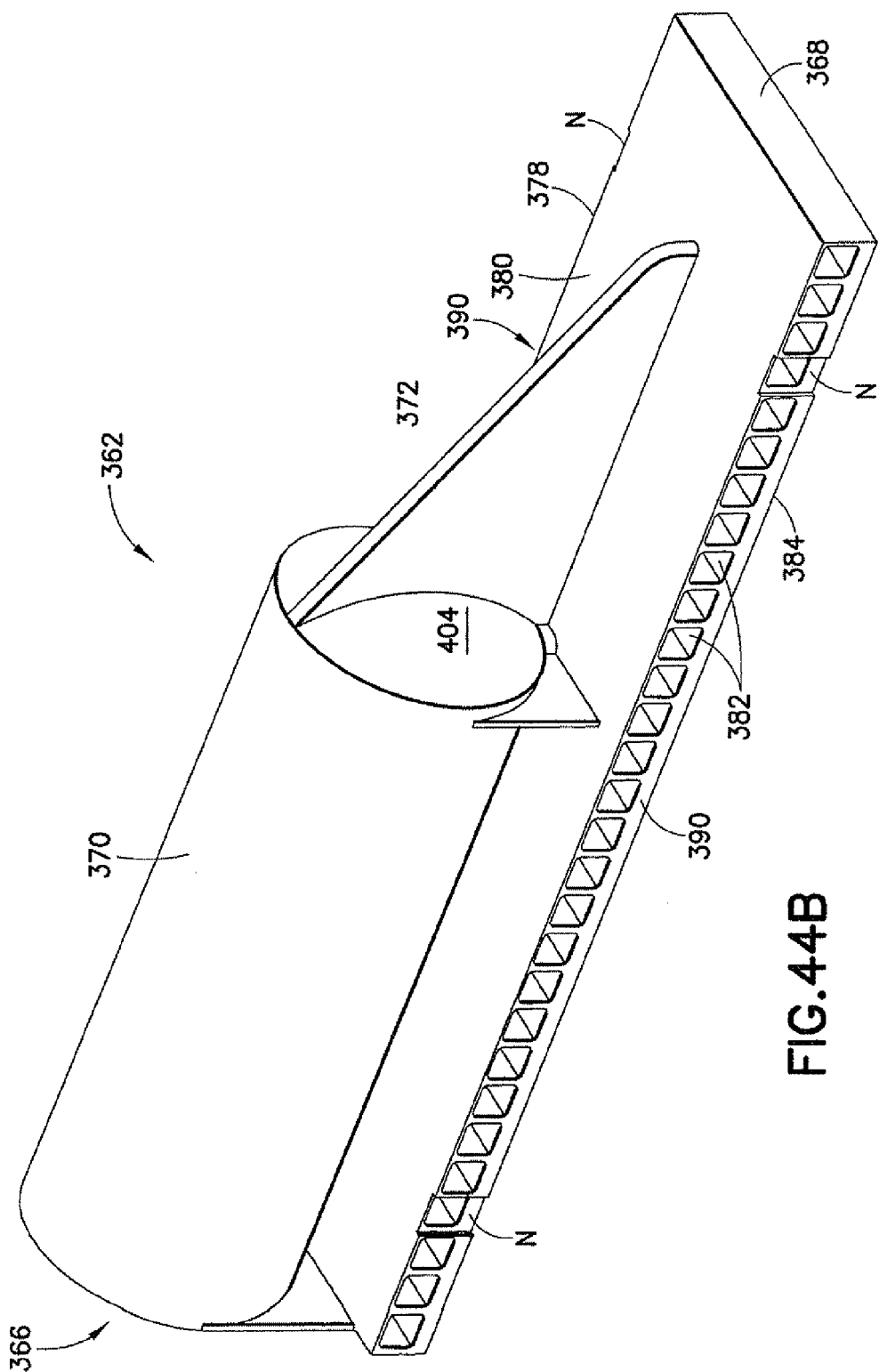
FIG. 44B is a bottom perspective view of the sleeve piston shown in FIG. 44A.

However, in contrast to the previously embodiments of fluid pumping device 100, manifold openings 342 in base member 304 forming the pump housing 302 of fluid pumping device 300 may not exhibit the uniform spacing founding in the manifold openings 142 in base member 104 of fluid pumping device 100. As best shown in FIG. 38, isolation areas 440 may be provided between certain manifold openings 342 in base member 304. Such isolation areas or gaps 440 are provided between manifold openings 342 that carry different types of fluids, for example, saline $S_1$, $S_2$ versus contrast fluid $A_1$, $A_2$ and contrast fluid $B_1$, $B_2$. Isolation blanks or gaps 440 desirably prevent adjacent manifold ports 342 carrying different types of fluids from being connected together, even momentarily, while sleeve port 376 in sleeve portion 370 of sleeve piston 362 crosses over neighboring or adjacent O-ring fluid seal element 320 in the present embodiment. Such adjacent O-ring fluid seal elements 320 can potentially define a momentary shunting or "short circuit" fluid path as sleeve port 376 in sleeve portion 370 of sleeve piston 362 crosses over the adjacent O-rings; isolation blanks 440 desirably prevent this possible occurrence. When sleeve port 376 is aligned with a desired manifold opening 342, the surrounding O-ring fluid seal element 320 fluidly seals the sleeve port 376 to the selected manifold opening 342. When sleeve piston 362 is actuated to move away from this location, this O-ring fluid seal element 320 still seals the selected manifold opening 342 but the sleeve port 376 in the sleeve piston 362 is not re-sealed until it is substantially aligned with the next selected manifold port 342 and its surrounding fluid seal element 320. To prevent leakage of fluid and possible ingress of contaminants from around sleeve piston 362 entering pumping chamber 392 via sleeve port 376 while the sleeve piston 362 is in transition, the surrounding perimeter O-ring fluid seal element 320 disposed in circumferential or perimetrical groove 350 in the underside 310 of base member 304 surrounds the entire set of individual O-ring fluid seal elements 320 associated with the respective manifold openings 342. As it may be possible for fluid to leak from sleeve piston 362 while the sleeve piston 362 is in transit between manifold openings 342, an interior area 442 of the underside 310 of base member 304 that is enclosed by the circumferential or perimeter O-ring fluid seal element 320 is connected directly to waste outlet port 352 to allow fluid to drain via waste fluid line 22 to an appropriate medical fluid waste container.

An advantage of fluid pumping device 100, 300 described in the foregoing is that devices 100, 300 may deliver precisely controlled volumes of fluid (same volume) with each ejection stroke regardless of outlet back pressure encountered at patient manifold outlet port 146g and patient outlet port 358, respectively, in the foregoing devices 100, 300 by proper control of the displacement of piston 164, 364 in each fluid pump 160, 360. Likewise, flow rate delivered is also very repeatable, regardless of the outlet back pressure encountered by proper control of the velocity of piston 164, 364 in each fluid pump 160, 360. In certain instances, for example, if the selected manifold opening 142, 342 is unexpectedly restricted or blocked, operation of piston 164, 364 in sleeve piston 162, 362 results in an incomplete fill in pumping chamber 192, 392 because the operation of piston 162, 362 in it opposing sleeve piston 164, 364 is unable to fully fill the pumping chamber 192, 392 with the desired fluid volume. Such a blockage situation can occur, for example, upstream of the manifold opening 142, 342 such as a restriction or occlusion being present in fluid line 18 connecting a fluid container 16 to the selected manifold inlet port 146, 346 associated with the selected manifold opening 142, 342. In this situation, the fluid pumps 160, 360 in fluid pumping devices 100, 300 will not deliver the "expected" volume of fluid.

Figure 48:
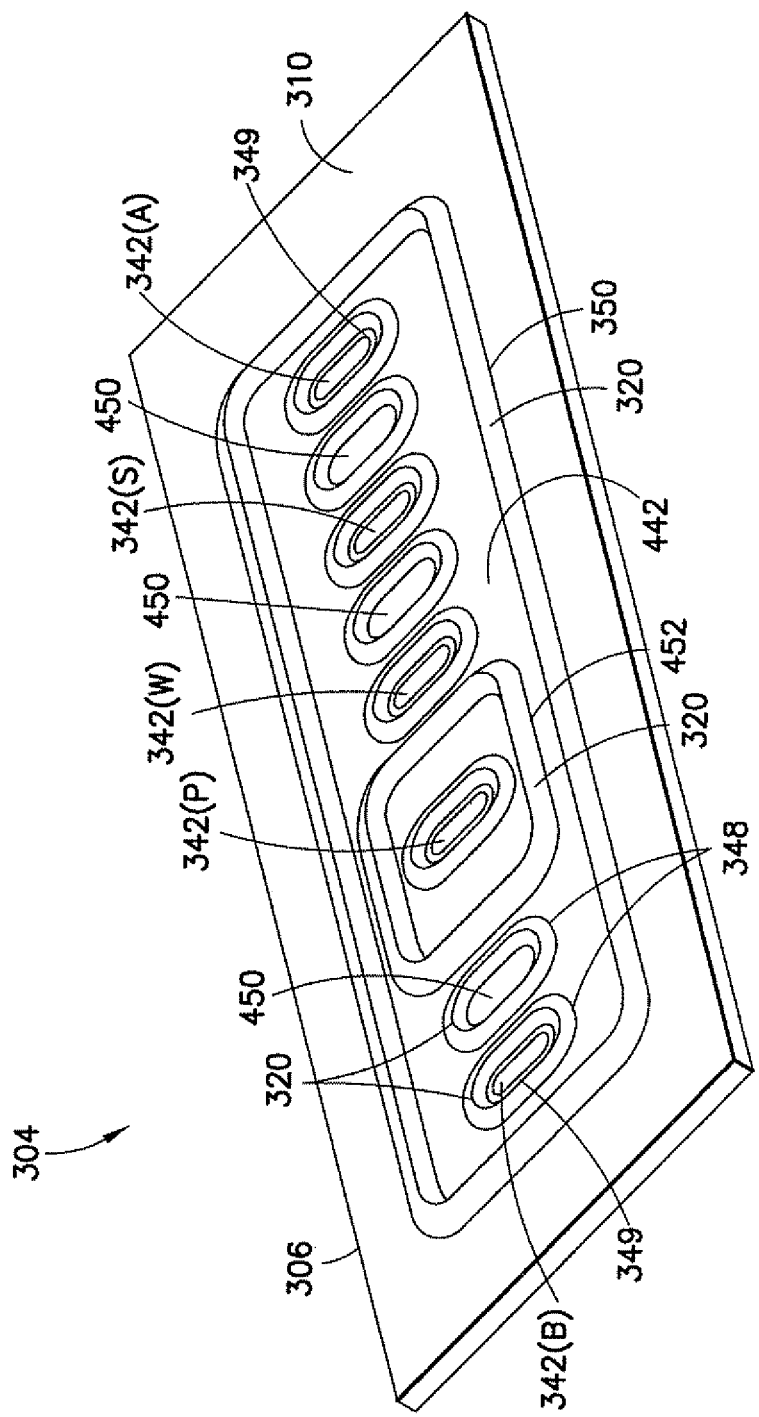
FIG. 48 is a bottom view of a cavity in the base member of the fluid pumping device of FIG. 36 showing an alternative configuration of the manifold openings and associated fluid seal elements shown in FIG. 38.
Figure 49:
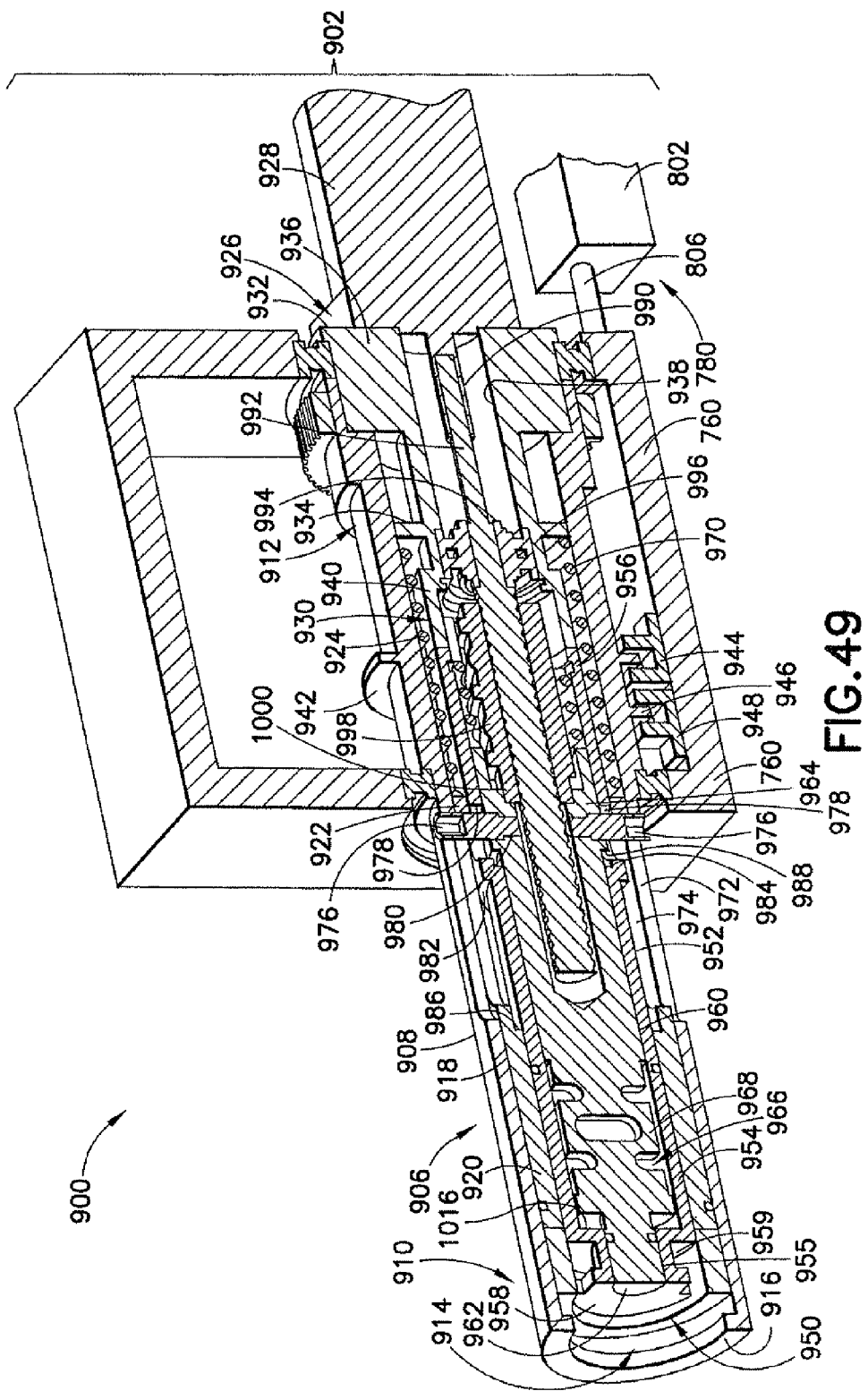
FIG. 49 is a perspective cross-sectional view of an alternative fluid pump actuator which may be used in the drive system shown in FIGS. 28-35.

The following discussion describes a process which may be used to detect this incomplete or under-fill condition, and FIG. 48 illustrates an alternative arrangement of manifold openings 342 in base member 304 and an alternative arrangement of fluid seal elements 320 in the underside 310 of the base member 304 to identify and address this situation. FIG. 48 is intended to illustrate an exemplary planar cavity 306 in base member 304 comprising the alternative arrangement of manifold openings 342 and fluid seal elements 320. It will be clear that the modified planar cavity 306 shown in FIG. 48 would be used in each fluid pump 360 in fluid pumping device 300 to implement the detection and correction process described herein and such a modification may also be made to the embodiments of fluid pumping device 100 described previously.

In a "normal" operational mode, meaning that a restriction or occlusion situation is not encountered, as piston 364 is retracted relative to a stationary sleeve piston 362, a known and substantially precise volume of fluid is pulled into the pumping chamber 392 and this known volume is ejected by reverse operation of piston 364 at a controlled velocity resulting in a desired and known flow rate. In a restriction or occlusion situation, retraction of piston 364 results in an incomplete or under-fill of pumping chamber 392 because the pumping chamber 392 does not fill quickly enough due to the restriction, for example, in the drawing fluid line 18. Because of the incomplete fill, air bubbles are likely present in pumping chamber 392 and pressure in the pumping chamber 392 is less than system pressure or under vacuum. As piston 364 moves in a pumping or ejection stroke, the air bubbles compress but the fluid volume ejected from pumping chamber 392 is less than expected and desired due to the presence of the air bubbles. One possible result of a vacuum condition is that contaminated fluid could be drawn into pumping chamber 392 via waste outlet port 352 and/or patient outlet port 358 when sleeve piston 362 is moved to place the pumping chamber 392 in fluid communication with one of these ports. Moreover, it is desirable to identify the under-fill situation and take corrective actions automatically or to alert an attendant operator of fluid delivery system 10.

To identify the foregoing restriction or occlusion situation, FIG. 48 illustrates a possible arrangement of manifold openings 342 in base member 304 and an alternative arrangement of fluid seal elements 320 in the underside 310 of the base member 304 to detect and address this situation. In FIG. 48, three manifold openings 342 comprise openings or ports for a contrast A fluid (342(A)), a contrast B fluid (342(B)), and saline S (342(S)). It will be appreciated that these three "inlet" manifold openings 342 connect to respective fluid passageways 340 connected to manifold ports 346 connected to respective sources of the foregoing fluids. Two outlet manifold openings 342 comprise a patient outlet manifold opening 342(P) associated with the fluid passageway 340 associated with patient outlet port 358 and a waste outlet manifold opening 342(W) associated with the fluid passageway 340 associated with waste outlet port 352. In addition, FIG. 48 shows that three blanked detection ports 450 between each manifold inlet opening 342 and the adjacent manifold inlet opening 342. The blanked detection ports 450 define one or more sealed areas where sleeve piston 362 in each fluid pump 360 may be moved to a "shut-off" position where the sleeve piston 362 is not connected to any inlet or outlet manifold opening 342 and so that sleeve port 376 in sleeve portion 370 of the sleeve piston 362 is completely sealed off. As shown, an O-ring fluid seal element 320 is disposed in the respective grooves 348 defined about each manifold opening 342 and a perimeter O-ring fluid seal element 320 is disposed in perimeter or circumferential groove 350 disposed about the entire set of sealed manifold openings 342. As also shown in FIG. 48, a second surrounding groove 452 may be defined in the underside 310 of base member 304 about the patient manifold outlet port 342(P) which carries an additional O-ring fluid seal element 320 for additional isolation of patient manifold outlet port 342(P).

In a general operating sequence for the foregoing arrangement in FIG. 48, sleeve piston 362 and insertion piston 364 are moved until sleeve port 376 in the sleeve portion 370 of the sleeve piston 362 is aligned with a selected manifold inlet opening 342. Piston 364 is retracted relative to sleeve piston 362 to pull fluid from the corresponding fluid passageway 340 connected to the selected manifold inlet opening 342. Once piston 364 has been retracted to fill pumping chamber 392 with a desired volume of fluid, pistons 362, 364 are moved together until sleeve port 376 in sleeve portion 370 of the sleeve piston 362 is aligned with a selected one of the blanked detection ports 450 and piston 364 is then advanced. If pumping chamber 392 contains air bubbles, piston 364 will advance until the air bubbles are compressed. The distance piston 364 advances into sleeve piston 362 for a given amount of applied force indicates the volume of air bubbles present in the pumping chamber 392. If pumping chamber 392 contains no air bubbles, no significant movement of piston 364 is possible and proper filling of the pumping chamber 392 has occurred and an ejection cycle may commence. Any movement of pistons 362, 364 is known from home sensors 746, 796 in drive system 700 as described previously.

It is possible to assess the degree of filling of pumping chamber 392. A first possibility is to use a force measurement sensor, such as a load cell in the drive system 900 to be described herein, to measure the force that is required to advance piston 364 a set, known distance. Such a force measurement sensor generally measures the force being applied to piston 364, and drive system 900 incorporates a load cell for this purpose. Alternatively, piston 364 may be advanced until the force measurement sensor registers a predetermined force level corresponding to a reasonably high pressure, for example, approximately 200 psi. The corresponding distance piston 364 advances may be obtained from home sensor 746. If it was possible to advance piston 364 a significant distance, for example, more than 0.020 or 0.030 inches, at a relatively low pressure, for example, less than 50 psi, then it may be concluded that pumping chamber 392 is not completely full of fluid. If piston 364 moved very little, for example, less than 0.020 or 0.030 inches, and developed a high force corresponding to a high fluid pressure, for example, more than 100-200 psi, then it may be concluded that pumping chamber 392 is completely full of fluid. If pumping chamber 392 is completely full of fluid, piston 364 may be returned to its original position by retracting the piston 364 by 0.020 or 0.030 inches or whatever distance the piston 364 was advanced. Pistons 362, 364 may be moved until sleeve port 376 in sleeve portion 370 of the sleeve piston 362 is aligned with manifold opening 342(P) associated with patient outlet port 358 and an ejection cycle may commence. If it is concluded that pumping chamber 392 is not full of fluid, the ejection cycle may be interrupted automatically by an associated control device and an error condition indicated. If the volume shortage is determined to be relatively small, an ejection cycle could continue, optionally with a warning message issued by the control device indicating the underdelivery of fluid. Other corrective action could include ejecting the contents of pumping chamber 392 to the waste outlet port 352.

Turning now to FIGS. 49-64, drive system 900 will now be described. As noted in the foregoing, fluid pumping device 300 may be adapted to operate with drive system 900 but it will be appreciated that the interface components associated with fluid pumping device 300 that make the fluid pumping device 300 operable with drive system 900 may also be added to fluid pumping device 100 described previously in connection with FIGS. 25-26 so that fluid pumping device 100 is likewise compatible with drive system 900. Generally, as fluid pumping devices 100, 300 are intended to deliver fluids under significant pressure to patient fluid path 12, it is desirable for there to be a robust interconnection between the components of the associated drive system and the driven components of fluid pumps 160, 360, namely pistons 162, 164 and 362, 364. In drive system 700 described previously, piston interface elements were detailed that enabled such robust connections to pistons 162, 164. Drive system 900 also enables robust connections between piston interface elements and pistons 362, 364 to be made wherein there are tight or close tolerance interconnections between the piston interface elements and pistons 362, 364. The following discussion of drive system 900 describes an alternative fluid pump actuator 902 which comprises a piston positioning device 904 that combines the piston interfacing functions of piston positioning devices 704(1), 704(2) discussed previously in connection with drive system 700 into one mechanical interfacing device. Generally, fluid pump actuator 902 in this embodiment comprises the same sled carriage 760 and sled drive system 780 discussed previously and a description of these components is omitted hereafter. In other words, piston positioning device 904 is disposed on sled carriage 760 in a similar manner to piston positioning devices 704(1), 704(2). It will be apparent from the schematic representation in FIG. 49 that sled drive system 780 is used to support fluid pump actuator 902 in the same manner as fluid pump actuator 702 described previously and, in particular, piston positioning devices 704(1), 704(2) of the fluid pump actuator 702.

In fluid pump actuator 902, piston positioning device 904 comprises a sleeve piston positioning device 906 and an insertion piston positioning device 950. Sleeve piston positioning device 906 comprises a sleeve outer drive tube 908 having a first or distal end 910 and a second or proximal end 912. Distal end 910 defines an open distal area 914 and comprises an inward extending radial flange 916 for engaging sleeve piston 362 as described herein. To aid in understanding the components of sleeve piston positioning device 906, it is noted that sleeve piston 362 is illustrated in various figures of FIGS. 49-64 without top portion 378 to simplify explanation of the interface between sleeve piston 362 and the sleeve piston positioning device 906. A sleeve inner drive tube 918 is concentrically positioned within sleeve outer drive tube 908. Sleeve inner drive tube 918 has a first or distal end portion 920 located within the sleeve outer drive tube 908 and a second or proximal end portion 922 disposed within the sleeve outer drive tube 908 to interface with a first spring 924. First spring 924 acts between the proximal end portion 922 of sleeve inner drive tube 918 and an interface element 926 extending at least partially into the proximal end 912 of sleeve outer drive tube 908.

Interface element 926 is generally adapted to associate the sleeve positioning device 906 and the insertion piston positioning device 950 with a drive motor 928. In particular, interface element 926 comprises a distal end 930 extending into sleeve outer drive tube 908 and a proximal end 932 which is seated within the proximal end 912 of the sleeve outer drive tube 908 and which engages drive motor 928. Desirably, the proximal end 932 of interface element 926 is secured to the motor housing of the drive motor 928. Interface element 926 further comprises, in an intermediate location between the distal and proximal ends 930, 932, a radial flange 934 against which first spring 924 engages. Accordingly, first spring 924 acts between the proximal end portion 922 of sleeve inner drive tube 918 and radial flange 934. The proximal end 932 of interface element 926 comprises a proximal cylindrical portion 936 that seats into the open proximal end 912 of sleeve outer drive tube 908. Interface element 926 defines a central bore 938 therethrough and further comprises a slightly enlarged distal cylindrical portion 940.

In the assembled configuration, sleeve inner drive tube 918 is disposed within sleeve outer drive tube 908 with first spring 924 extending between the proximal end portion 922 of the sleeve inner drive tube 918 and radial flange 934 on interface element 926. A radial sensor flange 942 is desirably provided on sleeve outer drive tube 908 and may extend circumferentially about the sleeve outer drive tube 908. Radial sensor flange 942 may be formed integral with sleeve outer drive tube 908 or, if desired, be a separate component secured to the body of the sleeve outer drive tube 908. Radial sensor flange 942 is adapted to be associated with a first sensor 944 mounted to sled carriage 760. If desired, an additional or second sensor flange 946 may be provided on sleeve outer drive tube 908 distally forward of sensor flange 942 and which is associated with an additional or second sensor 948 mounted to sled carriage 760. Sensors 944, 948 provide inputs to an associated control device of the angular or rotational positioning of sleeve outer drive tube 908 relative to sled carriage 760; the position of sled carriage 760 may be obtained or known from sensor plate 772 and home sensor 794 as described previously.

Insertion piston positioning device 950 is generally disposed concentrically within sleeve inner drive tube 918 of sleeve positioning device 906. Insertion piston positioning device 950 comprises a piston outer drive tube 952 comprising a distal end portion 954 defining a central aperture 955 and a proximal end portion 956. Distal end portion 954 comprises a distal flange 958 adapted to engage or interface with drive interface flange 398 and, in particular, the U-shaped slot 400 defined by flange lip 399 of the drive interface flange 398 formed at the proximal end of piston rod 396 of insertion piston 364, described previously. Distal end portion 954 defines a perimetrical or circumferential recess 959 so that distal flange 958 and drive interface flange 398 may seat together in a corresponding mating engagement. A piston drive shaft 960 is disposed internally in piston outer drive tube 952 and comprises a solid distal end portion or tip 962, a generally hollow proximal end portion 964, and intermediate portion 966 which is desirably a force measurement sensor 968, such as a load cell, which allows an associated control device to measure total force applied to the insertion piston 362, for example, for the reasons noted previously in connection with FIG. 48. Solid distal end portion 962 is adapted for inserted engagement in central aperture 955 defined in the distal end portion 954 of piston outer drive tube 952. Proximal end portion 956 of piston outer drive tube 952 is desirably adapted for abutting relationship with the distal cylindrical portion 940 of interface element 926. A second spring 970 is situated within piston outer drive tube 952 to engage the proximal end portion 964 of piston drive shaft 960. Desirably, second spring 970 is secured within the piston outer drive tube 952 to act between the proximal end portion 964 of piston drive shaft 960 and the proximal end portion 956 of the piston outer drive tube 952, for example, by engagement within a supporting structure disposed in the hollow proximal end portion 956 which, in the present embodiment, comprises a simple snap ring as described later herein.

Sleeve outer and inner drive tubes 908, 918 respectively define a pair of top and bottom slots 972, 974 that accept a pair of anti-rotation pins 976 which extend through the slots 972, 974. While the slots 972, 974 are shown at the top and bottom locations of sleeve outer drive tube 908 and sleeve inner drive tube 918 this is intended to be merely exemplary and such slots 972, 974 may be oriented at other locations around the circumference of the sleeve outer drive tube 908 and sleeve inner drive tube 918 for accepting the anti-rotation pins 976. The anti-rotation pins 976 further extending radially inward and pass through opposed, top and bottom, radial openings 978 in piston outer drive tube 952 to engage and seat in registered radial openings 980 defined in the hollow proximal end 964 in piston drive shaft 960. The radial openings 978 in piston outer drive tube 952 are sized larger than the diameter of anti-rotation pins 976 to allow translational movement of the piston outer drive tube 952 relative to piston drive shaft 960 as described herein. Anti-rotation pins 976 generally prevent relative rotation between the sleeve outer and inner drive tubes 908, 918 and relative rotation between the piston outer drive tube 952 and piston drive shaft 960. Moreover, relative rotation of sleeve outer and inner drive tubes 908, 918 between the piston outer drive tube 952 and piston drive shaft 960 is likewise prevented.

The proximal end portion 956 of piston outer drive tube 952 has a slightly larger external diameter than the distal end portion 954 so as to form an external abutment shoulder 982 and an internal abutment shoulder 984. Correspondingly, sleeve inner drive tube 918 has a slightly smaller inner diameter at the distal end portion 920 than at the proximal end portion 922 so as to form an inner abutment shoulder 986 opposing external abutment shoulder 982 associated with piston outer drive tube 952. In a generally analogous manner to the foregoing, the proximal end portion 964 of piston drive shaft 960 has a slightly larger outer diameter than the distal end portion 962 of the piston drive shaft 960 to form a raised abutment shoulder 988 which is opposite from the internal abutment shoulder 984 associated with piston outer drive tube 952. It will be appreciated from the accompanying figures that the radial openings 980 in piston drive shaft 960 are formed just proximal of raised abutment shoulder 988.

Drive motor 928 comprises a drive shaft 990 engaged with a ball screw shaft 992 disposed concentrically within or generally coaxial with piston drive shaft 960, piston outer drive tube 952, and interface element 926. Ball screw shaft 992 is supported by a conventional thrust bearing 994 disposed within a bearing cavity 996 defined internally in interface element 926 just proximal of distal cylindrical portion 940 of interface element 926. Thrust bearing 994 rotationally and axially supports ball screw shaft 992 in central bore 938 in interface element 926 in a conventional manner. Accordingly, thrust bearing 994 is desirably secured within bearing cavity 996 by a mechanical connection, press-fit connection, and like connections. Ball screw shaft 992 extends distally into the hollow proximal end portion 964 of piston drive shaft 960. Ball screw shaft 992 may be similar to ball screw shafts 628, 728 discussed previously in this disclosure. Ball screw shaft 992 is rotationally engaged with a ball screw nut 998 seated in the hollow proximal end portion 964 of piston drive shaft 960. In particular, proximal end portion 964 defines an internal rim 1000 in which the forward or distal end of ball screw nut 998 is secured. A snap ring 1002 is disposed in an annular groove 1004 defined in the inner wall of piston outer drive tube 952 at the proximal end portion 956 of the piston outer drive tube 952. As illustrated, second spring 970 is secured within the piston outer drive tube 952 to act between the proximal end portion 964 of piston drive shaft 960 and snap ring 1002. As described previously, ball screw shaft 992 is in rotational threaded engagement with ball screw nut 998 and "forward" rotational movement of ball screw shaft 992 causes advancement of ball screw nut 998 which advances piston drive shaft 960.

As will be apparent from the foregoing, in fluid pump actuator 902, sleeve piston positioning device 906 generally comprises sleeve outer drive tube 908 interfacing with sleeve piston 362 and insertion piston positioning device 950 generally comprises piston outer drive tube 952 interfacing with insertion piston 364. With the various components of drive system 900 set forth in the foregoing, this disclosure now turns to an exemplary sequence for interfacing sleeve piston 362 with sleeve piston positioning device 906, and interfacing insertion piston 364 with insertion piston positioning device 950. This sequence is generally shown in FIGS. 61A-61G discussed herein and is intended only to be exemplary to indicate how pistons 362, 364 interface with the sleeve piston positioning device 906 and insertion piston positioning device 950, respectively, which together comprise piston positioning device 904 in the fluid pump actuator 902 for each fluid pump 360.

Before referring to FIGS. 61A-61G, reference is made to FIGS. 50-55, wherein an interfacing sequence for interfacing sleeve piston 362 with sleeve outer drive tube 908 is shown. As described previously, sleeve piston 362 comprises an end flange 410 with two spaced apart rim flange elements 412 defining an intervening space 414. End flange 410 comprises lateral ribs 416 extending between rim flange elements 412 in intervening space 414 to section the intervening space 414 into an engagement or receiving space 418 adapted to receive radial flange 916 at the distal end 910 of sleeve outer drive tube 908. Additionally, as mentioned previously, it may be desirable to ensure that the engagement of end flange 410 with radial flange 916 is orientation specific, meaning that the end flange 410 has only one possible or "correct" orientation for interfacing with radial flange 916. As noted previously, additional intervening ribs 420 are provided in intervening space 414 for this purpose to ensure that only receiving space 418 is capable of full engagement with radial flange 916, thereby blocking any potential incorrect association or interface of sleeve piston 362 with sleeve outer drive tube 908. Accordingly, only one possible engagement orientation is provided due to the presence of intervening ribs 420. Opposing ends 1006 on radial flange 916 contact and abut the lateral ribs 416 on end flange 410 to secure the engagement of radial flange 916 with receiving space 418 and this abutting engagement has the advantage of preventing rotation of sleeve piston 362 relative to sleeve outer drive tube 908.

Figure 56:
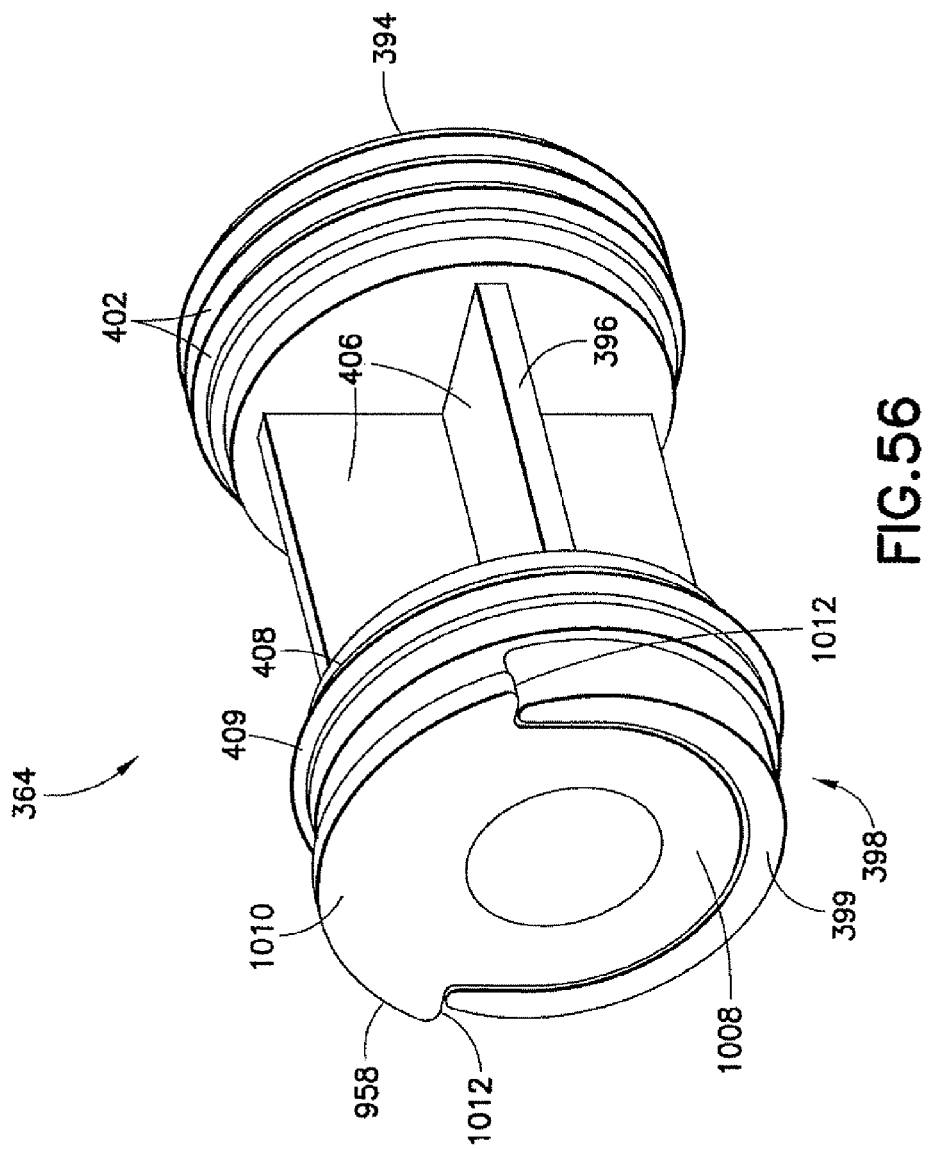
FIG. 56 is a perspective view of an insertion piston adapted to interface with the fluid pump actuator shown in FIG. 49.
Figure 57:
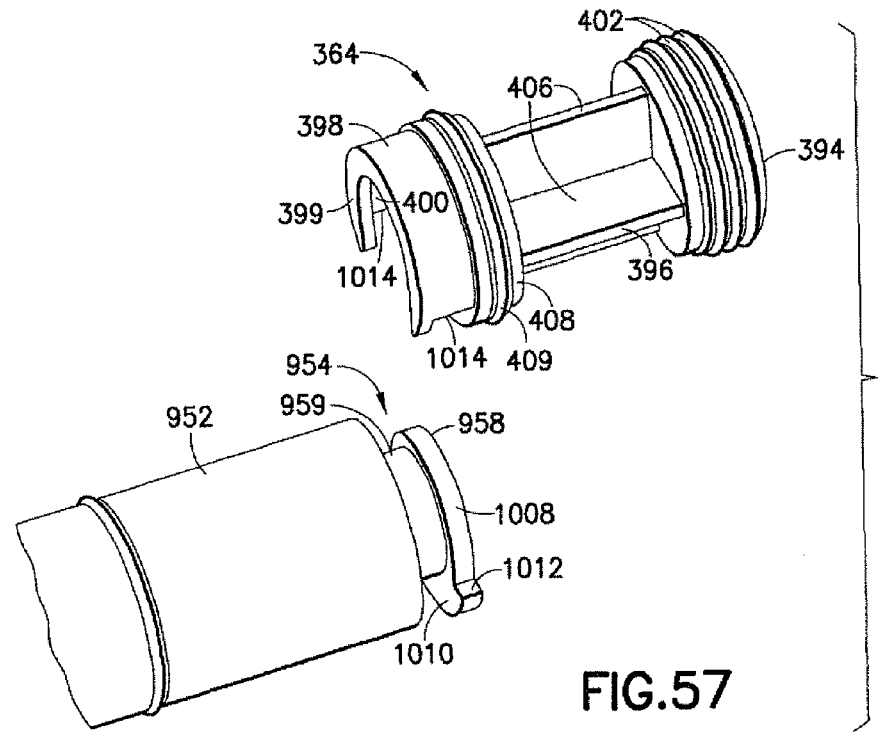
FIG. 57 is a perspective view illustrating a sequence for connecting the insertion piston shown in FIG. 56 with a piston positioning device of the fluid pump actuator shown in FIG. 49.
Figure 58:
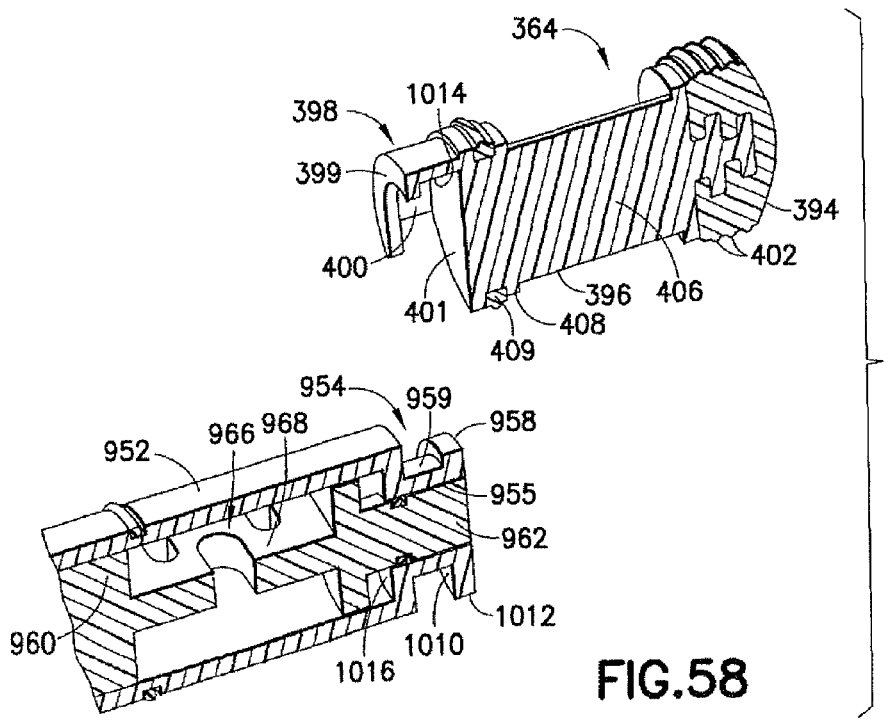
FIG. 58 is a cross-sectional view of the sequence shown in FIG. 57.
Figure 59:
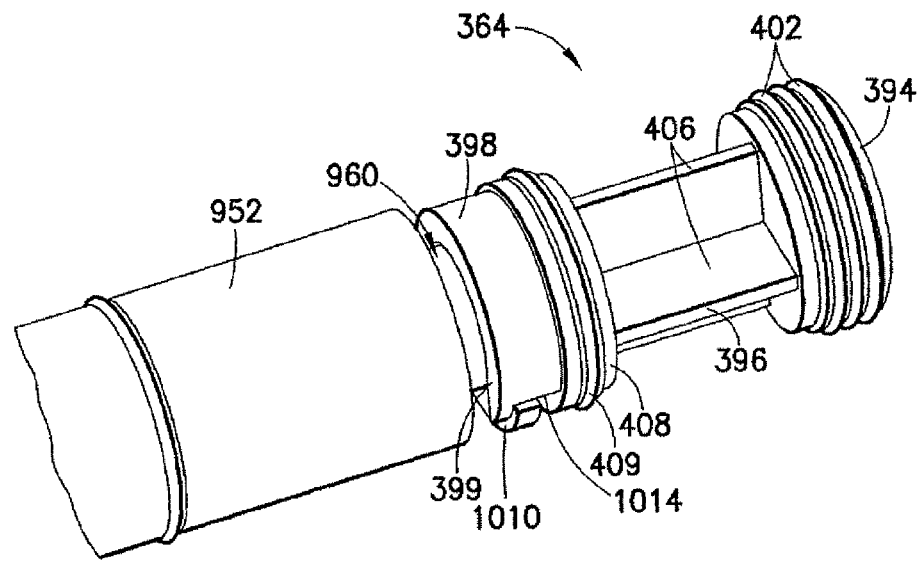
FIG. 59 is a perspective view illustrating the connection of the insertion piston with the piston positioning device resulting from the sequence shown in FIGS. 57-58.
Figure 60:
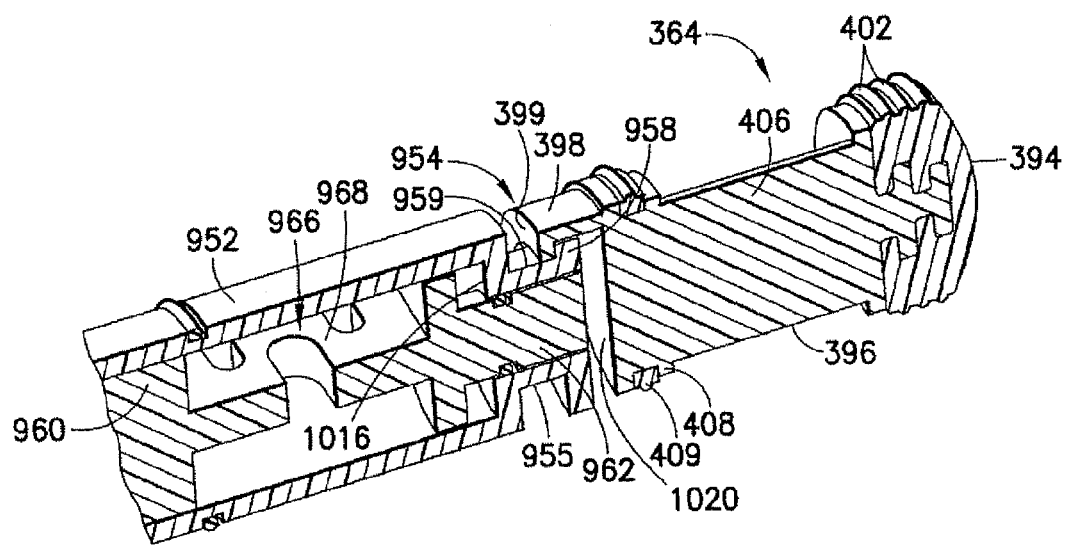
FIG. 60 is a cross-sectional view of the connection shown in FIG. 59.

Similarly, with reference to FIGS. 56-60, an exemplary sequence for engaging or interfacing insertion piston 364 with piston outer drive tube 952 is shown. In FIGS. 56-60, insertion piston 364 is shown again, wherein the proximal end of piston rod 396 comprises drive interface flange 398 with a flange lip 399 defining a U-shaped slot 400. In the interface of the insertion piston 364 with piston outer drive tube 952, distal flange 958 at the distal end portion 954 of piston outer drive tube 952 comprises a generally U-shaped portion 1008 which is shaped to engage or seat in the U-shaped slot 400 of drive interface flange 398. An arcuate portion 1010 of distal flange 958, which is desirably integral with the U-shaped portion 1008, defines opposing tab ends 1012 which are adapted to engage lateral edges or ends 1014 of flange lip 399 of drive interface flange 398 which defines or forms the U-shaped slot 400. This abutting engagement between tab ends 1012 and lateral edges 1014 prevents rotation of insertion piston 364 relative to piston outer drive tube 952 and, once the foregoing engagement is made, ensures that the engagement between insertion piston 364 and piston outer drive tube 952 is orientation specific, meaning that drive interface flange 398 and distal flange 958 will only cooperatively interface together when insertion piston 364 is properly oriented with respect to piston outer drive tube 952 thereby eliminating the possibility of incorrectly associating the piston 364 with insertion piston positioning device 950. Once in engagement, flange lip 399 of drive interface flange 398 is generally received in intervening recess 959 defined in the distal end portion 954 of piston outer drive tube 952 so that the U-shaped shaped portion 1008 of the distal flange 958 may correspondingly seat into engagement in the U-shaped slot 400 defined by the flange lip 399 of drive interface flange 398. FIG. 56 illustrates just distal flange 958 in association with drive interface flange 398 for clarity purposes.

Figure 61A:
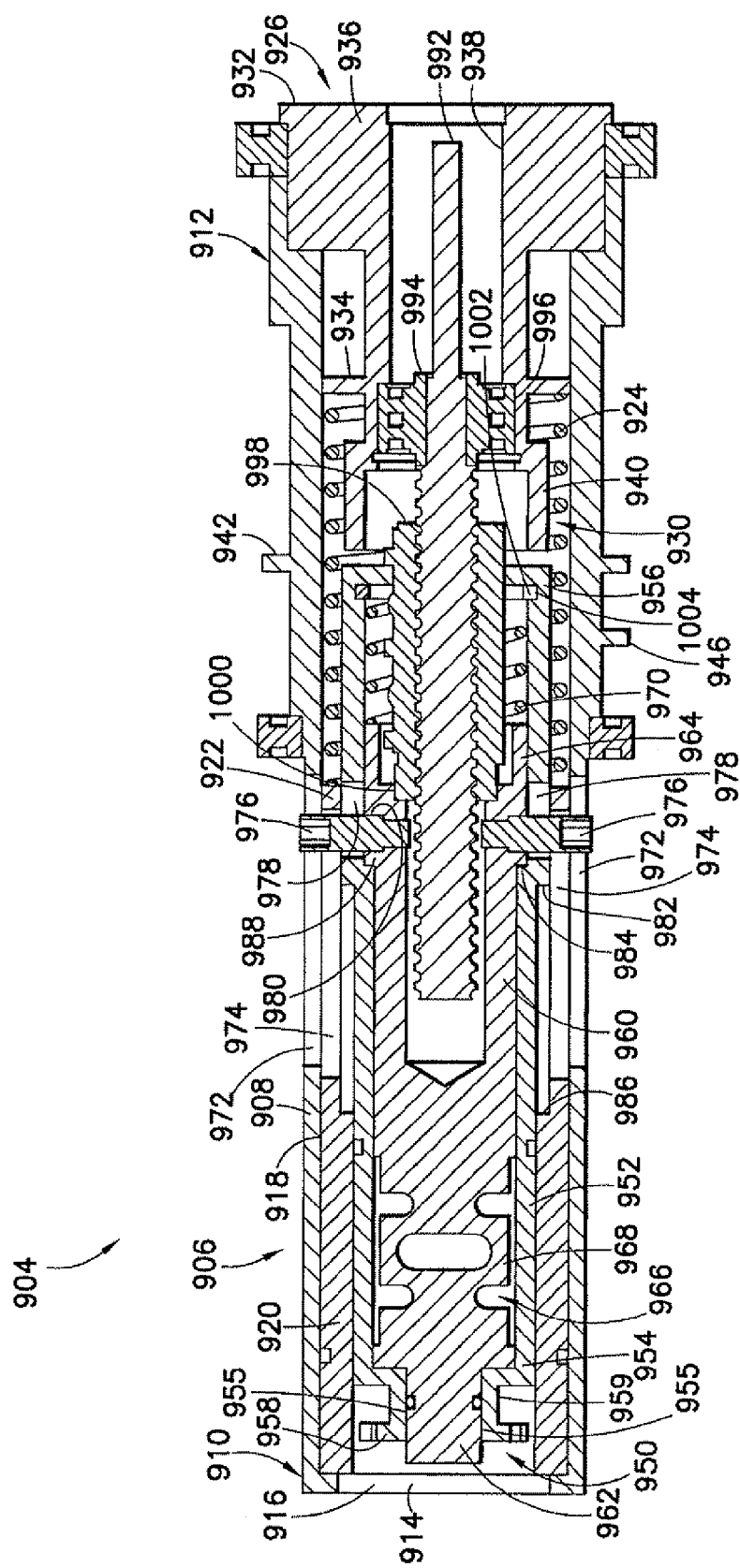

Referring further to FIGS. 61-64 inclusive, FIG. 61A illustrates an initial or home position of the various components of piston positioning device 904 is shown. In this position, it is generally noted that first spring 924 acts upon the proximal end portion 922 of sleeve inner drive tube 918 so that the distal end portion 920 of sleeve inner drive tube 918 to urge the sleeve inner drive tube 918 forward to engage radial flange 916 at the distal end 910 of sleeve outer drive tube 908. Similarly, second spring 970 acts upon the proximal end portion 964 of piston drive shaft 960 so that load cell 968, in the present embodiment, contacts an inner distal end wall 1016 of piston outer drive tube 952. Inner end wall 1016 is defined generally by the formation of intervening recess 959 in the distal end portion 954 of piston outer drive tube 952. FIG. 62A illustrates just piston outer drive tube 952, piston drive shaft 960, and second spring 970, wherein second spring 970 acts upon the proximal end portion 964 of piston drive shaft 960 so that load cell 968, in the present embodiment, contacts against inner distal end wall 1016 of piston outer drive tube 952 to clarify the initial "free" state of the piston outer drive tube 952 and piston drive shaft 960. In this position or state, abutment shoulder 988 on piston drive shaft 960 desirably seats against internal abutment shoulder 984 on piston outer drive tube 952.

Figure 61B:
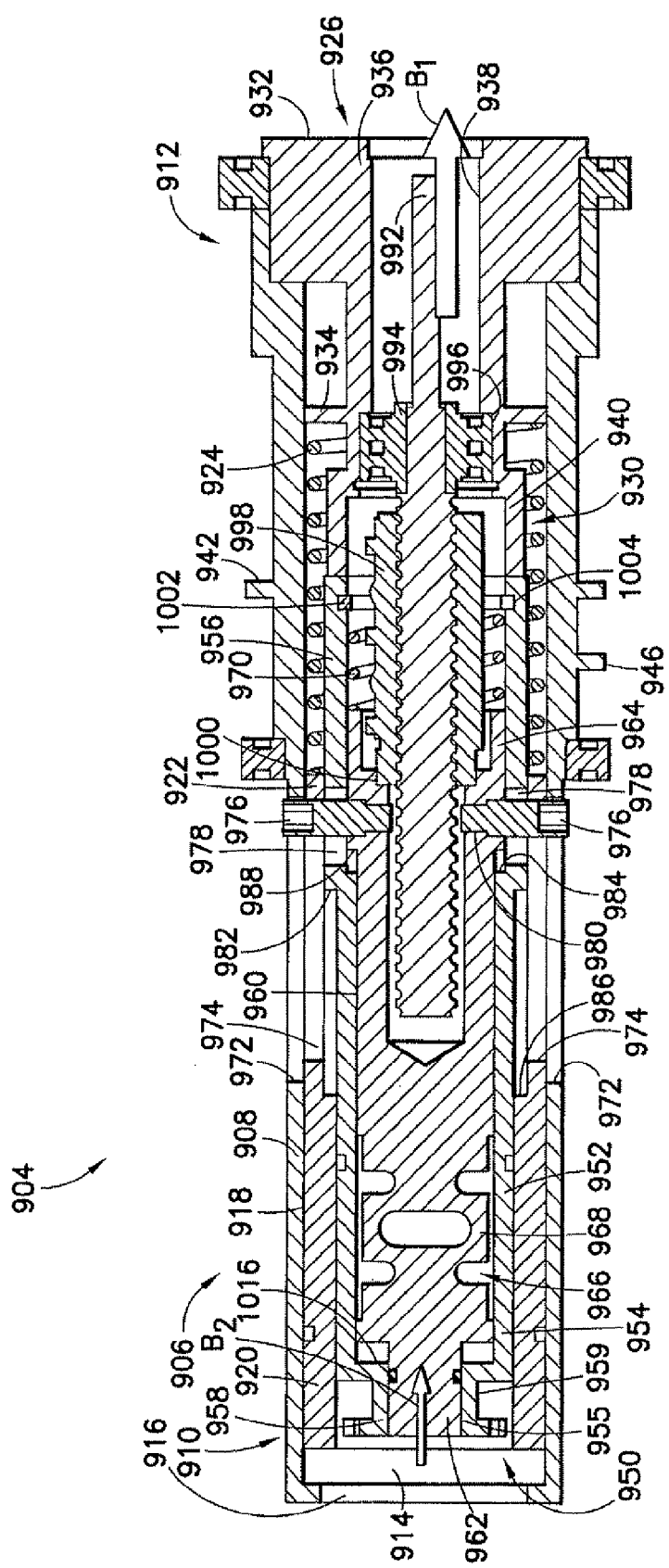
Figure 62A:
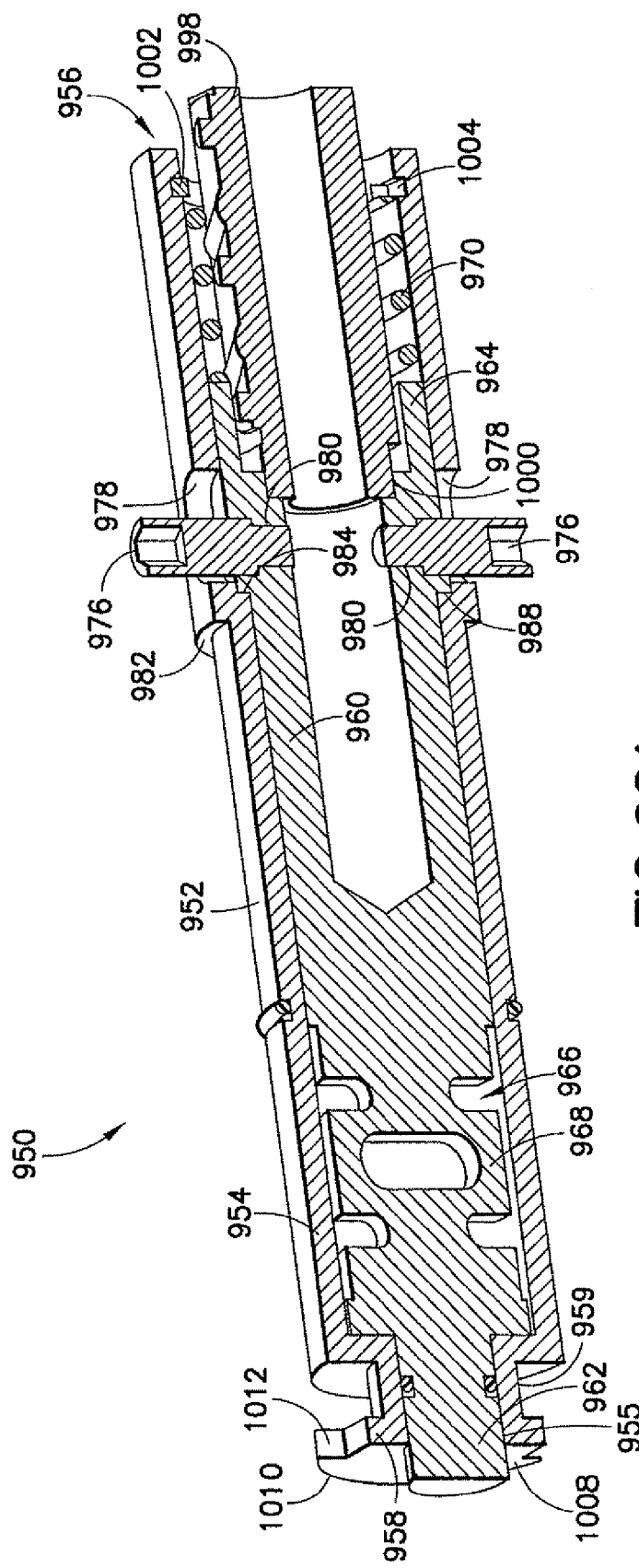
FIGS. 62A-62C are cross-sectional views illustrating the sequence for associating the insertion piston with the piston positioning device of the fluid pump actuator shown in FIG. 49.
Figure 62B:
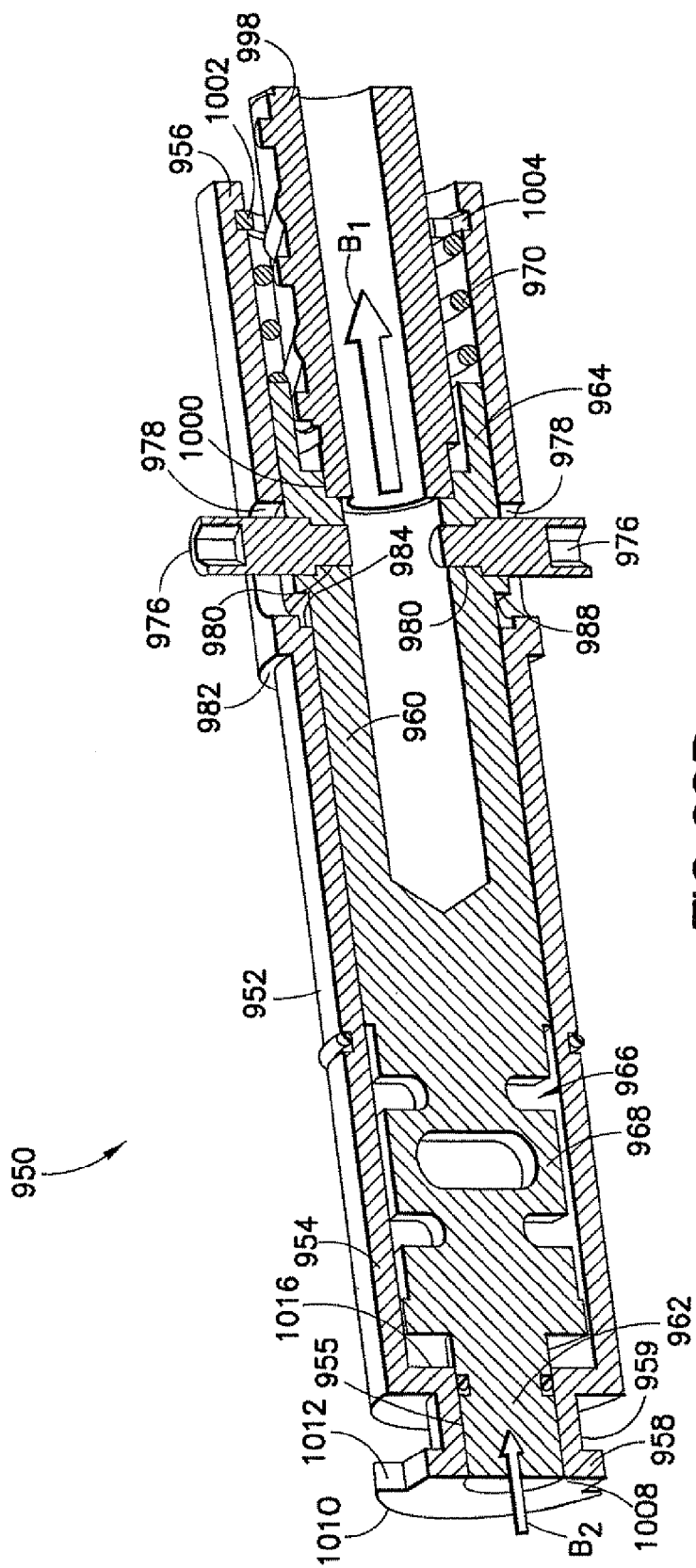

In FIG. 61B, ball screw shaft 992 has been driven in reverse by drive motor 928. Piston outer drive tube 952 moves rearward or proximally due to the interference engagement between second spring 970 and snap ring 1002 residing annular groove 1004 defined in the inner wall of piston outer drive tube 952 at the proximal end portion 956 of the piston outer drive tube 952. This rearward movement of piston outer drive tube 952 continues until the proximal end portion 956 of the piston outer drive tube 952 abuts against the distal end 930 of interface element 926 and, accordingly, seats against the distal cylindrical portion 940 of the interface element 926. Additional reverse rotation of ball screw shaft 992 causes piston drive shaft 960 to retract until the solid distal end portion 962 of piston drive shaft 960 is retracted into the distal opening 955 in the distal end portion 954 of piston outer drive tube 952. Desirably, solid distal end portion 962 is retracted to be at least substantially flush with distal flange 958 on the distal end portion 954 of piston outer drive tube 952, which provides sufficient clearance to allow insertion piston 364 to be interfaced with piston outer drive tube 952. This interface comprises, as indicated, positioning insertion piston 364 so that U-shaped slot 400 defined by flange lip 399 of drive interface flange 398 may placed in engagement with distal flange 958 at the distal end portion 954 of piston outer drive tube 952. This additional rotation of ball screw shaft 992 also compresses second spring 970 between the proximal end portion 964 of piston drive shaft 960 and snap ring 1002. FIG. 62B illustrates the foregoing "loading" state of piston drive shaft 960 when retracted relative to piston outer drive tube 952 by illustrating just these components and, additionally, second spring 970. Arrow $B_1$ in FIGS. 61B and 62B illustrates the retracting movement of piston drive shaft 960 relative to piston outer drive tube 952. Arrow $B_2$ in FIG. 61B illustrates the retraction of solid distal end portion 962 of piston drive shaft 960 into the distal opening 955 in the distal end portion 954 of piston outer drive tube 952.

Figure 61C:
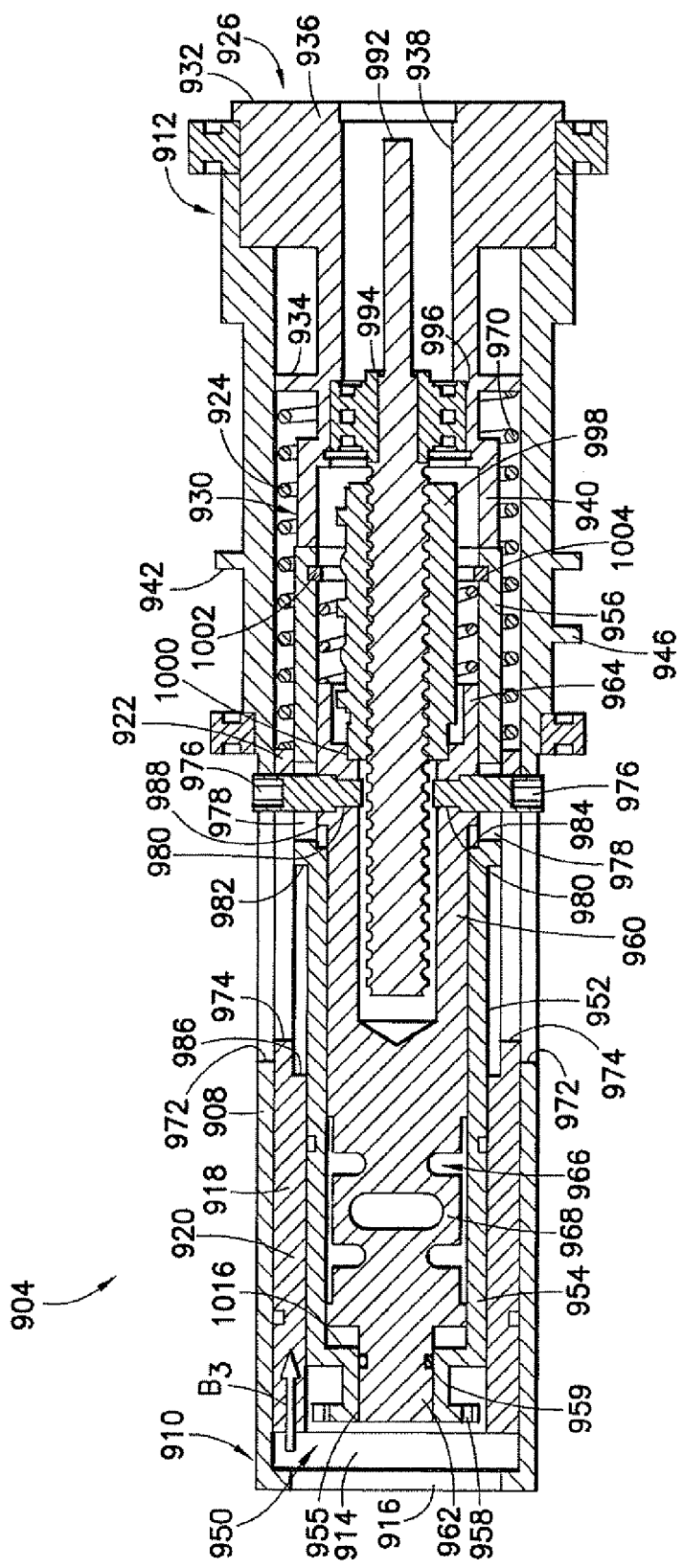

As shown in FIG. 61C, concurrently with retraction of the piston drive shaft 960, anti-rotation pins 976 reach an end of travel position in opposed slots 974 in sleeve inner drive tube 918 and additional rotation of ball screw shaft 992 causes the sleeve inner drive tube 918 to compress first spring 924 between the proximal end portion 922 of the sleeve inner drive tube 918 and radial flange 934 on interface element 926. This action retracts sleeve inner drive tube 918 relative to sleeve outer drive tube 908, as represented by arrow $B_3$, sufficiently to expose the radial flange 916 at the distal end of sleeve outer drive tube 908 so that sleeve piston 362 may be interfaced with the sleeve outer drive tube 908. This interface comprises engaging engagement space 418 on end flange 410 of sleeve piston 362 with the radial flange 916 at the distal end 910 of sleeve outer drive tube 908 as described previously.

FIG. 61D illustrates the initial association of pistons 362, 364 with sleeve outer drive tube 908 and piston outer drive tube 952, respectively, by the foregoing process. It will be appreciated that a gap or clearance 1018 is provided between the rear rim flange element 412 on end flange 410 of sleeve piston 362 and the distal end portion 920 of sleeve inner drive tube 918. Likewise, a second gap or clearance 1020 is provided between distal flange 958 at the distal end portion 954 of piston outer drive tube 952 and end wall 401 so that the distal flange 958 may engage the U-shaped slot 400 defined by flange lip 399 of drive interface flange 398 at the proximal end of piston rod 396 of insertion piston 364. More particularly, the U-shaped portion 1008 of distal flange 958 engages the U-shaped slot 400 defined by flange lip 399 of drive interface flange 398 at the proximal end of piston rod 396 of insertion piston 364. Referring to FIG. 61E, when ball screw shaft 992 is rotated to advance ball screw nut 998 forward or distally, as represented by Arrow $B_4$, whereby the solid distal end portion 962 of the piston drive shaft 960 engages end wall 401 of drive interface flange 398 at the proximal end of piston rod 396 of piston 364, as represented by arrow $B_5$. Second spring 970 acts between the proximal end portion 964 of piston drive shaft 960 and snap ring 1002 to maintain the piston outer drive tube 952 substantially in place. Similarly, as ball screw nut 998 moves forward or distally, first spring 924 continuously acts between the proximal end portion 922 of sleeve inner drive tube 918 and radial flange 934 on interface element 926 to substantially simultaneously urge the sleeve inner drive tube 918 forward or distally to contact the rear rim flange element 412 on end flange 410 of sleeve piston 362. The forward or distal, substantially simultaneous movement of the sleeve inner drive tube 918 and piston drive shaft 960 are similarly represented by arrows $B_5$ in FIG. 61E.

Figure 62C:
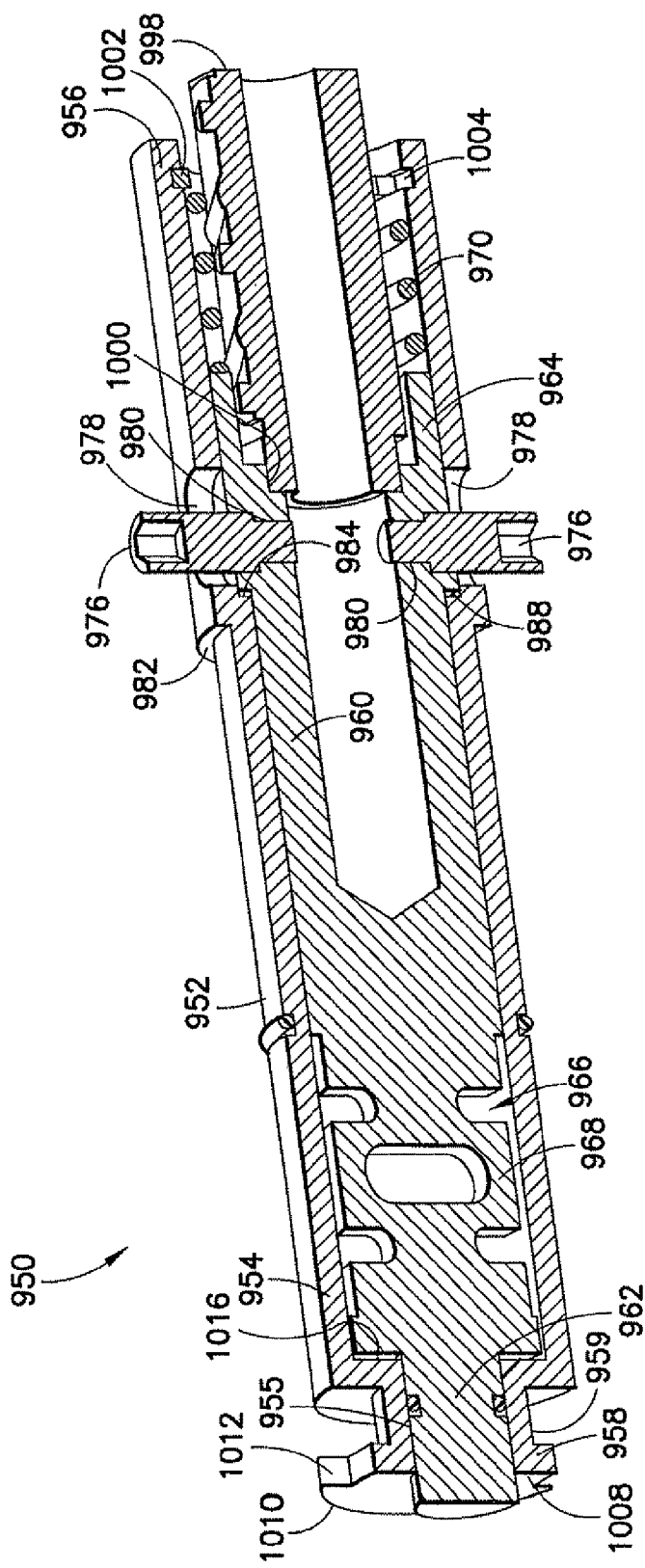
Figure 63A:
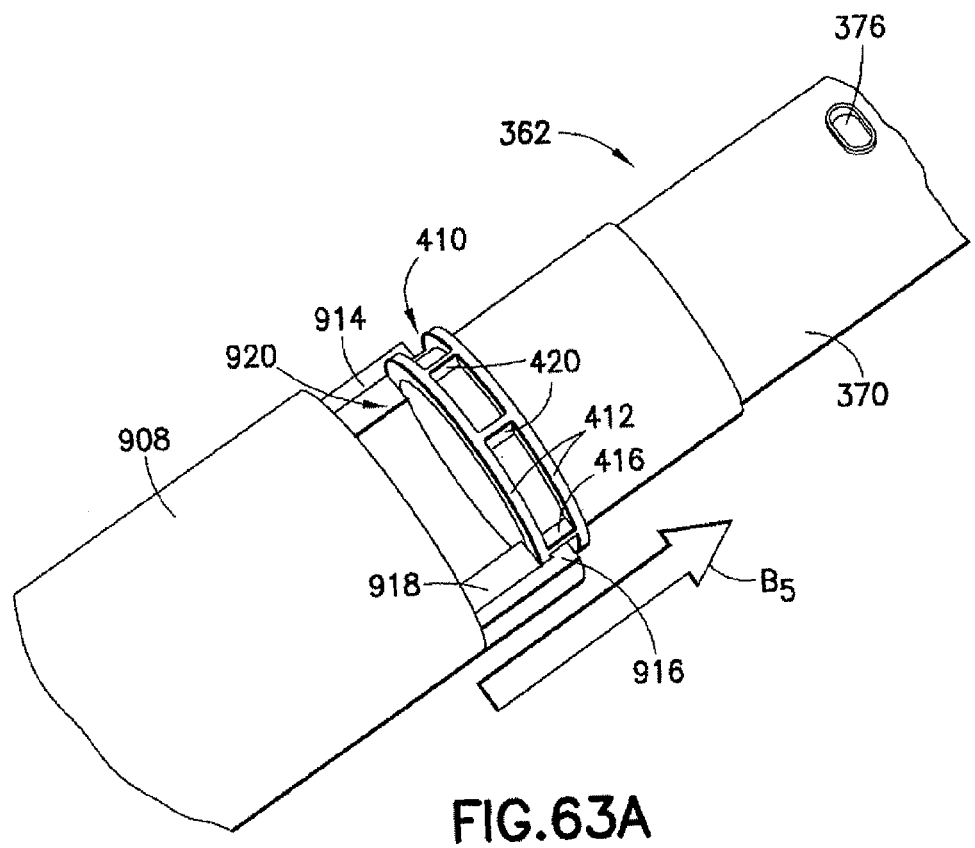
FIGS. 63A-63B are a perspective view and a perspective cross-sectional view, respectively, illustrating a sequence for securing the connection of the sleeve piston with the sleeve piston positioning device of the fluid pump actuator shown in FIG. 49.
Figure 63B:
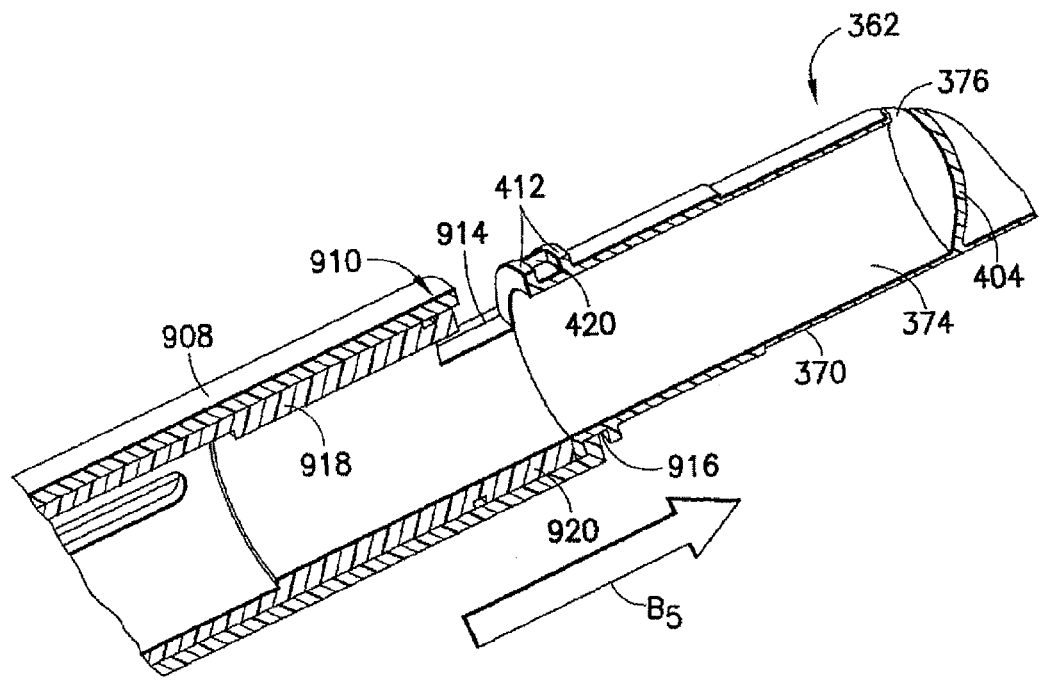
Figure 64A:
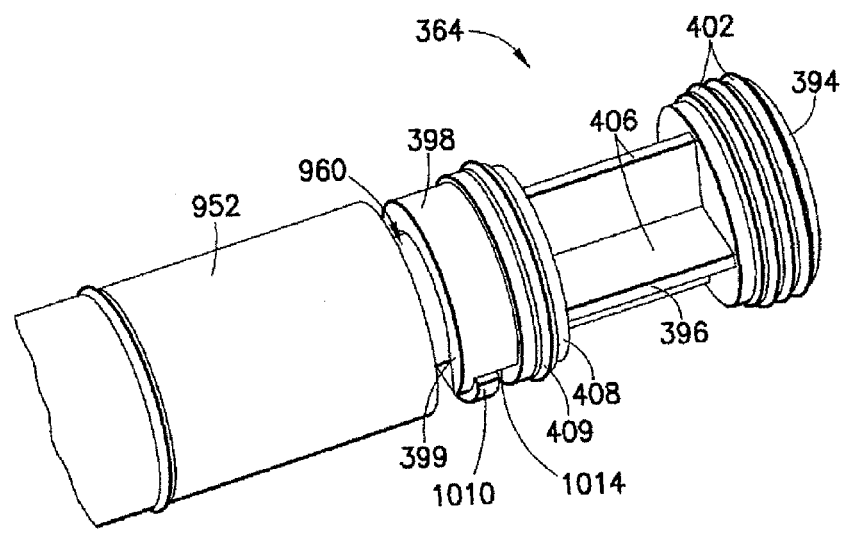
FIGS. 64A-64B are a perspective view and a perspective cross-sectional view, respectively, illustrating a sequence for securing the connection of the insertion piston with the piston positioning device of the fluid pump actuator shown in FIG. 49.
Figure 64B:
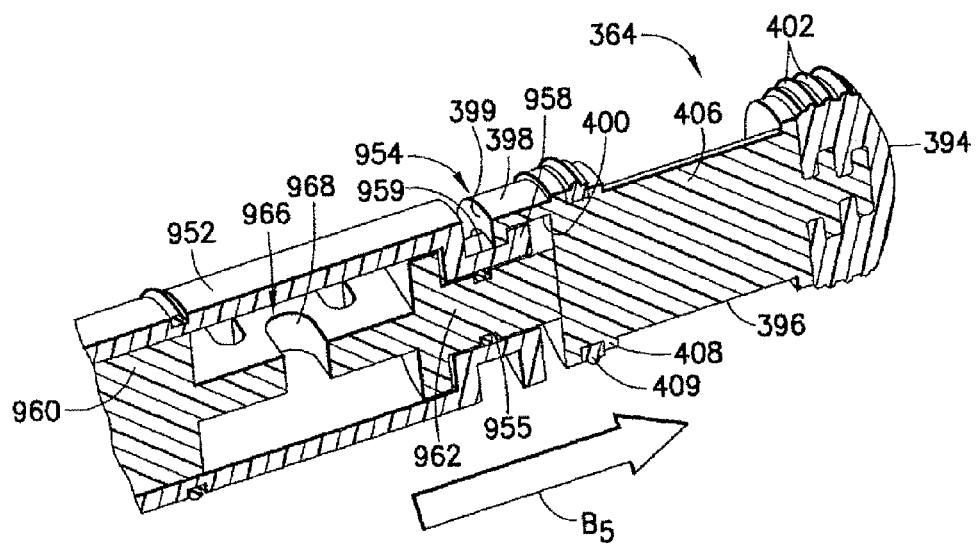
Figure 65:
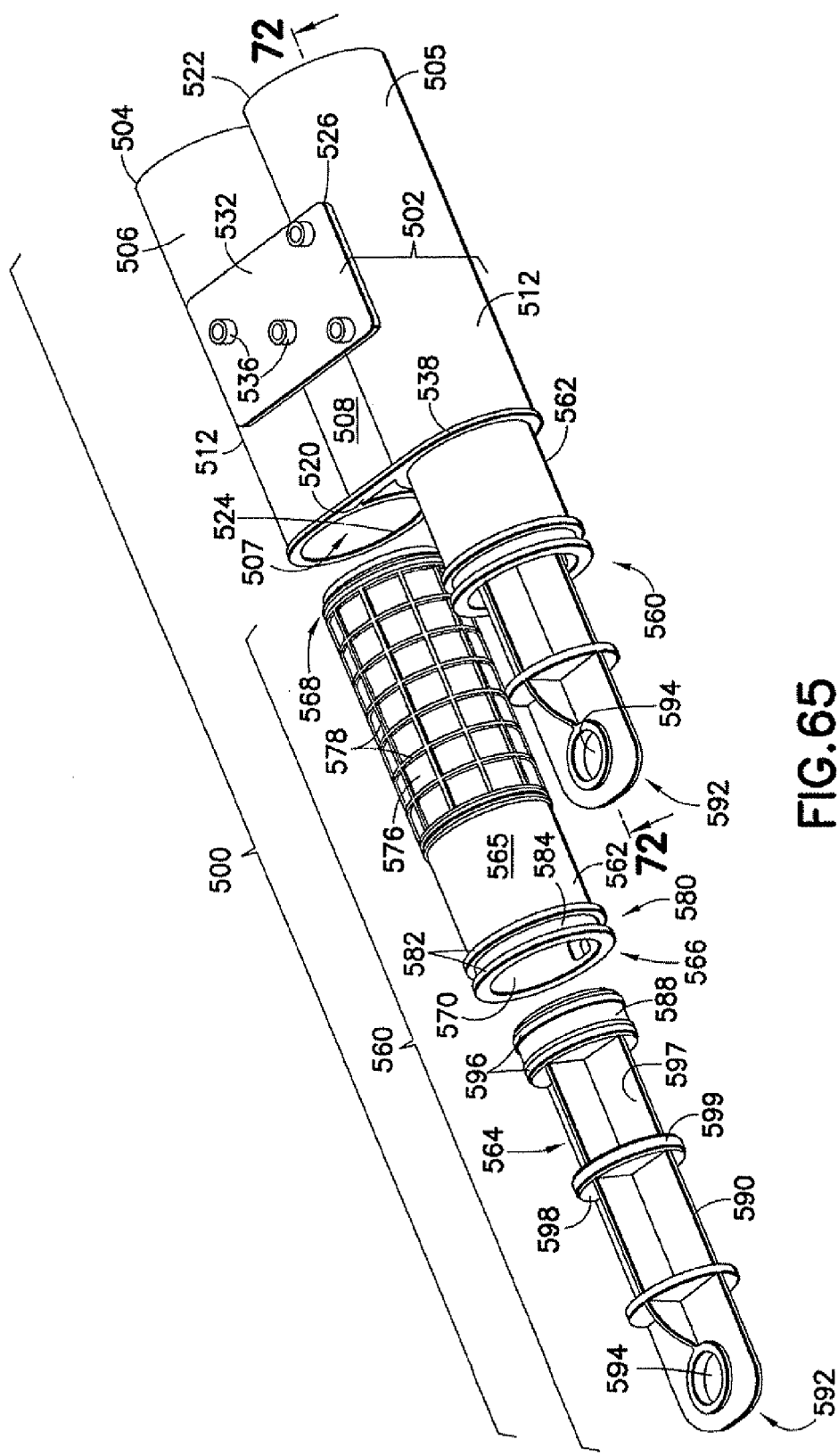
FIG. 65 is an exploded perspective view of another embodiment of a fluid pumping device in accordance with the disclosure herein.
Figure 66:
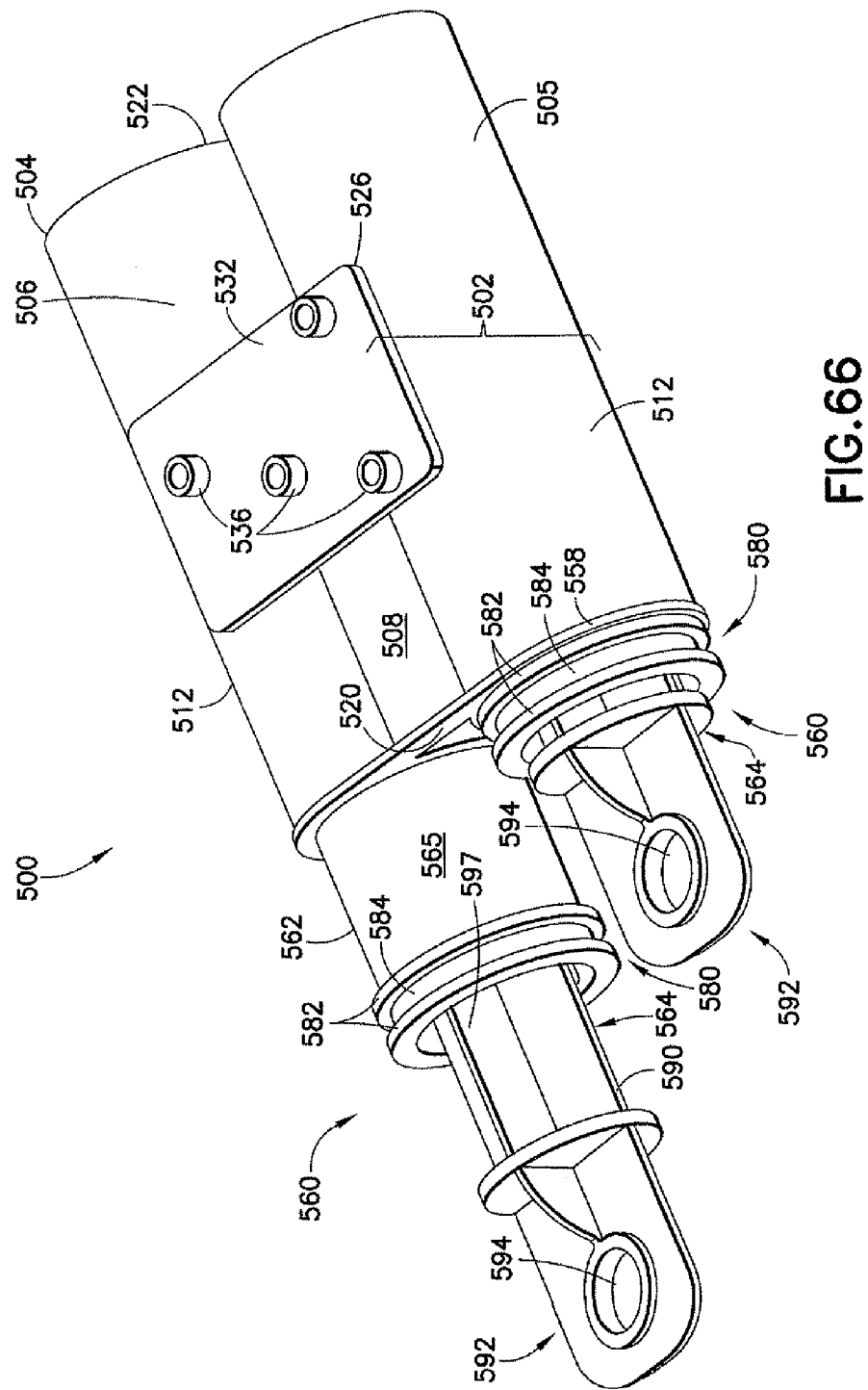
FIG. 66 is an assembled top perspective view of the fluid pumping device of FIG. 65.
Figure 67:
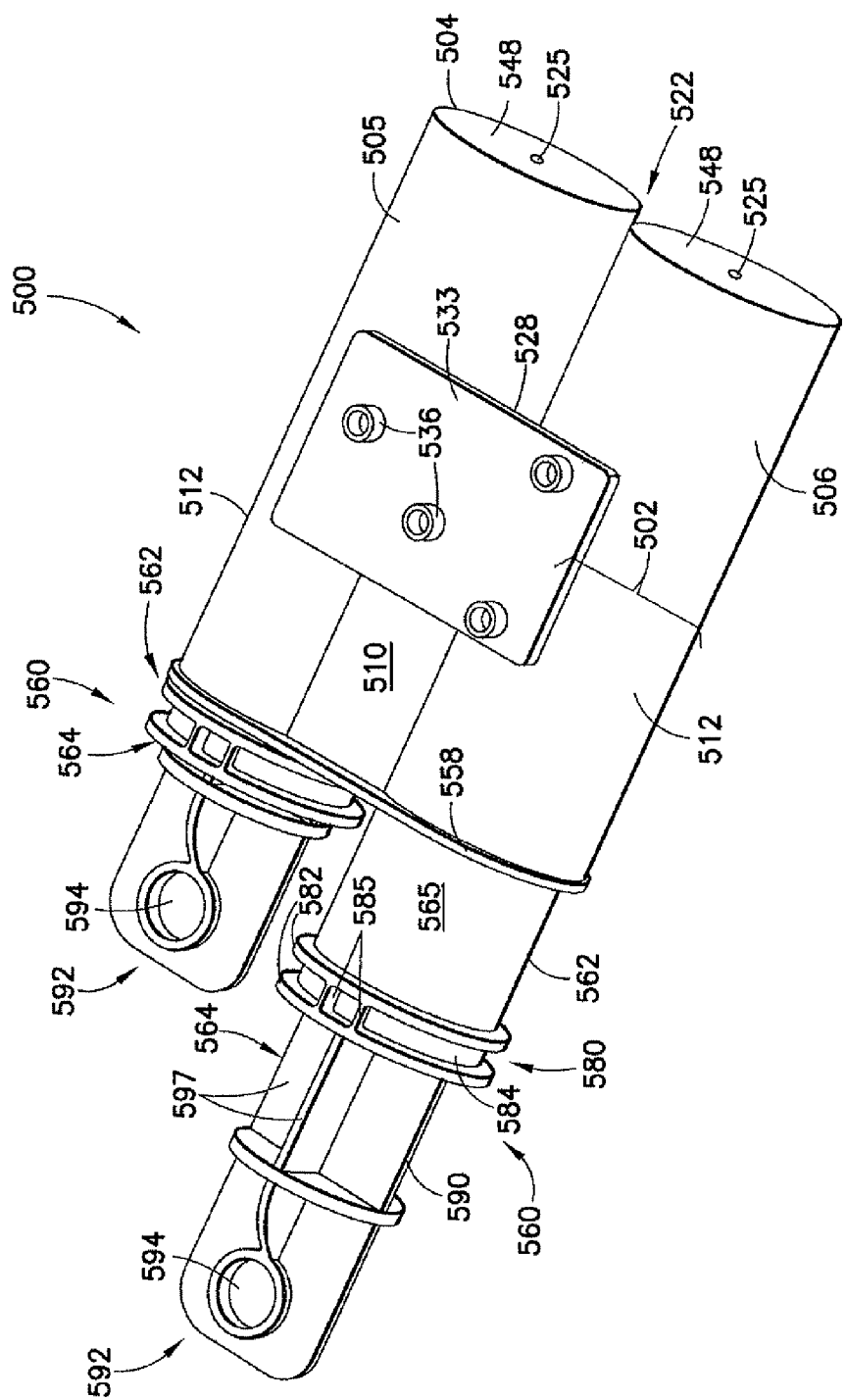
FIG. 67 is an assembled bottom perspective view of the fluid pumping device of FIG. 65.

The forward movement of ball screw nut 998 results in the solid distal end portion 962 of piston drive shaft 960 engaging the end wall 401 of drive interface flange 398 at the proximal end of piston rod 396 of piston 364. The force provided by first spring 924 substantially simultaneously urges sleeve inner drive tube 918 forward against the rear flange element 412 of the two flange elements 412 on end flange 410 of sleeve piston 362 and clamps this rear flange element 412 between the distal end of sleeve inner drive tube 918 and radial flange 916 at the distal end 910 of sleeve outer drive tube 908. This double engagement ensures a tight connection between sleeve piston 362 and sleeve outer drive tube 908 and sleeve inner drive tube 918 of sleeve piston positioning device 906 and a similarly tight connection or engagement between insertion piston 364 and piston outer drive tube 952 and piston drive shaft 960 of insertion piston positioning device 950. FIG. 62C illustrates just piston outer drive tube 952, piston drive shaft 960, and second spring 970 in the foregoing forward "clamping" position of the piston drive shaft 960 relative to the piston outer drive tube 952. As stated, in this position, solid distal end portion 962 of the piston drive shaft 960 contacts end wall 401 of drive interface flange 398 at the proximal end of piston rod 396 of piston 364. Also in this position or state, abutment shoulder 988 on piston drive shaft 960 is not seated against internal abutment shoulder 984 on piston outer drive tube 952. Further, FIGS. 63A-63B illustrate just the "clamping" interface of sleeve piston 362 with sleeve outer drive tube 908 and sleeve inner drive tube 918, with arrow $B_5$ again indicating the forward movement of sleeve inner drive tube 918 relative to sleeve outer drive tube 908 used to capture rear flange element 412 of the two flange elements 412 on end flange 410 of sleeve piston 362 and clamp this rear flange element 412 between the distal end portion 920 of sleeve inner drive tube 918 and radial flange 916 at the distal end 910 of sleeve outer drive tube 908. Similarly, FIGS. 64A-64B illustrate just the "clamping" interface between insertion piston 364 with piston outer drive tube 952 and piston drive shaft 960, with arrow $B_5$ again indicating the forward movement of piston drive shaft 960 relative to piston outer drive tube 952 which causes the solid distal end portion 962 of piston drive shaft 960 to engage with the end wall 401 of drive interface flange 398 at the proximal end of piston rod 396 of piston 364 and exert forward pressure thereto which, in turn, causes distal flange 958 to seat tightly against the flange lip 399 of drive interface flange 398. This forward movement of the solid distal end portion 962 of piston drive shaft 960 to engage end wall 401 and apply pressure thereto also causes corresponding rearward pressure to be applied by sleeve outer drive tube 908 on the front side of the rear flange element 412 of end flange 410 of sleeve piston 362 and enhances the "clamping" pressure on this rear flange element 412 between the distal end portion 920 of sleeve inner drive tube 918 and radial flange 916 at the distal end 910 of sleeve outer drive tube 908.

FIG. 61F shows that further rotation of ball screw shaft 992 causes forward movement of ball screw nut 998 and corresponding forward movement of insertion piston 364 in sleeve piston 362 until, as shown in FIG. 61G, piston head 394 of piston 364 contacts end wall 404 in the sleeve portion 370 of the sleeve piston 362 and, thus, an end of travel location of insertion piston 364 within sleeve piston 362 is reached. Forward movement of insertion piston 364 caused by rotating ball screw shaft 992 is indicated by arrows $B_6$ in FIG. 61F. At the end of the stroke of insertion piston 364 in sleeve piston 362, it is desirable that external abutment shoulder 982 on piston outer drive tube 952 contact and engage inner abutment shoulder 986 on sleeve inner drive tube 918 to prevent any damage to end wall 404 in the sleeve portion 370 of the sleeve piston 362.

While the foregoing discussion centered on the engagement of pistons 362, 364 with interfacing components of drive system 900, it will be appreciated that the foregoing components of drive system 900 may be adapted into a powered injector device used to operate a syringe plunger within a syringe body and the foregoing concepts may be used to secure such a syringe plunger and syringe body to the powered injector device comprising the foregoing described components of drive system 900. Accordingly, the foregoing components of drive system 900 may be used in a powered syringe injector platform, wherein such a syringe would have the structure of end flange 410 described previously and the corresponding syringe plunger would have the same general configuration as insertion piston 364 described previously.

Referring to FIGS. 65-72, another embodiment of a fluid pumping device 500 is illustrated. Fluid pumping device 500 is generally similar to fluid pumping devices 100 and 300 described previously. Fluid pumping device 500 may also be used as part of fluid delivery system 10 comprising, as in previous embodiments, fluid pumping device 500 and an associated drive system, typically one of drive systems 700, 900 discussed previously. FIG. 1B, discussed previously, illustrates association of fluid pumping device 100 with various bulk fluid sources 14 and fluid pumping device 500 may be similarly adapted to fluid pumping device 100 to associate with bulk fluid sources 14 via the fluid path elements described previously associating the bulk fluid sources 14 with fluid pumping device 100. In contrast to previous embodiments, fluid pumping device 500 comprises fluid pumps 560 that operate such that at least one piston may be actuated to move in both a reciprocating and rotating fashion as discussed hereinafter. Such a modification in operation likewise requires certain changes to the operation of the associated drive system 700, 900 which will be discussed herein.

As in previous embodiments, fluid pumping device 500 is a multi-component device comprising a pump housing 502 and one or more fluid pumps 560 which again constitute the movable components of fluid pumping device 500 for delivering fluid under pressure to a desired end point such as to patient fluid path 12. Pump housing 502 serves as a support component or structure for the movable components of fluid pumping device 500, namely, fluid pumps 560, as well as a connection point for connecting the fluid path elements shown in FIG. 1B to pump housing 502 of the fluid pumping device 500. Pump housing 502, in contrast to previous embodiments, desirably comprises a multi-barrel base member 504 to which an upper manifold cap 532 and a lower manifold cap 533 are secured. Manifold caps 532 and 533 may be considered to be a component or part of pump housing 502 in accordance with this disclosure and may optionally be formed integral with base member 504. Accordingly, pump housing 502 may be considered to be a multi-piece component comprising at least base member 504, upper manifold cap 532, and lower manifold cap 533. Base member 504 and manifold caps 532, 533 may be injection-molded plastic components or pieces which are assembled together to form or complete pump housing 502 by suitable assembly methods such as ultrasonic welding, laser welding, adhesive, solvent bonding, by direct mechanical attachment, and like methods.

Base member 504 may have any desirable configuration but in this embodiment comprises a pair of cylindrical members 505, 506 desirably integrally coupled with each other along their respective longitudinal axes, thereby defining at least two adjacent and generally parallel receiving barrels 507. The configuration of base member 504 as a multi-barrel component is in keeping with previous discussion in this disclosure that base member 104 may include cylindrical formations to accept two cylindrical-type fluid pumps 160. Barrels 507 are adapted to accept two identical fluid pumps 560 which form the movable components of fluid pumping device 500 as identified previously and which are described in detail herein. While the illustrated configuration of base member 504 comprises two adjacent barrels 507 defined by base member 504 for accepting two like fluid pumps 560, this illustration is not intended to restrict the possibility of base member 504 forming an additional or several additional barrels 507 to accept an additional or several fluid pumps 560 respectively therein. Again, for simplicity and expediency, the following discussion describes fluid pumping device 500 with two like fluid pumps 560 as a non-limiting embodiment of fluid pumping device 500. As shown, barrels 507 define a generally cylindrical shape to receive generally cylindrical-shaped fluid pumps 560 therein. For purposes of explaining the spatial orientation of features or components of fluid pumping device 500, base member 504 may be considered to have a first or top side 508, a second, bottom, or underside 510, and opposing lateral sides 512. Base member 504 generally comprises two opposing ends 520, 522. First end 520 of base member 504 defines two barrel openings 524 to permit access to barrels 507 and barrels 507 are substantially closed by end walls 548 at second end 522 which define two small vent openings 525 therein. The purpose of vent holes 525 will be discussed in greater detail hereinafter.

Figure 68:
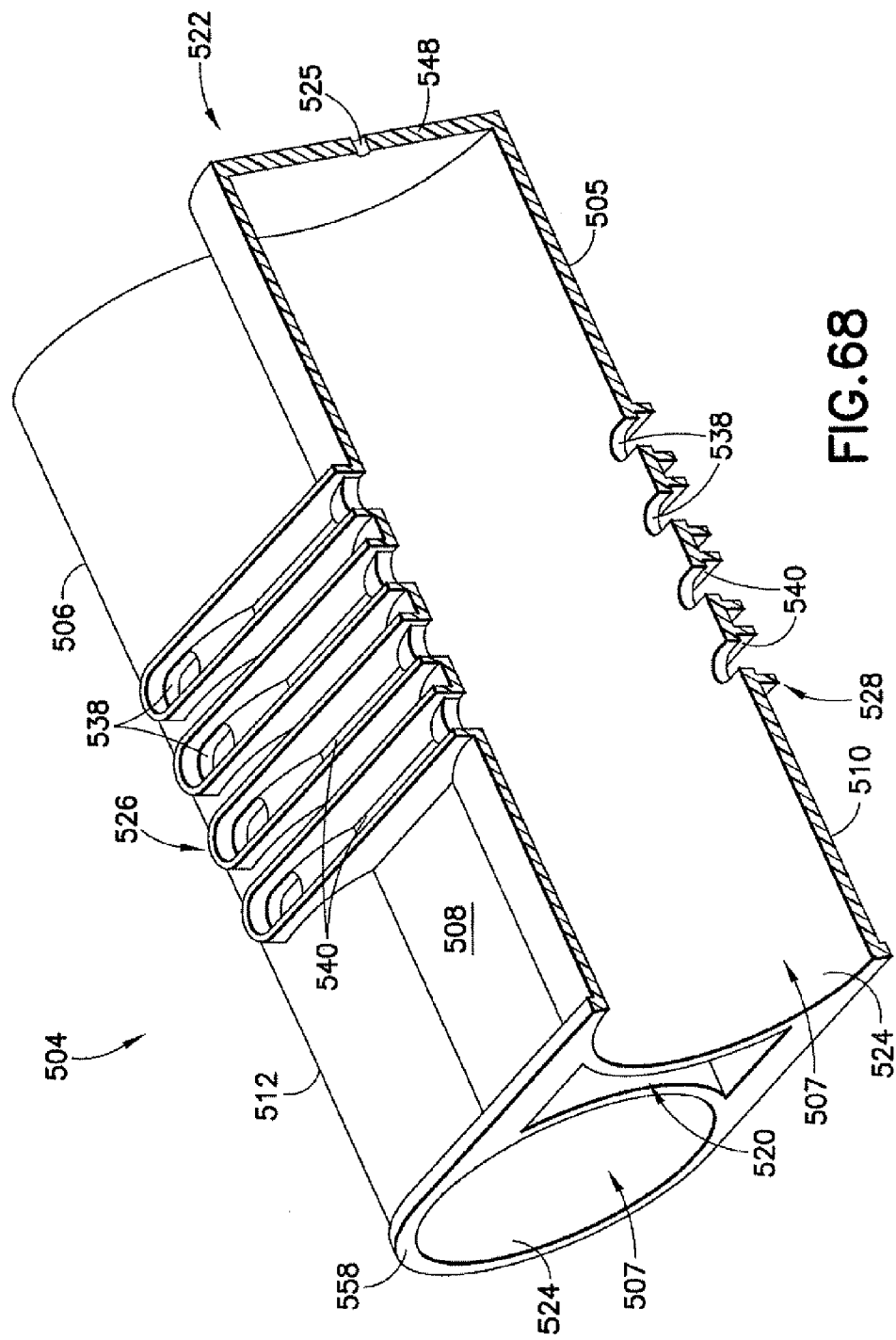
FIG. 68 is a perspective and partial cross-sectional view of a base member of a pump housing of the fluid pumping device of FIG. 65.
Figure 69:
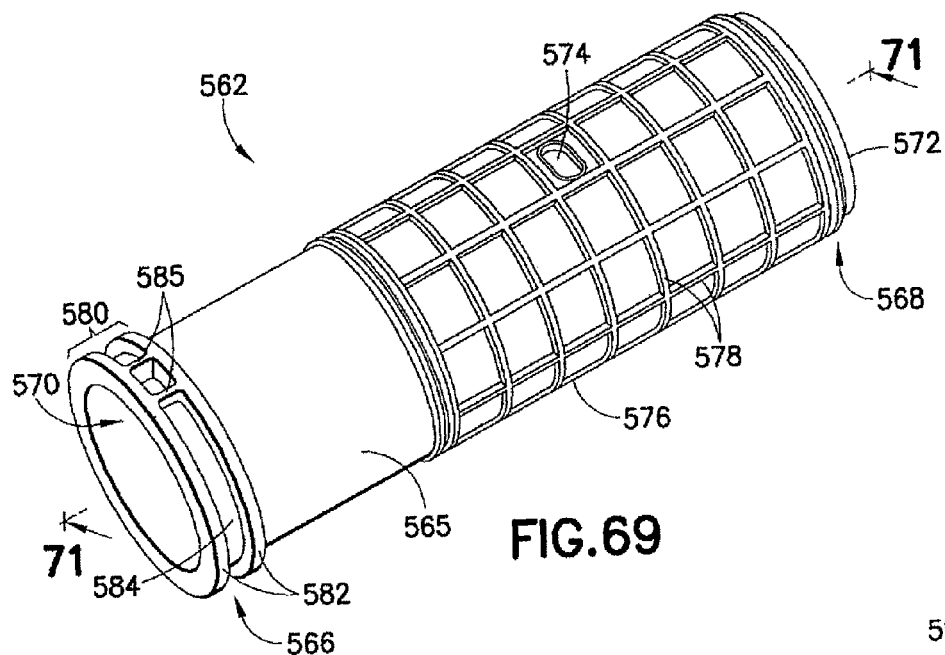
FIG. 69 is a perspective view of a sleeve piston of a fluid pump in the fluid pumping device of FIG. 65.
Figure 70:
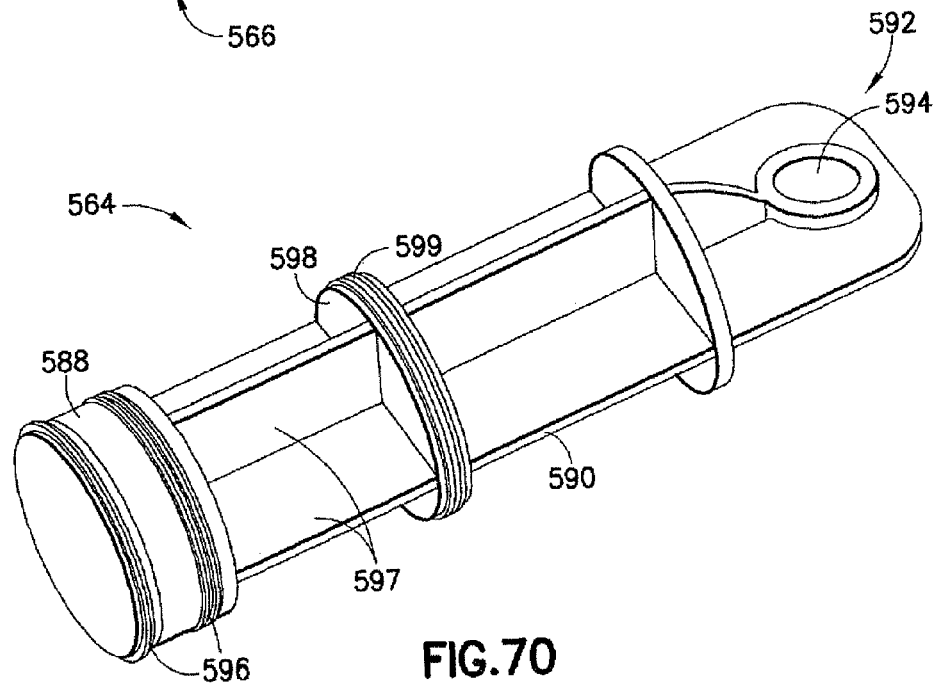
FIG. 70 is a perspective view of an insertion piston in the fluid pump of the fluid pumping device of FIG. 65.
Figure 71:
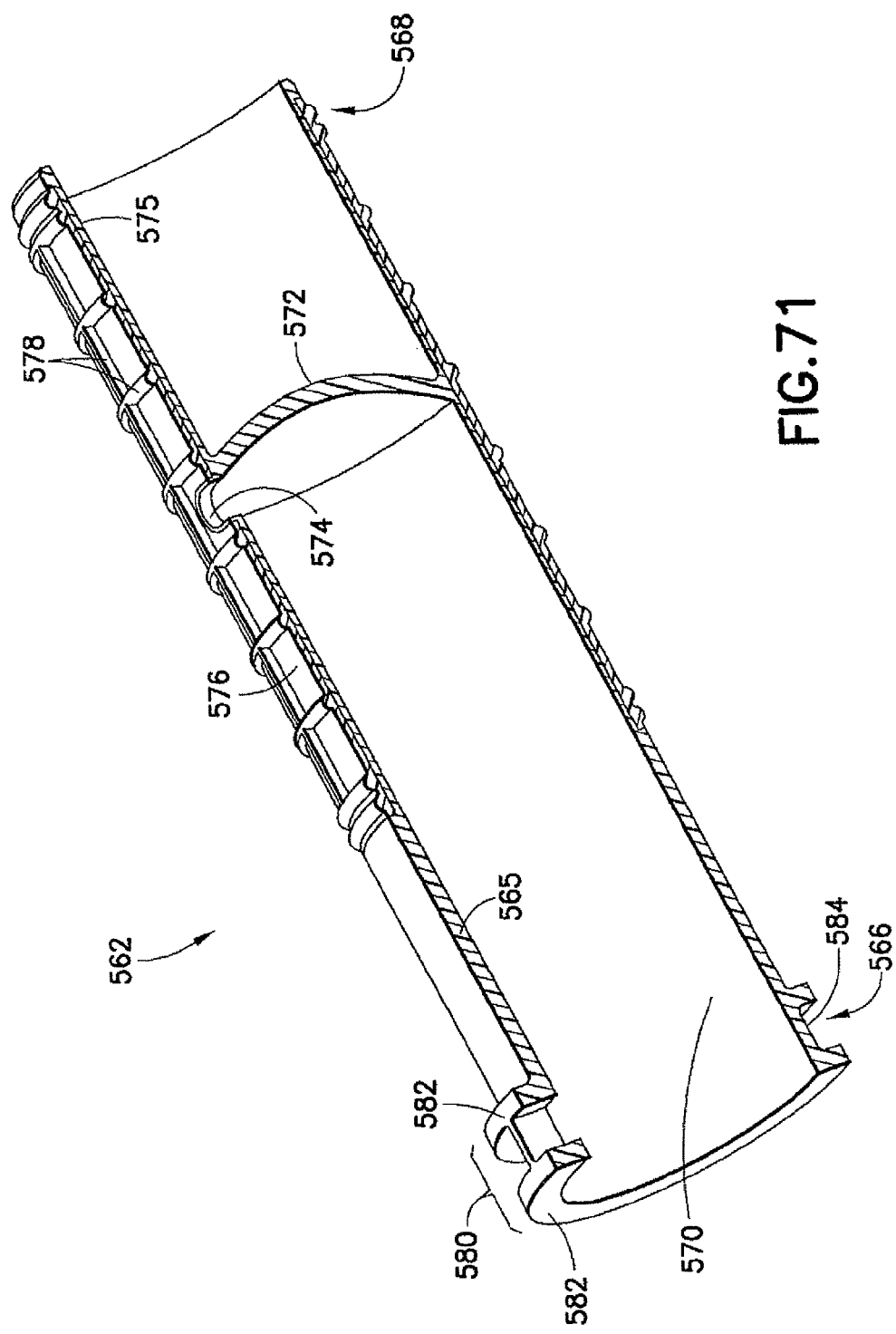
FIG. 71 is a cross-sectional view taken along line 71-71 in FIG. 69.
Figure 72:
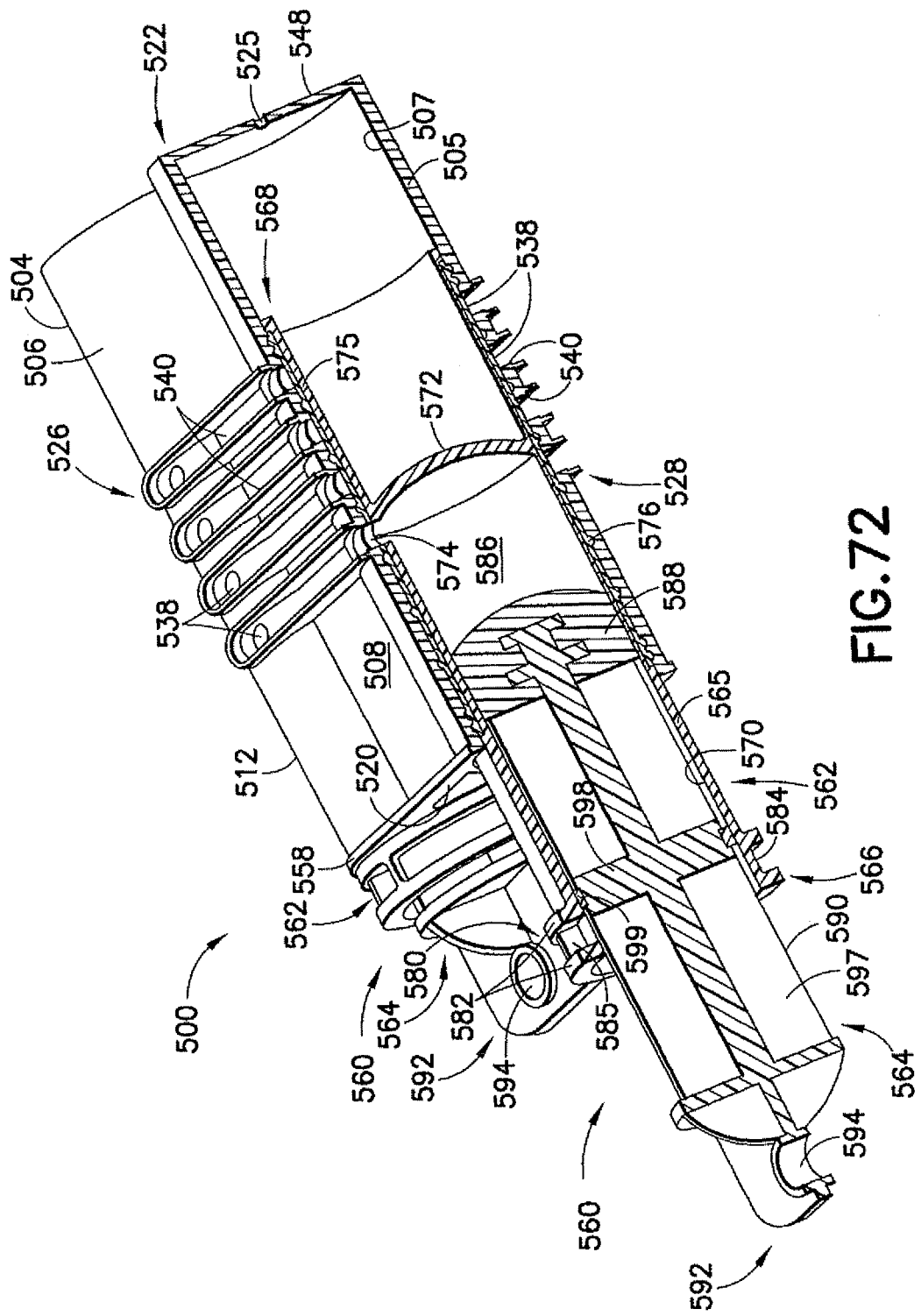
FIG. 72 is a cross-sectional view taken along line 72-72 in FIG. 65.

With specific reference to FIG. 68, base member 504 further comprises a first manifold portion 526 on top side 508 and a second manifold portion 528 on the bottom side 510. First manifold portion 526 and second manifold portion 528 are identical except that first manifold portion 526 is positioned on top side 508 of base member 504 and second manifold portion 528 is positioned on bottom side 510 of base member 504. First manifold portion 526 and second manifold portion 528 are generally centered between opposing ends 520, 522 of base member 504. First manifold portion 526 extends upward or is generally upstanding from the top side 508 of base member 504 and second manifold portion 528 extends downward from the bottom side 510 of base member 504. In the illustrated embodiment, first manifold portion 526 and second manifold portion 528 are formed integrally with base member 504. Alternatively, manifold portions 526 and 528 may also be formed as separate components that are joined to base member 504 by joining methods customary in the art such as ultrasonic welding, laser welding, adhesive, by direct mechanical attachment, and like methods.

Manifold caps 532, 533 each define a series of fluid connector ports 536. Connector ports 536 are similar to connector ports 136 described previously and generally connector ports 536 and are adapted to interface with connectors 20 at the end of fluid lines 18 associated with the respective fluid containers 16 shown in FIG. 1B to form a generally leak proof connection with the connectors 20. Manifold portions 526, 528 each comprise a series of fluid ports 538 defined in base member 504 each having an associated or connected fluid passageway 540. Fluid ports 538 provide fluid communication with the respective fluid pumps 560. Generally, connector ports 536 on manifold caps 532, 533 fluidly connect with one of the fluid ports 538, respectively, defined by the respective manifold portions 526, 528 thereby fluidly linking the respective fluid passageways 540 formed in manifold portions 526, 528 with a respective one of the connector ports 536. In the accompanying figures, each associated or connected connector port 536, fluid port 538, and fluid passageway 540 is given a designated and like numeric identifier for ease in discerning one associated connector port 536, fluid port 538, and fluid passageway 540 from an adjacent associate connector port 536, fluid port 538, and fluid passageway 540. When manifold caps 532, 533 are secured to manifold portions 526, 528 of base member 504, the respective fluid ports 538 and connected fluid passageways 540 are enclosed. Accordingly, connectors ports 536 are adapted as inlet ports for associating one or more fluids to fluid pumps 560 or as one or more outlet ports for delivering a single fluid or a mixture of fluids to a downstream process, for example, patient fluid path 12 or waste fluid line 22 coupled to a suitable medical fluid waste container (not shown). Base member 504 also comprises a radial end flange 558 at first end 520.

Fluid pumps 560 are located within the respective barrels 507 defined in base member 504, as generally described previously. Fluid pumps 560 each comprise two opposing pistons 562, 564, which may be referred to herein as a first piston or sleeve piston 562 and a second piston or insertion piston 564 for identification purposes. As each fluid pump 560 is identical having identical operating pistons 562, 564, the following discussion outlines the structure of one such fluid pump 560 used in fluid pumping device 500. A suitable configuration for pistons 562, 564 of fluid pump 560, in a similar manner to previous embodiments, comprises insertion piston 564 disposed or inserted at least partially into sleeve piston 562. For this purpose, sleeve piston 562 may have a generally cylindrical configuration comprising a cylindrical sleeve body 565 with opposing first and second ends 566, 568. Sleeve body 565 defines an internal cavity or chamber 570 wherein insertion piston 564 may be inserted or disposed. The second end 568 of sleeve body 565 defines an arcuate or curved end wall 572. A sleeve access opening or sleeve port 574 is defined in sleeve body 565 to provide access to internal cavity 570. A distal cylindrical portion 575 of sleeve body 565 encloses end wall 572 and provides a structure adapted to contact the closed end wall or end face 548 in each cylindrical member 505, 506 during operation of fluid pumps 560.

A sleeve-shaped elastomeric seal or sleeve 576 is desirably provided about sleeve body 565 to encompass a substantial portion of the sleeve body 565 from the closed second end 568 forward toward the open first end 566 of the sleeve body 565. Elastomeric sleeve 576 includes a plurality of intersecting ribs 578. Elastomeric sleeve 576 fluidly seals sleeve body 565 in its receiving barrel 507 in base member 504 of pump housing 502. Elastomeric sleeve 576 may be formed separately from sleeve piston 562 and then assembled to sleeve body 565 of sleeve piston 562 or the elastomeric sleeve 576 may be formed integrally with the sleeve body 565 during a subsequent overmolding technique and like processes. Elastomeric sleeve 576 generally replaces the fluid seal elements 120, 320 described previously in this disclosure, but such seals may be provided in association with manifold portions 526, 528 if desired.

Fluid pumping device 500 is generally adapted such that pistons 562, 564 for each fluid pump 560 may be "driven" from the same side of the fluid pumping device 500 utilizing drive system 700 described previously. More particularly, pistons 562, 564 for each fluid pump 560 are adapted to be driven from the same end 520 of base member 504 of fluid pumping device 500 by drive system 700. In like manner to previous embodiments, sleeve body 565 of sleeve piston 562 may comprise a dual or double rim end flange 580 which is formed as part of the sleeve body 565 and forms the first end 566 of the sleeve body 565. End flange 580 comprises two spaced apart rim flange elements 582 which define an intervening space 584 for interfacing with the U-shaped saddle element 750 associated with piston interface structure 748 discussed previously in connection with drive system 700 and now also suited to operation of fluid pumping device 500 according to the present embodiment. A distal or "interior" one of the two spaced rim flange elements 582 still forms an interfering structure at first end 566 of sleeve body 565 of sleeve piston 562 to engage radial end flange 558 at end 522 of base member 504 to limit linear travel of the sleeve piston 562 into base member 504, in a similar manner to that described previously in this disclosure. It will be appreciated that drive system 700 may be altered to effect both reciprocal linear movement, and, desirably, at least limited rotational movement sleeve piston 562 within barrel 507 of base member 504 by appropriate modification to piston interface structure 748. One such modification could include providing a separate actuating device associated with piston interface structure 748 to allow at least limited rotation of U-shaped saddle element 750. A limited rotational movement capability of U-shaped saddle element 750, in turn, would effect limited rotational movement of sleeve piston 562 in barrel 507 of base member 504. For this purpose, intervening ribs 585 may be provided in intervening space 584 to engage structure on U-shaped saddle element 750 such that any limited rotational movement of U-shaped saddle element 750 is transmitted to sleeve piston 562 via engagement with ribs 585. With respect to drive system 900, at least a limited rotational capability may be provided to sleeve piston positioning device 906 and to sleeve outer drive tube 908 in particular which would interface with sleeve piston 562.

As noted previously, insertion piston 564 is adapted to access internal cavity 570 defined by sleeve body 565 of sleeve piston 562. Insertion piston 564 is reciprocally movable within sleeve body 565, and may be actuated in the manner described previously in connection with drive system 700 relating to insertion piston 164. As described herein, insertion piston 564 is desirably similarly configured to insertion piston 164 to interface with drive system 700 in the manner described previously. With insertion piston 564 engaged in sleeve piston 562 disposed within sleeve portion 570, pistons 562, 564 cooperate to form or define a pumping chamber 586 of fluid pumping device 500.

Piston 564 comprises a piston head 588 and a proximally extending piston rod 590. Piston rod 590 comprises a generally X-shaped configuration and terminates at a proximal end thereof with a disc element having a drive interface portion 592 extending therefrom. Drive interface portion 592 defines an attachment aperture 594. Drive interface portion 592 and attachment aperture 594 are desirably identical to drive interface portion 198 described previously in this disclosure, wherein an interface aperture or attachment aperture 200 is used to associate previously-described piston rod 196 with drive system 700 described previously. Accordingly, drive system 700 may also be used to operate piston 564 in fluid pumps 560 of fluid pumping device 500 in the manner detailed previously within this disclosure.

Piston rod 590 is desirably formed of a generally rigid plastic material such as polycarbonate and piston head 588 is desirably formed of a polymeric material, such as polyurethane and the like, that is overmolded onto a distal end of piston rod 590. The generally X-shaped cross-section of piston head 588 may be formed by individual flange elements 597. Piston head 588 exhibits a generally curved or arcuate-shaped configuration to engage end wall 572 of sleeve body 565 of sleeve piston 562 which desirably has a corresponding arcuate or "domed" shape for strength purposes as detailed previously in this disclosure. The polymeric material defining piston head 588 desirably defines one or more circumferential sealing ribs 596 to form a fluid seal with the inner wall of sleeve body 565 of sleeve piston 562. While a pair of sealing ribs 596 is shown on piston head 588, additional spaced ribs or a single such rib may be provided as desired.

As indicated, the generally X-shaped cross-section of piston rod 396 may be formed by individual flange elements 597 and is desirably reinforced with an additional disc element 598 located distally forward of drive interface portion 592 as illustrated. Additional disc element 598 may comprise an overmolded polymeric layer 599 in a generally similar manner to the polymeric material forming piston head 588. The polymeric-covered additional disc element 598 generally provides stability to piston 564 as it operates within sleeve body 565 of sleeve piston 562. It will be appreciated that sealing ribs 596 on piston head 588 form a generally fluid tight seal between piston head 588 and sleeve body 565 of sleeve piston 562 such that pumping chamber 586 is a generally fluid tight chamber during a static, non-moving situation involving pistons 562, 564 or during dynamic, operational movement of pistons 562, 564. Specific materials for forming piston head 588 and polymeric layer 599 may be any of those identified in the foregoing in connection with piston head 194, 394, other suitable materials may be used such as those detailed previously in connection with fluid seal elements 120. Desirably, the polymeric material forming piston head 588 and polymeric layer 599 are the same material, for example, polyurethane. If desired, polymeric layer 599 may be formed onto flange elements 597 so that polymeric layer 599 encompasses the circumferential edge of disc element 598 and the outward facing edges of the individual flange elements 597 defining piston rod 590 in the manner described previously in this disclosure. As in previous embodiments, end flange 580 on sleeve body 565 of sleeve piston 562 may be configured in a similar manner to end flange 410 described previously and drive interface portion 592 of piston rod 590 of insertion piston 564 may be configured in a similar manner to drive interface flange 398 described previously so that pistons 562, 564 are suitable for operation by drive system 900.

Referring further to FIGS. 73-80, basic operation of fluid pumping device 500 will now be described. As noted previously, fluid pumping device 500 comprises two fluid pumps 560 in the illustrated and non-limiting embodiment in the accompanying figures. Moreover, first manifold portion 526 and first manifold cap 532 along with second manifold portion 528 and second manifold cap 533 together comprise a series of eight connector ports 536 having the configuration described hereinabove. Of these eight connector ports 536, it may be desirable to have six of these connector ports 536 be inlet connector ports, 536(1)-536(6), and the remaining two fluid ports 536 be outlet connector ports, 536(7), 536(8). As an example, in the context of using fluid pumping device 500 for delivering contrast media fluid to a patient during a radiographic imaging procedure, the six inlet fluid connector ports 536 may be divided as follows: two connector inlet ports 536 for saline 536(1), 536(4); two connector inlet ports 536 for one type, concentration, or brand of contrast media fluid 536(2), 536(5); and two connector inlet ports 536 for a different type, concentration, or brand of contrast media fluid of contrast media fluid 536(3), 536(6). The two remaining connector ports 536 may be divided into a patient connector port 536(7) and a waste connector port 536(8). While the foregoing example limits the discussion to eight fluid connector ports 536, it is possible within the scope of this disclosure to add additional such ports for additional inlet and outlet ports if desired based on the details provided hereinabove.

As noted previously, fluid pumps 560 are configured such that, under the action of drive system 700, pistons 562, 564 in each fluid pump 560 may be separately controlled and, therefore, are separately positionable relative to one another. Stated another way, each sleeve piston 562 is movable relative to its opposing insertion piston 564 and vice versa. Accordingly, it is possible for insertion piston 564 to move while the opposed sleeve piston 562 remains stationary and vice versa. In addition, in the present embodiment, each sleeve piston 562 is capable of being moved in both a linearly reciprocal and at least in a limited rotational manner. For clarity in explaining operation of fluid pumps 560 in fluid pumping device 500, the following discussion will describe the operation of one fluid pump 560. It will be appreciated that the additional or "second" fluid pump 560 in fluid pumping device 500 may be operated in the same manner and, additionally, in a staggered mode from the "first" fluid pump 560 so that continuous fluid delivery may be provided at patient connector port 536(7); staggered operation of fluid pumps 160 has been described in detail herein and such operation is applicable to fluid pumps 560. As will be appreciated and apparent from the accompanying figures, both fluid pumps 560 are capable of sharing inlet connector inlet ports 536(1)-536(6) and outlet connector ports 536(7) and 536(8) due to the configuration of fluid passageways 540 and associated fluid ports 538 in base member 504.

Figure 73:
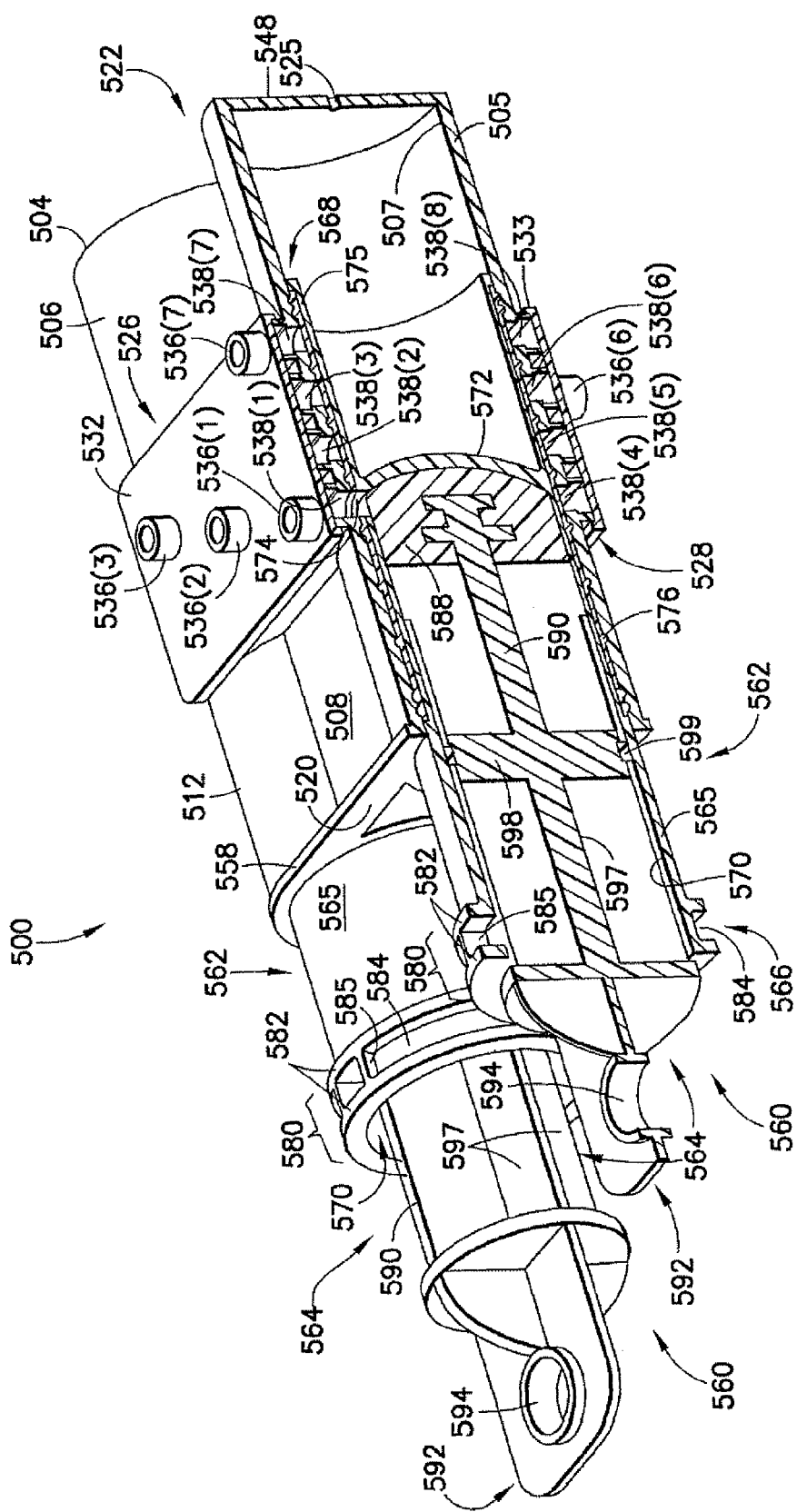
FIGS. 73-80 are cross-sectional views showing one complete fluid fill and ejection cycle of one of the fluid pumps of the fluid pumping device of FIG. 65.
Figure 74:
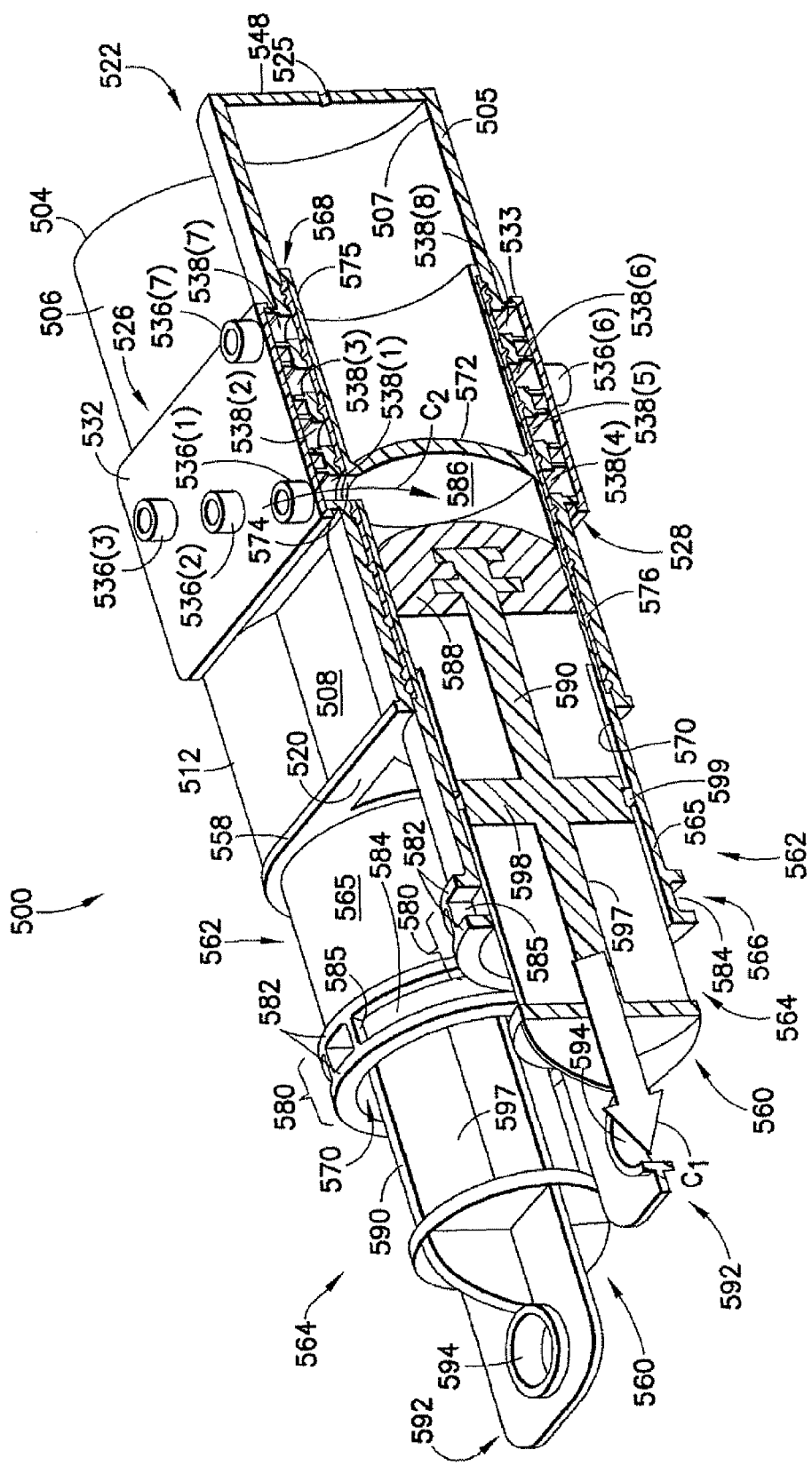
Figure 75:
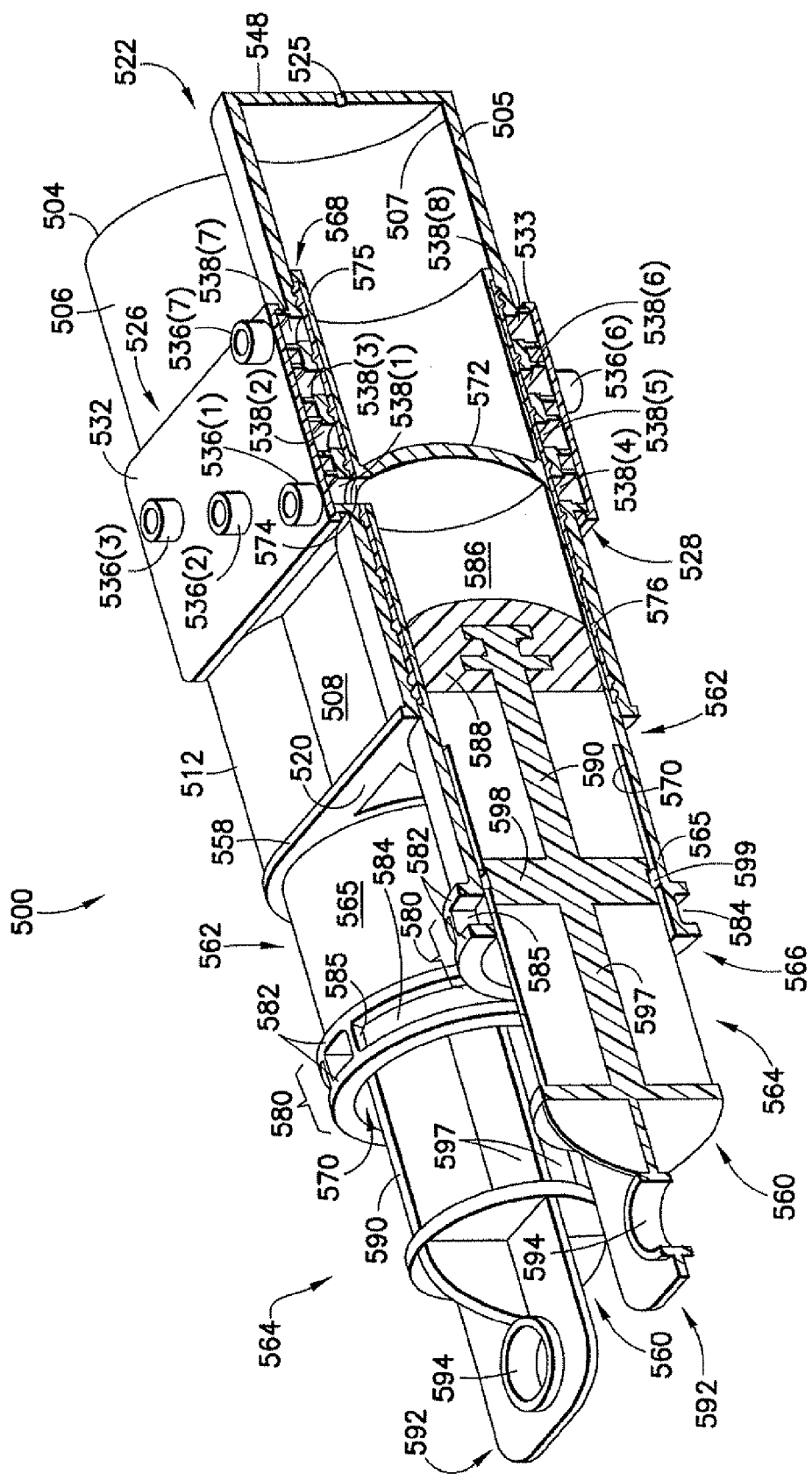
Figure 76:
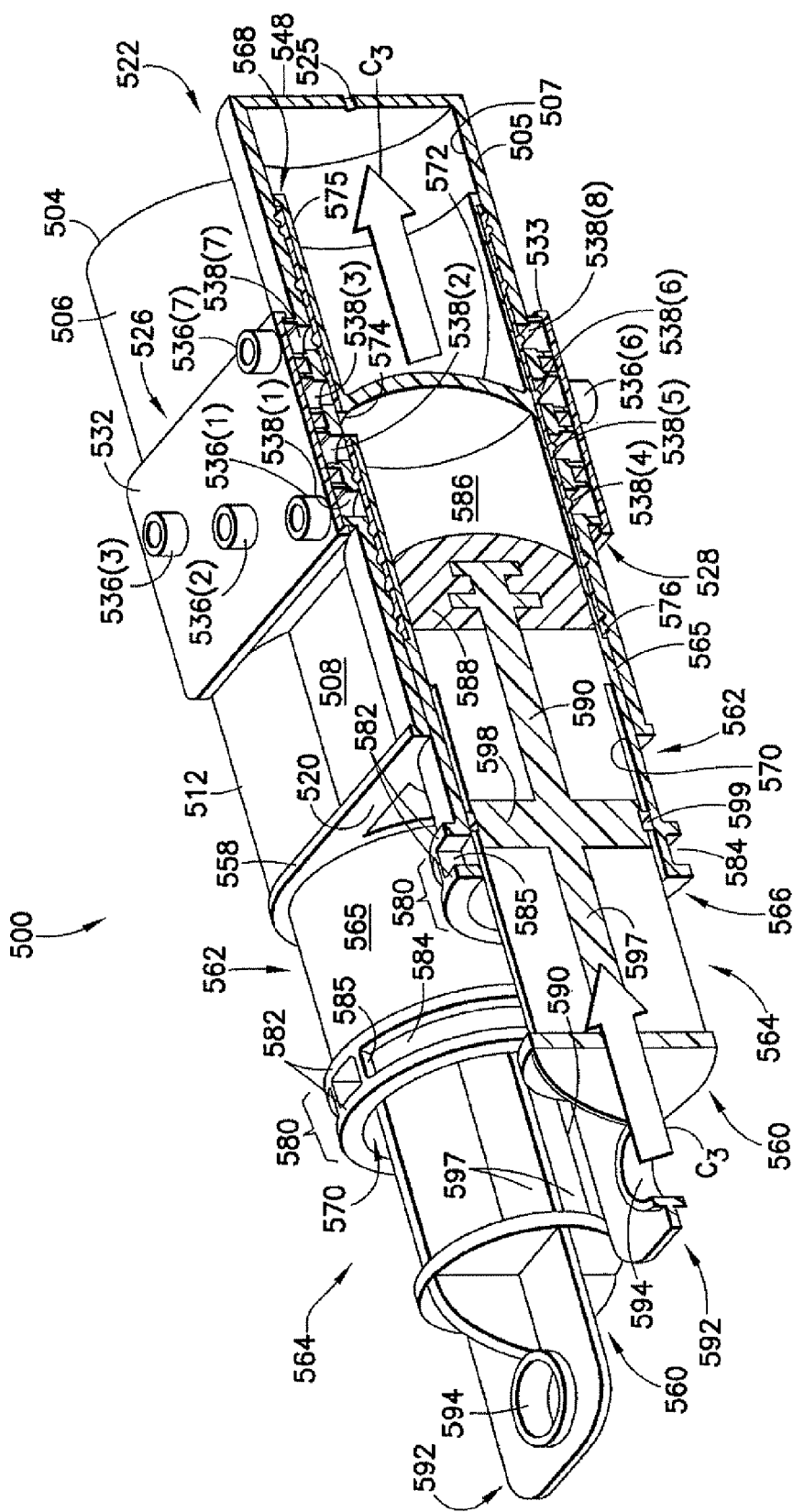

The ability of pistons 562, 564 to move independently under the motive forces provided by drive system 700 allows, for example, sleeve piston 562 to remain stationary proximate to one of inlet fluid ports 538(1)-538(6) so sleeve port 574 in sleeve body 565 of sleeve piston 562 is associated with a selected one of the inlet fluid ports 538(1)-538(6). For example, as illustrated in FIG. 73, fluid pump 560 may begin in a position where sleeve port 574 of sleeve body 565 of sleeve piston 562 is aligned with inlet fluid port 538(1). As sleeve piston 562 is held stationary at inlet fluid port 538(1) by drive system 700, opposing piston 564 may be moved axially and generally linearly away from sleeve piston 562 by drive system 700. As this movement occurs, as represented by an arrow $C_1$ in FIG. 74, piston head 588 generally clears sleeve port 574, so that a substantially unimpeded inlet fluid path is established between a source of saline, for instance, and pumping chamber 586. This fluid path is denoted by an arrow $C_2$ in FIG. 74. As piston 564 continues to move in the direction of arrow $C_1$, fluid is pulled into pumping chamber 586 from a source of saline, for instance, through connector port 536(1) under negative pressure caused by this relative movement. The remaining fluid ports 538(2)-538(8) are blocked by the sleeve body 565 of sleeve piston 562 preventing fluid communication with pumping chamber 586. When a desired amount of fluid is drawn into pumping chamber 586 under the withdrawing action of piston 564, the movement of piston 564 is stopped by drive system 700. Both pistons 562, 564 may be moved to another inlet fluid port 538(2)-538(6), if desired, or alternatively, to the patient outlet port 538(7) or waste outlet port 538(8). During movement to another inlet fluid port, pistons 562, 564 are driven or moved substantially in synch with one another by the drive system 700 in order to prevent unwanted pressure or vacuum in pumping chamber 586. During movement of sleeve piston 562 in barrel 507, air in the barrel 507 is expelled through vent opening 525. An example of the synchronous movement of pistons 562, 564 is illustrated by arrows $C_3$ in FIG. 76.

Figure 77:
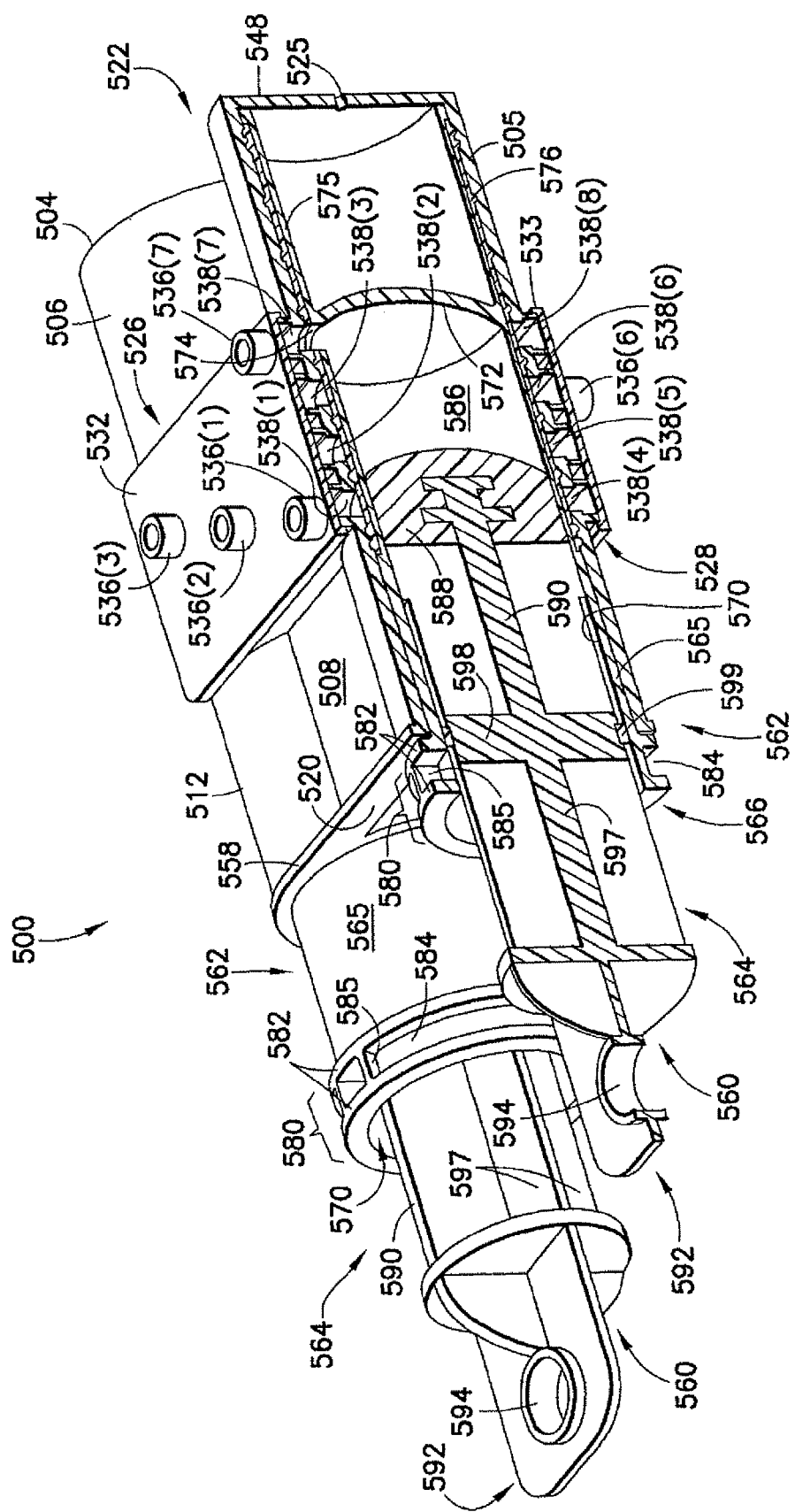
Figure 78:
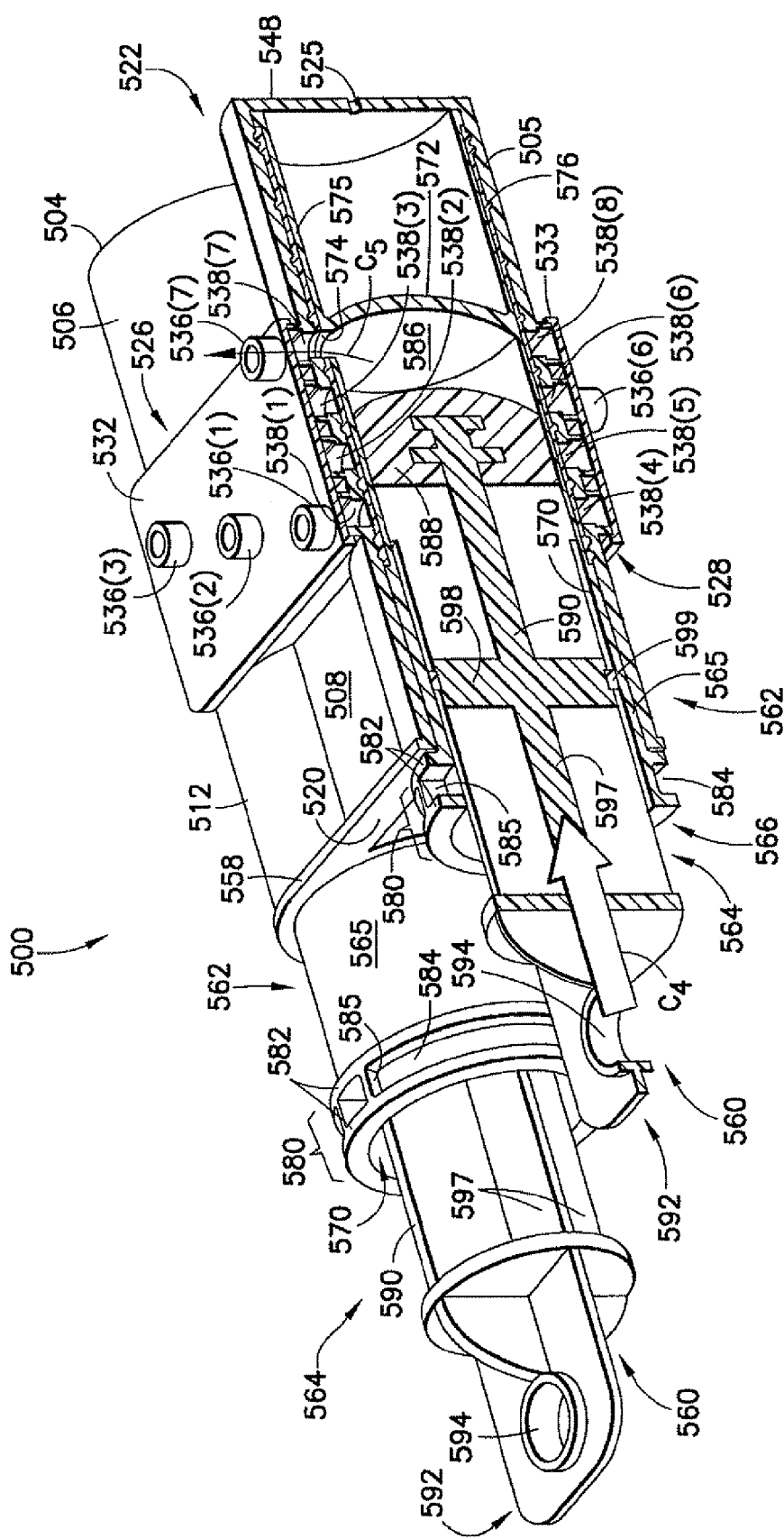
Figure 79:
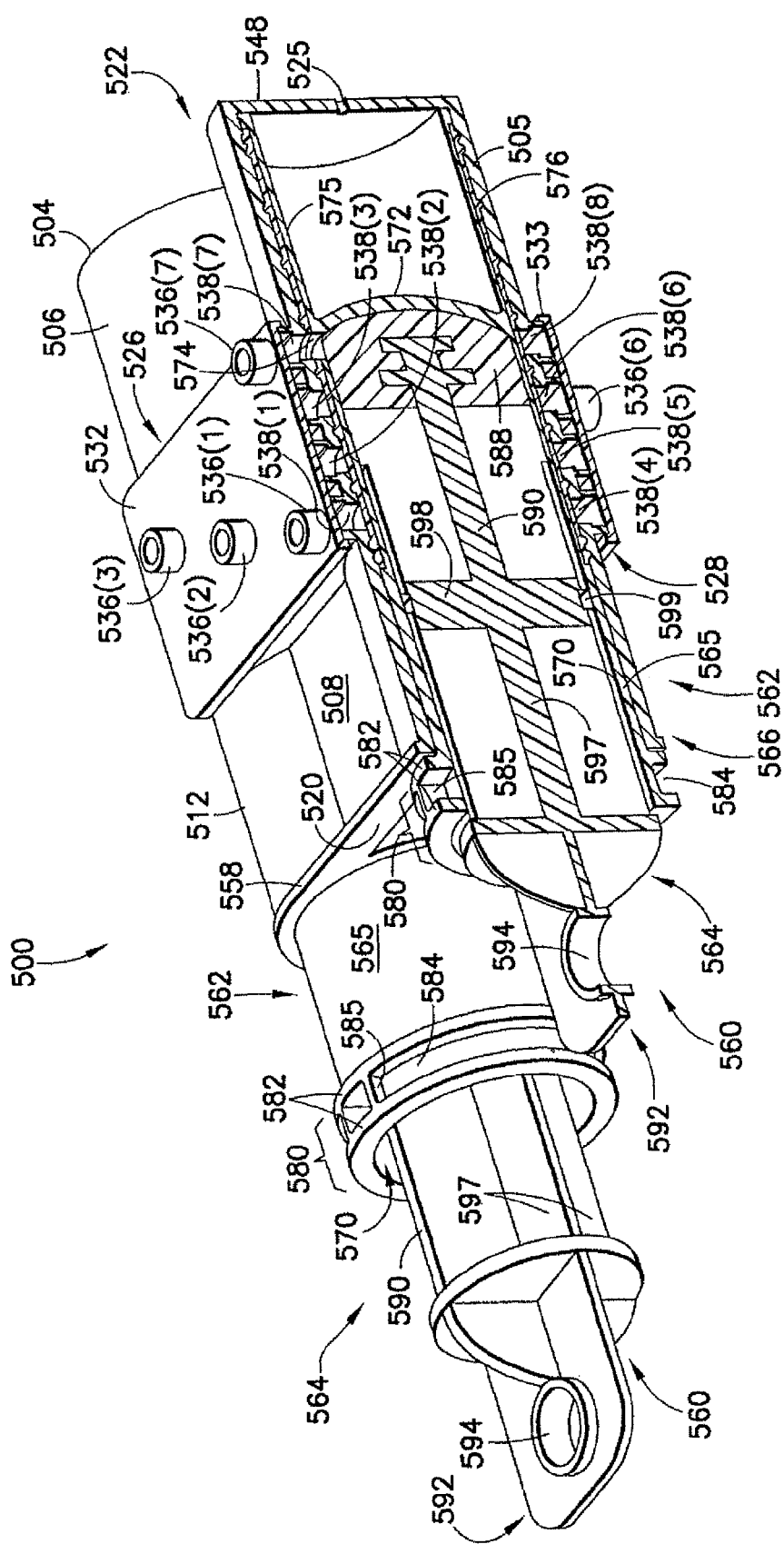
Figure 80:
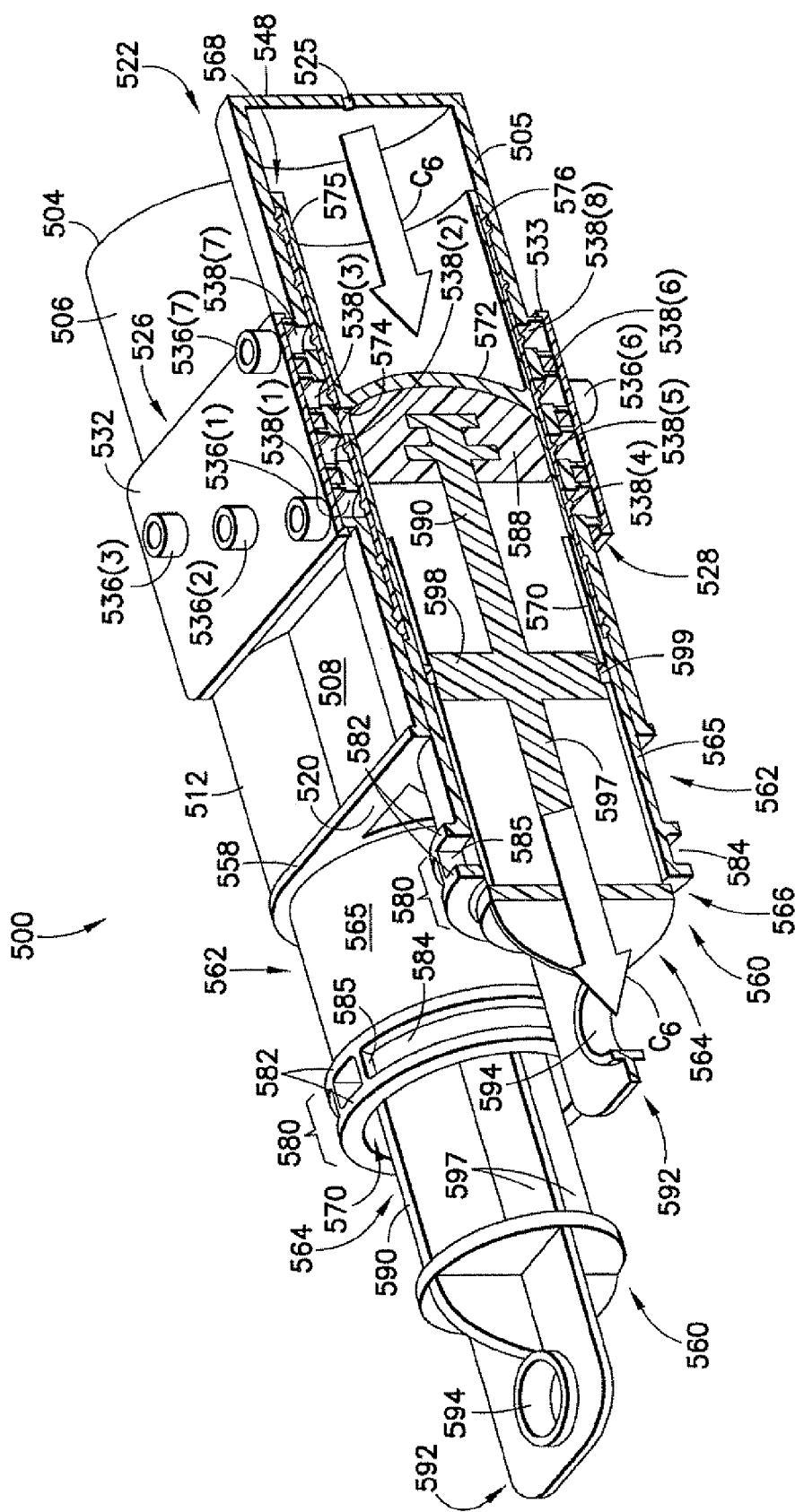

If it is desired to eject fluid into patient fluid path 12, patient outlet port 538(7) may be selected and, with alignment of sleeve port 574 with patient outlet port 538(7), an outlet fluid path is established from pumping chamber 586 to connector port 536(7) as shown in FIG. 77. Once the foregoing fluid path is established, drive system 700 "fixes" the location of sleeve piston 562. As sleeve piston 562 is held substantially stationary, insertion piston 564 may be operated by drive system 700 to begin a pumping or ejection stroke or movement. In the pumping or ejection stroke, as illustrated in FIGS. 78 and 79, piston 564 moves into the sleeve body 565 of sleeve piston 562 as represented by arrow $C_4$ in FIG. 78 to pressurize the fluid contained in pumping chamber 586 and expel this fluid through sleeve port 574, patient outlet port 538(7), connecting fluid passageway 540(7) and patient connector port 536(7), and into the patient fluid path 12. In FIG. 78, the expelling or ejection fluid from pumping chamber 586 in this manner is represented by arrow $C_5$. In FIG. 79, at the conclusion of the ejection stroke, the curved or arcuate shape of piston head 594 mates with the curved or arcuate shape of inner end wall 572 in sleeve body 565 of sleeve piston 562. As in previous embodiments, it is desirable for sealing ribs 596 on piston head 588 to be located just proximal of sleeve port 574 such that there is desirably a slight clearance around the distal end of piston head 588 and the inner wall of sleeve portion 574 to enable substantially all fluid to be ejected from pumping chamber 586 during the foregoing ejection or pumping stroke of insertion piston 564. As the ejection cycle is now complete, a fill cycle as described previously may begin again by substantially synchronously moving piston 562, 564 to desired inlet fluid port 538 as shown by arrows $C_6$ in FIG. 80.

Figure 81:
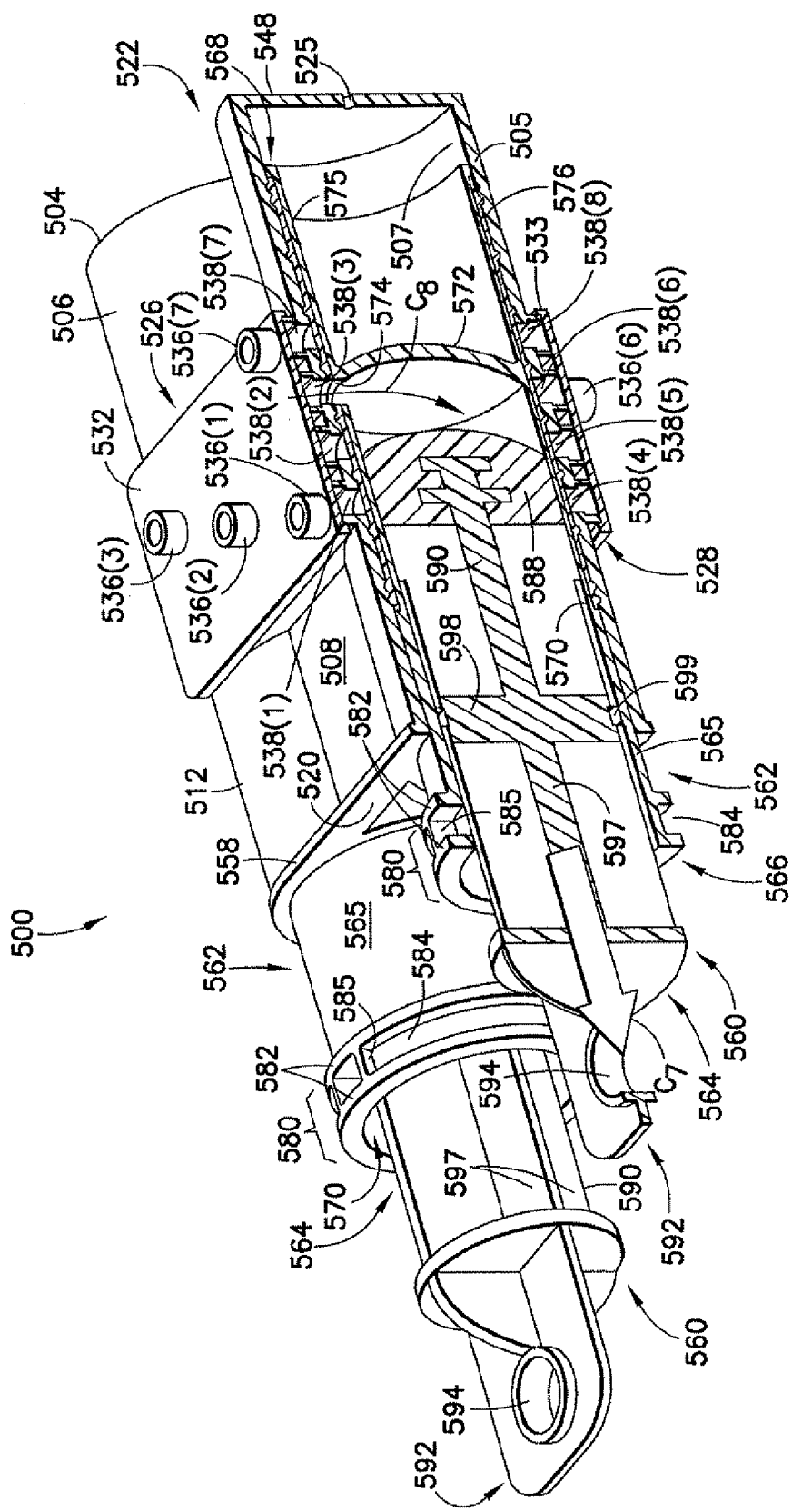
FIGS. 81 and 82 are cross-sectional views showing the fluid pumping device of FIG. 65 mixing fluids within the pumping chamber of one of the fluid pumps.
Figure 82:
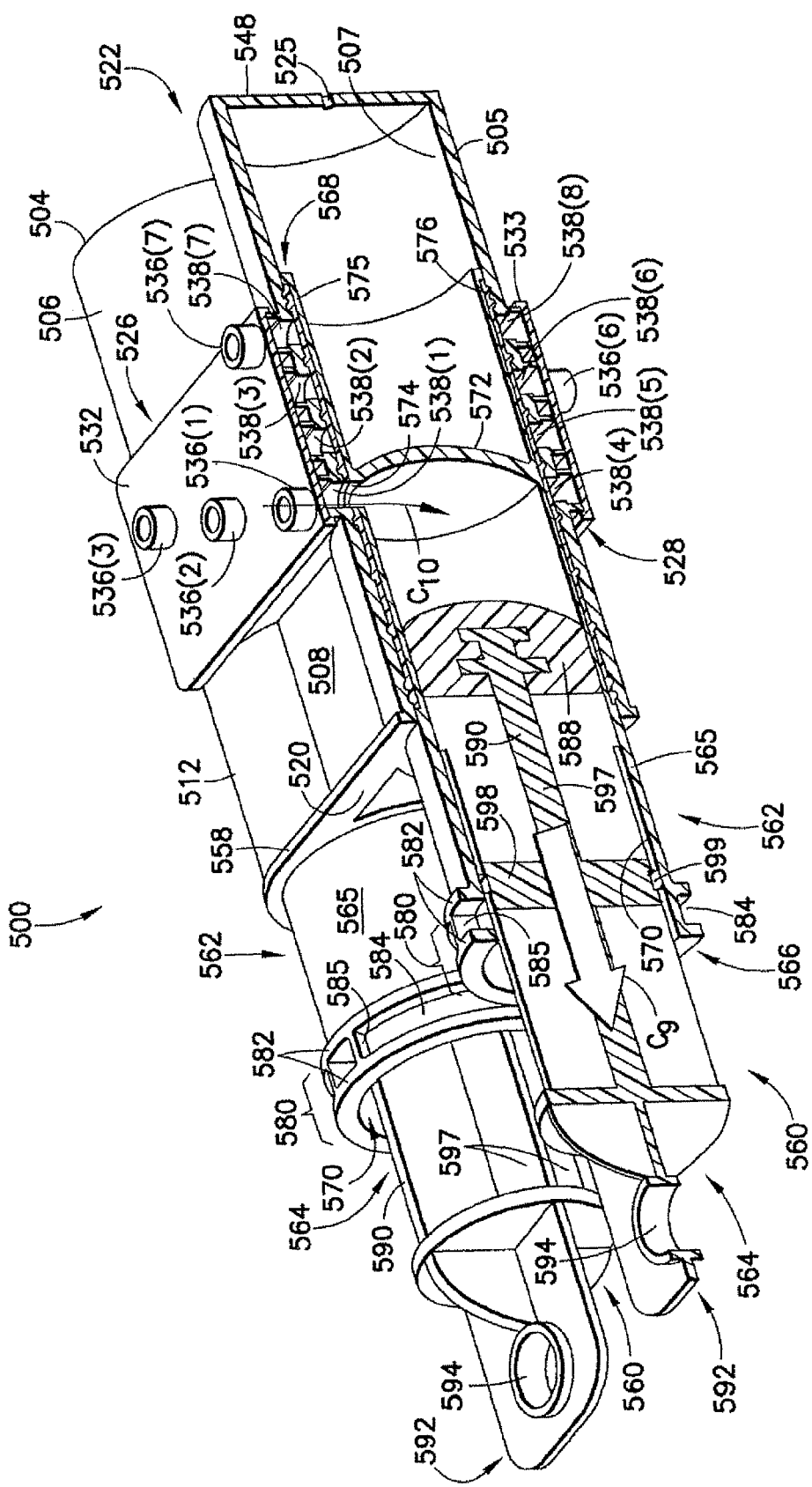

With reference to FIGS. 81 and 82, fluid pumping device 500 may also be configured to deliver a controlled mixture of two fluids, such as contrast and saline. This process is performed as generally follows. First, sleeve piston 562 is held stationary at a selected inlet fluid port 538, such as inlet fluid port 538(3), by drive system 700, and the opposing insertion piston 564 may be moved axially and generally linearly away from sleeve piston 562 by drive system 700 as described previously. As this movement occurs, as represented by an arrow $C_7$ in FIG. 74, piston head 588 again generally clears sleeve port 574, so that a substantially unimpeded inlet fluid path is established between a source of contrast media fluid, for instance, and pumping chamber 586. This fluid path is denoted by an arrow $C_8$ in FIG. 81. As noted in the forgoing, a slight clearance is always present around the distal end of piston head 588 and the inner wall of sleeve portion 574. As piston 564 continues to move in the direction of arrow $C_7$, fluid is drawn into pumping chamber 586 from a source of contrast media fluid connected to inlet connector port 536(3), into fluid passageway 540(3), and through inlet fluid port 538(3) under negative pressure generated by this movement.

Pistons 562, 564 are then substantially synchronously and linearly moved to select another port. Once the next port is selected, for example, inlet fluid port 538(1) as shown in FIG. 82, sleeve piston 562 is halted with sleeve body 565 positioned such that sleeve port 574 aligns with inlet fluid port 538(1) to allow fluid communication between pumping chamber 586 and inlet fluid port 538(1). As sleeve piston 562 is held stationary, opposing piston 564 may again be moved axially and generally linearly away from sleeve piston 562 as shown by arrow $C_9$ in FIG. 82. As this movement occurs, fluid, now saline from a source connected to inlet connector port 536(1), is drawn into pumping chamber 586, as shown by arrow $C_{10}$, under the negative pressure caused by the movement of piston 564. As saline enters pumping chamber 586, the saline mixes with the contrast media fluid already present in pumping chamber 586 which dilutes the contrast media fluid. It will be appreciated that the amount of saline and contrast media fluid drawn into pumping chamber 586 may be controlled by the amount or distance piston 564 is retracted relative to sleeve piston 562 in each of the foregoing "fill" procedures as detailed previously in this disclosure.

When a desired amount of saline is drawn into pumping chamber 586 under the moving action of piston 564, both pistons 562, 564 may be moved to another inlet fluid port 538(2), to receive a different contrast media fluid or another fluid altogether by the methodology described in the foregoing. Pistons 562, 564 may then be moved (desirably substantially in synch for the reasons noted previously) to an outlet fluid port 538, such as the patient outlet port 538(7) connected via fluid passageway 540(7) to patient connector port 536(7) which serves as the patient fluid administration port in the instant example.

With reference to FIGS. 83-88, the ability for sleeve piston 562 to be driven both axially and rotationally and the benefits of such movement will now be described. A possible limitation of the foregoing described operation of fluid pumping device 500 is that sleeve port 574 in sleeve body 565 of sleeve piston 562 must pass across most or all of fluid ports 538 as sleeve piston 562 moves axially. If pumping chamber 586 is under a slight negative pressure, fluid, either contrast media fluid or saline in the instant example, could be inadvertently drawn via one of the fluid ports 538 through sleeve port 574 into pumping chamber 586 as the sleeve port 574 passes over the fluid ports 538. A solution to this problem is to rotationally move sleeve piston 562 to an intermediate "shut off" position where sleeve port 574 is sealed off by the interior of barrel 507 in base member 504 before moving the sleeve piston 562 to another location. This may be done by rotating sleeve piston 562 with drive system 700 so that sleeve port 574 does not align with any of the fluid ports 538, moving sleeve piston 562 to a desired fluid port 538, and then rotating the sleeve piston 562 so that the sleeve port 574 in the sleeve body 565 of the sleeve piston 562 aligns with the selected fluid port 538 as will be described in greater detail hereinafter with reference to FIGS. 83-88.

Figure 83:
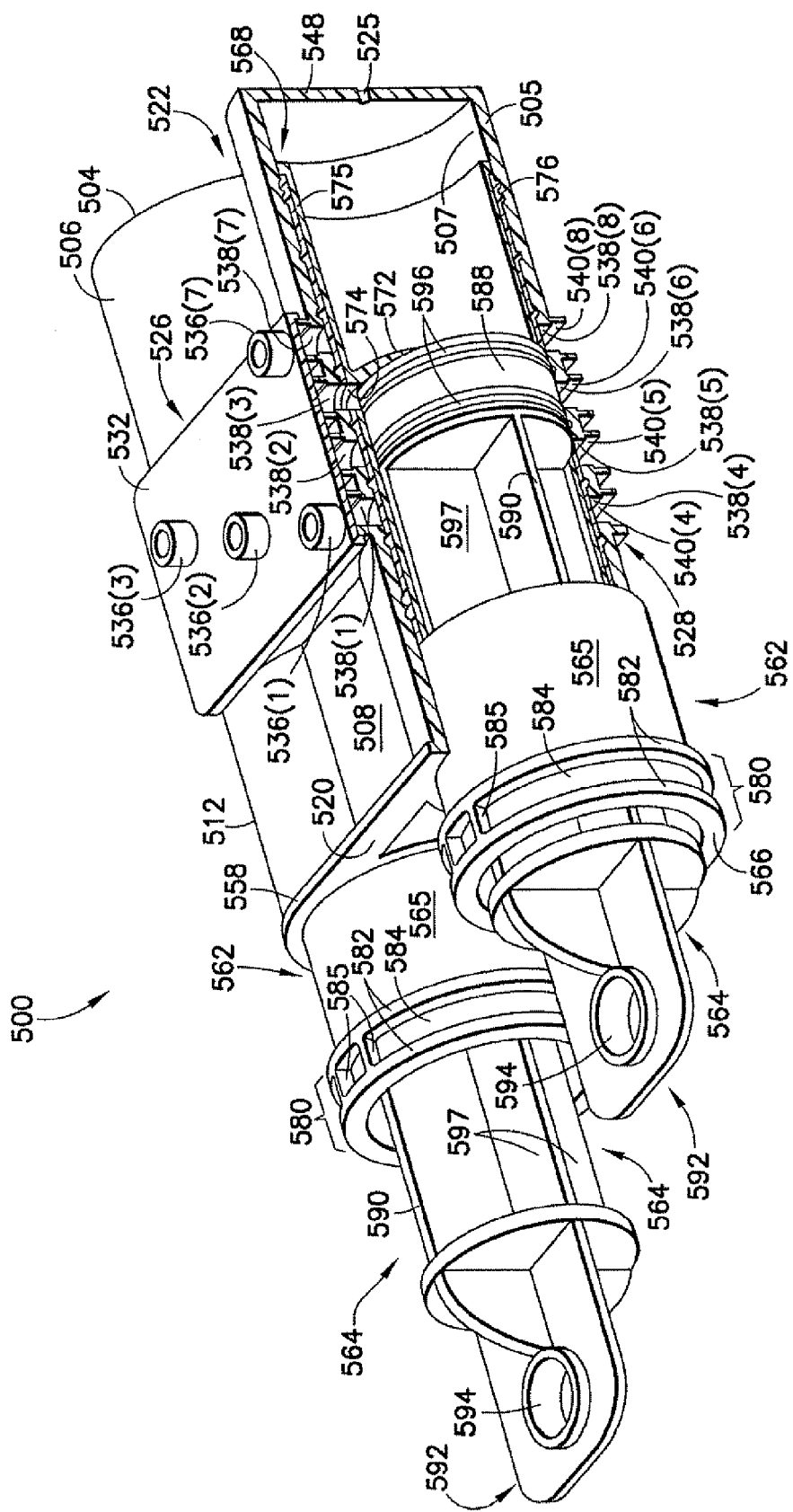
FIGS. 83-88 are cross-sectional views showing the sleeve piston of a fluid pump of the fluid pumping device of FIG. 65 isolating fluid ports in the base member of the pump housing during stages of a fluid fill and ejection cycle.
Figure 84:
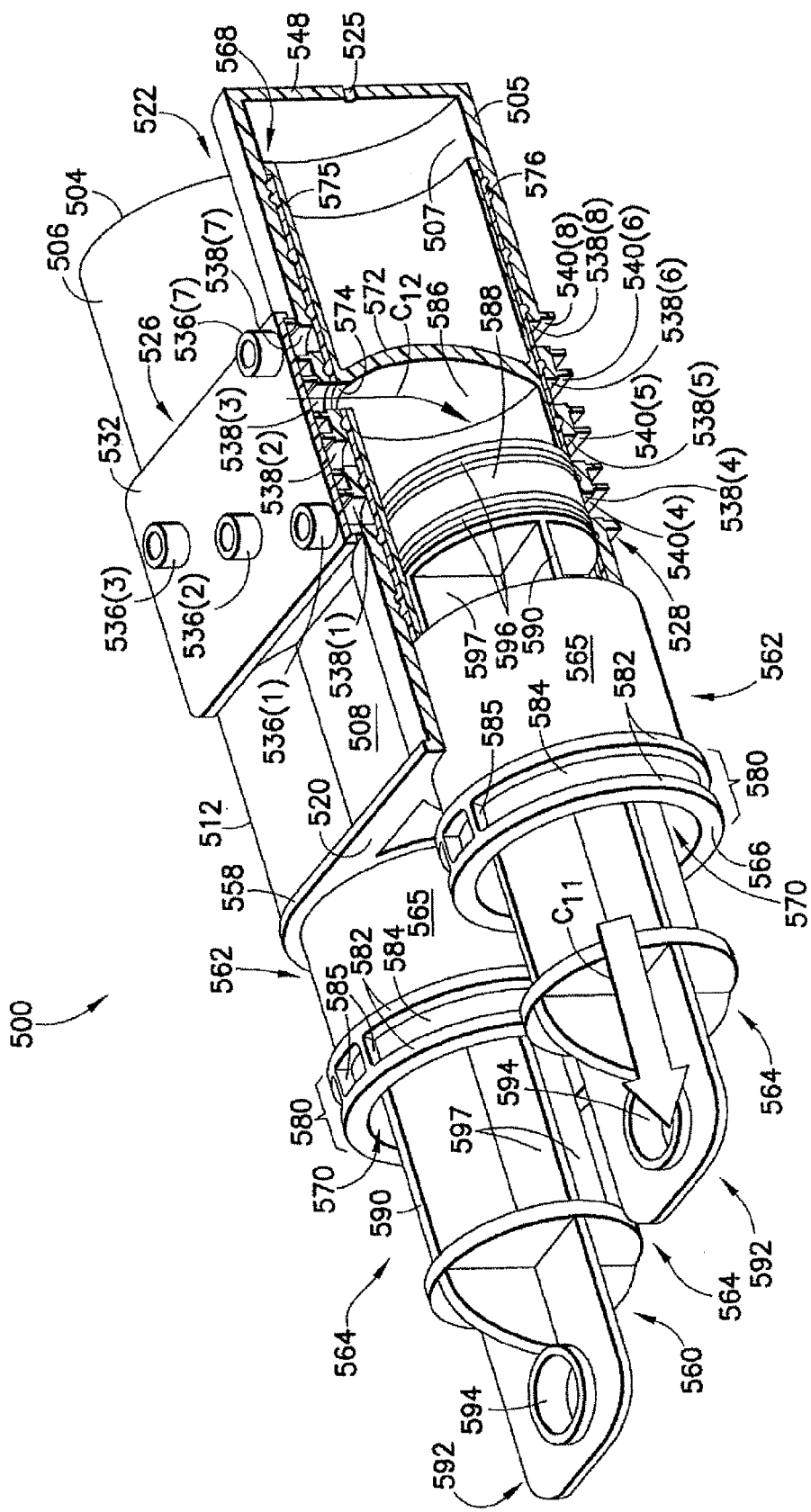
Figure 85:
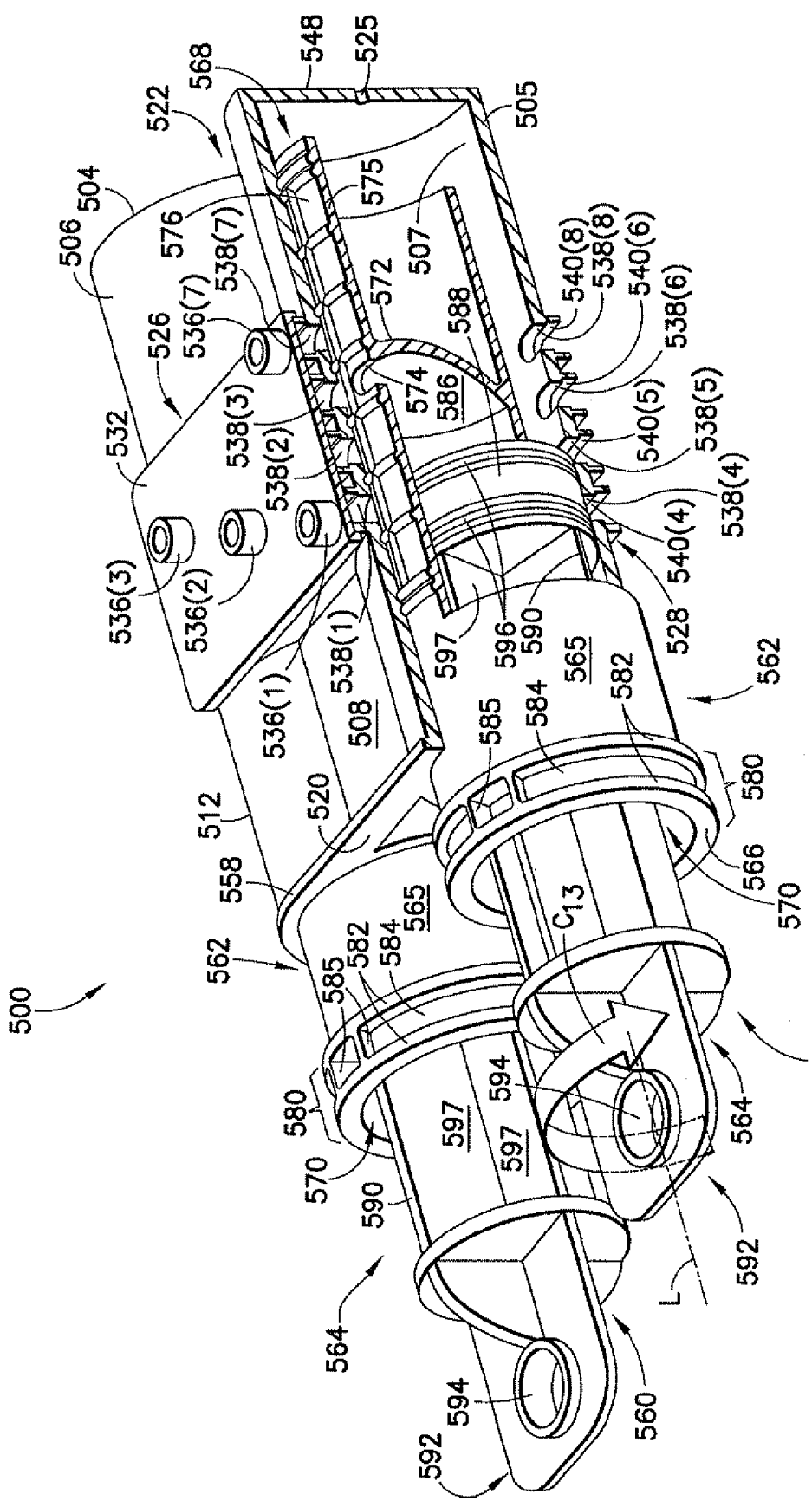
Figure 86:
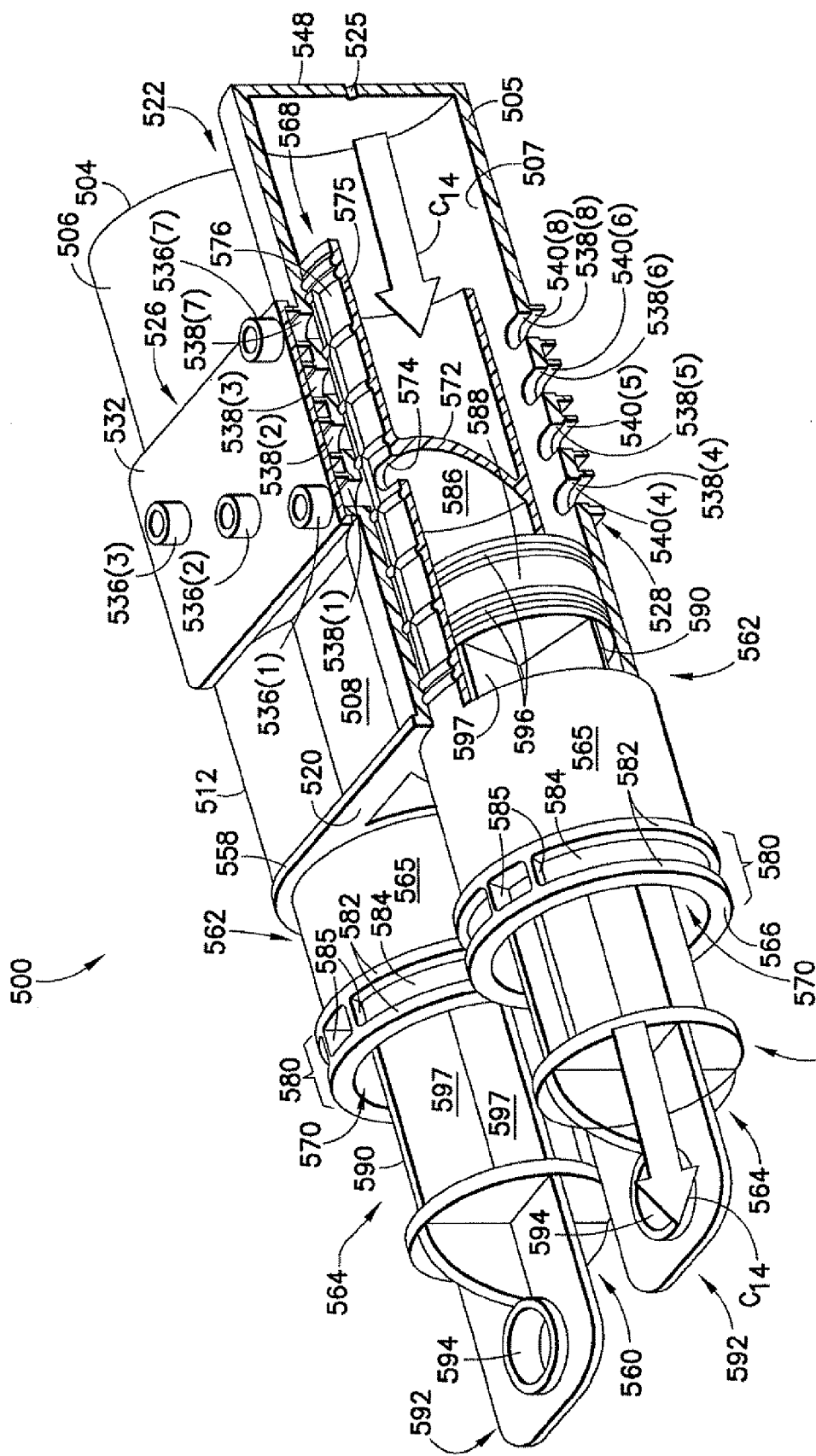

As illustrated in FIG. 83, fluid pump 560 may begin in a position where sleeve port 574 in sleeve body 565 of sleeve piston 562 is aligned with inlet fluid port 538(3). As sleeve piston 562 is held stationary by drive system 700, opposing piston 564 may be moved axially and generally linearly away from the sleeve piston 562 by the drive system 700. As this movement occurs, as represented by an arrow $C_{11}$ in FIG. 84, an inlet fluid path is established between a source of contrast media fluid, for instance, and pumping chamber 586 according to the methodology described previously. This fluid path is denoted by an arrow $C_{12}$ in FIG. 84. As piston 564 continues to move in the direction of arrow $C_{11}$, fluid is drawn into pumping chamber 586 via connector port 536(3), fluid passageway 540(3), and inlet fluid port 538(3) under negative pressure caused by this movement. When a desired amount of fluid is drawn into pumping chamber 586 under the withdrawing action of piston 564, the movement of the piston 564 is stopped by drive system 700. Thereafter, as illustrated in FIG. 85, sleeve piston 562 is rotated in the direction of arrow $C_{13}$ so that sleeve port 574 is no longer in alignment with any of fluid ports 538, thereby placing the sleeve port 574 in a "shut-off" position. In this position, each of fluid ports 538 are covered by the sleeve body 565 which prevents fluid from these ports from being inadvertently drawn into pumping chamber 586. Pistons 562, 564 are then substantially synchronously moved to another inlet fluid port 538 or, alternatively, to one of the outlet fluid ports 538(7) (patient), 538(8) (waste container). An example of this substantially synchronous movement is illustrated by arrows $C_{14}$ in FIG. 86. It is noted that the sleeve port 574 in sleeve piston 562 remains in the "shut-off" position.

Figure 87:
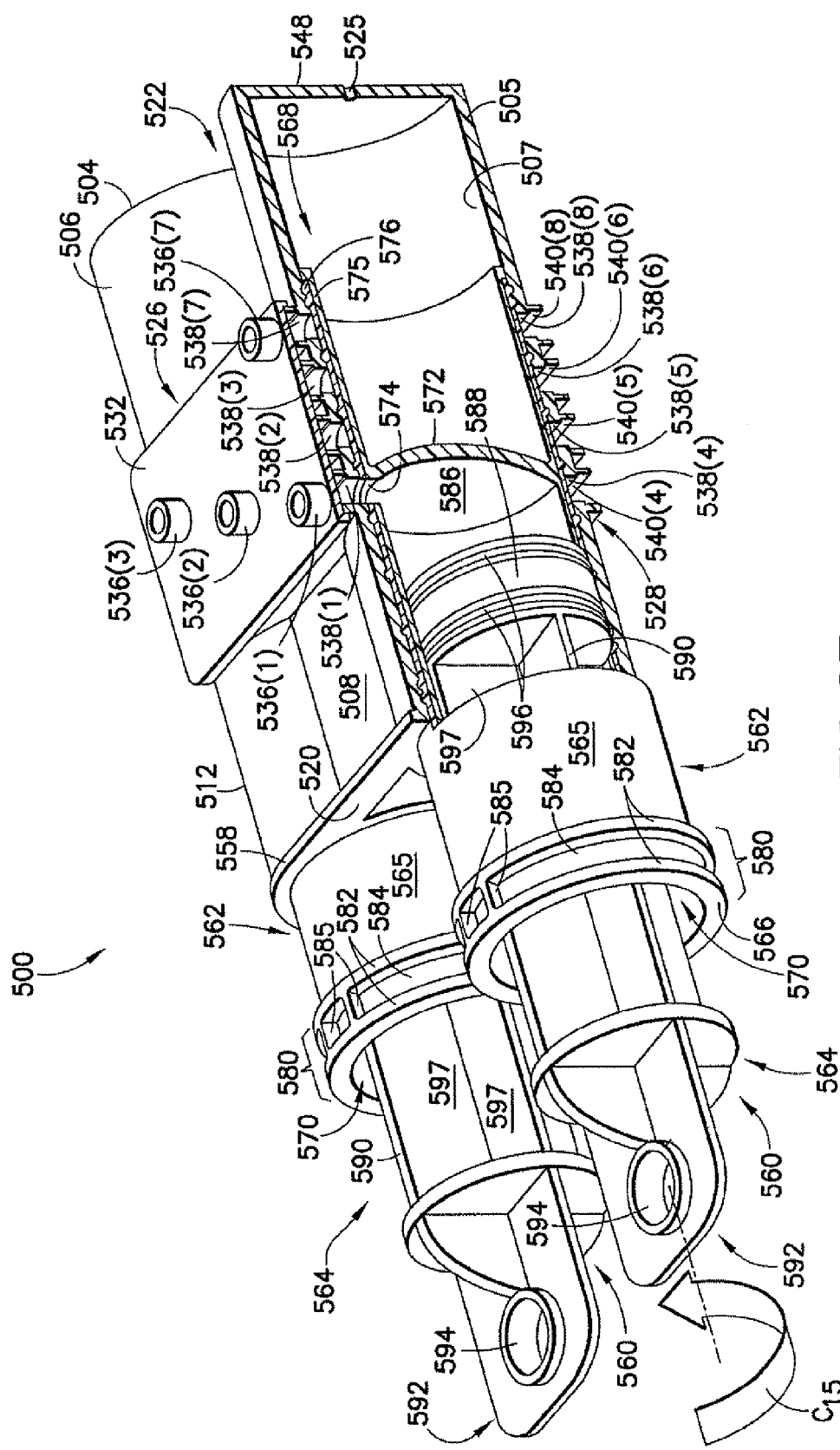
Figure 88:
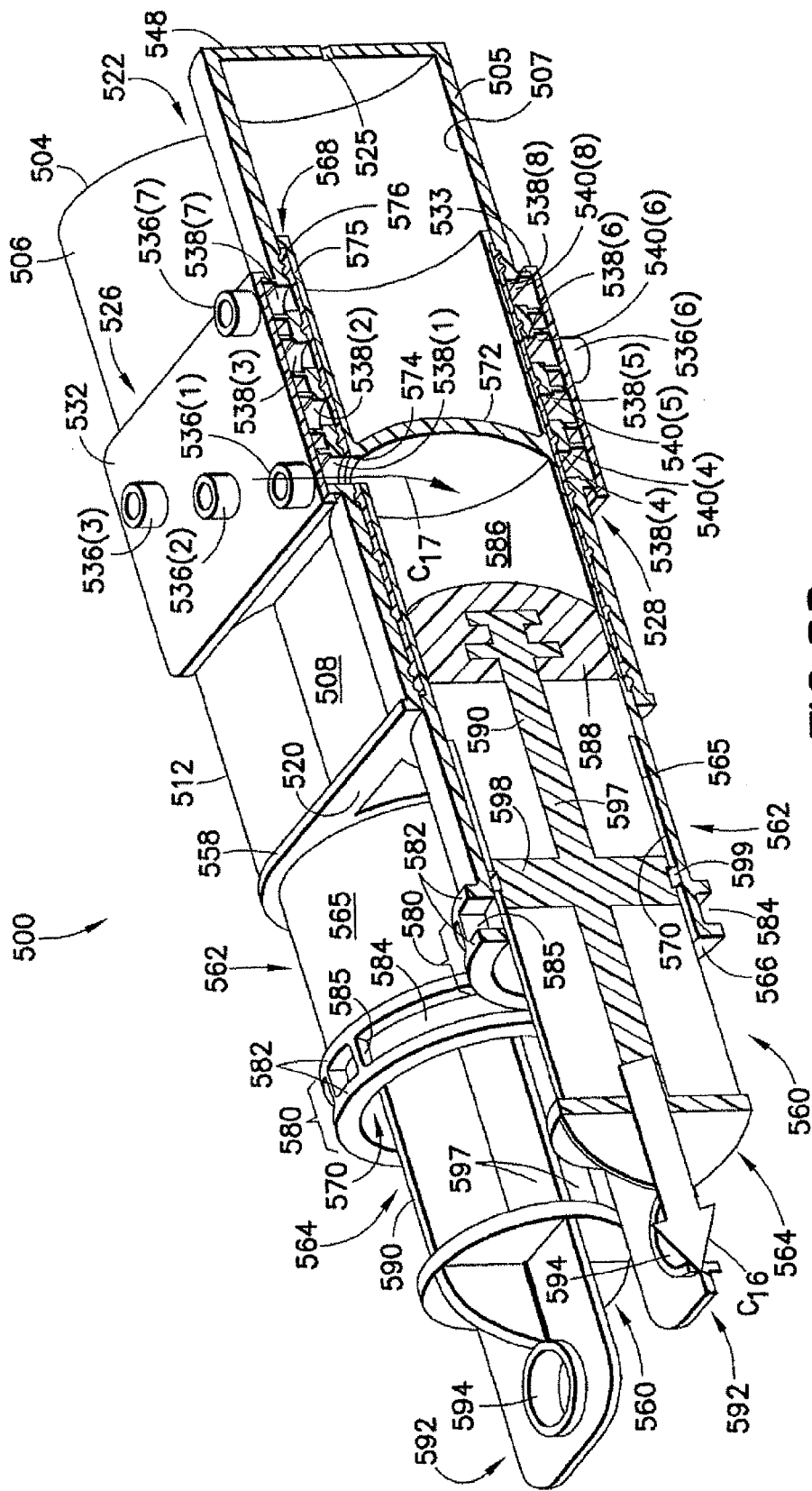

As shown in FIG. 87, once the next fluid port 538 is selected, for instance inlet fluid port 538(1), an inlet fluid path is established from pumping chamber 586 to "saline" connector inlet port 538(1) by rotating sleeve piston 562 in the direction of arrow $C_{15}$ so that sleeve port 574 aligns with inlet fluid port 538(1). Once the foregoing fluid path is established, drive system 700 "fixes" the location of sleeve piston 562. As sleeve piston 562 is held stationary at the selected inlet fluid port 538(1), opposing piston 564 may again be moved axially and generally linearly away from sleeve piston 562 as shown by arrow $C_{16}$ in FIG. 88. As this movement occurs, fluid, now saline from a bulk saline fluid source 14 connected to connector inlet port 536(1) is drawn into pumping chamber 586, as shown by arrow $C_{17}$, under the negative pressure caused by the movement of piston 564. As saline enters pumping chamber 586, the saline mixes with the contrast media fluid already present in pumping chamber 586 which dilutes the contrast media fluid. When a desired amount of saline is drawn into pumping chamber 586, pistons 562, 564 may be moved to establish another inlet fluid path, if desired, such as an inlet fluid path associated with inlet fluid port 538(2) connected to another type of contrast media fluid in the present example or another fluid altogether or, alternatively, pistons 562, 564 may be moved to patient outlet port 538(7) to eject the contents of pumping chamber 586 into the patient fluid path 12.

If it is assumed that patient outlet port 538(7) is selected, sleeve piston 562 is rotated such that it places sleeve port 574 in the "shut-off" position and then pistons 562, 564 are moved substantially in synch to patient outlet port 538(7). When pistons 562, 564 reach patient outlet port 538(7), sleeve piston 562 is rotated to align sleeve port 574 with patient outlet port 538(7), thereby establishing an outlet fluid path from pumping chamber 586 to patient connector port 536(7) via patient outlet port 538(7) and connecting fluid passageway 540(7). A suitable fluid connection is desirably present between patient connector port 536(7) and patient fluid path 12 to the patient. Once the foregoing fluid communication path is established, drive system 700 "fixes" the location of sleeve piston 562 and causes insertion piston 564 to begin a pumping or ejection stroke or movement to expel the fluid mixture in pumping chamber 586 to the patient fluid path 12.

Figure 89:
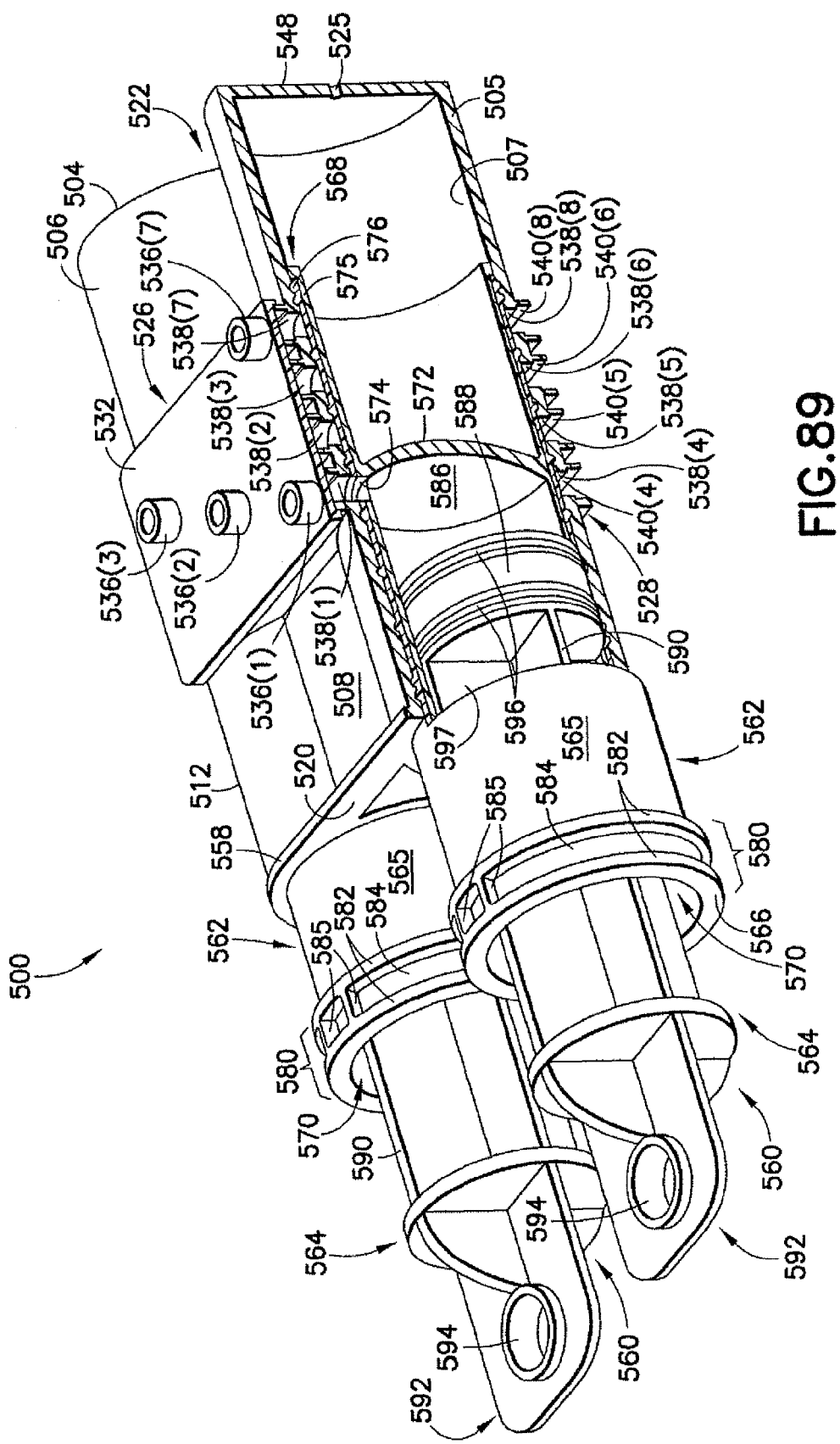
FIGS. 89-91 are cross-sectional views showing the fluid pumping device of FIG. 65 accessing a bank of fluid ports in the base member of the pump housing which are positioned on a bottom portion of the base member.
Figure 90:
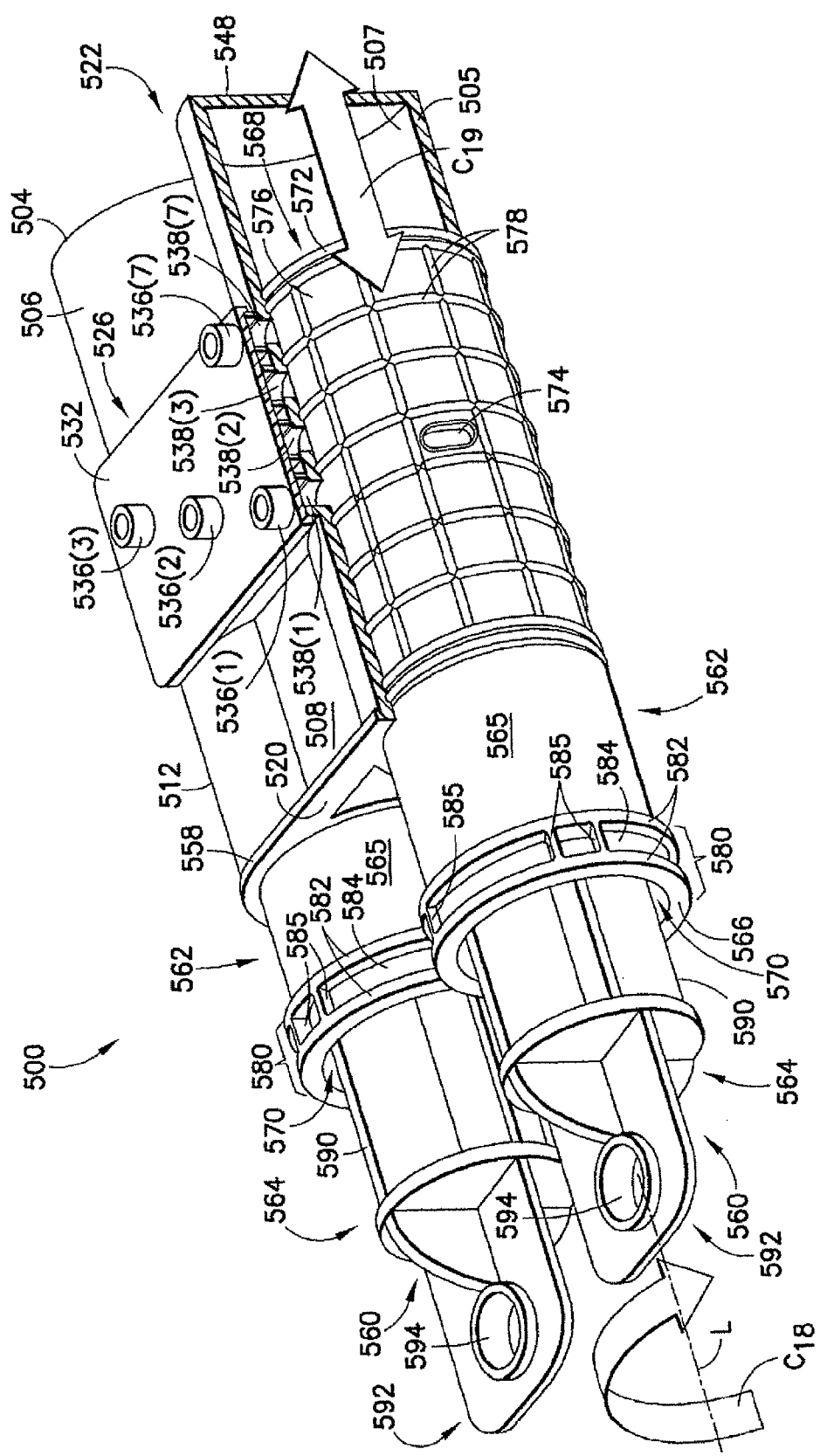
Figure 91:
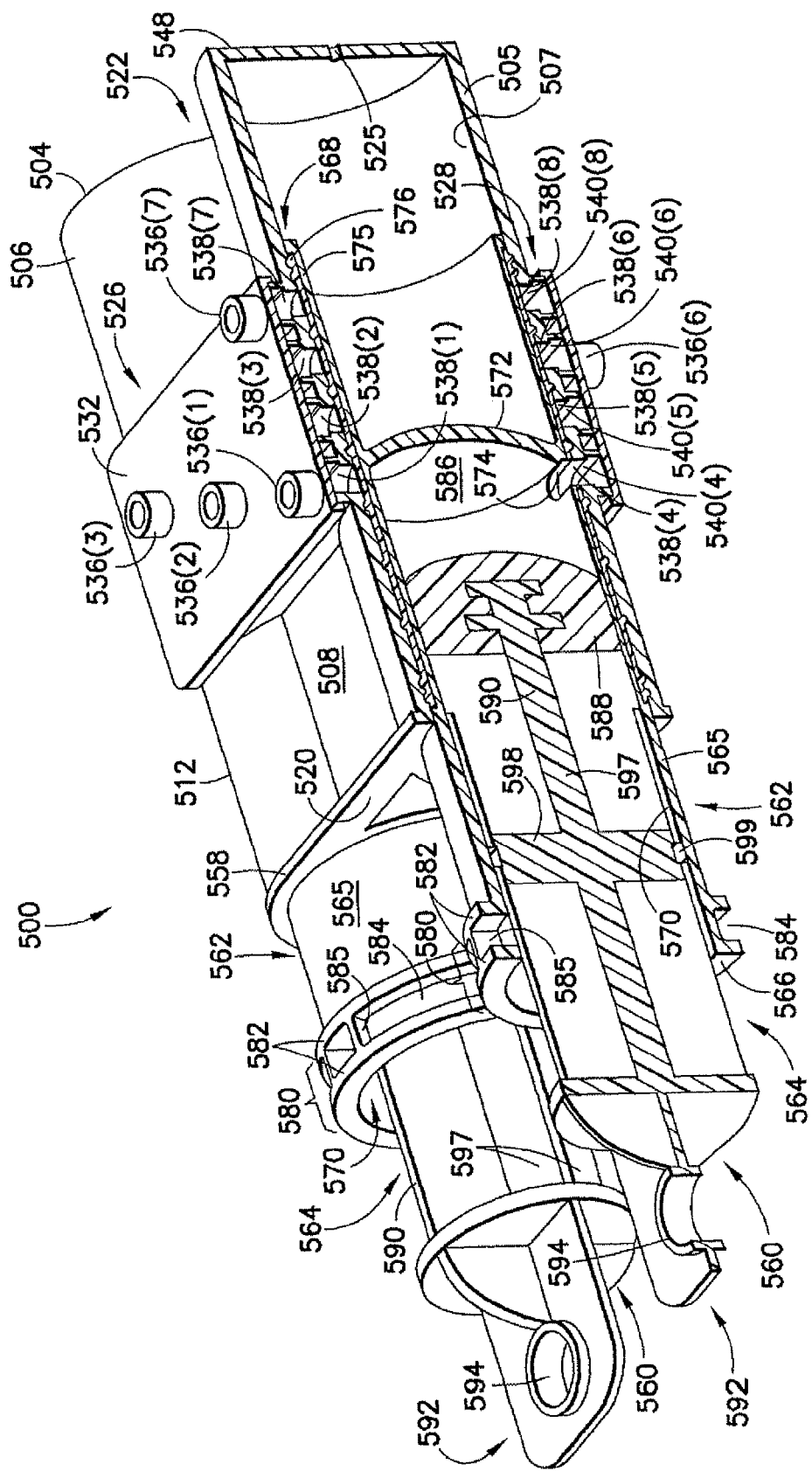

While the foregoing operational examples were limiting to discussions of selecting respective bulk fluid sources connected to connector ports 536(1)-536(3) on the "top" manifold portion 526 and a patient connector port 536(7) also associated with top manifold portion 526, it will be understood that sleeve piston 562 may exhibit rotational movement to access the bottom fluid ports 538(4)-538(6) and 538(8) by drive system 700, modified to operate sleeve piston 562 in this rotational manner. For example, with reference to FIGS. 89-91, after insertion piston 564 has moved axially to draw fluid into pumping chamber 586 through fluid port 538(1) as shown in FIG. 89, sleeve piston 562 may optionally be rotated in the direction of arrow $C_{15}$ and/or axially translated in the direction of arrow $C_{19}$ by drive system 700 to select one of fluid ports 538(4)-538(6) and 538(8) as shown in FIG. 90. FIG. 91 illustrates that sleeve piston 562 has rotated 180° to fluid port 538(4) without translational movement.

It should be noted that fluid pumping device 500 is not intended to be limited to linearly arranged fluid ports 538 in the cylindrical members 505, 506 of base member 504. Various other arrangements may be provided in cylindrical members 505, 506 of base member 504. Several of exemplary options are illustrated in FIGS. 92A-92I. For exemplary purposes, each of these figures only illustrates one of cylindrical members 505, 506 of base member 504 and omits pistons 562, 564 disposed in barrels 507 of cylindrical members 505, 506. Unless noted otherwise, the arrangement and operation of pistons 562, 564 is identical to the foregoing description of these components. It is noted that modifications are required to manifold portions 526, 528 to effect access to the respective arrangements of fluid ports 538 described herein and such changes are within the skill of those skilled in art.

Figure 92B:
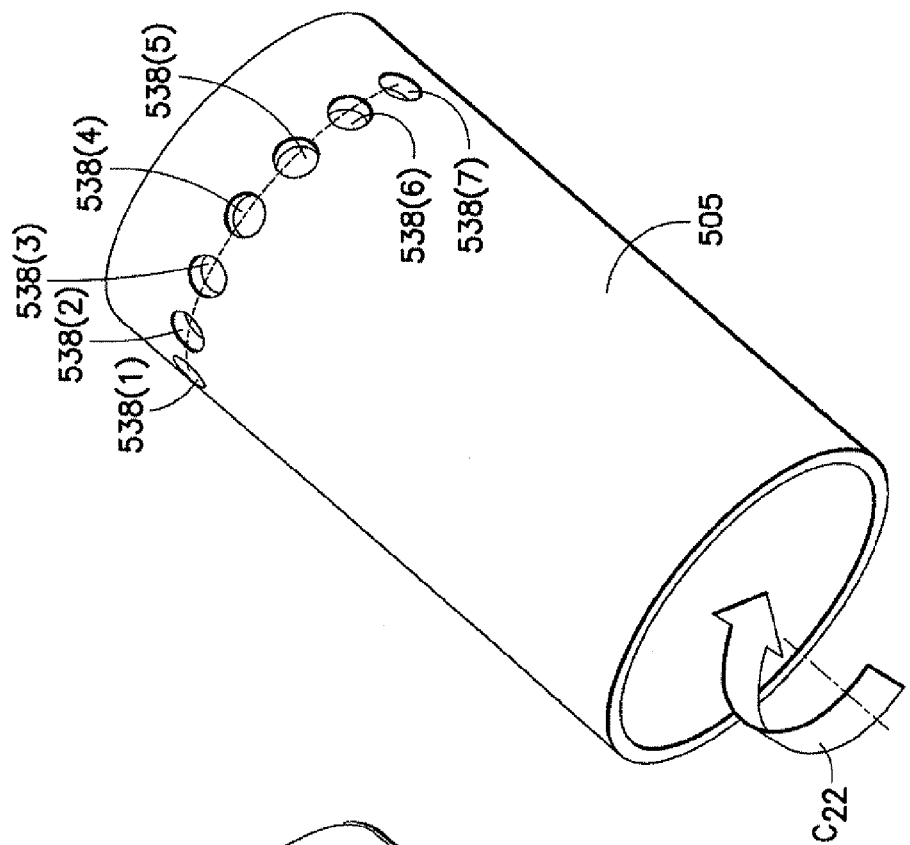
Figure 92A:
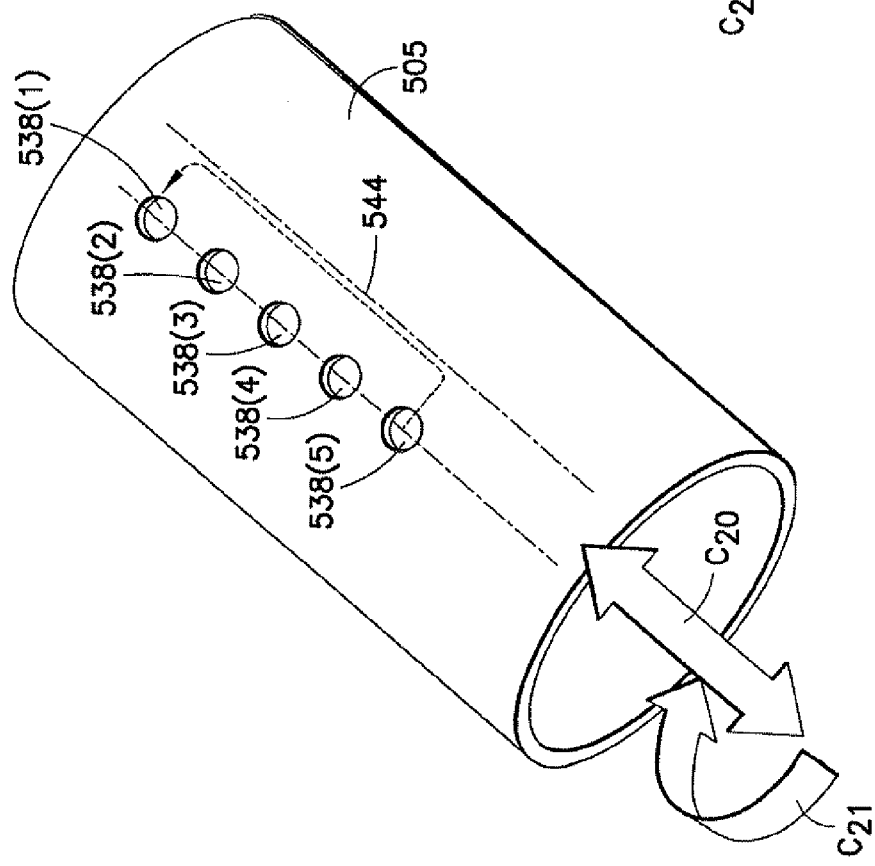

With reference to FIG. 92A, cylindrical member 505 includes a plurality of fluid ports 538 arranged in an axial row. In the illustrated embodiment, five fluid ports 538 are provided. For exemplary and non-limiting purposes, fluid ports 538 may be defined as inlet or outlet ports as follows. Fluid ports 538(1), 538(2), and 538(5) may each be defined as inlet ports. Inlet fluid port 538(1) may be for a first type of contrast media fluid, inlet fluid port 538(2) may be for saline, and inlet fluid port 538(5) may be for a second type of contrast media. Fluid ports 538(3) and 538(4) may each be defined as outlet ports. Outlet fluid port 538(3) may be a patient outlet port and outlet fluid port 538(4) may be a waste fluid port. Movement of sleeve piston 562 in bidirectional axial movement is denoted by arrow $C_{20}$ and this bidirectional axial movement is used to select one of the fluid ports 538. Prior to moving sleeve piston 562 in an axial direction, sleeve piston 562 is rotated in the direction of arrow $C_{21}$ to a "shut-off" position 544 of sleeve port 574 when moving between fluid ports 538. This rotation minimizes or prevents fluid from inadvertently being drawn into pumping chamber 586 when sleeve port 574 moves past each of the fluid ports 538 during axial movement (without such rotation).

With reference to FIG. 92B, cylindrical member 505 includes a plurality of fluid ports 538 positioned within a single circumferential row. In the illustrated embodiment, seven fluid ports 538 are provided. For exemplary and non-limiting purposes, fluid ports 538 may be defined as inlet or outlet ports as follows. Fluid ports 538(1), 538(2), 538(6), and 538(7) may each be defined as inlet ports. Fluid port 538(1) may be an inlet port for a first type of contrast media fluid, fluid ports 538(2) and 538(6) may be inlet ports for saline and fluid port 538(7) may be an inlet port for a second type of contrast media fluid. Fluid ports 538(3)-538(5) may each be defined as outlet ports. More specifically, fluid port 538(4) may be a patient outlet port and fluid ports 538(3) and 538(5) may each be a waste outlet port. Movement of sleeve piston 562 in a rotational direction only is denoted by arrow $C_{22}$ and this allows for the desired fluid port 538 to be selected. Sleeve piston 562 in this embodiment only moves rotationally because each of the fluid ports 538 is provided in the same circumferential row. However, this configuration desirably includes multiple saline fluid ports 538(2), 538(6) and multiple waste fluid ports 538(3), 538(5) to prevent cross contamination between fluid ports 538 during rotation of the first piston 562.

With reference to FIG. 92C, cylindrical member 505 includes a plurality of manifold fluid ports 538 again arranged in a single circumferential row. In the illustrated embodiment, five fluid ports 538 are provided. For exemplary and non-limiting purposes, fluid ports 538 may be defined as inlet or outlet ports as follows. Fluid ports 538(1)-538(3) may each be defined as inlet ports. Fluid port 538(1) may be an inlet port for a first type of contrast media fluid, fluid port 538(3) may be an inlet port for saline, and fluid port 538(2) may be an inlet port for a second type of contrast media fluid. Fluid ports 538(4) and 538(5) may each be defined as outlet fluid ports. More specifically, fluid port 538(5) may be a patient outlet port and fluid port 538(4) may be a waste material port. Movement of sleeve piston 562 in a rotational direction is denoted by arrow $C_{23}$ and this movement is used to select one of the fluid ports 538. Prior to moving sleeve piston 562 in a rotational direction, sleeve piston 562 may be moved axially in the direction of arrow $C_{24}$ to a "shut-off" position 544 of sleeve port 574 formed in sleeve body 565 of sleeve piston 562 when moving between fluid ports 538. This axial movement minimizes or prevents fluid from being inadvertently drawn into pumping chamber 586 when sleeve port 574 moves past each of the fluid ports 538 during rotational movement.

With reference to FIG. 92D, cylindrical member 505 includes a plurality of fluid ports 538 arranged in a pair of adjacent circumferential rows. In the illustrated embodiment, eight fluid ports 538 are provided and are divided into two circumferential rows having four fluid ports 538 each. For exemplary and non-limiting purposes, fluid ports 538 may be defined as inlet or outlet ports as follows. Fluid ports 538(1)-538(4) may each be defined as inlet ports. Fluid port 538(1) may be an inlet port for a first type of contrast media fluid, fluid ports 538(3) and 538(4) may be inlet ports for saline, and fluid port 538(2) may be an inlet port for a second type of contrast media fluid. Fluid ports 538(5)-538(8) may each be defined as outlet ports. More specifically, fluid ports 538(7) and 538(8) may each be patient outlet ports and fluid ports 538(5) and 538(6) may each be waste outlet ports. Movement of sleeve piston 562 in a rotational direction is denoted by arrow $C_{25}$ and is used to select one of the fluid ports 538. Prior to moving sleeve piston 562 in a rotational direction, sleeve piston 562 is moved axially in the direction of arrow $C_{26}$ to a "shut-off" position 544 of sleeve port 574 formed in sleeve body 565 of sleeve piston 562 when moving between fluid ports 538. This axial movement minimizes or prevents fluid from being inadvertently drawn into pumping chamber 586 when sleeve port 574 moves past each of the fluid ports 538 during rotational movement. Sleeve piston 562 is also moved in the axial direction to select either a first row of fluid ports 538 including fluid ports 538(1), 538(3), 538(5), and 538(7) or a second row of fluid ports 538 including fluid ports 538(2), 538(4), 538(6), and 538(8).

With reference to FIG. 92E, cylindrical member 505 is identical to the one shown in FIG. 92D except that the plurality of fluid ports 538 is arranged in a pair of axial rows rather than a pair of circumferential rows. In the illustrated embodiment, eight fluid ports 538 are provided and are divided into two axial rows having four fluid ports 538 each. For exemplary and non-limiting purposes, fluid ports 538 may be defined as inlet or outlet ports as follows. Fluid ports 538(1)-538(4) may each be defined as inlet ports. Fluid port 538(1) may be an inlet port for a first type of contrast media fluid, fluid ports 538(3) and 538(4) may be inlet ports for saline, and fluid port 538(2) may be an inlet port for a second type of contrast media fluid. Fluid ports 538(4)-538(8) may each be defined as outlet ports. More specifically, fluid ports 538(7) and 538(8) may each be patient outlet ports and fluid ports 538(5) and 538(6) may each be waste outlet ports. Movement of sleeve piston 562 in an axial direction is denoted by arrow $C_{27}$ and is used to select one of the fluid ports 538. Prior to moving sleeve piston 562 in an axial direction, sleeve piston 562 is moved rotationally in the direction of arrow $C_{28}$ to a "shut-off" position 544 of sleeve port 574 formed in sleeve body 565 of sleeve piston 562 when moving between fluid ports 538. This axial movement minimizes or prevents fluid from being inadvertently pulled into pumping chamber 586 when sleeve port 574 moves past each of the fluid ports 538 during rotational movement. Sleeve piston 562 is also moved in the rotational direction to select either a first row of fluid ports 538 including fluid ports 538(1), 538(3), 538(5), and 538(7) or a second row of fluid ports 538 including fluid ports 538(2), 538(4), 538(6), and 538(8).

With reference to FIG. 92F, cylindrical member 505 includes a plurality of fluid ports 538 arranged in a pair of circumferential rows. In the illustrated embodiment, five fluid ports 538 are provided and are divided into two circumferential rows with the fluid ports 538 acting as fluid inlets provided in a first circumferential row and the fluid ports 538 acting as outlets provided in a second circumferential row. For exemplary and non-limiting purposes, fluid ports 538 may be defined as inlet or outlet ports as follows. Fluid ports 538(1)-538(3) may each be defined as inlet ports. Fluid port 538(1) may be an inlet port for a first type of contrast media fluid, fluid port 538(3) may be an inlet port for saline, and fluid port 538(2) may be an inlet port for a second type of contrast media fluid. Fluid ports 538(4) and 538(5), provided in a different circumferential row than manifold portion inlet ports 538(1)-538(3), are each defined as outlet fluid ports. More specifically, fluid port 538(5) may be a patient outlet port and fluid port 538(4) may be a waste outlet port. Movement of sleeve piston 562 in a rotational direction is denoted by arrow $C_{29}$ and is used to select one of the fluid ports 538 in a given row. Movement of sleeve piston 562 in an axial direction is denoted by arrow $C_{30}$ and allows for selection of either the output row or the input row of fluid ports 538. "Dead" spaces 546 in the output row and the input row allow for a "shut-off" position of sleeve port 574 formed in sleeve body 565 of sleeve piston 562 when moving between fluid ports 538.

The embodiment of cylindrical member 505 illustrated in FIG. 92G is identical to the one shown in FIG. 92F except that the plurality of fluid ports 538 is arranged in a pair of axial rows rather than a pair of circumferential rows. In the illustrated embodiment, five fluid ports 538 are provided and are divided into two axial rows with the fluid ports 538 acting as inlets provided in a first axial row and the fluid ports 538 acting as outlets provided in a second axial row. For exemplary and non-limiting purposes, fluid ports 538 may be defined as inlet or outlet ports as follows. Fluid ports 538(1)-538(3) may each be defined as inlet ports. Fluid port 538(1) may be an inlet port for a first type of contrast media fluid, fluid port 538(3) may be an inlet port for saline, and fluid port 538(2) may be an inlet port for a second type of contrast media fluid. Fluid ports 538(4) and 538(5), provided in a different axial row than inlet fluid ports 538(1)-538(3), are each defined as outlet ports. More specifically, fluid port 538(5) may be a patient outlet port and fluid port 538(4) may be a waste outlet port. Movement of sleeve piston 562 in an axial direction is denoted by arrow $C_{31}$ and is used to select one of the fluid ports 538 in a given row. Movement of sleeve piston 562 in a rotational direction is denoted by arrow $C_{32}$ and allows for selection of either the output row or the input row of fluid ports 538. "Dead" spaces 546 in the output row and the input row allow for a "shut-off" position of sleeve port 574 in sleeve body 565 of sleeve piston 562 when moving between fluid ports 538.

With reference to FIG. 92H, cylindrical member 505 includes a plurality of fluid ports 538 positioned within a single helical row. In the illustrated embodiment, seven fluid ports 538 are provided. For exemplary and non-limiting purposes, fluid ports 538 may be defined as inlet or outlet ports as follows. Fluid ports 538(1), 538(2), 538(6), and 538(7) may each be defined as inlet ports. Fluid port 538(1) may be an inlet port for a first type of contrast media fluid, fluid ports 538(2) and 538(6) may be inlet ports for saline and fluid port 538(7) may be an inlet port for a second type of contrast media fluid. Fluid ports 538(3)-538(5) may each be defined as outlet ports. More specifically, fluid port 538(4) may be a patient outlet port and fluid ports 538(3) and 538(5) may be waste outlet ports. Movement of sleeve piston 562 in a simultaneous rotational and axial direction allows for the desired fluid port 538 to be selected. Alternatively, sleeve piston 562 in this embodiment may also be moved in a rotational direction first to a "dead" space 546 and then in an axial direction to a desired fluid port 538 which allows for a "shut-off" position 544 of sleeve port 574 formed in sleeve body 565 of sleeve piston 562 when moving between fluid ports 538

The embodiments of cylindrical member 505 illustrated in FIGS. 92I and 92J each require a sleeve piston 562 having at least one sleeve port 574 (not shown) defined in a desirably planar end wall 572 of sleeve body 565 of the sleeve piston 562 rather than in the elongated sidewall of the sleeve body 565 as shown in previous embodiments. With reference to FIG. 92I, an alternative embodiment of cylindrical member 505 includes a plurality of fluid ports 538 positioned within a single circular row on an end face 548 of cylindrical member 505. In the illustrated embodiment, seven fluid ports 538 are provided. For exemplary and non-limiting purposes, fluid ports 538 may be defined as inlet or outlet ports as follows. Fluid ports 538(1), 538(2), 538(6), and 538(7) may each be defined as inlet ports. Fluid port 538(1) may be an inlet port for a first type of contrast media fluid, fluid ports 538(2) and 538(6) may be inlet ports for saline, and fluid port 538(7) may be an inlet port for a second type of contrast media fluid. Fluid ports 538(3)-538(5) may each be defined as outlet ports. More specifically, fluid port 538(4) may be a patient outlet port and fluid ports 538(3) and 538(5) may be waste outlet ports. Movement of sleeve piston 562 in a rotational direction is denoted by arrow $C_{33}$ in FIGS. 92I and 92J and allows for the desired fluid port 538 to be aligned with sleeve port 574 formed in the end wall 572 of sleeve body 565 of sleeve piston 562. Sleeve piston 562 in this embodiment only moves rotationally because each fluid port 538 is provided in the same circumferential row.

With reference to FIG. 92J, this embodiment of cylindrical member 505 includes a plurality of fluid ports 538 positioned within a single helical row on end face 548 of cylindrical member 505. In the illustrated embodiment, seven fluid ports 538 are provided. For exemplary and non-limiting purposes, fluid ports 538 may be defined as inlet or outlet ports as follows. Fluid ports 538(1), 538(2), 538(6), and 538(7) may each be defined as inlet ports. Fluid port 538(1) may be an inlet port for a first type of contrast media fluid, fluid ports 538(2) and 538(6) may be inlet ports for saline, and fluid port 538(7) may be an inlet port for a second type of contrast media fluid. Fluid ports 538(3)-538(5) may each be defined as outlet ports. More specifically, fluid port 538(4) may be a patient outlet port and fluid ports 538(3) and 538(5) may be waste outlet ports. With this embodiment, sleeve piston 562 has four sleeve ports 574 (not shown) that are equally spaced along a radius of the end wall 572 of sleeve piston 562. Movement of such a configured sleeve piston 562 in a rotational direction allows for the desired fluid port 538 to be selected by aligning one of the four sleeve ports 574 with the desired fluid port 538.

While embodiments of a fluid pumping device and a fluid delivery system incorporating the fluid pumping device and associated drive systems were provided in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A fluid pumping device, comprising:
a pump housing comprising a base member comprising a plurality of inlet ports and at least one outlet port; and
a pair of opposing pistons movably associated with the base member, wherein the pair of opposing pistons at least in part define a pumping chamber of the fluid pumping device therebetween, and are independently controlled such that any one of the plurality of inlet ports or the at least one outlet port is independently selectable to be in fluid communication with the pumping chamber.

2. The fluid pumping device of claim 1, wherein the base member supports the pair of opposing pistons to at least reciprocally operate relative to the base member.

3. The fluid pumping device of claim 1, wherein the base member comprises a manifold portion defining the plurality of inlet ports and the at least one outlet port.

4. The fluid pumping device of claim 3, further comprising a manifold cap on the manifold portion and defining the plurality of inlet ports and the at least one outlet port in combination with the manifold portion.

5. The fluid pumping device of claim 3, wherein the manifold portion comprises a plurality of fluid passageways respectively connected to the plurality of inlet ports and the at least one outlet port.

6. The fluid pumping device of claim 5, wherein the base member comprises at least one opening in each of the fluid passageways to enable fluid communication between the pumping chamber and the plurality of inlet ports and the at least one outlet port via the plurality of fluid passageways.

7. The fluid pumping device of claim 1, wherein the base member comprises a manifold portion defining the plurality of inlet ports and the at least one outlet port, and wherein the plurality of inlet ports and the at least one outlet port are disposed on lateral sides of the manifold portion.

8. A fluid pumping device, comprising:
a pump housing comprising a base member comprising a plurality of inlet ports and at least one outlet port; and
a pair of opposing pistons movably associated with the base member, wherein the pair of opposing pistons at least in part define a pumping chamber of the fluid pumping device therebetween, and are independently controlled such that any one of the plurality of inlet ports or the at least one outlet port is independently selectable to be in fluid communication with the pumping chamber; and
wherein one of the pair of opposing pistons comprises a sleeve portion and the other of the pair of opposing pistons is at least partially disposed in the sleeve portion to define the pumping chamber.

9. The fluid pumping device of claim 8, wherein the sleeve portion defines an opening for fluid communication with a selected inlet port or the at least one outlet port to establish fluid communication between the selected inlet port or the at least one outlet port and the pumping chamber.

10. The fluid pumping device of claim 8, further comprising a fluid seal element disposed between the base member and the sleeve portion.

11. A fluid delivery system, comprising:
a pump housing comprising a base member comprising a plurality of inlet ports and at least one outlet port;
a pair of opposing pistons movably associated with the base member, wherein the pair of opposing pistons at least in part define a pumping chamber of the fluid pumping device therebetween, and are independently controlled such that any one of the plurality of inlet ports or the at least one outlet port is independently selectable to be in fluid communication with the pumping chamber; and
a drive system interfaced with the pair of opposing pistons to at least reciprocally operate the pistons relative to the base member.

12. The fluid delivery system of claim 11, wherein the drive system comprises respective piston positioning devices interfaced with each piston of the pair of opposing pistons.

13. The fluid delivery system of claim 12, wherein the piston positioning devices are disposed on opposite sides of the base member to interface with the respective pistons.

14. The fluid delivery system of claim 12, wherein the piston positioning devices are each disposed on a same side of the base member to interface with the respective pistons.

15. The fluid delivery system of claim 11, further comprising a support device to support at least one of the pair of opposing pistons in the drive system.

16. The fluid delivery system of claim 12, further comprising a position sensor associated with the drive system to interface with at least one of the piston positioning devices to ascertain at least one position of the piston positioning device.

17. The fluid delivery system of claim 14, wherein the piston positioning devices are disposed commonly on a carriage.

18. The fluid delivery system of claim 17, wherein the carriage is movable by a carriage drive system.

19. The fluid delivery system of claim 18, wherein the carriage is bi-directional linearly movable by the carriage drive system.

20. The fluid delivery system of claim 17, further comprising a position sensor associated with the drive system to interface with the carriage to ascertain at least one position of the carriage.

* * * * *

UNITED STATES PATENT AND TRADEMARK OFFICE
CERTIFICATE OF CORRECTION

| | | |
|---|---|---|
| PATENT NO. | : 9,057,363 B2 | Page 1 of 1 |
| APPLICATION NO. | : 12/745849 | |
| DATED | : June 16, 2015 | |
| INVENTOR(S) | : Capone et al. | |

It is certified that error appears in the above-identified patent and that said Letters Patent is hereby corrected as shown below:

IN THE SPECIFICATION:

In Column 21, Line 55, delete "146b as" and insert -- 146h as --, therefor.
In Column 32, Line 15, delete "sled carnage" and insert -- sled carriage --, therefor.
In Column 45, Line 60, delete "manifold ports 342" and insert -- manifold ports 346 --, therefor.
In Column 46, Line 10, delete "manifold port 342" and insert -- manifold port 346 --, therefor.

Signed and Sealed this
Twenty-sixth Day of January, 2016

Michelle K. Lee
*Director of the United States Patent and Trademark Office*